(12) United States Patent
Zhang et al.

(10) Patent No.: US 11,997,994 B2
(45) Date of Patent: Jun. 4, 2024

(54) GENETICALLY MODIFIED NON-HUMAN ANIMALS WITH COMMON LIGHT CHAIN IMMUNOGLOBULIN LOCUS

(71) Applicant: Biocytogen Pharmaceuticals (Beijing) Co., Ltd., Beijing (CN)

(72) Inventors: Yabo Zhang, Beijing (CN); Hui Lu, Beijing (CN); Huizhen Zhao, Beijing (CN); Jiawei Yao, Beijing (CN); Yi Yang, Beijing (CN); Yuelei Shen, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/969,254

(22) Filed: Oct. 19, 2022

(65) Prior Publication Data

US 2023/0128645 A1   Apr. 27, 2023

Related U.S. Application Data

(63) Continuation of application No. PCT/CN2021/097652, filed on Jun. 1, 2021.

(30) Foreign Application Priority Data

Jun. 2, 2020  (WO) ............... PCT/CN2020/094000
Apr. 7, 2021  (WO) ............... PCT/CN2021/085839

(51) Int. Cl.
  *A01K 67/0278*  (2024.01)
(52) U.S. Cl.
  CPC ...... *A01K 67/0278* (2013.01); *A01K 2207/15* (2013.01); *A01K 2227/105* (2013.01); *A01K 2267/01* (2013.01)
(58) Field of Classification Search
  CPC .............................................. A01K 67/0278
  See application file for complete search history.

(56) References Cited

U.S. PATENT DOCUMENTS

| | | | |
|---|---|---|---|
| 4,522,811 A | 6/1985 | Eppstein et al. | |
| 4,603,112 A | 7/1986 | Paoletti et al. | |
| 4,769,330 A | 9/1988 | Paoletti et al. | |
| 4,777,127 A | 10/1988 | Suni et al. | |
| 5,017,487 A | 5/1991 | Stunnenberg et al. | |
| 6,586,251 B2 | 7/2003 | Economides et al. | |
| 6,596,541 B2 | 7/2003 | Murphy et al. | |
| 7,105,348 B2 | 9/2006 | Murphy et al. | |
| 7,129,084 B2 | 10/2006 | Buelow et al. | |
| 7,262,028 B2 | 8/2007 | Van Berkel | |
| 7,541,513 B2 | 6/2009 | Bruggeman et al. | |
| 7,816,578 B2 | 10/2010 | Tomizuka et al. | |
| 8,367,888 B2 | 2/2013 | Bruggemann et al. | |
| 8,502,018 B2 | 8/2013 | Murphy et al. | |
| 8,759,105 B2 | 6/2014 | Economides et al. | |
| 8,791,323 B2 | 7/2014 | Murphy et al. | |
| 8,846,402 B2 | 9/2014 | Economides et al. | |
| 8,877,688 B2 * | 11/2014 | Vasquez ............... | C07K 16/005 506/17 |
| 8,907,157 B2 | 12/2014 | Buelow | |
| 9,253,965 B2 | 2/2016 | Bradley et al. | |
| 9,353,394 B2 | 5/2016 | Murphy et al. | |
| 9,371,553 B2 | 6/2016 | Murphy et al. | |
| 9,376,699 B2 | 6/2016 | Murphy et al. | |
| 9,382,567 B2 | 7/2016 | Murphy et al. | |
| 9,388,446 B2 | 7/2016 | Murphy et al. | |
| 9,434,782 B2 | 9/2016 | Bradley et al. | |
| 9,439,405 B2 | 9/2016 | Bruggemann et al. | |
| 9,445,581 B2 | 9/2016 | Bradley et al. | |
| 9,447,177 B2 | 9/2016 | Bradley et al. | |
| 9,504,236 B2 | 11/2016 | Bradley et al. | |
| 9,505,827 B2 | 11/2016 | Bradley et al. | |
| 9,528,136 B2 | 12/2016 | Murphy et al. | |
| 9,677,129 B2 | 6/2017 | Economides et al. | |
| 9,708,635 B2 | 7/2017 | Murphy et al. | |
| 9,783,593 B2 | 10/2017 | Bradley et al. | |
| 9,788,534 B2 | 10/2017 | Bradley et al. | |
| 9,896,516 B2 | 2/2018 | Bradley et al. | |
| 9,924,705 B2 | 3/2018 | Liang et al. | |
| 9,938,357 B2 | 4/2018 | Bradley et al. | |
| 9,938,358 B2 | 4/2018 | Bradley et al. | |
| 9,963,501 B2 | 5/2018 | Haynes et al. | |
| 10,064,398 B2 | 9/2018 | Bradley et al. | |
| 10,149,462 B2 | 12/2018 | Lee et al. | |
| 10,165,763 B2 | 1/2019 | Bradley et al. | |

(Continued)

FOREIGN PATENT DOCUMENTS

| | | |
|---|---|---|
| AU | 2001284703 | 2/2002 |
| AU | 2002220048 | 5/2002 |

(Continued)

OTHER PUBLICATIONS

Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*

(Continued)

*Primary Examiner* — Anoop K Singh
*Assistant Examiner* — David A Montanari
(74) *Attorney, Agent, or Firm* — Fish & Richardson P.C.

(57) ABSTRACT

This disclosure relates to genetically modified animals and cells with humanized light chain immunoglobulin locus and/or humanized heavy chain immunoglobulin locus. In one aspect, the endogenous light chain immunoglobulin locus comprises a limit number of human IGKV genes and human IGKJ genes.

18 Claims, 115 Drawing Sheets

Specification includes a Sequence Listing.

(56) References Cited

U.S. PATENT DOCUMENTS

| | | | |
|---|---|---|---|
| 10,194,645 B2 | 2/2019 | Bruggemann et al. |
| 10,226,033 B2 | 3/2019 | Bradley et al. |
| 10,227,625 B2 | 3/2019 | Murphy et al. |
| 10,251,377 B2 | 4/2019 | Clube |
| 10,344,299 B2 | 7/2019 | Economides et al. |
| 10,378,037 B2 | 8/2019 | Murphy et al. |
| 10,378,038 B2 | 8/2019 | Murphy et al. |
| 10,378,039 B2 | 8/2019 | Murphy et al. |
| 10,378,040 B2 | 8/2019 | Murphy et al. |
| 10,526,630 B2 | 1/2020 | Murphy et al. |
| 2009/0253902 A1 | 10/2009 | Tomizuka et al. |
| 2010/0122361 A1 | 5/2010 | Smith et al. |
| 2012/0093785 A1 | 4/2012 | Oshimura et al. |
| 2014/0033336 A1 | 1/2014 | Murphy et al. |
| 2014/0041067 A1 | 2/2014 | Bradley et al. |
| 2014/0331343 A1 | 11/2014 | Bradley et al. |
| 2016/0219847 A1 | 8/2016 | Mcwhirter et al. |
| 2016/0316731 A1 | 11/2016 | Murphy et al. |
| 2017/0320936 A1 | 11/2017 | Bradley et al. |
| 2019/0174729 A1 | 6/2019 | Lee et al. |
| 2020/0390073 A1 | 12/2020 | Shen et al. |
| 2023/0064196 A1 | 3/2023 | Shen et al. |

FOREIGN PATENT DOCUMENTS

| | | | | |
|---|---|---|---|---|
| AU | 2002239422 | 6/2002 | | |
| AU | 2002244023 | 9/2002 | | |
| AU | 2008259939 | 12/2008 | | |
| AU | 2010269978 | 1/2011 | | |
| AU | 2011266843 | 12/2011 | | |
| AU | 2011286185 | 2/2012 | | |
| AU | 2012311286 | 3/2013 | | |
| AU | 2012311288 | 3/2013 | | |
| AU | 2012343587 | 6/2013 | | |
| AU | 2013239501 | 10/2013 | | |
| AU | 2014214863 | 8/2014 | | |
| AU | 2016101604 | 10/2016 | | |
| CA | 2362098 | 8/2000 | | |
| CA | 2430013 | 6/2002 | | |
| CA | 2438390 | 8/2002 | | |
| CA | 2688834 | 12/2008 | | |
| CN | 1200014 | 11/1998 | | |
| CN | 1717483 | 1/2006 | | |
| CN | 101688228 | 3/2010 | | |
| CN | 102791866 | 11/2012 | | |
| CN | 103228130 | 7/2013 | | |
| CN | 103571872 | 2/2014 | | |
| CN | 104244709 | 12/2014 | | |
| CN | 104334732 | 2/2015 | | |
| CN | 104540383 | 4/2015 | | |
| CN | 104994729 | 10/2015 | | |
| CN | 104994730 | 10/2015 | | |
| CN | 105308184 | 2/2016 | | |
| CN | 107602696 | 1/2018 | | |
| CN | 109837307 | 6/2019 | | |
| EP | 0345242 | 12/1989 | | |
| EP | 1151010 | 11/2001 | | |
| EP | 1354034 | 10/2003 | | |
| EP | 1360287 | 11/2003 | | |
| EP | 1399559 | 3/2004 | | |
| EP | 2003960 | 12/2008 | | |
| EP | 2152880 | 2/2010 | | |
| EP | 2264163 | 12/2010 | | |
| EP | 2421357 | 2/2012 | | |
| EP | 2501817 | 9/2012 | | |
| EP | 2505654 | 10/2012 | | |
| EP | 2517556 | 10/2012 | | |
| EP | 2517557 | 10/2012 | | |
| EP | 2564695 | 3/2013 | | |
| EP | 2602323 | 6/2013 | | |
| EP | 2604110 | 6/2013 | | |
| EP | 2649184 | 10/2013 | | |
| EP | 2757875 | 7/2014 | | |
| EP | 2758535 | 7/2014 | | |
| EP | 2786657 | 10/2014 | | |
| EP | 2787075 | 10/2014 | | |
| EP | 2792236 | 10/2014 | | |
| EP | 2798950 | 11/2014 | | |
| EP | 2831244 | 2/2015 | | |
| EP | 2877571 | 6/2015 | | |
| EP | 2967013 | 1/2016 | | |
| EP | 3028564 | 6/2016 | | |
| EP | 3028565 | 6/2016 | | |
| EP | 3051942 | 8/2016 | | |
| EP | 3085779 | 10/2016 | | |
| EP | 3085780 | 10/2016 | | |
| GB | 2200651 | 8/1988 | | |
| JP | 2001-505059 | 4/2001 | | |
| WO | WO 1989/001973 | 3/1989 | | |
| WO | WO 1991/002805 | 3/1991 | | |
| WO | WO 1996/27011 | 9/1996 | | |
| WO | WO 1998/024893 | 6/1998 | | |
| WO | WO 2000/46251 | 8/2000 | | |
| WO | WO 2002/12437 | 2/2002 | | |
| WO | WO 2002/36789 | 5/2002 | | |
| WO | WO 2002/43478 | 6/2002 | | |
| WO | WO 2002/066630 | 8/2002 | | |
| WO | WO 2003/000737 | 1/2003 | | |
| WO | WO-2005097185 A2 | * | 10/2005 | ........... C07K 16/283 |
| WO | WO 2007/117410 | 10/2007 | | |
| WO | WO 2008/077546 | 7/2008 | | |
| WO | WO 2008/151081 | 12/2008 | | |
| WO | 2009157771 A2 | 12/2009 | | |
| WO | WO 2011/004192 | 1/2011 | | |
| WO | 2011097603 A1 | 8/2011 | | |
| WO | WO-2011097603 A1 | * | 8/2011 | ......... A01K 67/0276 |
| WO | WO 2011/158009 | 12/2011 | | |
| WO | WO 2012/018610 | 2/2012 | | |
| WO | WO 2012/141798 | 10/2012 | | |
| WO | WO 2013/041844 | 3/2013 | | |
| WO | WO 2013/041845 | 3/2013 | | |
| WO | WO 2013/041846 | 3/2013 | | |
| WO | WO 2013/061098 | 5/2013 | | |
| WO | WO 2013/079953 | 6/2013 | | |
| WO | WO 2013/144566 | 10/2013 | | |
| WO | WO 2013/144567 | 10/2013 | | |
| WO | WO 2013/171505 | 11/2013 | | |
| WO | WO 2014/124156 | 8/2014 | | |
| WO | WO 2015/040402 | 3/2015 | | |
| WO | WO 2015/049517 | 4/2015 | | |
| WO | WO 2017/201476 | 11/2017 | | |
| WO | WO 2018/001241 | 1/2018 | | |
| WO | WO 2018/041118 | 3/2018 | | |
| WO | WO 2018/041119 | 3/2018 | | |
| WO | WO 2018/041120 | 3/2018 | | |
| WO | WO 2018/041121 | 3/2018 | | |
| WO | WO 2018/068756 | 4/2018 | | |
| WO | WO 2018/086583 | 5/2018 | | |
| WO | WO 2018/086594 | 5/2018 | | |
| WO | WO 2018/121787 | 7/2018 | | |
| WO | WO 2018/136823 | 7/2018 | | |
| WO | WO 2018/177440 | 10/2018 | | |
| WO | WO 2018/177441 | 10/2018 | | |
| WO | 2019008123 A2 | 1/2019 | | |
| WO | 2020169022 A1 | 8/2020 | | |
| WO | WO 2020/169022 | 8/2020 | | |
| WO | WO 2023/284850 | 1/2023 | | |

OTHER PUBLICATIONS

Gomez et al. (2010, Theriogenology, vol. 74, pp. 498-515) (Year: 2010).*

Buta et al. (2013, Stem Cell Res., vol. 11, pp. 552-562) (Year: 2013).*

Tong et al. (2010, Nature, vol. 467(7312), pp. 211-213) (Year: 2010).*

Hong et al. (2012, Stem Cells and Development, vol. 21(9), pp. 1571-1586) (Year: 2012).*

Kakoki et al. (2004, Developmental Cell, vol. 6, pp. 597-606). (Year: 2004).*

Boyd et al., "Individual variation in the germline Ig gene repertoire inferred from variable region gene rearrangements," The Journal of Immunology, Jun. 15, 2010, 184(12):6986-6992.

(56) References Cited

OTHER PUBLICATIONS

Brensing-Küppers et al., "The human immunoglobulin κ locus on yeast artificial chromosomes (YACs)," Gene, Jun. 3, 1997, 191(2):173-181.

Call et al., "A cre-lox recombination system for the targeted integration of circular yeast artificial chromosomes into embryonic stem cells," Human molecular genetics, Jul. 22, 2000, 9(12):1745-1751.

Davies et al., "Creation of mice expressing human antibody light chains by introduction of a yeast artificial chromosome containing the core region of the human immunoglobulin κ locus," Bio/Technology, Aug. 1, 1993, 11(8): Abstract 1 page.

Jackson et al., "Divergent human populations show extensive shared IGK rearrangements in peripheral blood B cells," Immunogenetics, Jan. 2012, 64:3-14.

Li et al., "Generation of transgenic mice with megabase-sized human yeast artificial chromosomes by yeast spheroplast—embryonic stem cell fusion," Nature protocols, Aug. 2013, 8(8): Abstract 1 page.

Matsuda et al., "The complete nucleotide sequence of the human immunoglobulin heavy chain variable region locus," The Journal of experimental medicine, Dec. 7, 1998, 188(11):2151-2162.

Abhinandan, et al. "Analysis and improvements to Kabat and structurally correct numbering of antibody variable domains," Molecular Immunology, 2008, 45(14):3832-3839.

Auerbach et al., "Establishment and Chimera Analysis of 129/SvEv- and C57BL/6-Derived Mouse Embryonic Stem Cell Lines," BioTechniques, 2000, 29(5): 1-6.

Chothia et al., "Conformations of immunoglobulin hypervariable regions," Nature, 1989, 342(6252):877-883.

Extended European Search Report in European Appln. No. 20760285.5, mailed on Oct. 27, 2022, 14 pages.

Festing et al., "Revised nomenclature for strain 129 mice," Mammalian Genome, 1999, 10:836.

Genbank Accession No. AB019437, "*Homo sapiens* DNA, immunoglobulin heavy-chain variable region, complete sequence, 1 of 5," Earliest priority 1998, 82 pages.

GenBank Accession No. NC_000002.12, "*Homo sapiens* chromosome 2, GRCh38.p7 Primary Assembly," Jun. 6, 2016, 3 pages.

GenBank Accession No. NC_000078.6, "Mus musculus strain C57BL/6J chromosome 12, GRCm38.p4 C57BL/6J," Jun. 22, 2016, 2 pages.

Green et al., "Regulation of B cell development by variable gene complexity in mice reconstituted with human immunoglobulin yeast artificial chromosomes," The Journal of experimental medicine, Aug. 3, 1998, 188(3):483-495.

IMGT Repertoire (IG and TR) Gene Positions: Human (*Homo sapiens*) IGH. [online database], downloaded on Feb. 23, 2021 from http://irngt.org/IMGTrepertoire/index.php?section=LocusGenes&repertoire=GenePositions&species=hurnan&group=IGH, last updated Mar. 29, 2016; 8 pages.

IMGT Repertoire (IG and TR) Gene Positions: IGH Mouse (Mus musculus) C57BL/6J in GRCnn38.93 assembly, [online database] downloaded on Feb. 23, 2021 from http://inngt.org/IMGTrepertoire/index.php?section=LocusGenes&repertoire=GenePositions&species=nnouse&group=IGH, updated May 27, 2016, 7 pages.

IMGT Repertoire (IG and TR) Gene Table: Human (*Homo sapiens*) IGHV. [online database], downloaded on Jun. 18, 2021 from http://www.irngt.org/IMGTrepertoire/index.php?section=LocusGenes&repertoire=genetable&species=hurnan&group=IGHV, last updated Apr. 10, 2018; 16 pages.

IMGT Repertoire (IG and TR) Gene Table: Human (*Homo sapiens*) IGKJ. [online database] downloaded on Feb. 23, 2021 from http://irngt.org/IMGTrepertoire/index.php?section=LocusGenes&repertoire=genetable&species=hurnan&group=IGKJ; last updated Dec. 3, 2015; 3 pages.

IMGT Repertoire (IG and TR) Gene Table: Human (*Homo sapiens*) IGKV. [online database] downloaded on Feb. 23, 2021 from http://irngt.org/IMGTrepertoire/index.php?section=LocusGenes&repertoire=genetable&species=hurnan&group=IGKV; last updated Mar. 4, 2015; 9 pages.

International Preliminary Report on Patentability in International Appln. No. PCT/CN2020/075698, dated Aug. 26, 2021, 6 pages.

International Search Report and Written Opinion in International Appln. No. PCT/CN2020/075698, mailed May 20, 2020, 11 pages.

International Search Report and Written Opinion in International Appln. No. PCT/CN2021/097652, mailed Aug. 31, 2021, 13 pages.

Irani, et al. "Molecular properties of human IgG subclasses and their implications for designing therapeutic monoclonal antibodies against infectious diseases." Molecular Immunology, 2015, 67(2):171-182.

Janssens et al., "Generation of heavy-chain-only antibodies in mice," Proceedings of the National Academy of Sciences, Oct. 2006, 103(41):15130-15135.

Karlsson et al., "Kinetic and concentration analysis using BIA technology," Methods, Jun. 1, 1994, (2):99-110.

Kohler et al., "Continuous cultures of fused cells secreting antibody of predefined specificity," Nature, Aug. 1975, 256:495-497.

Kozbor et al., "The production of monoclonal antibodies from human lymphocytes," Immunol. Today, 1983, 4:72-79.

Kuroiwa et al., "Manipulation of human minichromosomes to carry greater than megabase-sized chromosome inserts," Nature Biotechnology, 2000, 18(10):1086-1090.

Lee et al. Supplementary Material, "Massive genome engineering: Complete Humanization of the Mouse Immunoglobulin Loci for Therapeutic Antibody Discovery," Nature Biotechnology, Apr. 2014, 32(4): 356-567, 16 pages.

Lee et al., "Complete humanization of the mouse immunoglobulin loci enables efficient therapeutic antibody discovery," Nature Biotechnology, Apr. 2014, 4(32):356-366.

Lefranc et al., "Chromosomal localization, organization of the loci and potential repertoire," in The Immunoglobulin Facts Book, 1st Ed., pp. 45-68, London: Academic Press, 2001.

Lefranc, "Nomenclature of the Human Immunoglobulin Genes," Current Protocols Immunol., 2000, 40(1): 37 Pages.

Macdonald et al, "Precise and in situ genetic humanization of 6 Mb of mouse immunoglobulin genes," PNAS, 2014, 111(14): 5147-5152.

Macdonald, et al, "Velocigene Technology Extended to Humanization of Several Megabases of Complex Loci," presented at the 1st International MUGEN Conference on Animal Models for Human Immunological Disease, Athens, Greece, Sep. 2006, 1 page Abstract.

Martin et al., "Molecular modeling of antibody combining sites," Methods Enzymol., 1991, 203:121-153.

Martin, "Protein sequence and structure analysis of antibody variable domains," Antibody engineering, Springer Berlin Heidelberg, 2001, 422-439.

Mendez et al., "Functional transplant of megabase human immunoglobulin loci recapitulates human antibody response in mice," Nature genetics, Feb. 1997, 15(2):146-156.

Morea et al., "Antibody structure, prediction and redesign ," Biophys Chem., 1997, 68(1-3):9-16.

Morea et al., "Conformations of the third hypervariable region in the VH domain of immunoglobulins," J Mol Biol., 1998, 275(2):269-294.

Murphy et al., "Mice with megabase humanization of their immunoglobulin genes generate antibodies as efficiently as normal mice," Proceedings of the National Academy of Sciences, Apr. 8, 2014, 111(14):5153-5158.

Murphy et al., Supporting Information for "Mice with megabase humanization of their immunoglobulin genes generate antibodies as efficiently as normal mice," Proceedings of the National Academy of Sciences, Apr. 8, 2014, 111(14):5153-5158, 6 pages.

Murphy, "VelocImmune: immunoglobulin variable region humanized mice," Recombinant antibodies for immunotherapy, Jul. 27, 2009, 100-107.

Paulis, "Chromosome Transfer Via Cell Fusion," Methods in Molecular Biology, 2011, 738:57-67.

Pink et al., "Pseudogenes: pseudo-functional or key regulators in health and disease?" RNA, May 1, 2011, 17(5):792-798.

(56) References Cited

OTHER PUBLICATIONS

Ponomarenko et al., "Antibody-protein interactions: benchmark datasets and prediction tools evaluation ," BMC Structural Biology, 2007, 7:64, 19 pages.
*Regeneron Pharmaceuticals, Inc.*, v. *Merus B.V.*, Case No. 14 Civ. 1650(KBF), dated Nov. 21, 2014, 21 pages.
Sanford et al., "General protocol for microcell-mediated chromosome transfer," Somatic Cell and Molecular Genetics, May 1987, 13(3):279-284.
Shinohara et al., "Stability of transferred human chromosome fragments in cultured cells and in mice," Chromosome Research, Nov. 2000, 8:713-725.
Shiraiwa et al., "Engineering a bispecific antibody with a common light chain: Identification and optimization of an anti-CD3 epsilon and anti-GPC3 bispecific antibody, ERY974," Methods, Feb. 1, 2019, 154:10-20, Abstract only.
Stevens, S, et al, "Velocimmune: Humanization of Immunoglobulin Loci Using Velocigene Technology, presented at the 1st International MUGEN Conference on Animal Models for Human Immunoglobulin Disease," Athens, Greece, Sep. 2006, 1 page Abstract.
Takehara et al., "A novel transchromosomic system: stable maintenance of an engineered Mb-sized human genomic fragment translocated to a mouse chromosome terminal region," Transgenic research, Jun. 2014, 23(3):441-453.
Tomizuka et al., "Functional expression and germline atransmission of a human chromosome fragment in chimaeric mice," Nature Genetics, 1997, 16(2):133-143.
Vidarsson, et al, "IgG subclasses and allotypes: from structure to effector functions," Frontiers in Immunology, Oct. 2014, 5(520):1-17.
Vihinen, "Contribution of pseudogenes to sequence diversity," Pseudogenes, 2014:15-24.
Voronina et al., "Deletion of Adam6 in Mus musculus leads to male subfertility and deficits in sperm ascent into the oviduct," Biology of reproduction, Mar. 1, 2019, 100(3):686-696.
Williams et al., "CO-FISH, COD-FISH, ReD-FISH, SKY-FISH," Genes, Chromosomes & Cancer, 1995, 14:126127, 113-124.
Wolff et al., "Monoclonal antibody homodimers: enhanced antitumor activity in nude mice," Cancer Res., 1993, 53:2560-2565.
Wu et al., "An analysis of the sequences of the variable regions of Bence Jones proteins and myeloma light chains and their implications for antibody complementarity," J. Exp. Med., 1970, 132:211-250.
Xu et al., "Production of bispecific antibodies in 'knobs-into-holes' using a cell-free expression system," mAbs, Jan. 2015, 7(1):231-242.
Yin et al., "Delivery technologies for genome editing," Nature Reviews Drug Discovery, 2017, 16(6):387-399.
Zhu et al., "Humanising the mouse genome piece by piece," Nature communications, Apr. 23, 2019, 10(1):1-13.
Lefranc, M. P. Nomenclature of the Human Immunoglobulin Genes Current Protocols Immunol. 40(1): A.1P.1-A.1P.37, 2000.
De Wildt et al. Analysis of Heavy and Light Chain Pairings Indicates that Receptor Editing Shapes the Human Antibody Repertoire. 1999. J. of Mol. Biol. 285(3): 895-901.
Haldi et al., "Large human YACs constructed in a rad52 strain show a reduced rate of chimerism," Genomics, Dec. 1, 1994, 24(3):478-484.
Blanco, et al., "Age-associated distribution of normal B-cell and plasma cell subsets in peripheral blood," Journal of Allergy and Clinical Immunology, 2018, 141(6):2208-2219e16.

Candelaria et al., "Antibodies Targeting the Transferrin Receptor 1 (TfR1) as Direct Anti-cancer Agents," Frontiers in Immunology, 2021, 12(607692):1-21.
Dennis, "Welfare issues of genetically modified animals," ILAR Journal, 2002, 43(2): 100-109.
Devoy et al., "Genomically humanised mice: technologies and promise," Nature Reviews Genetics, 2011, 13(1):14-20 (Author Manuscript; available in PMC on Mar. 8, 2016).
Estep et al., "High throughput solution-based measurement of antibody-antigen affinity and epitope binning," mAbs, 2013, 5(2):270-278.
Feng et al., "Site-specific chromosomal integration in mammalian cells: highly efficient CRE recombinase-mediated cassette exchange," Journal of Molecular Biology, Oct. 1, 1999, 292(4):779-785.
Fisher-Hoch et al., "Protection of rhesus monkeys from fatal Lassa fever by vaccination with a recombinant vaccinia virus containing the Lassa virus glycoprotein gene," Proc. Natl. Acad. Sci. USA, 1989, 86:317-321.
GenBank Accession No. NC_000078.7, "Mus musculus strain C57BL/6J chromosome 12, GRCm39," Sep. 22, 2020, 2 pages.
Guzman et al., "Efficient and selective adenovirus-mediated gene transfer into vascular neointima," Circulation, 1993, 88(6):2838-2848.
Guzman et al., "Efficient gene transfer into myocardium by direct injection of adenovirus vectors," Circulation Research, 1993, 73(6):1202-1207.
Joyce et al., "Comparisons of the antibody repertoires of a humanized rodent and humans by high throughput sequencing," Scientific Reports, 2020, 10(1120):1-9 (plus supplement pp. 1-8).
Kass-Eisler et al., "Quantitative determination of adenovirus-mediated gene delivery to rat cardiac myocytes in vitro and in vivo," 1993, Proc. Natl. Acad. Sci. USA, 90(24):11498-11502.
Kolls et al., "Prolonged and effective blockade of tumor necrosis factor activity through adenovirus-mediated gene transfer," 1994, Proc. Natl. Acad. Sci. USA, 91(1):215-219.
Ma et al., "Genome-wide analysis of pseudogenes reveals HBBP1's human-specific essentiality in erythropoiesis and implication in ß-thalassemia," Developmental Cell, 2021, 56:478-493.
Moore et al., "Antibody cross-competition analysis of the human immunodeficiency virus type 1 gp120 exterior envelope glycoprotein," Journal of Virology, 1996, 70(3):1863-1872.
Shen et al., "Transferrin receptor 1 in cancer: a new sight for cancer therapy," American Journal of Cancer Research, 2018, 8(6):916-931.
Takeda et al., "Deletion of the immunoglobulin K chain intron enhancer abolishes K chain gene rearrangement in cis hut not γ chain gene rearrangement in trans," The EMBO Journal, 1993, 12(6):2329-2336.
Zhou et al., "Developing tTA transgenic rats for inducible and reversible gene expression," International Journal of Biological Sciences, 2009, 5(2):171-181.
Zou et al., "Block in development at the pre-B-II to immature B cell stage in mice without Igk and Igλ Light Chain," The Journal of Immunology, 2003, 170(3):1354-1361.
Zou et al., "Gene targeting in the Ig kappa locus: efficient generation of lambda chain-expressing B cells, independent of gene rearrangements in Ig kappa," The EMBO Journal, 1993, 12(3):811-820.
Zou et al., "Subtle differences in antibody responses and hypermutation of lambda light chains in mice with a disrupted chi constant region," Eur J Immunol., 1995, 25(8):2154-2162.

* cited by examiner

| Proximal V-CLUSTER from 3' (top of column) to 5' (bottom of column) | Distal V-CLUSTER from 3' (bottom of column) to 5' (top of column) |
|---|---|
| IGKV4-1 | |
| IGKV5-2 | |
| IGKV7-3 | |
| IGKV2-4 | |
| IGKV1-5 | |
| IGKV1-6 | |
| IGKV3-7 | IGKV3D-7 |
| IGKV1-8 | IGKV1D-8 |
| | IGKV1D-43 |
| | IGKV1D-42 |
| IGKV1-9 | |
| IGKV2-10 | IGKV2D-10 |
| IGKV3-11 | IGKV3D-11 |
| IGKV1-12 | IGKV1D-12 |
| IGKV1-13 | IGKV1D-13 |
| IGKV2-14 | IGKV2D-14 |
| IGKV3-15 | IGKV3D-15 |
| IGKV1-16 | IGKV1D-16 |
| IGKV1-17 | IGKV1D-17 |
| | IGKV6D-41 |
| IGKV2-18 | IGKV2D-18 |
| IGKV2-19 | IGKV2D-19 |
| IGKV3-20 | IGKV3D-20 |
| IGKV6-21 | IGKV6D-21 |
| IGKV1-22 | IGKV1D-22 |
| IGKV2-23 | IGKV2D-23 |
| IGKV2-24 | IGKV2D-24 |
| IGKV3-25 | IGKV3D-25 |
| IGKV2-26 | IGKV2D-26 |
| IGKV1-27 | IGKV1D-27 |
| IGKV2-28 | IGKV2D-28 |
| IGKV2-29 | IGKV2D-29 |
| IGKV2-30 | IGKV2D-30 |
| IGKV3-31 | IGKV3D-31 |
| IGKV1-32 | IGKV1D-32 |
| IGKV1-33 | IGKV1D-33 |
| IGKV3-34 | IGKV3D-34 |
| IGKV1-35 | IGKV1D-35 |
| IGKV2-36 | IGKV2D-36 |
| IGKV1-37 | IGKV1D-37 |
| IGKV2-38 | IGKV2D-38 |
| IGKV1-39 | IGKV1D-39 |
| IGKV2-40 | IGKV2D-40 |

| Gene | Location | Orientation | IMGT Locus | IMGT Position | Accession number | Positions | Gene positions on chromosome | NCBI Accession number | Gene positions in sequences |
|---|---|---|---|---|---|---|---|---|---|
| IGHA2 | 14q32.33 | REV | IGH | | J00221 | 1227..1618 | 105124322..105124713 | NT_026437.11 | 87054322..87054713 |
| IGHA2 | 14q32.33 | REV | IGH | | J00221 | 684..1004 | 105124936..105125256 | NT_026437.11 | 87054936..87055256 |
| IGHA2 | 14q32.33 | REV | IGH | | J00221 | 164..469 | 105125474..105125776 | NT_026437.11 | 87055474..87055776 |
| IGHE | 14q32.33 | REV | IGH | | J00222 | 2540..2868 | 105137451..105137779 | NT_026437.11 | 87067451..87067779 |
| IGHE | 14q32.33 | REV | IGH | | J00222 | 2133..2456 | 105137863..105138186 | NT_026437.11 | 87067863..87068186 |
| IGHE | 14q32.33 | REV | IGH | | J00222 | 1726..2046 | 105138273..105138593 | NT_026437.11 | 87068273..87068593 |
| IGHE | 14q32.33 | REV | IGH | | J00222 | 1210..1518 | 105138801..105139109 | NT_026437.11 | 87068801..87069109 |
| IGHG4 | 14q32.33 | REV | IGH | | K01316 | 1481..1800 | 105161861..105162180 | NT_026437.11 | 87091861..87092180 |
| IGHG4 | 14q32.33 | REV | IGH | | K01316 | 1054..1383 | 105162278..105162607 | NT_026437.11 | 87092278..87092607 |
| IGHG4 | 14q32.33 | REV | IGH | | K01316 | 900..935 | 105162726..105162761 | NT_026437.11 | 87092726..87092761 |
| IGHG4 | 14q32.33 | REV | IGH | | K01316 | 216..509 | 105163154..105163447 | NT_026437.11 | 87093154..87093447 |
| IGHG2 | 14q32.33 | REV | IGH | | J00230 | 1480..1799 | 105180588..105180907 | NT_026437.11 | 87110588..87110907 |
| IGHG2 | 14q32.33 | REV | IGH | | J00230 | 1056..1382 | 105181005..105181331 | NT_026437.11 | 87111005..87111331 |

| | | | | | | | |
|---|---|---|---|---|---|---|---|
| IGHG2 | 14q32.33 | REV | IGH | J00230 | 902..937 | 105181450..105181485 | NT_026437.11 | 871111450..871111485 |
| IGHG2P | 14q32.33 | REV | IGH | J00230 | 216..509 | 105181878..105182171 | NT_026437.11 | 871111878..871112171 |
| IGHGP | 14q32.33 | REV | IGH | X06766 | 1474..1790 | 105205635..105205947 | NT_026437.11 | 871135635..871135947 |
| IGHGP | 14q32.33 | REV | IGH | X06766 | 1047..1376 | 105206045..105206374 | NT_026437.11 | 871136045..871136374 |
| IGHGP | 14q32.33 | REV | IGH | X06766 | 878..928 | 105206493..105206543 | NT_026437.11 | 871136493..871136543 |
| IGHGP | 14q32.33 | REV | IGH | X06766 | 195..488 | 105206933..105207226 | NT_026437.11 | 871136933..871137226 |
| IGHA1 | 14q32.33 | REV | IGH | J00220 | 1244..1635 | 105244553..105244944 | NT_026437.11 | 871174553..871174944 |
| IGHA1 | 14q32.33 | REV | IGH | J00220 | 662..1021 | 105245167..105245526 | NT_026437.11 | 871175167..871175526 |
| IGHA1 | 14q32.33 | REV | IGH | J00220 | 142..447 | 105245741..105246046 | NT_026437.11 | 871175741..871176046 |
| IGHEP1 | 14q32.33 | REV | IGH | J00223 | 849..1177 | 105259179..105259507 | NT_026437.11 | 871189179..871189507 |
| IGHEP1 | 14q32.33 | REV | IGH | J00223 | 447..765 | 105259591..105259909 | NT_026437.11 | 871189591..871189909 |
| IGHG1 | 14q32.33 | REV | IGH | J00228 | 1481..1800 | 105278858..105279177 | NT_026437.11 | 872208858..872209177 |
| IGHG1 | 14q32.33 | REV | IGH | J00228 | 1055..1384 | 105279275..105279604 | NT_026437.11 | 872209275..872209604 |
| IGHG1 | 14q32.33 | REV | IGH | J00228 | 892..936 | 105279723..105279767 | NT_026437.11 | 872209723..872209767 |
| IGHG1 | 14q32.33 | REV | IGH | J00228 | 210..503 | 105280159..105280452 | NT_026437.11 | 872210159..872210452 |
| IGHG3 | 14q32.33 | REV | IGH | X03604 | 2061..2380 | 105306622..105306941 | NT_026437.11 | 872236622..872236941 |

FIG. 20 (Continued)

| | | | | | | | | |
|---|---|---|---|---|---|---|---|---|
| IGHG3 | 14q32.33 | REV | IGH | X03604 | 1634..1963 | 105307039..105307368 | NT_026437.11 | 87237039.872..37368 |
| IGHG3 | 14q32.33 | REV | IGH | X03604 | 1471..1515 | 105307487..105307531 | NT_026437.11 | 87237487.872..37531 |
| IGHG3 | 14q32.33 | REV | IGH | X03604 | 1283..1327 | 105307675..105307719 | NT_026437.11 | 87237675.872..37719 |
| IGHG3 | 14q32.33 | REV | IGH | X03604 | 1095..1139 | 105307863..105307907 | NT_026437.11 | 87237863.872..37907 |
| IGHG3 | 14q32.33 | REV | IGH | X03604 | 901..951 | 105308051..105308101 | NT_026437.11 | 87238051.872..38101 |
| IGHG3 | 14q32.33 | REV | IGH | X03604 | 216..509 | 105308494..105308787 | NT_026437.11 | 87238494.872..38787 |
| IGHD | 14q32.33 | REV | IGH | K02880 | 25..50 | 105375785..105375810 | NT_026437.11 | 87305785.873..05810 |
| IGHD | 14q32.33 | REV | IGH | K02879 | 101..424 | 105377748..105378071 | NT_026437.11 | 87307748.873..08071 |
| IGHD | 14q32.33 | REV | IGH | K02878 | 101..424 | 105378282..105378605 | NT_026437.11 | 87308282.873..08605 |
| IGHD | 14q32.33 | REV | IGH | K02877 | 101..172 | 105379342..105379413 | NT_026437.11 | 87309342.873..09413 |
| IGHD | 14q32.33 | REV | IGH | K02876 | 101..202 | 105382203..105382304 | NT_026437.11 | 87312203.873..12304 |
| IGHD | 14q32.33 | REV | IGH | K02875 | 101..403 | 105382753..105383055 | NT_026437.11 | 87312753.873..13055 |
| IGHM | 14q32.33 | REV | IGH | X14940 | 1708..2096 | 105391496..105391887 | NT_026437.11 | 87321496.873..21887 |
| IGHM | 14q32.33 | REV | IGH | X14940 | 1212..1529 | 105392067..105392384 | NT_026437.11 | 87322067.873..22384 |
| IGHM | 14q32.33 | REV | IGH | X14940 | 631..966 | 105392630..105392965 | NT_026437.11 | 87322630.873..22965 |
| IGHM | 14q32.33 | REV | IGH | X14940 | 233..544 | 105393056..105393367 | NT_026437.11 | 87323056.873..23367 |

FIG. 20 (Continued)

| | | | | | | | |
|---|---|---|---|---|---|---|---|
| IGHJ6 | 14q32.33 | REV | IGH | 960175.960275 | J00256 | 2909..3009 | 105400453..105400553 | NT_02643 7.11 | 87330453.873 30553 |
| IGHJ3P | 14q32.33 | REV | IGH | 959970.960057 | J00256 | 2709..2797 | 105400671..105400758 | NT_02643 7.11 | 87330671.873 30758 |
| IGHJ5 | 14q32.33 | REV | IGH | 959571.959659 | J00256 | 2317..2404 | 105401084..105401156 | NT_02643 7.11 | 87331069.873 31141 |
| IGHJ4 | 14q32.33 | REV | IGH | 959172.959258 | J00256 | 1873..1959 | 105401470..105401556 | NT_02643 7.11 | 87331470.873 31556 |
| IGHJ3 | 14q32.33 | REV | IGH | 958789.958886 | J00256 | 1498..1586 | 105401865..105401930 | NT_02643 7.11 | 87331842.873 31907 |
| IGHJ2P | 14q32.33 | REV | IGH | 958583.958682 | J00256 | 1284..1380 | 105402046..105402145 | NT_02643 7.11 | 87332046.873 32145 |
| IGHJ2 | 14q32.33 | REV | IGH | 958184.958274 | J00256 | 893..984 | 105402454..105402544 | NT_02643 7.11 | 87332454.873 32544 |
| IGHJ1 | 14q32.33 | REV | IGH | 957977.958066 | J00256 | 686..774 | 105402662..105402751 | NT_02643 7.11 | 87332662.873 32751 |
| IGHD7-27 | 14q32.33 | REV | IGH | 957884.957950 | J00256 | 592..659 | 105402781..105402845 | NT_02643 7.11 | 87332778.873 32842 |
| IGHJ1P | 14q32.33 | REV | IGH | 957759.957849 | J00256 | 467..557 | 105402879..105402969 | NT_02643 7.11 | 87332879.873 32969 |
| IGHD1-26 | 14q32.33 | REV | IGH | 942598.942673 | X97051 | 72141..72216 | 105417909..105417984 | NT_02643 7.11 | 87347909.873 47984 |
| IGHD6-25 | 14q32.33 | REV | IGH | 942095.942168 | X97051 | 71638..71711 | 105418414..105418487 | NT_02643 7.11 | 87348414.873 48487 |
| IGHD5-24 | 14q32.33 | REV | IGH | 939730.939805 | X97051 | 69272..69347 | 105420778..105420853 | NT_02643 7.11 | 87350778.873 50853 |
| IGHD4-23 | 14q32.33 | REV | IGH | 938765.938839 | X97051 | 68306..68380 | 105421745..105421819 | NT_02643 7.11 | 87351745.873 51819 |
| IGHD3-22 | 14q32.33 | REV | IGH | 937592.937678 | X93616 | 2..88 | 105422906..105422992 | NT_02643 7.11 | 87352906.873 52992 |
| IGHD2-21 | 14q32.33 | REV | IGH | 935075.935158 | J00235 | 1..63 | 105425447..105425509 | NT_02643 7.11 | 87355447.873 55509 |

FIG. 20 (Continued)

| IGHD1 -20 | 14q32 .33 | REV | IGH | 932446.93 2518 | X9705 1 | 61987.620 59 | 105428066..105 428138 | NT_02643 7.11 | 87358066..873 58138 |
|---|---|---|---|---|---|---|---|---|---|
| IGHD6 -19 | 14q32 .33 | REV | IGH | 931934.93 2010 | X9705 1 | 61475.615 51 | 105428574..105 428650 | NT_02643 7.11 | 87358574..873 58650 |
| IGHD5 -18 | 14q32 .33 | REV | IGH | 930093.93 0168 | X1397 2 | 2885.2960 | 105430417..105 430492 | NT_02643 7.11 | 87360417..873 60492 |
| IGHD4 -17 | 14q32 .33 | REV | IGH | 929131.92 9202 | X9705 1 | 58671..587 42 | 105431383..105 431454 | NT_02643 7.11 | 87361383..873 61454 |
| IGHD3 -16 | 14q32 .33 | REV | IGH | 927984.92 8076 | X9361 4 | 2..94 | 105432511..105 432601 | NT_02643 7.11 | 87362511..873 62601 |
| IGHD2 -15 | 14q32 .33 | REV | IGH | 925668.92 5753 | J00234 | 1..66 | 105434853..105 434918 | NT_02643 7.11 | 87364853..873 64918 |
| IGHD1 -14 | 14q32 .33 | REV | IGH | 923001.92 3073 | X1397 2 | 14490..145 62 | 105437513..105 437585 | NT_02643 7.11 | 87367513..873 67585 |
| IGHD6 -13 | 14q32 .33 | REV | IGH | 922493.92 2569 | X1397 2 | 13983.140 59 | 105438017..105 438093 | NT_02643 7.11 | 87368017..873 68093 |
| IGHD5 -12 | 14q32 .33 | REV | IGH | 920984.92 1062 | X1397 2 | 12478..125 56 | 105439524..105 439602 | NT_02643 7.11 | 87369524..873 69602 |
| IGHD4 -11 | 14q32 .33 | REV | IGH | 920024.92 0095 | X1397 2 | 11522..115 93 | 105440491..105 440562 | NT_02643 7.11 | 87370491..873 70562 |
| IGHD3 -10 | 14q32 .33 | REV | IGH | 919128.91 9214 | X1397 2 | 10631..107 17 | 105441372..105 441458 | NT_02643 7.11 | 87371372..873 71458 |
| IGHD3 -9 | 14q32 .33 | REV | IGH | 918944.91 9030 | X1397 2 | 10447..105 33 | 105441556..105 441642 | NT_02643 7.11 | 87371556..873 71642 |
| IGHD2 -8 | 14q32 .33 | REV | IGH | 916414.91 6500 | X1397 2 | 7921.8007 | 105444086..105 444172 | NT_02643 7.11 | 87374086..873 74172 |
| IGHD1 -7 | 14q32 .33 | REV | IGH | 913731.91 3803 | X1397 2 | 5238..5310 | 105446783..105 446855 | NT_02643 7.11 | 87376783..873 76855 |
| IGHD6 -6 | 14q32 .33 | REV | IGH | 913227.91 3300 | X1397 2 | 4734..4807 | 105447287..105 447359 | NT_02643 7.11 | 87377286..873 77358 |
| IGHD5 -5 | 14q32 .33 | REV | IGH | 911378.91 1453 | X9705 1 | 59633..597 08 | 105449133..105 449208 | NT_02643 7.11 | 87379133..873 79208 |

FIG. 20 (Continued)

| | | | | | | | |
|---|---|---|---|---|---|---|---|
| IGHD4-4 | 14q32.33 | REV | IGH | 910417..910488 | X13972 | 1924..1995 | 105450098..105450169 | NT_02643 7.11 | 87380098..87380169 .873 |
| IGHD3-3 | 14q32.33 | REV | IGH | 909265..909351 .90 | X13972 | 776..862 | 105451235..105451321 | NT_02643 7.11 | 87381235..87381321 .873 |
| IGHD2-2 | 14q32.33 | REV | IGH | 906798..906884 .90 | J00232 | 1..66 | 105453723..105453788 | NT_02643 7.11 | 87383723..87383788 .873 |
| IGHD1-1 | 14q32.33 | REV | IGH | 904136..904208 .90 | X97051 | 33686..33758 .337 | 105456378..105456450 | NT_02643 7.11 | 87386378..87386450 .873 |
| IGHV4-30-2 | 14q32.33 | REV | IGH | | L10089 | 1..297 | 105476885..105476952 | NT_02643 7.11 | 87406660..87406727 .874 |
| IGHV4-4 | 14q32.33 | REV | IGH | 811002..811472 .81 | L10098 | 1..325 | 105476906..105476984 | NT_02643 7.11 | 87406894..87406972 .874 |
| IGHV(II)-1-1 | 14q32.33 | REV | IGH | 878294..878475 .87 | AB019441 | 78294..78475 .784 | 105482111..105482292 | NT_02643 7.11 | 87412111..87412292 .874 |
| IGHV3-21 | 14q32.33 | REV | IGH | 597417..597909 .59 | AB019439 | 197417..197909 .19 | 106282330..106282428 | NT_02643 7.11 | 88211936..88212034 .882 |
| IGHV1-2 | 14q32.33 | REV | IGH | 836435..836911 .83 | X07448 | 126..603 | 105523675..105524151 | NT_02643 7.11 | 87453675..87454151 .874 |
| IGHV3-41 | 14q32.33 | REV | IGH | 390047..390538 .39 | M99670 | 189..680 | 106119868..106120165 | NT_02643 7.11 | 88049868..88050165 .880 |
| IGHV1-3 | 14q32.33 | REV | IGH | 817860..818336 .81 | X62109 | 21..497 | 105542250..105542726 | NT_02643 7.11 | 87472250..87472726 .874 |
| IGHV4-59 | 14q32.33 | REV | IGH | 205856..206326 .20 | AB019438 | 1..291 | 106154301..106154591 | NT_02643 7.11 | 88084301..88084591 .880 |
| IGHV2-5 | 14q32.33 | REV | IGH | 794964..795446 .79 | X62111 | 71..553 | 105565140..105565622 | NT_02643 7.11 | 87495140..87495622 .874 |
| IGHV(II)-5-1 | 14q32.33 | REV | IGH | 793545..793643 .79 | AB019440 | 193545..193643 .19 | 105566943..105567041 | NT_02643 7.11 | 87496943..87497041 .874 |
| IGHV(II)-5-2 | 14q32.33 | REV | IGH | 787450..787749 .78 | AB019440 | 187450..187749 .18 | 105572837..105573136 | NT_02643 7.11 | 87502837..87503136 .875 |
| IGHV3-6 | 14q32.33 | REV | IGH | 777310..777803 .77 | M99650 | 13..506 | 105582783..105583276 | NT_02643 7.11 | 87512783..87513276 .875 |

FIG. 20 (Continued)

| IGHV3-7 | 14q32.33 | REV | IGH | 770688.771182 | M99649 | 184..678 | 105589404..105589898 | NT_026437.11 | 87519404.87519898 |
|---|---|---|---|---|---|---|---|---|---|
| IGHV6-1 | 14q32.33 | REV | IGH | 883485.883971 | J04097 | 337..823 | 105763091..105763163 | NT_026437.11 | 87692677.87692749 |
| IGHV3-9 | 14q32.33 | REV | IGH | 736812.737296 | M99651 | 132..616 | 105623290..105623774 | NT_026437.11 | 87553290.87553774 |
| IGHV2-10 | 14q32.33 | REV | IGH | 729561.730040 | M99647 | 71..550 | 105630549..105631025 | NT_026437.11 | 87560549.87561025 |
| IGHV3-11 | 14q32.33 | REV | IGH | 715861.716349 | M99652 | 48..536 | 105644237..105644725 | NT_026437.11 | 87574237.87574725 |
| IGHV(II)-11-1 | 14q32.33 | REV | IGH | 712240.712656 | AB019440 | 112240.112656 | 105647930..105648346 | NT_026437.11 | 87577930.87578346 |
| IGHV1-12 | 14q32.33 | REV | IGH | 710238.710527 | X92210 | 191..628 | 105649911..105650348 | NT_026437.11 | 87579911.87580348 |
| IGHV3-13 | 14q32.33 | REV | IGH | 702954.703445 | X92217 | 2..493 | 105657141..105657632 | NT_026437.11 | 87587141.87587632 |
| IGHV(II)-13-1 | 14q32.33 | REV | IGH | 690249.690586 | AB019440 | 90249.90586 | 105670000..105670337 | NT_026437.11 | 87600000.87600337 |
| IGHV1-14 | 14q32.33 | REV | IGH | 686675.687009 | AB019440 | 86675.87009 | 105673577..105673911 | NT_026437.11 | 87603577.87603911 |
| IGHV3-15 | 14q32.33 | REV | IGH | 678769.679269 | X92216 | 2..502 | 105681317..105681817 | NT_026437.11 | 87611317.87611817 |
| IGHV(II)-15-1 | 14q32.33 | REV | IGH | 669050.669320 | AB019440 | 69050.69320 | 105691266..105691536 | NT_026437.11 | 87621266.87621536 |
| IGHV3-16 | 14q32.33 | REV | IGH | 667196.667688 | M99655 | 30..522 | 105692898..105693390 | NT_026437.11 | 87622898.87623390 |
| IGHV(II)-16-1 | 14q32.33 | REV | IGH | 661801.662105 | AB019440 | 61801.62105 | 105698481..105698785 | NT_026437.11 | 87628481.87628785 |

FIG. 20 (Continued)

| | | | | | | | |
|---|---|---|---|---|---|---|---|
| IGHV1-17 | 14q32.33 | REV | IGH | 658074.658549 | M99640 | 45..521 | 105702037..105702512 | NT_02643 7.11 | 87632037..87632512 |
| IGHV1-18 | 14q32.33 | REV | IGH | 647544.648019 | M99641 | 47..522 | 105712567..105713042 | NT_02643 7.11 | 87642567..87643042 |
| IGHV3-19 | 14q32.33 | REV | IGH | 635792.636211 | M99656 | 211..630 | 105724375..105724794 | NT_02643 7.11 | 87654375..87654794 |
| IGHV1-20 | 14q32.33 | REV | IGH | 621508.622001 | M99657 | 10..504 | 105738585..105739078 | NT_02643 7.11 | 87668585..87669078 |
| IGHV(I)-20-1 | 14q32.33 | REV | IGH | 619576.620076 | AB019440 | 19576..20076 | 105740510..105741010 | NT_02643 7.11 | 87670510..87671010 |
| IGHV1-58 | 14q32.33 | REV | IGH | 210733.211209 | M29809 | 151..627 | 106149377..106149853 | NT_02643 7.11 | 88079377..88079853 |
| IGHV3-22 | 14q32.33 | REV | IGH | 574720.575220 | M99659 | 85..585 | 105785366..105785866 | NT_02643 7.11 | 87715366..87715866 |
| IGHV(I)-22-1 | 14q32.33 | REV | IGH | 569320.569588 | AB019439 | 169320..169588 | 105790998..105791266 | NT_02643 7.11 | 87720998..87721266 |
| IGHV(II)-22-2 | 14q32.33 | REV | IGH | 568065.568262 | AB019439 | 168065..168262 | 105792324..105792521 | NT_02643 7.11 | 87722324..87722521 |
| IGHV3-23 | 14q32.33 | REV | IGH | 563887.564381 | M99660 | 10..504 | 105796205..105796699 | NT_02643 7.11 | 87726205..87726699 |
| IGHV1-24 | 14q32.33 | REV | IGH | 555962.556438 | M99642 | 68..544 | 105804148..105804624 | NT_02643 7.11 | 87734148..87734624 |
| IGHV3-25 | 14q32.33 | REV | IGH | 543468.543960 | M99661 | 78..570 | 105816626..105817118 | NT_02643 7.11 | 87746626..87747118 |
| IGHV(II)-25-1 | 14q32.33 | REV | IGH | 539140.539381 | AB019439 | 139140..139381 | 105821205..105821446 | NT_02643 7.11 | 87751205..87751446 |
| IGHV2-26 | 14q32.33 | REV | IGH | 531449.531931 | M99648 | 21..503 | 105828655..105829137 | NT_02643 7.11 | 87758655..87759137 |

FIG. 20 (Continued)

| | | | | | | | | |
|---|---|---|---|---|---|---|---|---|
| IGHV(II)-26-1 | 14q32.33 | REV | IGH | 523568.523874 | AB019439 | 123568.123874 | 105836712..105837018 | NT_027.11643 | 87766712..87767018877 |
| IGHV(I)-26-2 | 14q32.33 | REV | IGH | 518318.518630 | AB019439 | 118318.118630 | 105841956..105842268 | NT_027.11643 | 87771956..87772268877 |
| IGHV7-27 | 14q32.33 | REV | IGH | 515042.515455 | M99643 | 65..526 | 105845083..105845544 | NT_027.11643 | 87775083..87775544877 |
| IGHV4-31 | 14q32.33 | REV | IGH | 483897.484373 | X05713 | 153..626 | 105851517..105851990 | NT_027.11643 | 87781517..87781990877 |
| IGHV(I)-28-1 | 14q32.33 | REV | IGH | 503603.503855 | AB019439 | 103603.103855 | 105856731..105856983 | NT_027.11643 | 87786731..87786983877 |
| IGHV3-29 | 14q32.33 | REV | IGH | 501726.502222 | AB019439 | 101726.102222 | 105858364..105858860 | NT_027.11643 | 87788364..87788860877 |
| IGHV(II)-30 | 14q32.33 | REV | IGH | 498085.498577 | M83134 | 1782..2274 | 105862009..105862501 | NT_027.11643 | 87792009..87792501877 |
| IGHV(I)-30-1 | 14q32.33 | REV | IGH | 490666.490939 | AB019439 | 90666..90939 | 105869647..105869920 | NT_027.11643 | 87799647..87799920877 |
| IGHV3-30-1 | 14q32.33 | REV | IGH | 488784.489232 | AB019439 | 88784..89232 | 105871354..105871802 | NT_027.11643 | 87801354..87801802878 |
| IGHV3-30-2 | 14q32.33 | REV | IGH | 508596.509069 | X05714 | 151..624 | 105549114..105549584 | NT_027.11643 | 87479114..87479584874 |
| IGHV4-28 | 14q32.33 | REV | IGH | 478924.479232 | AB019439 | 78924..79232 | 105881354..105881662 | NT_027.11643 | 87811354..87811662878 |
| IGHV(I)-31-1 | 14q32.33 | REV | IGH | 477013.477509 | AB019439 | 77013..77509 | 105883077..105883573 | NT_027.11643 | 87813077..87813573878 |
| IGHV3-32 | 14q32.33 | REV | IGH | 473368.473860 | AB019439 | 73368..73860 | 105886726..105887218 | NT_027.11643 | 87816726..87817218878 |
| IGHV3-33 | 14q32.33 | REV | IGH | 465947.466220 | AB019439 | 65947..66220 | 105894366..105894639 | NT_027.11643 | 87824366..87824639878 |
| IGHV(I)-33-1 | 14q32.33 | REV | IGH | 464064.464512 | AB019439 | 64064..64512 | 105896074..105896522 | NT_027.11643 | 87826074..87826522878 |
| IGHV3-33-2 | | | | | | | | | |

FIG. 20 (Continued)

| | | | | | | | |
|---|---|---|---|---|---|---|---|
| IGHV4-34 | 14q32.33 | REV | IGH | 459517.45 9988 | AB019 439 | 1..343 | 105900598..105 900940 | NT_02643 7.11 | 87830598..878 30940 |
| IGHV7-34-1 | 14q32.33 | REV | IGH | 455877..45 6349 | AB019 439 | 55877..563 49 | 105904237..105 904709 | NT_02643 7.11 | 87834237..878 34709 |
| IGHV3-35 | 14q32.33 | REV | IGH | 443767..44 4259 | M9966 6 | 140..632 | 105916327..105 916819 | NT_02643 7.11 | 87846327..878 46819 |
| IGHV3-36 | 14q32.33 | REV | IGH | 440399..44 0861 | M9966 7 | 218..681 | 105919724..105 920187 | NT_02643 7.11 | 87849724..878 50187 |
| IGHV3-37 | 14q32.33 | REV | IGH | 436515..43 7003 | M9966 8 | 10..489 | 105923586..105 924071 | NT_02643 7.11 | 87853586..878 54071 |
| IGHV3-38 | 14q32.33 | REV | IGH | 422685..42 3175 | M9966 9 | 10..497 | 105937413..105 937901 | NT_02643 7.11 | 87867413..878 67901 |
| IGHV(II)-38-1 | 14q32.33 | REV | IGH | 415315..41 5645 | AB019 439 | 15315..156 45 | 105944941..105 945271 | NT_02643 7.11 | 87874941..878 75271 |
| IGHV4-30-4 | 14q32.33 | REV | IGH | | Z14238 | 1..438 | 105876252..105 876689 | NT_02643 7.11 | 87806252..878 06689 |
| IGHV7-40 | 14q32.33 | REV | IGH | 408075..40 8316 | M9964 4 | 164..497 | 105952270..105 952592 | NT_02643 7.11 | 87882270..878 82592 |
| IGHV(I)40-1 | 14q32.33 | REV | IGH | 392620..39 2696 | AB019 438 | 192620.19 2696 | 105967890..105 967966 | NT_02643 7.11 | 87897890..878 97966 |
| IGHV3-30-3 | 14q32.33 | REV | IGH | | X9228 3 | 1..294 | 105970093..105 970379 | NT_02643 7.11 | 87900093..879 00378 |
| IGHV3-42 | 14q32.33 | REV | IGH | 369925..37 0362 | M9967 1 | 1..461 | 105762906..105 763129 | NT_02643 7.11 | 87692869..876 93089 |
| IGHV3-43 | 14q32.33 | REV | IGH | 362897..36 3393 | M9967 2 | 170..666 | 105997193..105 997689 | NT_02643 7.11 | 87927193..879 27689 |
| IGHV(I)-43-1 | 14q32.33 | REV | IGH | 360618..36 0826 | AB019 438 | 160618.16 0826 | 105999760..105 999968 | NT_02643 7.11 | 87929760..879 29968 |
| IGHV(II)-44 | 14q32.33 | REV | IGH | 355142..35 5318 | M9967 3 | 62..511 | 106005056..106 005444 | NT_02643 7.11 | 87935056..879 35444 |

FIG. 20 (Continued)

| | | | | | | | |
|---|---|---|---|---|---|---|---|
| IGHV(IV)-44-1 | 14q32.33 | REV | IGH | 343764.344231 | AB019438 | 143764.144231 | 106016355..106016822 | NT_026437.11 | 87946355.87946822 |
| IGHV(II)-44-2 | 14q32.33 | REV | IGH | 339146.339382 | AB019438 | 136146.139382 | 106021204..106024440 | NT_026437.11 | 87951204.87954440 |
| IGHV1-45 | 14q32.33 | REV | IGH | 326175.326651 | X92209 | 2..478 | 106033935..106034411 | NT_026437.11 | 87963935.87964411 |
| IGHV1-46 | 14q32.33 | REV | IGH | 322057.322533 | X92343 | 153..629 | 106038053..106038529 | NT_026437.11 | 87968053.87968529 |
| IGHV(II)-46-1 | 14q32.33 | REV | IGH | 317614.317771 | AB019438 | 117614.117771 | 106042815..106042972 | NT_026437.11 | 87972815.87972972 |
| IGHV3-47 | 14q32.33 | REV | IGH | 314580.315074 | Z18900 | 1..291 | 106045553..106045843 | NT_026437.11 | 87975553.87975843 |
| IGHV(II)-47-1 | 14q32.33 | REV | IGH | 302103.302406 | AB019438 | 102103..102406 | 106058180..106058483 | NT_026437.11 | 87988180.87988483 |
| IGHV3-48 | 14q32.33 | REV | IGH | 295274.295768 | M99675 | 174..668 | 106064818..106065312 | NT_026437.11 | 87994818.87995312 |
| IGHV3-49 | 14q32.33 | REV | IGH | 276144.276644 | M99676 | 224..724 | 106083946..106084442 | NT_026437.11 | 88013946.88014442 |
| IGHV(II)-49-1 | 14q32.33 | REV | IGH | 268955.269225 | AB019438 | 68955.69225 | 106091361..106091631 | NT_026437.11 | 88021361.88021631 |
| IGHV3-50 | 14q32.33 | REV | IGH | 266998.267453 | M99677 | 10..283 | 106093318..106093588 | NT_026437.11 | 88023316.88023585 |
| IGHV5-51 | 14q32.33 | REV | IGH | 254379.254853 | M99686 | 168..641 | 106105734..106106207 | NT_026437.11 | 88035734.88036207 |
| IGHV(II)-51-1 | 14q32.33 | REV | IGH | 249747.250053 | AB019438 | 49747..5053 | 106110533..106110839 | NT_026437.11 | 88040533.88040839 |
| IGHV(II)-51-2 | 14q32.33 | REV | IGH | 248581.248843 | AB019438 | 48581..48843 | 106111743..106112005 | NT_026437.11 | 88041743.88042005 |

FIG. 20 (Continued)

| | | | | | | | |
|---|---|---|---|---|---|---|---|
| IGHV3-52 | 14q32.33 | REV | IGH | 246731.247220 | M99678 | 212.701 | 106113366.106113855 | NT_02643 7.11 | 88043366.88043855 |
| IGHV(I)-53-1 | 14q32.33 | REV | IGH | 240421.240910 | M99679 | 38.527 | 106282134.106282436 | NT_02643 7.11 | 88212134.88212436 |
| IGHV3-53 | 14q32.33 | REV | IGH | 233605.233874 | AB019438 | 33605.33874 | 106126712.106126981 | NT_02643 7.11 | 88056712.88056981 |
| IGHV3-54 | 14q32.33 | REV | IGH | 231746.232232 | M99680 | 147.631 | 106128356.106128840 | NT_02643 7.11 | 88058356.88058840 |
| IGHV4-55 | 14q32.33 | REV | IGH | 226980.227454 | M99685 | 230.704 | 106133132.106133606 | NT_02643 7.11 | 88063132.88063606 |
| IGHV7-56 | 14q32.33 | REV | IGH | 223335.223808 | M29810 | 136.429 | 106136958.106137251 | NT_02643 7.11 | 88066958.88067251 |
| IGHV3-57 | 14q32.33 | REV | IGH | 214314.214658 | M29815 | 7.568 | 106146106.106146421 | NT_02643 7.11 | 88076062.88076381 |
| IGHV1-8 | 14q32.33 | REV | IGH | 750026.750503 | M99637 | 58.535 | 105610083.105610560 | NT_02643 7.11 | 87540083.87540560 |
| IGHV4-39 | 14q32.33 | REV | IGH | 411486.411963 | AB019439 | 1.328 | 105948662.105948989 | NT_02643 7.11 | 87878662.87878989 |
| IGHV3-60 | 14q32.33 | REV | IGH | 201883.202375 | AB019438 | 1883.2375 | 106158211.106158703 | NT_02643 7.11 | 88088211.88088703 |
| IGHV(I)-60-1 | 14q32.33 | REV | IGH | 195563.195869 | AB019437 | 195563.195831 | 106164755.106165023 | NT_02643 7.11 | 88094755.88095023 |
| IGHV4-61 | 14q32.33 | REV | IGH | 193980.194456 | M29811 | 151.628 | 106166130.106166606 | NT_02643 7.11 | 88096130.88096606 |
| IGHV3-62 | 14q32.33 | REV | IGH | 189953.190447 | AB019437 | 189953.190447 | 106170139.106170633 | NT_02643 7.11 | 88100139.88100633 |
| IGHV(I)-62-1 | 14q32.33 | REV | IGH | 182749.183060 | AB019437 | 182749.183060 | 106177526.106177837 | NT_02643 7.11 | 88107526.88107837 |
| IGHV3-63 | 14q32.33 | REV | IGH | 180846.181313 | M99681 | 10.506 | 106179251.106179740 | NT_02643 7.11 | 88109251.88109740 |
| IGHV3-64 | 14q32.33 | REV | IGH | 175347.175841 | M99682 | 78.575 | 106184745.106185242 | NT_02643 7.11 | 88114745.88115242 |

FIG. 20 (Continued)

| | | | | | | | | |
|---|---|---|---|---|---|---|---|---|
| IGHV3-65 | 14q32.33 | REV | IGH | 166993..167487 | | 106193140..193440 | NT_02643 7.11 | 881123140..88123440 |
| IGHV(II)-65-1 | 14q32.33 | REV | IGH | 821563..821903 | Z27503 | 1..301 | | 87468683..87468874 69023 |
| IGHV(I)-65-1 | 14q32.33 | REV | IGH | 161481..161753 | AB019441 | 21563..21903 | NT_02643 7.11 | 881128833..881 29105 |
| IGHV3-66 | 14q32.33 | REV | IGH | 158060..158549 | AB019437 | 161481..161753 | NT_02643 7.11 | 881132037..881 32526 |
| IGHV1-67 | 14q32.33 | REV | IGH | 152482..152960 | X92218 | 2..491 | NT_02643 7.11 | 881137626..881 38059 |
| IGHV(I)-67-1 | 14q32.33 | REV | IGH | 146982..147131 | AB019437 | 1..434 | NT_02643 7.11 | 881143455..881 43604 |
| IGHV(II)-67-2 | 14q32.33 | REV | IGH | 146324..146422 | AB019437 | 146982..147131 | NT_02643 7.11 | 881144164..881 44262 |
| IGHV(II)-67-3 | 14q32.33 | REV | IGH | 140636..140910 | AB019437 | 146324..146422 | NT_02643 7.11 | 881149676..881 49950 |
| IGHV(II)-67-4 | 14q32.33 | REV | IGH | 138127..138432 | AB019437 | 140636..140910 | NT_02643 7.11 | 881152154..881 52459 |
| IGHV1-68 | 14q32.33 | REV | IGH | 129238..129717 | AB019437 | 138127..138432 | NT_02643 7.11 | 881160869..881 61348 |
| IGHV1-69 | 14q32.33 | REV | IGH | 119174..119651 | L22582 | 129238..129717 | NT_02643 7.11 | 881170935..881 71412 |
| IGHV2-70 | 14q32.33 | REV | IGH | 110279..110761 | L21969 | 233..710 | NT_02643 7.11 | 881179864..881 80307 |
| IGHV3-71 | 14q32.33 | REV | IGH | 105684..106184 | AB019437 | 1..444 | NT_02643 7.11 | 881184402..881 84902 |
| IGHV3-72 | 14q32.33 | REV | IGH | 90150..90650 | X92206 | 105684..106184 | NT_02643 7.11 | 881199936..882 00436 |
| | | | | | | 87..587 | | |

FIG. 20 (Continued)

| | | | | | | | | |
|---|---|---|---|---|---|---|---|---|
| IGHV3-73 | 14q32.33 | REV | IGH | 78150.78650 | X70197 | 1..300 | 105990226.105990526 | NT_026437.11 | 87920226.87920526.879.20526 |
| IGHV3-74 | 14q32.33 | REV | IGH | 70412.70906 | L33851 | 23..476 | 106289721..106290174 | NT_026437.11 | 88219721..88220174.882 |
| IGHV(I)-74-1 | 14q32.33 | REV | IGH | 59900..60068 | AB019437 | 59900..60068 | 106300518..106300686 | NT_026437.11 | 88230518..88230686.882 |
| IGHV3-75 | 14q32.33 | REV | IGH | 57164..57672 | Z27510 | 4..308 | 106302955..106303259 | NT_026437.11 | 88232955..88233259.882 |
| IGHV3-76 | 14q32.33 | REV | IGH | 53003..53492 | AB019437 | 1..292 | 106307134..106307425 | NT_026437.11 | 88237134..88237425.882 |
| IGHV(II)-76-1 | 14q32.33 | REV | IGH | 49245..49551 | AB019437 | 49245..49551 | 106311035..106311341 | NT_026437.11 | 88241035..88241341.882 |
| IGHV5-78 | 14q32.33 | REV | IGH | 29780..30228 | X92213 | 592..1027 | 106330373..106330806 | NT_026437.11 | 88260373..88260806.882 |
| IGHV(I)-78-1 | 14q32.33 | REV | IGH | 15431..15744 | AB019437 | 15431..15744 | 106344842..106345155 | NT_026437.11 | 88274842..88275155.882 |
| IGHV3-79 | 14q32.33 | REV | IGH | 13237..13688 | AB019437 | 13237..13688 | 106346898..106347349 | NT_026437.11 | 88276898..88277349.882 |
| IGHV4-80 | 14q32.33 | REV | IGH | 8147..8547 | AB019437 | 8147..8547 | 106352039..106352439 | NT_026437.11 | 88282039..88282439.882 |
| IGHV7-81 | 14q32.33 | REV | IGH | 6315..6790 | AB019437 | 6315..6790 | 106353796..106354271 | NT_026437.11 | 88283796..88284271.882 |
| IGHV(II)-82 | 14q32.33 | REV | IGH | 1490..1781 | AB019437 | 1490..1781 | 106358805..106359096 | NT_026437.11 | 88288805..88289096.882 |

| IMGT Gene | Chromosomal localization | Orientation | NCBI Gene ID | Reference GRCm38.p3 C57BL/6J | NCBI Gene positions in sequence | Orientation sequence | MGI ID | MGI symbol |
|---|---|---|---|---|---|---|---|---|
| IGHV1-86 | 12F2 (62.59 cM) | REV | 668599 | NC_000078.6 | 116009659..116009954 | -1 | MGI:3645729 | Ighv1-86 |
| IGHV1-85 | 12F2 (62.59 cM) | REV | 668597 | NC_000078.6 | 116000028..116000321 | -1 | MGI:3645723 | Ighv1-85 |
| IGHV1-84 | 12F2 (62.59 cM) | REV | 434609 | NC_000078.6 | 115980702..115981134 | -1 | MGI:3644235 | Ighv1-84 |
| IGHV1-83 | 12F2 (62.59 cM) | REV | 620140 | NC_000078.6 | 115963817..115964109 | -1 | MGI:3648939 | Ighv1-83 |
| IGHV1-82 | 12F2 (62.59 cM) | REV | 1.01E+08 | NC_000078.6 | 115952538..115952831 | -1 | MGI:4439671 | Ighv1-82 |
| IGHV1-81 | 12F2 (62.59 cM) | REV | 668591 | NC_000078.6 | 115920279..115920572 | -1 | MGI:4439635 | Ighv1-81 |
| IGHV1-80 | 12F2 (62.59 cM) | REV | 668589 | NC_000078.6 | 115912344..115912637 | -1 | MGI:4439738 | Ighv1-80 |
| IGHV1-79 | 12F2 (62.59 cM) | REV | 435331 | NC_000078.6 | 115888096..115888389 | -1 | MGI:3648258 | Ighv1-79 |
| IGHV1-78 | 12F2 (62.59 cM) | REV | 213570 | NC_000078.6 | 115868773..115869066 | -1 | MGI:4439736 | Ighv1-78 |
| IGHV1-77 | 12F2 (62.59 cM) | REV | 619994 | NC_000078.6 | 115861867..115862160 | -1 | MGI:4439670 | Ighv1-77 |
| IGHV8-16 | 12F2 (62.59 cM) | REV | 1.01E+08 | NC_000078.6 | 115858008..115858301 | -1 | MGI:5434409 | Ighv8-16 |
| IGHV1-76 | 12F2 (62.59 cM) | REV | 1.01E+08 | NC_000078.6 | 115847881..115848174 | -1 | MGI:4439737 | Ighv1-76 |

| | | | | | | |
|---|---|---|---|---|---|---|
| IGHV8-15 | 12F2 (62.59 cM) | REV | 1.01E+08 | NC_000078.6 | 115844016..115844309 | -1 | MGI:5434408 | Ighv8-15 |
| IGHV1-75 | 12F2 (62.59 cM) | REV | 622728 | NC_000078.6 | 115833950..115834243 | -1 | MGI:4439735 | Ighv1-75 |
| IGHV8-14 | 12F2 (62.59 cM) | REV | 668582 | NC_000078.6 | 115808427..115808727 | -1 | MGI:3648977 | Ighv8-14 |
| IGHV1-74 | 12F2 (62.59 cM) | REV | 1.01E+08 | NC_000078.6 | 115802690..115803080 | -1 | MGI:4439634 | Ighv1-74 |
| IGHV1-73 | 12F2 (62.59 cM) | REV | 668577 | NC_000078.6 | 115790593..115790887 | -1 | MGI:3645131 | Ighv1-73 |
| IGHV8-13 | 12F2 (62.59 cM) | REV | 1.01E+08 | NC_000078.6 | 115765335..115765635 | -1 | MGI:4439734 | Ighv8-13 |
| IGHV1-72 | 12F2 (62.59 cM) | REV | 619916 | NC_000078.6 | 115757984..115758277 | -1 | MGI:4439633 | Ighv1-72 |
| IGHV1-71 | 12F2 (62.59 cM) | REV | 619886 | NC_000078.6 | 115742205..115742506 | -1 | MGI:3643033 | Ighv1-71 |
| IGHV1-70 | 12F2 (62.59 cM) | REV | 638634 | NC_000078.6 | 115691889..115692182 | -1 | MGI:3644620 | Ighv1-70 |
| IGHV8-12 | 12F2 (62.59 cM) | REV | 780960 | NC_000078.6 | 115647945..115648245 | -1 | MGI:4432873 | Ighv8-12 |
| IGHV1-69 | 12F2 (62.59 cM) | REV | 619833 | NC_000078.6 | 115623203..115623595 | -1 | MGI:4439632 | Ighv1-69 |
| IGHV1-68 | 12F2 (62.59 cM) | REV | 780959 | NC_000078.6 | 115611340..115611633 | -1 | MGI:5009923 | Ighv1-68 |
| IGHV1-67 | 12F2 (62.59 cM) | REV | 435328 | NC_000078.6 | 115603940..115604233 | -1 | MGI:3645228 | Ighv1-67 |
| IGHV1-66 | 12F2 (62.59 cM) | REV | 380824 | NC_000078.6 | 115593110..115593403 | -1 | MGI:4439825 | Ighv1-66 |
| IGHV8-11 | 12F2 (62.59 cM) | REV | 636462 | NC_000078.6 | 115567149..115567449 | -1 | MGI:3644925 | Ighv8-11 |

| | | | | | | | |
|---|---|---|---|---|---|---|---|
| IGHV1-65 | 12F2 (62.58 cM) | REV | 780958 | NC_000078.6 | 115532055..115532347 | -1 | MGI:5009922 | Ighv1-65 |
| IGHV8-10 | 12F2 (62.58 cM) | REV | 780957 | NC_000078.6 | 115519340..115519640 | -1 | MGI:5009921 | Ighv8-10 |
| IGHV1-64 | 12F2 (62.58 cM) | REV | 380823 | NC_000078.6 | 115507587..115507977 | -1 | MGI:4439789 | Ighv1-64 |
| IGHV1-63 | 12F2 (62.58 cM) | REV | 780956 | NC_000078.6 | 115495625..115496058 | -1 | MGI:3642755 | Ighv1-63 |
| IGHV8-9 | 12F2 (62.57 cM) | REV | 432709 | NC_000078.6 | 115468331..115468632 | -1 | MGI:3644475 | Ighv8-9 |
| IGHV1-62-3 | 12F2 (62.57 cM) | REV | 668549 | NC_000078.6 | 115460999..115461431 | -1 | MGI:3648544 | Ighv1-62-3 |
| IGHV1-62-2 | 12F2 (62.57 cM) | REV | 238448 | NC_000078.6 | 115446417..115446710 | -1 | MGI:3644968 | Ighv1-62-2 |
| IGHV1-62-1 | 12F2 (62.55 cM) | REV | 668544 | NC_000078.6 | 115386707..115386988 | -1 | MGI:3704125 | Ighv1-62-1 |
| IGHV1-62 | 12F2 (62.55 cM) | REV | 668542 | NC_000078.6 | 115371986..115372278 | -1 | MGI:5009844 | Ighv1-62 |
| IGHV1-61 | 12F2 (62.55 cM) | REV | 674018 | NC_000078.6 | 115359140..115359433 | -1 | MGI:4439824 | Ighv1-61 |
| IGHV1-60 | 12F2 (62.54 cM) | REV | 780940 | NC_000078.6 | 115344537..115344830 | -1 | MGI:5009920 | Ighv1-60 |
| IGHV1-59 | 12F2 (62.54 cM) | REV | 432708 | NC_000078.6 | 115335057..115335513 | -1 | MGI:3644474 | Ighv1-59 |
| IGHV1-58 | 12F2 (62.54 cM) | REV | 780939 | NC_000078.6 | 115312166..115312597 | -1 | MGI:4439557 | Ighv1-58 |
| IGHV8-8 | 12F2 (62.54 cM) | REV | 780938 | NC_000078.6 | 115294066..115294362 | -1 | MGI:3815333 | Ighv8-8 |
| IGHV1-57 | 12F2 (62.53 cM) | REV | 780937 | NC_000078.6 | 115268424..115268715 | -1 | MGI:5009919 | Ighv1-57 |

| | | | | | | | |
|---|---|---|---|---|---|---|---|
| IGHV8-7 | 12F2 (62.53 cM) | REV | 780936 | NC_000078.6 | 115258139..115258432 | -1 | MGI:5009918 | Ighv8-7 |
| IGHV1-56 | 12F2 (62.53 cM) | REV | 382695 | NC_000078.6 | 115242802..115243095 | -1 | MGI:4439715 | Ighv1-56 |
| IGHV1-55 | 12F2 (62.52 cM) | REV | 780932 | NC_000078.6 | 115208137..115208527 | -1 | MGI:4439716 | Ighv1-55 |
| IGHV1-54 | 12F2 (62.52 cM) | REV | 211331 | NC_000078.6 | 115193675..115193968 | -1 | MGI:3647133 | Ighv1-54 |
| IGHV8-6 | 12F2 (62.51 cM) | REV | 629930 | NC_000078.6 | 115165777..115166077 | -1 | MGI:3645823 | Ighv8-6 |
| IGHV1-53 | 12F2 (62.51 cM) | REV | 780931 | NC_000078.6 | 115158445..115158835 | -1 | MGI:3576502 | Ighv1-53 |
| IGHV1-52 | 12F2 (62.51 cM) | REV | 382696 | NC_000078.6 | 115145487..115145780 | -1 | MGI:4439752 | Ighv1-52 |
| IGHV1-51 | 12F2 (62.51 cM) | REV | 780930 | NC_000078.6 | 115131375..115131668 | -1 | MGI:5009917 | Ighv1-51 |
| IGHV1-50 | 12F2 (62.5 cM) | REV | 780929 | NC_000078.6 | 115119748..115120041 | -1 | MGI:4439753 | Ighv1-50 |
| IGHV8-5 | 12F2 (62.49 cM) | REV | 640506 | NC_000078.6 | 115067560..115067860 | -1 | MGI:3645478 | Ighv8-5 |
| IGHV1-49 | 12F2 (62.49 cM) | REV | 629925 | NC_000078.6 | 115055223..115055516 | -1 | MGI:4439754 | Ighv1-49 |
| IGHV1-48 | 12F2 (62.49 cM) | REV | 780928 | NC_000078.6 | 115038227..115038520 | -1 | MGI:5009916 | Ighv1-48 |
| IGHV8-4 | 12F2 (62.48 cM) | REV | 629919 | NC_000078.6 | 115024026..115024318 | -1 | MGI:3646040 | Ighv8-4 |
| IGHV1-3 | 12F2 (62.48 cM) | REV | 780927 | NC_000078.6 | 115003418..115003712 | -1 | MGI:5009915 | Ighv1-3 |
| IGHV1-47 | 12F2 (62.48 cM) | REV | 629915 | NC_000078.6 | 114991108..114991401 | -1 | MGI:4439890 | Ighv1-47 |

FIG. 21 (Continued)

| | | | | | | |
|---|---|---|---|---|---|---|
| IGHV1-46 | 12F2 (62.48 cM) | REV | 668522 | NC_000078.6 | 114977693..114977986 | -1 | MGI:5009843 | Ighv1-46 |
| IGHV1-45 | 12F2 (62.47 cM) | REV | 780894 | NC_000078.6 | 114970055..114970348 | -1 | MGI:5009913 | Ighv1-45 |
| IGHV1-44 | 12F2 (62.47 cM) | REV | 668521 | NC_000078.6 | 114963380..114963674 | -1 | MGI:5009842 | Ighv1-44 |
| IGHV1-43 | 12F2 (62.47 cM) | REV | 629908 | NC_000078.6 | 114945950..114946243 | -1 | MGI:3704124 | Ighv1-43 |
| IGHV1-42 | 12F2 (62.47 cM) | REV | 629906 | NC_000078.6 | 114937154..114937544 | -1 | MGI:3704123 | Ighv1-42 |
| IGHV1-41 | 12F2 (62.47 cM) | REV | 629904 | NC_000078.6 | 114932371..114932664 | -1 | MGI:3649084 | Ighv1-41 |
| IGHV1-40 | 12F2 (62.47 cM) | REV | 780892 | NC_000078.6 | 114924941..114925233 | -1 | MGI:5009912 | Ighv1-40 |
| IGHV1-39 | 12F2 (62.46 cM) | REV | 780891 | NC_000078.6 | 114914599..114914892 | -1 | MGI:4439888 | Ighv1-39 |
| IGHV1-38 | 12F2 (62.46 cM) | REV | 780890 | NC_000078.6 | 114910011..114910303 | -1 | MGI:5009911 | Ighv1-38 |
| IGHV1-37 | 12F2 (62.46 cM) | REV | 668517 | NC_000078.6 | 114896238..114896531 | -1 | MGI:4439640 | Ighv1-37 |
| IGHV1-36 | 12F2 (62.46 cM) | REV | 629897 | NC_000078.6 | 114879888..114880181 | -1 | MGI:4439639 | Ighv1-36 |
| IGHV1-35 | 12F2 (62.46 cM) | REV | 668515 | NC_000078.6 | 114875302..114875597 | -1 | MGI:3644935 | Ighv1-35 |
| IGHV1-34 | 12F2 (62.45 cM) | REV | 628614 | NC_000078.6 | 114851190..114851483 | -1 | MGI:4439659 | Ighv1-34 |
| IGHV1-33 | 12F2 (62.45 cM) | REV | 641247 | NC_000078.6 | 114843693..114844083 | -1 | MGI:4439617 | Ighv1-33 |
| IGHV1-32 | 12F2 (62.45 cM) | REV | 780888 | NC_000078.6 | 114835223..114835516 | -1 | MGI:5009910 | Ighv1-32 |

FIG. 21 (Continued)

| IGHV1-31 | 12F2 (62.45 cM) | REV | 629893 | NC_000078.6 | 114829264..114829557 | | MGI:4439889 | -1 | Ighv1-31 |
| IGHV1-30 | 12F2 (62.44 cM) | REV | 668511 | NC_000078.6 | 114817099..114817390 | | MGI:4937173 | -1 | Ighv1-30 |
| IGHV1-29 | 12F2 (62.44 cM) | REV | 780887 | NC_000078.6 | 114812321..114812605 | | MGI:5009909 | -1 | Ighv1-29 |
| IGHV1-28 | 12F2 (62.44 cM) | REV | 668510 | NC_000078.6 | 114809421..114809714 | | MGI:3644938 | -1 | Ighv1-28 |
| IGHV1-27 | 12F2 (62.44 cM) | REV | 780886 | NC_000078.6 | 114804616..114804909 | | MGI:5009908 | -1 | Ighv1-27 |
| IGHV1-26 | 12F2 (62.44 cM) | REV | 629884 | NC_000078.6 | 114788372..114788665 | | MGI:4439641 | -1 | Ighv1-26 |
| IGHV1-25 | 12F2 (62.44 cM) | REV | 640497 | NC_000078.6 | 114781409..114781702 | | MGI:3648295 | -1 | Ighv1-25 |
| IGHV1-24 | 12F2 (62.44 cM) | REV | 780885 | NC_000078.6 | 114772928..114773221 | | MGI:3815052 | -1 | Ighv1-24 |
| IGHV1-23 | 12F2 (62.43 cM) | REV | 780884 | NC_000078.6 | 114764450..114764743 | | MGI:3815050 | -1 | Ighv1-23 |
| IGHV1-22 | 12F2 (62.43 cM) | REV | 780883 | NC_000078.6 | 114746273..114746566 | | MGI:4439784 | -1 | Ighv1-22 |
| IGHV1-21 | 12F2 (62.43 cM) | REV | 668499 | NC_000078.6 | 114740383..114740840 | | MGI:5009841 | -1 | Ighv1-21 |
| IGHV1-21-1 | 12F2 (62.43 cM) | REV | 631595 | NC_000078.6 | 114736245..114736538 | | MGI:3645737 | -1 | Ighv1-21-1 |
| IGHV1-20 | 12F2 (62.43 cM) | REV | 668497 | NC_000078.6 | 114723772..114724065 | | MGI:3644607 | -1 | Ighv1-20 |
| IGHV1-19 | 12F2 (62.42 cM) | REV | 382692 | NC_000078.6 | 114708648..114708941 | | MGI:4439779 | -1 | Ighv1-19 |
| IGHV1-19-1 | 12F2 (62.42 cM) | REV | 668493 | NC_000078.6 | 114704147..114704440 | | MGI:3644603 | -1 | Ighv1-19-1 |

FIG. 21 (Continued)

| IGHV1-18 | 12F2 (62.42 cM) | REV | 629871 | NC_000078.6 | 114682632..114682925 | -1 | MGI:4439780 | Ighv1-18 |
|---|---|---|---|---|---|---|---|---|
| IGHV1-17 | 12F2 (62.42 cM) | REV | 629869 | NC_000078.6 | 114676749..114677042 | -1 | MGI:3647700 | Ighv1-17 |
| IGHV1-17-1 | 12F2 (62.42 cM) | REV | 780926 | NC_000078.6 | 114671968..114672262 | -1 | MGI:5009914 | Ighv1-17-1 |
| IGHV1-16 | 12F2 (62.42 cM) | REV | 629866 | NC_000078.6 | 114665872..114666165 | -1 | MGI:3647704 | Ighv1-16 |
| IGHV1-15 | 12F2 (62.41 cM) | REV | 629865 | NC_000078.6 | 114657353..114657646 | -1 | MGI:4439782 | Ighv1-15 |
| IGHV1-14 | 12F2 (62.41 cM) | REV | 629863 | NC_000078.6 | 114646572..114646865 | -1 | MGI:4439781 | Ighv1-14 |
| IGHV1-13 | 12F2 (62.41 cM) | REV | 780865 | NC_000078.6 | 114630680..114630973 | -1 | MGI:5009907 | Ighv1-13 |
| IGHV1-12 | 12F2 (62.41 cM) | REV | 629860 | NC_000078.6 | 114615850..114616143 | -1 | MGI:3646284 | Ighv1-12 |
| IGHV1-11 | 12F2 (62.41 cM) | REV | 629859 | NC_000078.6 | 114612244..114612536 | -1 | MGI:5009835 | Ighv1-11 |
| IGHV1-10 | 12F2 (62.40 cM) | REV | 637050 | NC_000078.6 | 114597878..114598175 | -1 | MGI:5009837 | Ighv1-10 |
| IGHV1-9 | 12F2 (62.40 cM) | REV | 668478 | NC_000078.6 | 114583569..114583862 | -1 | MGI:4439621 | Ighv1-9 |
| IGHV1 5-2 | 12F2 (62.40 cM) | REV | 780864 | NC_000078.6 | 114564578..114564874 | -1 | MGI:4947963 | Ighv15-2 |
| IGHV1-8 | 12F2 (62.39 cM) | REV | 780863 | NC_000078.6 | 114555610..114555902 | -1 | MGI:5009906 | Ighv1-8 |
| IGHV1 0-4 | 12F2 (62.39 cM) | REV | 780862 | NC_000078.6 | 114547258..114547556 | -1 | MGI:5009905 | Ighv10-4 |
| IGHV1-7 | 12F2 (62.39 cM) | REV | 668474 | NC_000078.6 | 114538495..114538788 | -1 | MGI:3704122 | Ighv1-7 |

| | | | | | | |
|---|---|---|---|---|---|---|
| IGHV1-6 | 12F2 (62.39 cM) | REV | 780861 | NC_000078.6 | 114532972..114533264 | -1 | MGI:5009904 | Ighv1-6 |
| IGHV10-3 | 12F2 (62.39 cM) | REV | 380809 | NC_000078.6 | 114523441..114523887 | -1 | MGI:3648785 | Ighv10-3 |
| IGHV1-5 | 12F2 (62.39 cM) | REV | 668469 | NC_000078.6 | 114513330..114513623 | -1 | MGI:3704121 | Ighv1-5 |
| IGHV10-2 | 12F2 (62.38 cM) | REV | 780860 | NC_000078.6 | 114496003..114496300 | -1 | MGI:5009903 | Ighv10-2 |
| IGHV1-4 | 12F2 (62.38 cM) | REV | 432702 | NC_000078.6 | 114487136..114487429 | -1 | MGI:4439618 | Ighv1-4 |
| IGHV1-3 | 12F2 (62.38 cM) | REV | 780859 | NC_000078.6 | 114481615..114481916 | -1 | MGI:5009902 | Ighv1-3 |
| IGHV10-1 | 12F2 (62.38 cM) | REV | 380808 | NC_000078.6 | 114479007..114479451 | -1 | MGI:4439620 | Ighv10-1 |
| IGHV1-2 | 12F2 (62.38 cM) | REV | 238428 | NC_000078.6 | 114469075..114469371 | -1 | MGI:4439924 | Ighv1-2 |
| IGHV8-2 | 12F2 (62.38 cM) | REV | 629849 | NC_000078.6 | 114462290..114462589 | -1 | MGI:3647474 | Ighv8-2 |
| IGHV6-7 | 12F2 (62.38 cM) | REV | 432701 | NC_000078.6 | 114455626..114455925 | -1 | MGI:3644477 | Ighv6-7 |
| IGHV6-6 | 12F2 (62.38 cM) | REV | 238427 | NC_000078.6 | 114434788..114435087 | -1 | MGI:4439619 | Ighv6-6 |
| IGHV6-5 | 12F2 (62.37 cM) | REV | 639510 | NC_000078.6 | 114416596..114416895 | -1 | MGI:3647134 | Ighv6-5 |
| IGHV6-4 | 12F2 (62.37 cM) | REV | 628398 | NC_000078.6 | 114406474..114406773 | -1 | MGI:3704120 | Ighv6-4 |
| IGHV6-3 | 12F2 (62.36 cM) | REV | 629845 | NC_000078.6 | 114391712..114392010 | -1 | MGI:4439854 | Ighv6-3 |
| IGHV12-3 | 12F2 (62.36 cM) | REV | 435321 | NC_000078.6 | 114366526..114366819 | -1 | MGI:3646760 | Ighv12-3 |

| | | | | | | |
|---|---|---|---|---|---|---|
| IGHV13-2 | 12F2 (62.36 cM) | REV | 629842 | NC_000078.6 | 114357761..114358060 | -1 | MGI:3705861 | Ighv13-2 |
| IGHV1-1 | 12F2 (62.36 cM) | REV | 780834 | NC_000078.6 | 114351705..114351995 | -1 | MGI:5009901 | Ighv1-1 |
| IGHV8-1 | 12F2 (62.35 cM) | REV | 780833 | NC_000078.6 | 114332796..114333086 | -1 | MGI:5009900 | Ighv8-1 |
| IGHV3-8 | 12F2 (62.35 cM) | REV | 780831 | NC_000078.6 | 114322376..114322666 | -1 | MGI:3645298 | Ighv3-8 |
| IGHV5-21 | 12F2 (62.35 cM) | REV | 780832 | NC_000078.6 | 114320030..114320324 | -1 | MGI:5009899 | Ighv5-21 |
| IGHV3-7 | 12F2 (62.35 cM) | REV | 780830 | NC_000078.6 | 114314186..114314479 | -1 | MGI:5009898 | Ighv3-7 |
| IGHV9-4 | 12F2 (62.34 cM) | REV | 636260 | NC_000078.6 | 114299961..114300254 | -1 | MGI:3646379 | Ighv9-4 |
| IGHV3-6 | 12F2 (62.34 cM) | REV | 780829 | NC_000078.6 | 114288152..114288447 | -1 | MGI:4439856 | Ighv3-6 |
| IGHV13-1 | 12F2 (62.33 cM) | REV | 780828 | NC_000078.6 | 114267607..114267906 | -1 | MGI:4439855 | Ighv13-1 |
| IGHV3-5 | 12F2 (62.33 cM) | REV | 633457 | NC_000078.6 | 114262652..114262950 | -1 | MGI:3648045 | Ighv3-5 |
| IGHV3-4 | 12F2 (62.33 cM) | REV | 629833 | NC_000078.6 | 114253617..114253915 | -1 | MGI:3644034 | Ighv3-4 |
| IGHV7-4 | 12F2 (62.32 cM) | REV | 632654 | NC_000078.6 | 114222788..114223254 | -1 | MGI:4439763 | Ighv7-4 |
| IGHV3-3 | 12F2 (62.31 cM) | REV | 668438 | NC_000078.6 | 114196439..114196875 | -1 | MGI:3643949 | Ighv3-3 |
| IGHV14-4 | 12F2 (62.30 cM) | REV | 629826 | NC_000078.6 | 114176438..114176867 | -1 | MGI:4439765 | Ighv14-4 |
| IGHV15-1 | 12F2 (62.30 cM) | REV | 780827 | NC_000078.6 | 114158025..114158315 | -1 | MGI:5009897 | Ighv15-1 |

FIG. 21 (Continued)

| | | | | | | |
|---|---|---|---|---|---|---|
| IGHV7-3 | 12F2 (62.30 cM) | REV | 629822 | NC_000078.6 | 114153180..114153644 | -1 | MGI:4439766 | Ighv7-3 |
| IGHV9-3 | 12F2 (62.29 cM) | REV | 780825 | NC_000078.6 | 114140692..114141122 | -1 | MGI:3642720 | Ighv9-3 |
| IGHV12-2 | 12F2 (62.29 cM) | REV | 780824 | NC_000078.6 | 114127533..114127984 | -1 | MGI:5009896 | Ighv12-2 |
| IGHV9-2 | 12F2 (62.28 cM) | REV | 629818 | NC_000078.6 | 114109001..114109430 | -1 | MGI:3643816 | Ighv9-2 |
| IGHV12-1 | 12F2 (62.28 cM) | REV | 780823 | NC_000078.6 | 114107259..114107563 | -1 | MGI:5295669 | Ighv12-1 |
| IGHV9-1 | 12F2 (62.28 cM) | REV | 195180 | NC_000078.6 | 114093928..114094221 | -1 | MGI:4439911 | Ighv9-1 |
| IGHV6-2 | 12F2 (62.28 cM) | REV | 780822 | NC_000078.6 | 114089387..114089681 | -1 | MGI:5009895 | Ighv6-2 |
| IGHV16-1 | 12F2 (62.27 cM) | REV | 629812 | NC_000078.6 | 114068828..114069126 | -1 | MGI:3643819 | Ighv16-1 |
| IGHV14-3 | 12F2 (62.27 cM) | REV | 238418 | NC_000078.6 | 114059845..114060273 | -1 | MGI:4439764 | Ighv14-3 |
| IGHV11-2 | 12F2 (62.27 cM) | REV | 780818 | NC_000078.6 | 114048241..114048704 | -1 | MGI:4947968 | Ighv11-2 |
| IGHV3-2 | 12F2 (62.26 cM) | REV | 780817 | NC_000078.6 | 114033803..114034097 | -1 | MGI:4439923 | Ighv3-2 |
| IGHV4-2 | 12F2 (62.26 cM) | REV | 668423 | NC_000078.6 | 114013144..114013439 | -1 | MGI:5009840 | Ighv4-2 |
| IGHV14-2 | 12F2 (62.25 cM) | REV | 668421 | NC_000078.6 | 113994469..113994898 | -1 | MGI:4439607 | Ighv14-2 |
| IGHV1-1 | 12F2 (62.25 cM) | REV | 780804 | NC_000078.6 | 113981879..113982174 | -1 | MGI:4439535 | Ighv11-1 |
| IGHV3-1 | 12F2 (62.24 cM) | REV | 780803 | NC_000078.6 | 113964390..113964683 | -1 | MGI:4439534 | Ighv3-1 |

| | | | | | | |
|---|---|---|---|---|---|---|
| IGHV4-1 | 12F2 (62.24 cM) | REV | 780802 | NC_000078.6 | 113948284..113948577 | -1 | MGI:4439536 | Ighv4-1 |
| IGHV14-1 | 12F2 (62.23 cM) | REV | 780801 | NC_000078.6 | 113931953..113932246 | -1 | MGI:4439920 | Ighv14-1 |
| IGHV7-2 | 12F2 (62.23 cM) | REV | 780800 | NC_000078.6 | 113912025..113912483 | -1 | MGI:4439623 | Ighv7-2 |
| IGHV7-1 | 12F2 (62.22 cM) | REV | 780799 | NC_000078.6 | 113896408..113896946 | -1 | MGI:4439622 | Ighv7-1 |
| IGHV5-19 | 12F2 (62.22 cM) | REV | 780798 | NC_000078.6 | 113884761..113885342 | -1 | MGI:5009894 | Ighv5-19 |
| IGHV2-9 | 12F2 (62.22 cM) | REV | 640046 | NC_000078.6 | 113879097..113879388 | -1 | MGI:4439624 | Ighv2-9 |
| IGHV2-8 | 12F2 (62.22 cM) | REV | 780797 | NC_000078.6 | 113877361..113877659 | -1 | MGI:5009893 | Ighv2-8 |
| IGHV5-18 | 12F2 (62.22 cM) | REV | 780796 | NC_000078.6 | 113875772..113876239 | -1 | MGI:5009892 | Ighv5-18 |
| IGHV5-17 | 12F2 (62.21 cM) | REV | 780794 | NC_000078.6 | 113859149..113859442 | -1 | MGI:4439533 | Ighv5-17 |
| IGHV5-16 | 12F2 (62.21 cM) | REV | 633568 | NC_000078.6 | 113838528..113838821 | -1 | MGI:4439556 | Ighv5-16 |
| IGHV5-15 | 12F2 (62.20 cM) | REV | 780792 | NC_000078.6 | 113826648..113826941 | -1 | MGI:4439812 | Ighv5-15 |
| IGHV2-7 | 12F2 (62.20 cM) | REV | 780793 | NC_000078.6 | 113807314..113807747 | -1 | MGI:4439521 | Ighv2-7 |
| IGHV2-6-8 | 12F2 (62.19 cM) | REV | 791090 | NC_000078.6 | 113796138..113796430 | -1 | MGI:4439811 | Ighv2-6-8 |
| IGHV2-9-1 | 12F2 (62.18 cM) | REV | 791089 | NC_000078.6 | 113769857..113770142 | -1 | MGI:4439519 | Ighv2-9-1 |
| IGHV5-12-4 | 12F2 (62.18 cM) | REV | 628098 | NC_000078.6 | 113762251..113762544 | -1 | MGI:3645977 | Ighv5-12-4 |

| | | | | | | | |
|---|---|---|---|---|---|---|---|
| IGHV5-9-1 | 12F2 (62.17 cM) | REV | 641178 | NC_000078.6 | 113736113..113736406 | -1 | MGI:4439810 | Ighv5-9-1 |
| IGHV2-6 | 12F2 (62.17 cM) | REV | 630486 | NC_000078.6 | 113716672..113716962 | -1 | MGI:4439518 | Ighv2-6 |
| IGHV5-12 | 12F2 (62.16 cM) | REV | 668395 | NC_000078.6 | 113702126..113702419 | -1 | MGI:4439516 | Ighv5-12 |
| IGHV5-11 | 12F2 (62.16 cM) | REV | 777784 | NC_000078.6 | 113687229..113687505 | -1 | MGI:5009891 | Ighv5-11 |
| IGHV2-5 | 12F2 (62.16 cM) | REV | 638605 | NC_000078.6 | 113685482..113685774 | -1 | MGI:4439517 | Ighv2-5 |
| IGHV5-10 | 12F2 (62.16 cM) | REV | 777783 | NC_000078.6 | 113669673..113669968 | -1 | MGI:3642589 | Ighv5-10 |
| IGHV5-9 | 12F2 (62.15 cM) | REV | 544896 | NC_000078.6 | 113661771..113662228 | -1 | MGI:4439873 | Ighv5-9 |
| IGHV5-8 | 12F2 (62.15 cM) | REV | 777782 | NC_000078.6 | 113654967..113655245 | -1 | MGI:5009890 | Ighv5-8 |
| IGHV2-4 | 12F2 (62.15 cM) | REV | 668389 | NC_000078.6 | 113653291..113653583 | -1 | MGI:3643263 | Ighv2-4 |
| IGHV5-7 | 12F2 (62.14 cM) | REV | 777781 | NC_000078.6 | 113634686..113634981 | -1 | MGI:3642590 | Ighv5-7 |
| IGHV5-6 | 12F2 (62.14 cM) | REV | 777780 | NC_000078.6 | 113625508..113625801 | -1 | MGI:4439815 | Ighv5-6 |
| IGHV5-5 | 12F2 (62.14 cM) | REV | 777779 | NC_000078.6 | 113612965..113613442 | -1 | MGI:5009889 | Ighv5-5 |
| IGHV2-3 | 12F2 (62.14 cM) | REV | 238412 | NC_000078.6 | 113611184..113611476 | -1 | MGI:4439872 | Ighv2-3 |
| IGHV6-1 | 12F2 (62.14 cM) | REV | 777689 | NC_000078.6 | 113603460..113603928 | -1 | MGI:5009888 | Ighv6-1 |
| IGHV5-4 | 12F2 (62.13 cM) | REV | 777688 | NC_000078.6 | 113597448..113597741 | -1 | MGI:4439895 | Ighv5-4 |

FIG. 21 (Continued)

| | | | | | | | |
|---|---|---|---|---|---|---|---|
| IGHV5-3 | 12F2 (62.13 cM) | REV | 777687 | NC_000078.6 | 113589967..113590243 | -1 | MGI:5009887 | Ighv5-3 |
| IGHV2-2 | 12F2 (62.13 cM) | REV | 777686 | NC_000078.6 | 113588267..113588700 | -1 | MGI:4439894 | Ighv2-2 |
| IGHV5-2 | 12F2 (62.13 cM) | REV | 777685 | NC_000078.6 | 113578504..113578990 | -1 | MGI:4439893 | Ighv5-2 |
| IGHV2-1 | 12F2 (62.13 cM) | REV | 777684 | NC_000078.6 | 113574247..113574540 | -1 | MGI:4936981 | Ighv2-1 |
| IGHV5-1 | 12F2 (62.13 cM) | REV | 777683 | NC_000078.6 | 113572929..113573222 | -1 | MGI:5009886 | Ighv5-1 |
| IGHD5-1 | 12F2 (62.11 cM) | REV | 777682 | NC_000078.6 | 113526800..113526809 | -1 | MGI:4937117 | Ighd5-1 |
| IGHD3-1 | 12F2 (62.11 cM) | REV | 777681 | NC_000078.6 | 113525313..113525329 | -1 | MGI:4439891 | Ighd3-1 |
| IGHD1-1 | 12F2 (62.10 cM) | REV | 777657 | NC_000078.6 | 113482170..113482192 | -1 | MGI:4939871 | Ighd1-1 |
| IGHD6-1 | 12F2 (62.10 cM) | REV | 777680 | NC_000078.6 | 113480143..113480171 | -1 | MGI:4937254 | Ighd6-1 |
| IGHD2-3 | 12F2 (62.10 cM) | REV | 777679 | NC_000078.6 | 113475400..113475416 | -1 | MGI:4439708 | Ighd2-3 |
| IGHD6-2 | 12F2 (62.10 cM) | REV | 777678 | NC_000078.6 | 113474875..113474903 | -1 | MGI:4937120 | Ighd6-2 |
| IGHD2-4 | 12F2 (62.10 cM) | REV | 777677 | NC_000078.6 | 113470694..113470710 | -1 | MGI:4439709 | Ighd2-4 |
| IGHD5-2 | 12F2 (62.10 cM) | REV | 777676 | NC_000078.6 | 113469426..113469435 | -1 | MGI:4936898 | Ighd5-2 |
| IGHD2-5 | 12F2 (62.10 cM) | REV | 777675 | NC_000078.6 | 113466027..113466043 | -1 | MGI:4439705 | Ighd2-5 |
| IGHD5-3 | 12F2 (62.10 cM) | REV | 777674 | NC_000078.6 | 113464761..113464770 | -1 | MGI:4937297 | Ighd5-3 |

FIG. 21 (Continued)

| | | | | | | |
|---|---|---|---|---|---|---|
| IGHD5-7 | 12F2 (62.10 cM) | REV | 777673 | NC_000078.6 | 113464524..113464552 | -1 | MGI:4936973 | Ighd5-7 |
| IGHD2-6 | 12F2 (62.10 cM) | REV | 777672 | NC_000078.6 | 113461369..113461385 | -1 | MGI:4439865 | Ighd2-6 |
| IGHD5-4 | 12F2 (62.10 cM) | REV | 777670 | NC_000078.6 | 113460101..113460110 | -1 | MGI:4937058 | Ighd5-4 |
| IGHD5-8 | 12F2 (62.10 cM) | REV | 777669 | NC_000078.6 | 113459864..113459892 | -1 | MGI:4937171 | Ighd5-8 |
| IGHD2-7 | 12F2 (62.10 cM) | REV | 777667 | NC_000078.6 | 113456720..113456736 | -1 | MGI:4439866 | Ighd2-7 |
| IGHD5-5 | 12F2 (62.10 cM) | REV | 777665 | NC_000078.6 | 113454942..113454951 | -1 | MGI:4937334 | Ighd5-5 |
| IGHD2-8 | 12F2 (62.10 cM) | REV | 777664 | NC_000078.6 | 113450851..113450867 | -1 | MGI:4439706 | Ighd2-8 |
| IGHD5-6 | 12F2 (62.10 cM) | REV | 777663 | NC_000078.6 | 113449588..113449597 | -1 | MGI:4937234 | Ighd5-6 |
| IGHD3-2 | 12F2 (62.10 cM) | REV | 777662 | NC_000078.6 | 113448214..113448229 | -1 | MGI:4439707 | Ighd3-2 |
| IGHD4-1 | 12F2 (62.10 cM) | REV | 777661 | NC_000078.6 | 113430528..113430538 | -1 | MGI:4439801 | Ighd4-1 |
| IGHJ1 | 12F2 (62.10 cM) | REV | 777648 | NC_000078.6 | 113429781..113429833 | -1 | MGI:4439802 | Ighj1 |
| IGHJ2 | 12F2 (62.10 cM) | REV | 777654 | NC_000078.6 | 113429468..113429515 | -1 | MGI:4439803 | Ighj2 |
| IGHJ3 | 12F2 (62.10 cM) | REV | 777655 | NC_000078.6 | 113429085..113429132 | -1 | MGI:4439767 | Ighj3 |
| IGHJ4 | 12F2 (62.10 cM) | REV | 777656 | NC_000078.6 | 113428514..113428567 | -1 | MGI:4439658 | Ighj4 |
| IGHM | 12F2 (62.10 cM) | REV | 16019 | NC_000078.6 | 113418826..113422730 | -1 | MGI:96448 | Ighm |

FIG. 21 (Continued)

| | | | | | | |
|---|---|---|---|---|---|---|
| IGHD | 12F2 (62.10 cM) | REV | 380797 | NC_000078.6 | 113407535..113416324 | -1 | MGI:96447 | Ighd |
| IGHG3 | 12F2 (62.10 cM) | REV | 380795 | NC_000078.6 | 113357442..113361232 | -1 | MGI:2144790 | Ighg3 |
| IGHG1 | 12F2 (62.10 cM) | REV | 16017 | NC_000078.6 | 113326544..113330523 | -1 | MGI:96446 | Ighg1 |
| IGHG2B | 12F2 (62.10 cM) | REV | 16016 | NC_000078.6 | 113304314..113307933 | -1 | MGI:96445 | Ighg2b |
| IGHG2C | 12F2 (62.10 cM) | REV | 404711 | NC_000078.6 | 113287389..113288932 | -1 | MGI:2686979 | Ighg2c |
| IGHE | 12F2 (62.10 cM) | REV | 380792 | NC_000078.6 | 113269263..113273248 | -1 | MGI:2685746 | Ighe |
| IGHA | 12F2 (62.09 cM) | REV | 238447 | NC_000078.6 | 113256204..113260236 | -1 | MGI:96444 | Igha |

| IMGT | | | | | | NCBI | | | |
|---|---|---|---|---|---|---|---|---|---|
| Gene | Loc. | Orient. | Locus | Position | Accession number | Positions | Gene positions on chromosome | Accession number | Gene positions in sequences |
| IGKC | 2q11.2 | REV | IGK | | J00241 | 334..653 | 88937992..88938311 | NT_022184.14 | 67900421..67900740 |
| IGKJ5 | 2q11.2 | REV | IGK | 1714339..171441 7 | J00242 | 1536..1612 | 88941195..88941271 | NT_022184.14 | 67903624..67903700 |
| IGKJ4 | 2q11.2 | REV | IGK | 1714024..171410 2 | J00242 | 1221..1297 | 88941513..88941589 | NT_022184.14 | 67903942..67904018 |
| IGKJ3 | 2q11.2 | REV | IGK | 1713683..171376 0 | J00242 | 880..955 | 88941848..88941923 | NT_022184.14 | 67904277..67904352 |
| IGKJ2 | 2q11.2 | REV | IGK | 1713376..171343 55 | J00242 | 573..650 | 88942152..88942229 | NT_022184.14 | 67904581..67904658 |
| IGKJ1 | 2q11.2 | REV | IGK | 1713015..171307 93 | J00242 | 212..288 | 88942513..88942589 | NT_022184.14 | 67904942..67905018 |
| IGKV4-1 | 2q11.2 | FWD | IGK | 1688795..168940 6 | Z00023 | 98..709 | 88966203..88966814 | NT_022184.14 | 67928632..67929243 |
| IGKV5-2 | 2q11.2 | FWD | IGK | 1677164..167768 2 | X02485 | 304..822 | 88977926..88978445 | NT_022184.14 | 67940355..67940874 |
| IGKV7-3 | 2q11.2 | REV | IGK | 1659301..165997 29 | X12682 | 683..1281 | 88995711..88996309 | NT_022184.14 | 67958140..67958738 |
| IGKV2-4 | 2q11.2 | REV | IGK | 1642592..164339 49 | X72814 | 569..1296 | 89012284..89013011 | NT_022184.14 | 67974713..67975440 |
| IGKV1-5 | 2q11.2 | REV | IGK | 1627192..162769 97 | Z00001 | 297..802 | 89027904..89028409 | NT_022184.14 | 67990333..67990838 |

| IGKV1-6 | 2q11.2 | REV | IGK | 1608228..16087 34 | M64858 | 131..637 | 89046866..89047 372 | NT_022184. 14 | 68009295..68009 801 |
|---|---|---|---|---|---|---|---|---|---|
| IGKV3-7 | 2q11.2 | REV | IGK | 1595982..15965 28 | X02725 | 134..680 | 89059072..89059 618 | NT_022184. 14 | 68021501..68022 047 |
| IGKV1-8 | 2q11.2 | REV | IGK | 1582087..15825 86 | K02097 | 950..1427 | 89073041..89073 518 | NT_022184. 14 | 68035470..68035 947 |
| IGKV1-9 | 2q11.2 | REV | IGK | 1564529..15650 34 | K02096 | 691..1168 | 89090592..89091 069 | NT_022184. 14 | 68053021..68053 498 |
| IGKV2-10 | 2q11.2 | REV | IGK | 1554301..15550 22 | Z00012 | 121..814 | 89100604..89101 297 | NT_022184. 14 | 68063033..68063 726 |
| IGKV3-11 | 2q11.2 | REV | IGK | 1547302..15478 45 | X01668 | 134..677 | 89107753..89108 296 | NT_022184. 14 | 68070182..68070 725 |
| IGKV1-12 | 2q11.2 | REV | IGK | 1534288..15347 92 | V01577 | 1170..1674 | 89120806..89121 310 | NT_022184. 14 | 68083235..68083 739 |
| IGKV1-13 | 2q11.2 | REV | IGK | 1528520..15290 26 | K02093 | 427..903 | 89126602..89127 078 | NT_022184. 14 | 68089031..68089 507 |
| IGKV2-14 | 2q11.2 | REV | IGK | 1496203..14969 96 | X72810 | 191..956 | 89158630..89159 395 | NT_022184. 14 | 68121059..68121 824 |
| IGKV3-15 | 2q11.2 | REV | IGK | 1489297..14898 40 | M23090 | 676..1219 | 89165758..89166 301 | NT_022184. 14 | 68128187..68128 730 |
| IGKV1-16 | 2q11.2 | REV | IGK | 1474657..14751 62 | J00248 | 131..636 | 89180437..89180 942 | NT_022184. 14 | 68142866..68143 371 |
| IGKV1-17 | 2q11.2 | REV | IGK | 1457171..14576 76 | X72808 | 397..902 | 89197918..89198 423 | NT_022184. 14 | 68160347..68160 852 |
| IGKV2-18 | 2q11.2 | REV | IGK | 1445516..14463 22 | X63400 | 341..1117 | 89209304..89210 080 | NT_022184. 14 | 68171733..68172 509 |
| IGKV2-19 | 2q11.2 | REV | IGK | 1439747..14400 43 | X12692 | 814..1080 | 89215579..89215 845 | NT_022184. 14 | 68178008..68178 274 |
| IGKV3-20 | 2q11.2 | REV | IGK | 1431886..14324 50 | X12686 | 108..672 | 89223142..89223 706 | NT_022184. 14 | 68185571..68186 135 |

FIG. 22 (Continued)

| | | | | | | | |
|---|---|---|---|---|---|---|---|
| IGKV6-21 | 2q11.2 | REV | IGK | 1414698..1415279 | X63399 | 507..1088 | 89240320..89240901 | NT_022184.14 | 68202749..68203330 |
| IGKV1-22 | 2q11.2 | REV | IGK | 1403796..1404293 | X71885 | 2665..3132 | 89251344..89251811 | NT_022184.14 | 68213773..68214240 |
| IGKV2-23 | 2q11.2 | REV | IGK | 1401965..1403001 | X71885 | 834..1549 | 89252927..89253642 | NT_022184.14 | 68215356..68216071 |
| IGKV2-24 | 2q11.2 | REV | IGK | 1397878..1398710 | X12684 | 154..986 | 89256897..89257729 | NT_022184.14 | 68219326..68220158 |
| IGKV3-25 | 2q11.2 | REV | IGK | 1380742..1381345 | X06583 | 636..2411 | 89273094..89273871 | NT_022184.14 | 68235523..68237300 |
| IGKV2-26 | 2q11.2 | REV | IGK | 1378180..1378960 | X71884 | 505..1257 | 89276679..89277432 | NT_022184.14 | 68239108..68239861 |
| IGKV1-27 | 2q11.2 | REV | IGK | 1361116..1361620 | X63398 | 323..827 | 89293993..89294497 | NT_022184.14 | 68256422..68256926 |
| IGKV2-28 | 2q11.2 | REV | IGK | 1352578..1353341 | X63397 | 305..1068 | 89302264..89303027 | NT_022184.14 | 68264693..68265456 |
| IGKV2-29 | 2q11.2 | REV | IGK | 1340097..1340853 | X63396 | 322..1078 | 89314751..89315507 | NT_022184.14 | 68277180..68277936 |
| IGKV2-30 | 2q11.2 | REV | IGK | 1329442..1330257 | X63403 | 898..1713 | 89325349..89326164 | NT_022184.14 | 68287778..68288593 |
| IGKV3-31 | 2q11.2 | REV | IGK | 1322273..1323239 | X71883 | 1839..2376 | 89332799..89333336 | NT_022184.14 | 68295228..68295765 |
| IGKV1-32 | 2q11.2 | REV | IGK | 1320994..1321488 | X71883 | 560..1034 | 89334142..89334616 | NT_022184.14 | 68296571..68297045 |
| IGKV1-33 | 2q11.2 | REV | IGK | 1306433..1306937 | M64856 | 131..635 | 89348843..89349347 | NT_022184.14 | 68311272..68311776 |
| IGKV3-34 | 2q11.2 | REV | IGK | 1299120..1299680 | X71891 | 588..1120 | 89356128..89356660 | NT_022184.14 | 68318557..68319089 |
| IGKV1-35 | 2q11.2 | REV | IGK | 1287738..1288241 | X71890 | 456..930 | 89367568..89368042 | NT_022184.14 | 68329997..68330471 |

FIG. 22 (Continued)

| | | | | | | | |
|---|---|---|---|---|---|---|---|
| IGKV2-36 | 2q11.2 | REV | IGK | 1279452..1279685 | X71889 | 144..377 | 89376096..89376329 | NT_022184.14 | 68338525..68338758 |
| IGKV1-37 | 2q11.2 | REV | IGK | 1277171..1277775 | X59316 | 356..860 | 89378106..89378610 | NT_022184.14 | 68340535..68341039 |
| IGKV2-38 | 2q11.2 | REV | IGK | 1264765..1265034 | X71888 | 580..819 | 89390775..89391014 | NT_022184.14 | 68353204..68353443 |
| IGKV1-39 | 2q11.2 | REV | IGK | 1254806..1255310 | X59315 | 134..638 | 89400468..89400972 | NT_022184.14 | 68362897..68363401 |
| IGKV2-40 | 2q11.2 | REV | IGK | 1244063..1244826 | X59314 | 889..1652 | 89411128..89411721 | NT_022184.14 | 68373387..68373980 |
| IGKV2D-36 | 2q11.2 | FWD | IGK | 387386..387619 | X71893 | 2718..2951 | 89562873..89563106 | NT_032994.5 | 1322..1555 |
| IGKV1D-35 | 2q11.2 | FWD | IGK | 378827..379330 | X71894 | 121..595 | 89571166..89571640 | NT_032994.5 | 9615..10089 |
| IGKV3D-34 | 2q11.2 | FWD | IGK | 367325..367885 | X71895 | 588..1120 | 89582610..89583142 | NT_032994.5 | 21059..21591 |
| IGKV1D-33 | 2q11.2 | FWD | IGK | 360069..360573 | M64855 | 131..635 | 89589921..89590425 | NT_032994.5 | 28370..28874 |
| IGKV1D-32 | 2q11.2 | FWD | IGK | 345540..346034 | X71896 | 578..1052 | 89604539..89605013 | NT_032994.5 | 42988..43462 |
| IGKV3D-31 | 2q11.2 | FWD | IGK | 344188..344755 | X71896 | 1857..2394 | 89605819..89606356 | NT_032994.5 | 44268..44805 |
| IGKV2D-30 | 2q11.2 | FWD | IGK | 336744..337559 | X63402 | 507..1322 | 89613009..89613824 | NT_032994.5 | 51458..52273 |
| IGKV2D-29 | 2q11.2 | FWD | IGK | 326154..326911 | M31952 | 324..1081 | 89623657..89624414 | NT_032994.5 | 62106..62863 |
| IGKV2D-28 | 2q11.2 | FWD | IGK | 313676..314439 | X12691 | 304..1067 | 89636130..89636893 | NT_032994.5 | 74579..75342 |
| IGKV1D-27 | 2q11.2 | FWD | IGK | 305082..305587 | Z00004 | 525..1030 | 89644980..89645485 | NT_032994.5 | 83429..83934 |

FIG. 22 (Continued)

| | | | | | | | |
|---|---|---|---|---|---|---|---|
| IGKV2D-26 | 2q11.2 | FWD | IGK | 287726..288491 | AP001216 | 30326.31106 | 89662063..89662843 | NT_0329945 | 100512..101292 |
| IGKV3D-25 | 2q11.2 | FWD | IGK | 284165..285949 | X71886 | 628.2412 | 89664611..89666397 | NT_0329945 | 103060..104846 |
| IGKV2D-24 | 2q11.2 | FWD | IGK | 268793..269625 | X63401 | 185.1017 | 89680942..89681774 | NT_0329945 | 119391..120223 |
| IGKV2D-23 | 2q11.2 | FWD | IGK | 264526..265540 | X71887 | 834.1839 | 89685026..89686031 | NT_0329945 | 123475..124480 |
| IGKV1D-22 | 2q11.2 | FWD | IGK | 263213..263710 | X71887 | 2664.3131 | 89686856..89687323 | NT_0329945 | 125305..125772 |
| IGKV6D-21 | 2q11.2 | FWD | IGK | 252235..252816 | X12683 | 378.959 | 89697749..89698330 | NT_0329945 | 136198..136779 |
| IGKV3D-20 | 2q11.2 | FWD | IGK | 234918..235482 | X12687 | 108.672 | 89715082..89715646 | NT_0329945 | 153531..154095 |
| IGKV2D-19 | 2q11.2 | FWD | IGK | 227325..227621 | X71882 | 433.699 | 89722943..89723209 | NT_0329945 | 161392..161658 |
| IGKV2D-18 | 2q11.2 | FWD | IGK | 221028..221834 | X63395 | 308.1084 | 89728733..89729509 | NT_0329945 | 167182..167958 |
| IGKV6D-41 | 2q11.2 | FWD | IGK | 204147..204727 | M27751 | 220.772 | 89745835..89746387 | NT_0329945 | 184284..184836 |
| IGKV1D-17 | 2q11.2 | FWD | IGK | 191094..191599 | X63392 | 986.1491 | 89758963..89759468 | NT_0329945 | 197412..197917 |
| IGKV1D-16 | 2q11.2 | FWD | IGK | 173645..174150 | K01323 | 131.636 | 89776410..89776915 | NT_0329945 | 214859..215364 |
| IGKV3D-15 | 2q11.2 | FWD | IGK | 158967..159510 | X72815 | 71.614 | 89791050..89791593 | NT_0329945 | 229499..230042 |
| IGKV2D-14 | 2q11.2 | FWD | IGK | 151823..152616 | X72811 | 221.986 | 89797944..89798709 | NT_0329945 | 236393..237158 |
| IGKV1D-13 | 2q11.2 | FWD | IGK | 119800..120306 | X17262 | 130.636 | 89830253..89830759 | NT_0329945 | 268702..269208 |

FIG. 22 (Continued)

| IGKV1D-12 | 2q11.2 | FWD | IGK | 114055..114538 | X17263 | 131..607 | 89836021..89836497 | NT_0329945 | 274470..274946 |
| IGKV3D-11 | 2q11.2 | FWD | IGK | 100971..101514 | X17264 | 83..626 | 89849045..89849588 | NT_0329945 | 287494..288037 |
| IGKV2D-10 | 2q11.2 | FWD | IGK | 93730..94523 | X17265 | 122..887 | 89856036..89856801 | NT_0329945 | 294485..295250 |
| IGKV1D-42 | 2q11.2 | FWD | IGK | 83687..84183 | X72816 | 209..705 | 89866370..89866866 | NT_0329945 | 304819..305315 |
| IGKV1D-43 | 2q11.2 | FWD | IGK | 63823..64328 | X72817 | 150..655 | 89886225..89886730 | NT_0329945 | 324674..325179 |
| IGKV1D-8 | 2q11.2 | FWD | IGK | 52970..53474 | Z00008 | 305..781 | 89897079..89897555 | NT_0329945 | 335528..336004 |
| IGKV3D-7 | 2q11.2 | FWD | IGK | 39007..39568 | X72820 | 441..1002 | 89911009..89911570 | NT_0329945 | 349458..350019 |

| IMGT Gene | Chromosomal localization | Orientation | NCBI Gene ID | Reference GRCm38.p3 C57BL/6J | NCBI Gene positions in sequence | Orientation sequence | MGI ID | MGI symbol |
|---|---|---|---|---|---|---|---|---|
| IGKV2-137 | 6C1 (30.89 cM) | FWD | 692187 | NC_000072.6 | 67555636..67556216 | 1 | MGI:4439879 | Igkv2-137 |
| IGKV1-136 | 6C1 (30.90 cM) | FWD | 692186 | NC_000072.6 | 67593876..67594430 | 1 | MGI:4947614 | Igkv1-136 |
| IGKV1-135 | 6C1 (30.91 cM) | FWD | 243420 | NC_000072.6 | 67609745..67610508 | 1 | MGI:3819952 | Igkv1-135 |
| IGKV14-134-1 | 6C1 (30.94 cM) | REV | 692185 | NC_000072.6 | 67711174..67711628 | -1 | MGI:5009883 | Igkv14-134-1 |
| IGKV17-134 | 6C1 (30.94 cM) | REV | 692184 | NC_000072.6 | 67720729..67721225 | -1 | MGI:4936953 | Igkv17-134 |
| IGKV1-133 | 6C1 (30.95 cM) | FWD | 628027 | NC_000072.6 | 67724914..67725661 | 1 | MGI:3648380 | Igkv1-133 |
| IGKV1-132 | 6C1 (30.96 cM) | FWD | 243423 | NC_000072.6 | 67759700..67760413 | 1 | MGI:3648800 | Igkv1-132 |
| IGKV1-131 | 6C1 (30.96 cM) | REV | 628056 | NC_000072.6 | 67766036..67766772 | -1 | MGI:3645551 | Igkv1-131 |
| IGKV14-130 | 6C1 (30.97 cM) | FWD | 628072 | NC_000072.6 | 67791046..67791511 | 1 | MGI:3645770 | Igkv14-130 |
| IGKV9-129 | 6C1 (30.98 cM) | FWD | 692182 | NC_000072.6 | 67839793..67840266 | 1 | MGI:3525017 | Igkv9-129 |
| IGKV9-128 | 6C1 (30.99 cM) | FWD | 692181 | NC_000072.6 | 67847409..67847874 | 1 | MGI:3809196 | Igkv9-128 |

| | | | | | | | |
|---|---|---|---|---|---|---|---|
| IGKV17-127 | 6C1 (30.99 cM) | FWD | 243433 | NC_000072.6 | 67861159..67861659 | 1 | MGI:3646891 | Igkv17-127 |
| IGKV14-126-1 | 6C1 (30.99 cM) | FWD | 692180 | NC_000072.6 | 67876011..67876477 | 1 | MGI:5009882 | Igkv14-126-1 |
| IGKV14-126 | 6C1 (31.00 cM) | FWD | 628127 | NC_000072.6 | 67896177..67896664 | 1 | MGI:3643131 | Igkv14-126 |
| IGKV11-125 | 6C1 (31.01 cM) | FWD | 243428 | NC_000072.6 | 67913573..67914052 | 1 | MGI:3642338 | Igkv11-125 |
| IGKV9-124 | 6C1 (31.02 cM) | REV | 243431 | NC_000072.6 | 67942076..67942540 | -1 | MGI:3646892 | Igkv9-124 |
| IGKV9-123 | 6C1 (31.02 cM) | REV | 628144 | NC_000072.6 | 67954230..67954690 | -1 | MGI:3643848 | Igkv9-123 |
| IGKV1-122 | 6C1 (31.04 cM) | FWD | 434024 | NC_000072.6 | 68016742..68017488 | 1 | MGI:4439722 | Igkv1-122 |
| IGKV17-121 | 6C1 (31.05 cM) | FWD | 667435 | NC_000072.6 | 68036818..68037318 | 1 | MGI:3647671 | Igkv17-121 |
| IGKV9-120 | 6C1 (31.05 cM) | FWD | 434025 | NC_000072.6 | 68049983..68050454 | 1 | MGI:3647784 | Igkv9-120 |
| IGKV9-119 | 6C1 (31.06 cM) | FWD | 692177 | NC_000072.6 | 68056345..68056810 | 1 | MGI:5009881 | Igkv9-119 |
| IGKV14-118-2 | 6C1 (31.06 cM) | FWD | 692176 | NC_000072.6 | 68066369..68066828 | 1 | MGI:5009880 | Igkv14-118-2 |
| IGKV14-118-1 | 6C1 (31.07 cM) | FWD | 692175 | NC_000072.6 | 68082547..68083145 | 1 | MGI:5009879 | Igkv14-118-1 |
| IGKV11-118 | 6C1 (31.06 cM) | FWD | 692174 | NC_000072.6 | 68105414..68105880 | 1 | MGI:5009878 | Igkv11-118 |
| IGKV1-117 | 6C1 (31.06 cM) | FWD | 16098 | NC_000072.6 | 68121091..68121825 | 1 | MGI:4439721 | Igkv1-117 |
| IGKV1-115 | 6C1 (31.09 cM) | FWD | 628206 | NC_000072.6 | 68160797..68161716 | 1 | MGI:3644873 | Igkv1-115 |

FIG. 23 (Continued)

| | | | | | | | |
|---|---|---|---|---|---|---|---|
| IGKV11-114 | 6C1 (31.09 cM) | FWD | 692173 | NC_000072.6 | 68164459..68164923 | 1 | MGI:5009877 | Igkv11-114 |
| IGKV2-113 | 6C1 (31.09 cM) | FWD | 692172 | NC_000072.6 | 68178801..68179564 | 1 | MGI:5009876 | Igkv2-113 |
| IGKV2-112 | 6C1 (31.11 cM) | FWD | 381776 | NC_000072.6 | 68219981..68220705 | 1 | MGI:3644894 | Igkv2-112 |
| IGKV14-111 | 6C1 (31.12 cM) | FWD | 545847 | NC_000072.6 | 68256404..68256869 | 1 | MGI:4439863 | Igkv14-111 |
| IGKV1-110 | 6C1 (31.12 cM) | FWD | 381777 | NC_000072.6 | 68270527..68271265 | 1 | MGI:4439558 | Igkv1-110 |
| IGKV2-109 | 6C1 (31.13 cM) | FWD | 628268 | NC_000072.6 | 68302439..68303158 | 1 | MGI:3642626 | Igkv2-109 |
| IGKV1-108 | 6C1 (31.13 cM) | FWD | 628272 | NC_000072.6 | 68312054..68312359 | 1 | MGI:3644576 | Igkv1-108 |
| IGKV2-107 | 6C1 (31.14 cM) | FWD | 628283 | NC_000072.6 | 68326098..68326752 | 1 | MGI:3645630 | Igkv2-107 |
| IGKV11-106 | 6C1 (31.14 cM) | FWD | 628293 | NC_000072.6 | 68339527..68333999 | 1 | MGI:3648899 | Igkv11-106 |
| IGKV2-105 | 6C1 (31.15 cM) | FWD | 692170 | NC_000072.6 | 68348661..68334944 | 1 | MGI:5009874 | Igkv2-105 |
| IGKV16-104 | 6C1 (31.17 cM) | FWD | 381778 | NC_000072.6 | 68425605..68342607 | 1 | MGI:2685913 | Igkv16-104 |
| IGKV15-103 | 6C1 (31.18 cM) | FWD | 692169 | NC_000072.6 | 68437468..68343792 | 1 | MGI:96513 | Igkv15-103 |
| IGKV15-102 | 6C1 (31.18 cM) | REV | 692171 | NC_000072.6 | 68466126..68346659 | -1 | MGI:5009875 | Igkv15-102 |
| IGKV20-101-2 | 6C1 (31.19 cM) | FWD | 724035 | NC_000072.6 | 68474888..68347509 | 1 | MGI:5009884 | Igkv20-101-2 |
| IGKV15-101-1 | 6C1 (31.19 cM) | FWD | 692167 | NC_000072.6 | 68479082..68347953 | 1 | MGI:5009872 | Igkv15-101-1 |

FIG. 23 (Continued)

| IGKV15-101 | 6C1 (31.19 cM) | REV | 692168 | NC_000072.6 | 68481421..68481718 | -1 | MGI:5009873 | Igkv15-101 |
|---|---|---|---|---|---|---|---|---|
| IGKV14-100 | 6C1 (31.20 cM) | FWD | 243439 | NC_000072.6 | 68519012..68519477 | 1 | MGI:4439559 | Igkv14-100 |
| IGKV1-99 | 6C1 (31.21 cM) | FWD | 434028 | NC_000072.6 | 68541658..68542427 | 1 | MGI:4439724 | Igkv1-99 |
| IGKV12-98 | 6C1 (31.22 cM) | FWD | 435900 | NC_000072.6 | 68570763..68571235 | 1 | MGI:4439560 | Igkv12-98 |
| IGKV15-97 | 6C1 (31.22 cM) | FWD | 692166 | NC_000072.6 | 68591380..68591832 | 1 | MGI:5009871 | Igkv15-97 |
| IGKV10-96 | 6C1 (31.24 cM) | REV | 692165 | NC_000072.6 | 68631965..68632430 | -1 | MGI:4439561 | Igkv10-96 |
| IGKV2-95-2 | 6C1 (31.24 cM) | REV | 692164 | NC_000072.6 | 68647999..68648531 | -1 | MGI:4937167 | Igkv2-95-2 |
| IGKV2-95-1 | 6C1 (31.25 cM) | FWD | 692163 | NC_000072.6 | 68670752..68671335 | 1 | MGI:5009870 | Igkv2-95-1 |
| IGKV10-95 | 6C1 (31.25 cM) | FWD | 434031 | NC_000072.6 | 68680379..68680848 | 1 | MGI:4444598 | Igkv10-95 |
| IGKV10-94 | 6C1 (31.26 cM) | REV | 667550 | NC_000072.6 | 68704508..68704978 | -1 | MGI:4646140 | Igkv10-94 |
| IGKV2-93-1 | 6C1 (31.26 cM) | REV | 692162 | NC_000072.6 | 68712925..68713508 | -1 | MGI:5009869 | Igkv2-93-1 |
| IGKV19-93 | 6C1 (31.27 cM) | REV | 692161 | NC_000072.6 | 68736297..68736764 | -1 | MGI:1076177 | Igkv19-93 |
| IGKV4-92 | 6C1 (31.28 cM) | REV | 384410 | NC_000072.6 | 68755038..68755593 | -1 | MGI:2686254 | Igkv4-92 |
| IGKV4-91 | 6C1 (31.28 cM) | REV | 434033 | NC_000072.6 | 68768555..68769103 | -1 | MGI:3642277 | Igkv4-91 |
| IGKV4-90 | 6C1 (31.29 cM) | REV | 434034 | NC_000072.6 | 68807180..68807708 | -1 | MGI:4439830 | Igkv4-90 |

FIG. 23 (Continued)

| | | | | | | |
|---|---|---|---|---|---|---|
| IGKV13-89-1 | 6C1 (31.29 cM) | FWD | 692155 | NC_000072.6 | 68810495..68810543 | 1 | MGI:5009868 | Igkv13-89-1 |
| IGKV12-89 | 6C1 (31.29 cM) | REV | 384411 | NC_000072.6 | 68834846..68835307 | -1 | MGI:4439829 | Igkv12-89 |
| IGKV1-88 | 6C1 (31.31 cM) | REV | 692154 | NC_000072.6 | 68862265..68863030 | -1 | MGI:4439828 | Igkv1-88 |
| IGKV13-87 | 6C1 (31.32 cM) | FWD | 692153 | NC_000072.6 | 68902801..68903261 | 1 | MGI:3779399 | Igkv13-87 |
| IGKV4-86 | 6C1 (31.33 cM) | REV | 243451 | NC_000072.6 | 68910411..68910938 | -1 | MGI:2685305 | Igkv4-86 |
| IGKV13-85 | 6C1 (31.33 cM) | REV | 434036 | NC_000072.6 | 68930269..68930731 | -1 | MGI:4439827 | Igkv13-85 |
| IGKV13-84 | 6C1 (31.34 cM) | FWD | 692152 | NC_000072.6 | 68939602..68940064 | 1 | MGI:96514 | Igkv13-84 |
| IGKV4-83 | 6C1 (31.34 cM) | REV | 692145 | NC_000072.6 | 68961378..68961903 | -1 | MGI:5009867 | Igkv4-83 |
| IGKV13-82 | 6C1 (31.35 cM) | FWD | 692144 | NC_000072.6 | 68979198..68979660 | 1 | MGI:5009866 | Igkv13-82 |
| IGKV4-81 | 6C1 (31.35 cM) | REV | 243453 | NC_000072.6 | 68990758..68991283 | -1 | MGI:2685306 | Igkv4-81 |
| IGKV13-80-1 | 6C1 (31.36 cM) | FWD | 692143 | NC_000072.6 | 69009143..69009510 | 1 | MGI:5009865 | Igkv13-80-1 |
| IGKV4-80 | 6C1 (31.36 cM) | REV | 545848 | NC_000072.6 | 69016558..69017080 | -1 | MGI:4439653 | Igkv4-80 |
| IGKV4-79 | 6C1 (31.37 cM) | REV | 213684 | NC_000072.6 | 69042972..69043505 | -1 | MGI:2685040 | Igkv4-79 |
| IGKV13-78-1 | 6C1 (31.37 cM) | FWD | 628498 | NC_000072.6 | 69051444..69051794 | 1 | MGI:3647961 | Igkv13-78-1 |
| IGKV4-78 | 6C1 (31.38 cM) | REV | 545849 | NC_000072.6 | 69059690..69060224 | -1 | MGI:3819775 | Igkv4-78 |

FIG. 23 (Continued)

| | | | | | | |
|---|---|---|---|---|---|---|
| IGKV4-77 | 6C1 (31.39 cM) | REV | 667621 | NC_000072.6 | 69110904..69111432 | | | Igkv4-77 |
| IGKV13-76 | 6C1 (31.40 cM) | FWD | 692142 | NC_000072.6 | 69137866..69138332 | 1 | MGI:5009864 | Igkv13-76 |
| IGKV4-75 | 6C1 (31.41 cM) | REV | 692141 | NC_000072.6 | 69156118..69156659 | -1 | MGI:5009863 | Igkv4-75 |
| IGKV13-74-1 | 6C1 (31.41 cM) | FWD | 692140 | NC_000072.6 | 69177416..69177787 | 1 | MGI:5009862 | Igkv13-74-1 |
| IGKV4-74 | 6C1 (31.42 cM) | REV | 236047 | NC_000072.6 | 69184826..69185361 | -1 | MGI:3779447 | Igkv4-74 |
| IGKV13-73-1 | 6C1 (31.42 cM) | FWD | 692139 | NC_000072.6 | 69190073..69190282 | 1 | MGI:5009861 | Igkv13-73-1 |
| IGKV4-73 | 6C1 (31.42 cM) | REV | 628516 | NC_000072.6 | 69197583..69198116 | -1 | MGI:3645825 | Igkv4-73 |
| IGKV4-72 | 6C1 (31.43 cM) | REV | 385109 | NC_000072.6 | 69226854..69227383 | -1 | MGI:2686345 | Igkv4-72 |
| IGKV13-71-1 | 6C1 (31.43 cM) | FWD | 692138 | NC_000072.6 | 69235927..69236158 | 1 | MGI:5009860 | Igkv13-71-1 |
| IGKV4-71 | 6C1 (31.43 cM) | REV | 434586 | NC_000072.6 | 69243160..69243688 | -1 | MGI:4439654 | Igkv4-71 |
| IGKV4-70 | 6C1 (31.44 cM) | REV | 385120 | NC_000072.6 | 69267888..69268412 | -1 | MGI:2686348 | Igkv4-70 |
| IGKV4-69 | 6C1 (31.45 cM) | REV | 628541 | NC_000072.6 | 69283794..69284319 | -1 | MGI:3648668 | Igkv4-69 |
| IGKV4-68 | 6C1 (31.45 cM) | REV | 384515 | NC_000072.6 | 69304834..69305363 | -1 | MGI:2686265 | Igkv4-68 |
| IGKV12-67 | 6C1 (31.46 cM) | REV | 628551 | NC_000072.6 | 69324177..69324646 | -1 | MGI:3645399 | Igkv12-67 |
| IGKV12-66 | 6C1 (31.46 cM) | REV | 692133 | NC_000072.6 | 69334604..69335076 | -1 | MGI:5009859 | Igkv12-66 |

FIG. 23 (Continued)

| | | | | | | | | |
|---|---|---|---|---|---|---|---|---|
| IGKV4-65 | 6C1 (31.47 cM) | REV | 667670 | NC_000072.6 | 69342472..69934300 4 | | -1 | MGI:3644339 | Igkv4-65 |
| IGKV13-64 | 6C1 (31.47 cM) | FWD | 628564 | NC_000072.6 | 69362722..6936318 | | 1 | MGI:5009834 | Igkv13-64 |
| IGKV4-63 | 6C1 (31.48 cM) | REV | 628571 | NC_000072.6 | 69377944..6937847 2 | | -1 | MGI:3645235 | Igkv4-63 |
| IGKV13-62-1 | 6C1 (31.48 cM) | FWD | 692119 | NC_000072.6 | 69392439..6939281 5 | | 1 | MGI:5009858 | Igkv13-62-1 |
| IGKV4-62 | 6C1 (31.49 cM) | REV | 636752 | NC_000072.6 | 69399812..6940034 4 | | -1 | MGI:3643587 | Igkv4-62 |
| IGKV13-61-1 | 6C1 (31.49 cM) | FWD | 692118 | NC_000072.6 | 69409499..6940987 5 | | 1 | MGI:5009857 | Igkv13-61-1 |
| IGKV4-61 | 6C1 (31.49 cM) | REV | 546244 | NC_000072.6 | 69416893..6941742 5 | | -1 | MGI:4439819 | Igkv4-61 |
| IGKV4-59 | 6C1 (31.50 cM) | REV | 667683 | NC_000072.6 | 69438218..6943874 1 | | -1 | MGI:3646808 | Igkv4-59 |
| IGKV4-60 | 6C1 (31.51 cM) | REV | 385277 | NC_000072.6 | 69463288..6946372 5 | | -1 | MGI:3708737 | Igkv4-60 |
| IGKV4-58 | 6C1 (31.52 cM) | REV | 381831 | NC_000072.6 | 69500254..6950075 8 | | -1 | MGI:2685923 | Igkv4-58 |
| IGKV13-57-2 | 6C1 (31.52 cM) | FWD | 724106 | NC_000072.6 | 69523739..6952401 6 | | 1 | MGI:5009885 | Igkv13-57-2 |
| IGKV4-57-1 | 6C1 (31.53 cM) | REV | 384514 | NC_000072.6 | 69544368..6954489 2 | | -1 | MGI:3686264 | Igkv4-57-1 |
| IGKV13-57-1 | 6C1 (31.54 cM) | FWD | 692114 | NC_000072.6 | 69569737..6957010 9 | | 1 | MGI:5009856 | Igkv13-57-1 |
| IGKV4-57 | 6C1 (31.54 cM) | REV | 235952 | NC_000072.6 | 69575975..6957650 0 | | -1 | MGI:2685035 | Igkv4-57 |
| IGKV13-56-1 | 6C1 (31.54 cM) | FWD | 692113 | NC_000072.6 | 69581244..6958145 2 | | 1 | MGI:5009855 | Igkv13-56-1 |

FIG. 23 (Continued)

| | | | | | | |
|---|---|---|---|---|---|---|
| IGKV4-56 | 6C1 (31.54 cM) | REV | 619743 | NC_000072.6 | 69587295..69587810 | -1 | MGI:4439916 | Igkv4-56 |
| IGKV13-55-1 | 6C1 (31.55 cM) | FWD | 692112 | NC_000072.6 | 69599886..69600026 | 1 | MGI:5009854 | Igkv13-55-1 |
| IGKV4-55 | 6C1 (31.55 cM) | REV | 385253 | NC_000072.6 | 69607275..69607801 | -1 | MGI:2686370 | Igkv4-55 |
| IGKV13-54-1 | 6C1 (31.55 cM) | FWD | 692105 | NC_000072.6 | 69617048..69617423 | 1 | MGI:5009853 | Igkv13-54-1 |
| IGKV4-54 | 6C1 (31.56 cM) | REV | 385291 | NC_000072.6 | 69631648..69632178 | -1 | MGI:5009821 | Igkv4-54 |
| IGKV4-53 | 6C1 (31.56 cM) | REV | 546213 | NC_000072.6 | 69648824..69649354 | -1 | MGI:2686266 | Igkv4-53 |
| IGKV4-51 | 6C1 (31.58 cM) | REV | 619806 | NC_000072.6 | 69681406..69681939 | -1 | MGI:5009829 | Igkv4-51 |
| IGKV4-50 | 6C1 (31.58 cM) | REV | 381782 | NC_000072.6 | 69700767..69701287 | -1 | MGI:2685915 | Igkv4-50 |
| IGKV12-49 | 6C1 (31.59 cM) | REV | 619824 | NC_000072.6 | 69716498..69716956 | -1 | MGI:5009830 | Igkv12-49 |
| IGKV5-48 | 6C1 (31.59 cM) | REV | 619846 | NC_000072.6 | 69726573..69727125 | -1 | MGI:3642817 | Igkv5-48 |
| IGKV12-47 | 6C1 (31.60 cM) | REV | 434037 | NC_000072.6 | 69750854..69751310 | -1 | MGI:3644595 | Igkv12-47 |
| IGKV12-46 | 6C1 (31.61 cM) | REV | 692245 | NC_000072.6 | 69764523..69764992 | -1 | MGI:4439773 | Igkv12-46 |
| IGKV5-45 | 6C1 (31.61 cM) | REV | 545850 | NC_000072.6 | 69775750..69776306 | -1 | MGI:4439774 | Igkv5-45 |
| IGKV12-44 | 6C1 (31.63 cM) | REV | 545851 | NC_000072.6 | 69814631..69815100 | -1 | MGI:4439775 | Igkv12-44 |
| IGKV5-43 | 6C1 (31.63 cM) | REV | 381783 | NC_000072.6 | 69823355..69823911 | -1 | MGI:4943320 | Igkv5-43 |

FIG. 23 (Continued)

| | | | | | | |
|---|---|---|---|---|---|---|
| IGKV12-42 | 6C1 (31.64 cM) | REV | 677861 | NC_000072.6 | 69834792..69835245 | -1 | MGI:5009852 | Igkv12-42 |
| IGKV12-41 | 6C1 (31.65 cM) | REV | 619960 | NC_000072.6 | 69858420..69858884 | -1 | MGI:4439772 | Igkv12-41 |
| IGKV5-40-1 | 6C1 (31.65 cM) | REV | 619974 | NC_000072.6 | 69868595..69869193 | -1 | MGI:5009831 | Igkv5-40-1 |
| IGKV12-40 | 6C1 (31.66 cM) | REV | 435904 | NC_000072.6 | 69879350..69879813 | -1 | MGI:3643951 | Igkv12-40 |
| IGKV5-39 | 6C1 (31.67 cM) | REV | 620017 | NC_000072.6 | 69900424..69900977 | -1 | MGI:2686255 | Igkv5-39 |
| IGKV12-38 | 6C1 (31.69 cM) | REV | 620050 | NC_000072.6 | 69943186..69943648 | -1 | MGI:4439614 | Igkv12-38 |
| IGKV5-37 | 6C1 (31.69 cM) | REV | 384417 | NC_000072.6 | 69963312..69963861 | -1 | MGI:2686256 | Igkv5-37 |
| IGKV18-36 | 6C1 (31.71 cM) | REV | 620088 | NC_000072.6 | 69992465..69992977 | -1 | MGI:4439613 | Igkv18-36 |
| IGKV1-35 | 6C1 (31.72 cM) | REV | 620105 | NC_000072.6 | 70010949..70011673 | -1 | MGI:4439612 | Igkv1-35 |
| IGKV8-34 | 6C1 (31.73 cM) | REV | 620126 | NC_000072.6 | 70044112..70044678 | -1 | MGI:4949914 | Igkv8-34 |
| IGKV7-33 | 6C1 (31.74 cM) | REV | 243461 | NC_000072.6 | 70058632..70059199 | -1 | MGI:3577282 | Igkv7-33 |
| IGKV6-32 | 6C1 (31.74 cM) | REV | 434039 | NC_000072.6 | 70074024..70074584 | -1 | MGI:3641634 | Igkv6-32 |
| IGKV8-31 | 6C1 (31.76 cM) | REV | 546905 | NC_000072.6 | 70105860..70106179 | -1 | MGI:3644798 | Igkv8-31 |
| IGKV8-30 | 6C1 (31.76 cM) | REV | 384419 | NC_000072.6 | 70117061..70117617 | -1 | MGI:3642250 | Igkv8-30 |
| IGKV6-29 | 6C1 (31.77 cM) | REV | 620191 | NC_000072.6 | 70138462..70139082 | -1 | MGI:4439616 | Igkv6-29 |

FIG. 23 (Continued)

| | | | | | | | | |
|---|---|---|---|---|---|---|---|---|
| IGKV8-28 | 6C1 (31.78 cM) | REV | 434040 | NC_000072.6 | 70143593..70144416 | -1 | MGI:3642251 | Igkv8-28 |
| IGKV8-27 | 6C1 (31.79 cM) | REV | 434041 | NC_000072.6 | 70171809..70172270 | -1 | MGI:4439868 | Igkv8-27 |
| IGKV8-26 | 6C1 (31.80 cM) | FWD | 620240 | NC_000072.6 | 70193228..70193797 | 1 | MGI:4439869 | Igkv8-26 |
| IGKV6-25 | 6C1 (31.81 cM) | FWD | 381784 | NC_000072.6 | 70215433..70215957 | 1 | MGI:4439867 | Igkv6-25 |
| IGKV8-24 | 6C1 (31.81 cM) | REV | 677858 | NC_000072.6 | 70216858..70217421 | -1 | MGI:4947958 | Igkv8-24 |
| IGKV8-23-1 | 6C1 (31.82 cM) | FWD | 434685 | NC_000072.6 | 70240427..70240710 | 1 | MGI:4947960 | Igkv8-23-1 |
| IGKV6-23 | 6C1 (31.83 cM) | REV | 637227 | NC_000072.6 | 70260409..70260933 | -1 | MGI:3711980 | Igkv6-23 |
| IGKV8-22 | 6C1 (31.85 cM) | REV | 620387 | NC_000072.6 | 70297554..70297819 | -1 | MGI:5009833 | Igkv8-22 |
| IGKV8-21 | 6C1 (31.85 cM) | REV | 620400 | NC_000072.6 | 70314895..70315452 | -1 | MGI:1330840 | Igkv8-21 |
| IGKV6-20 | 6C1 (31.86 cM) | REV | 108024 | NC_000072.6 | 70335841..70336479 | -1 | MGI:1330836 | Igkv6-20 |
| IGKV8-19 | 6C1 (31.87 cM) | REV | 232065 | NC_000072.6 | 70340876..70341448 | -1 | MGI:1330844 | Igkv8-19 |
| IGKV8-18 | 6C1 (31.87 cM) | FWD | 667859 | NC_000072.6 | 70355877..70356445 | 1 | MGI:1330845 | Igkv8-18 |
| IGKV6-17 | 6C1 (31.88 cM) | FWD | 667865 | NC_000072.6 | 70371469..70371993 | 1 | MGI:1330833 | Igkv6-17 |
| IGKV8-16 | 6C1 (31.89 cM) | REV | 640340 | NC_000072.6 | 70386672..70387238 | -1 | MGI:1330843 | Igkv8-16 |
| IGKV6-15 | 6C1 (31.89 cM) | REV | 108022 | NC_000072.6 | 70406469..70406992 | -1 | MGI:1330831 | Igkv6-15 |

FIG. 23 (Continued)

| | | | | | | |
|---|---|---|---|---|---|---|
| IGKV6-14 | 6C1 (31.91 cM) | REV | 667881 | NC_000072.6 | 70434952..70435476 | -1 | MGI:1330830 | Igkv6-14 |
| IGKV6-13 | 6C1 (31.92 cM) | REV | 667899 | NC_000072.6 | 70457503..70458036 | -1 | MGI:1330829 | Igkv6-13 |
| IGKV3-12-1 | 6C1 (31.94 cM) | REV | 667908 | NC_000072.6 | 70497662..70498342 | -1 | MGI:3645632 | Igkv3-12-1 |
| IGKV3-12 | 6C1 (31.95 cM) | FWD | 667914 | NC_000072.6 | 70518250..70518849 | 1 | MGI:1330815 | Igkv3-12 |
| IGKV3-11 | 6C1 (31.96 cM) | FWD | 667917 | NC_000072.6 | 70553274..70554440 | 1 | MGI:1330820 | Igkv3-11 |
| IGKV3-10 | 6C1 (31.97 cM) | FWD | 667924 | NC_000072.6 | 70572633..70573230 | 1 | MGI:1330821 | Igkv3-10 |
| IGKV3-9 | 6C1 (31.98 cM) | FWD | 667928 | NC_000072.6 | 70588189..70588777 | 1 | MGI:1330856 | Igkv3-9 |
| IGKV3-8 | 6C1 (31.98 cM) | FWD | 108010 | NC_000072.6 | 70588871..70589452 | 1 | MGI:1330857 | Igkv3-8 |
| IGKV3-7 | 6C1 (31.99 cM) | FWD | 108005 | NC_000072.6 | 70607437..70608036 | 1 | MGI:1330852 | Igkv3-7 |
| IGKV3-6 | 6C1 (32.00 cM) | FWD | 667936 | NC_000072.6 | 70642405..70643565 | 1 | MGI:1330853 | Igkv3-6 |
| IGKV3-5 | 6C1 (32.01 cM) | FWD | 667940 | NC_000072.6 | 70663298..70663895 | 1 | MGI:1330854 | Igkv3-5 |
| IGKV3-4 | 6C1 (32.01 cM) | FWD | 626347 | NC_000072.6 | 70671789..70672377 | 1 | MGI:1330855 | Igkv3-4 |
| IGKV3-3 | 6C1 (32.02 cM) | FWD | 667946 | NC_000072.6 | 70686946..70687534 | 1 | MGI:1330849 | Igkv3-3 |
| IGKV3-2 | 6C1 (32.03 cM) | FWD | 626583 | NC_000072.6 | 70698468..70699067 | 1 | MGI:1330850 | Igkv3-2 |
| IGKV3-1 | 6C1 (32.03 cM) | FWD | 108004 | NC_000072.6 | 70703578..70704177 | 1 | MGI:1330851 | Igkv3-1 |

FIG. 23 (Continued)

| IGKJ1 | 6C1 (32.04 cM) | FWD | 110759 | NC_000072.6 | 70722562..70722259 | 1 | MGI:1316689 | Igkj1 |
|---|---|---|---|---|---|---|---|---|
| IGKJ2 | 6C1 (32.04 cM) | FWD | 110760 | NC_000072.6 | 70722916..70722954 | 1 | MGI:1316690 | Igkj2 |
| IGKJ3 | 6C1 (32.04 cM) | FWD | 110761 | NC_000072.6 | 70723223..70723260 | 1 | MGI:1316691 | Igkj3 |
| IGKJ4 | 6C1 (32.04 cM) | FWD | 110762 | NC_000072.6 | 70723548..70723585 | 1 | MGI:1316692 | Igkj4 |
| IGKJ5 | 6C1 (32.04 cM) | FWD | 110763 | NC_000072.6 | 70723886..70723923 | 1 | MGI:1316738 | Igkj5 |
| IGKC | 6C1 (32.04 cM) | FWD | 16071 | NC_000072.6 | 70726435..70726754 | 1 | MGI:96495 | Igkc |

FIG. 23 (Continued)

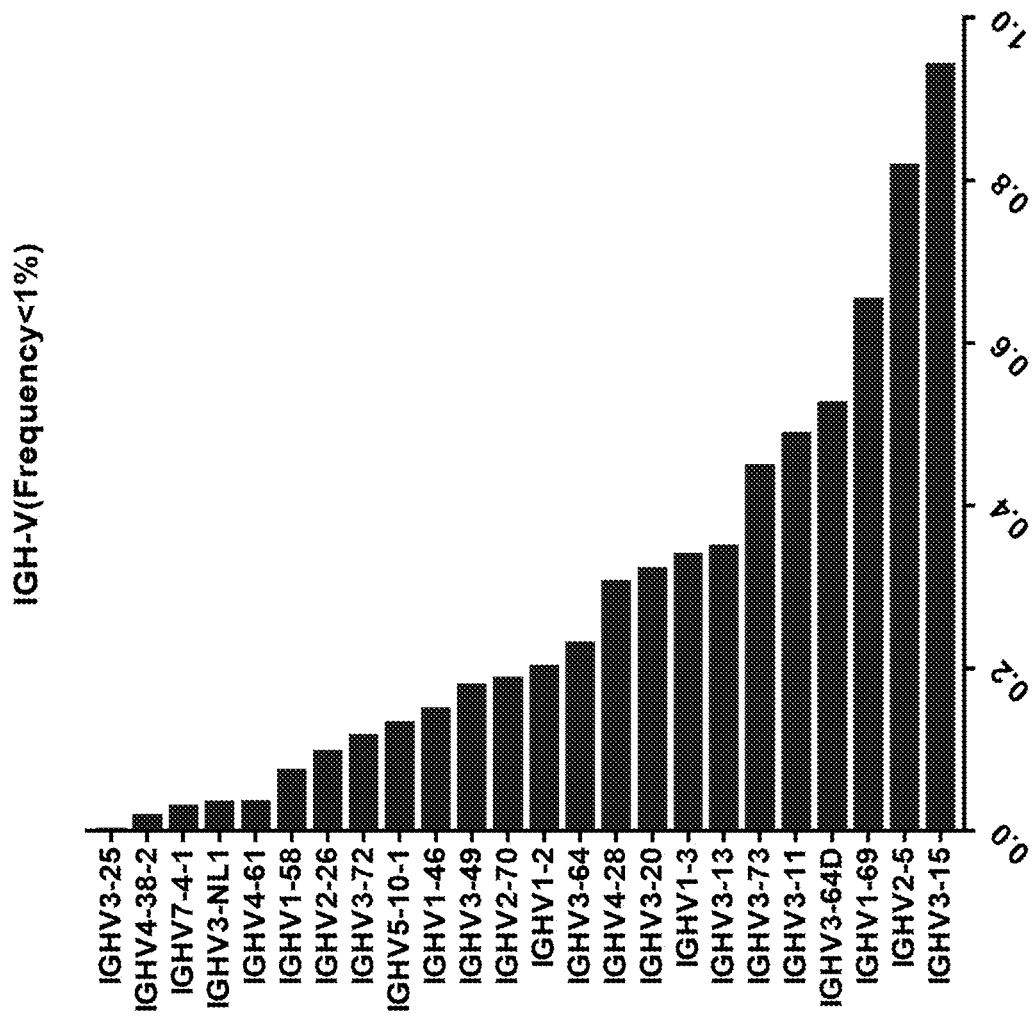

FIG. 32

IGKV1-39 (SEQ ID NO:1): 477bp, 89319623 to 89320099 of NCBI accession number NC_000002.12

Atggacatgagggtccccgctcagctcctggggctcctgctactctggctccgaggtgccagatgtgctc
agtactgactgactgaacttcagggaagttctctgtctgataacatgattaatagaacataggaatggagaacactaggaattactcagtgatgacatc
cagatgaccecagtctccatccetccctgtctctgtaggagacagatgccatccagtctcttgccggcaagtcagagcattagcagctatttaaattg
gtatcagcagaaaccaggaaagcccccaagcttctcatcttggatgctgatcctatgtctgtcaaactgctcaagttccatggcagttggcagttgatctg
ggacagatttcactctcaccatcagcagtctgcaacctgaagattttgcaactactgtcaacagagttacagtactacaccctcc

IGKV3-11 (SEQ ID NO:2): 516bp, 89027169 to 89027684 of NCBI accession number NC_000002.12

Atgaagcccccagctcagctctcctcctgctcctctgcctctgctcccaggtgagggaacatgagtgttgcacattagtgaaactcttgccac
ctctctagcaagaataattcaaaattcaaaagtatatcaaagatcttcctactcaaagacagtggttggtttgatcttgattacatgagtgcatt
tctgttttattccaattcagatataccaccggagctacttagcagttcagttggggcccagtctctgcccagtgccaccctctc
ctgcagggccagtcagagtgttagcagctaccttagcctggtaccagcagaaacctggccaggctccaggctcctcatcatcatggtgcatcaacagg
ccactgccatcccagacaggttccagtggcagtggggtctgggacagacttcactctcaccatcagcagctagcctgaagcctgaagattttgcagttattac
tgtcagcagcgtagcaactggcctcc

IGKV3-20 (SEQ ID NO: 3): 537bp, 89142572 to 89143108 of NCBI accession number NC_000002.12

Atgaaacccccagcgcagctcttcctcctgctcctctgcctctgctccccaggtgagggaacatggatggtttgcatgtcagtcagtgaaaccctctcaag
tcctgttactgtaccctggccaactctgcttttctctgcctgcaatactctcaataaagctcaataagtcctagtggaagacaaatgggttgattta
gattacatggggtgactttttcctccttcttagaggccagtcagatgttagcagcagctcactagccgtaccagcagaaacctggccaggctcctcca
ggaaagagcccaccctggcatcccagatagcagcggtcccagccaggttcagtggcagtgggtctgggacagacttcactctcaccatcagcagactggagcct
gaagattttgcagtgtattactgtcagcagtatggtagctcacctcc

IGKJ1 (SEQ ID NO:4): 38bp, 88861886 to 88861923 of NCBI accession number NC_000002.12 gtggacgttc ggccaaggga ccaaggtgga aatcaaac

IGKJ4 (SEQ ID NO:5): 38bp, 88860886 to 88860923 of NCBI accession number NC_000002.12 gctcacttc ggcggaggga ccaaggtgga gatcaaac

FIG. 32 (Continued)

Mouse 3' UTR sequence (SEQ ID NO 6) 1189bp gtaagtacacttttctctcatctttttatgtgtaagacacaggttttcatgttaggagtcagttcagaaatcttgagaaatggagaggc
tcattatcagttgacgtggcatacagtgtcagattttctgttttatcaagctagtgagttgaggtgcaaaagaggcttagttgaggaaagtaatt
aatactatggtcaccatccaagagattggatcggagaataagcatgtagtagttattgagatctggctgactgcagtagcgtgtcttctagacgt
ttaagtgggagatttggagggatgaaggaacttcaggatagaagaacttcagctgaagttcagctcgagagagctgagttcctaaaatgatgtgggagcaaac
tttgaagataactgtcttgagttttgcaataaaagtgggatagcagtgtttgaaagtgtttgactgtcttgccatgtgagctaggctgagttctctctttgtctcctaagttttatgac
ccacaagtactgtcttgagttttgcaataaaatggatagcagtgtttgaaagtgtttgactgtcttgccatgacgagtcctgacagacagctcaagggtttttttcctt
tacaaaaatcagtagtagtgtcctgaaataatcattaagctgtttgaaagtgtttgaaatgtgactgtcttgccatgacgagtcctgacagacagctcaagggtttttttcctt
ggtgtgactcttattctacatgaaagtaaatttgtcacaaaatgtcaaaatgagaagctctgtaggaaatgagaagactccttgaacagtacagtttggggtttgaactatatgttttaatggccacggtt
gtctcattcattcatcttaaaatttgaaagtaaatttgtttccccagttatactgagttaattttactgcgttattactgcagttattatcgccagccaaatcggtaccacctcttcttcttaca
ttgtaagacatttggtcctttgttgccagctgtgccagccatttggcgttcaaccttggcgtgcagctgtgccatccctgagcatcctgtccgcgtggacc
actgggtgacctcgcgctgtgccagccatttggcgttcaaccttggcgtgcagctgtgccatccctgagcatcctgtccgcgtggacc
ctttcctgaggcacagtgatagggacacagaacagaggccactaatctgaagagaacagagatgtgacagactacactaatgtgacagactacacaaaacaaggaaggtga
cttattggagatt Human 3' UTR sequence (SEQ ID NO: 7) 88860567 to 88860068 of NC_000002.12 gtaagtaattttcactattgtcttctgaaattgggtctgatgcctagttggccagtattgcctaaataggagtttgtaaagattggtaaatg
aggcattaagattgccatggttgcaaaactaaactcagctgcaaaaatgagtttggagaaaaaagattaaattgctctaaactgaatgacac
aaagtaacaaaagtgtaactaaaagaaccccttgtatttctaaggagcaaaagtaaattatttgttcactcttgccaaatattgtattgg
ttgttgctgattatgcatgatgacataaataacattttagtcttttcccttttgtttgataaattattttgtcagacaacaataaaa
atcaatagcacgccctaagaacagggaaaagtgaagtgaagtgaagttgaccctatttgctatgtagaagaggcagcttactgagaaatcagcagcagtgttgtt
tttagagtct Rearranged human IGKV1-39+J4 nucleic acid sequence 3012bp (SEQ ID NO: 35)
V1-39 Promoter    1-2000
V1-39             2001-2475  (the last 2 nucleotides in V1-39 are deleted)
J4                2476-2512  (the first nucleotide in J4 is deleted)
Human 3' UTR sequence  2513-3012 gcaggcagcatatattataatgcacactagaacactaggagagacaaggcagtgagagagagcagcgcgaaaatgtcctcagcgagaa
gctaccacagagggatgaatggagatcaagccacgtggaaacatgggaaaatgtctcagtatttttccacctaagaaggggaggatgggtatgta
tacacctccctgtcctcactgattcgagggctttcgagagggatgctcattccagggtgctgtgataggccatgtgtacaggcaggctgcctctccag
cttcagatagagccagtgaggaaaagatatggccatgggggtcagcagaagtacagcagaagtgcttctctctgaacctaatcttagcagagcagttaccagta
cacccccccacacacacacaccggcccctgaaagttcaggccctggaaaggagcaggggttgtgtacaggctataccacacagctctgcccacccttagtgatgcatgatgaatgct
actgcccctgaaattcaggccctggaaaggagcaggggttgtgtacaggctataccacacagctctgcccacccttagtgatgcatgatgaatgct
ccctgactccccaggttctcagtttctcatgtcgatgtagttgattccacttccctgctgcacaaccaggctggatgcctggcagaggcagaca FIG. 32 (Continued)

```
tgtgaggtatagggggttcaaatctgttctccaagtttatccagcttcaaagcattctccgtgtacatgagcgtggcttgacaggagatggagactc
tctttcctggatgtgaaggaggcaggcgtctgagtcaggatgatgtccactactgctttccagtgtctaaagagaaaagtgctttgatgtgcaggcagg
gaaatgcactgagtggtcgccaccctgaacactcacacactattgtgggaaaagcagatcagagcattaggcaagttgcattacctggccttctctt
atgattttgagagcaattgatgtgggttctagattgaccagagttcaagtttatcctgggaaataatacccaaggcagaaaaatgggcagaatgttttg
aagtaaacagatctagcattactactcaccctttcatatgattacagagacctatagtctggataatgtttaaggtcactacaaatactttggagtgtatt
caaaccaagacgaagctgctgccattgagactgcgcaggaattgcttgtaaatatactgtgacaatcacagaggtgttgttactatagcaaagatgttac
aatcacagcatcattatcgtgtcatctgcaggcatgttttctcactgtttttcgataagactgtttttctcacatgcctaagcaatataggaccaccctcaagct
aaatatgttctgatatagatactattaaatatactctaattttgactttttcctcaaaatatctcttgctcacacagcgct
tctccaatccactcaaatcccctcagaaacattccctccccagcaatctatgcctgctgatgattttgactttttcctcaaatatctcttgactgagtgagc
ccaatacacaactctaaatattattccagcaaatctatgcctgcctgattgatttgcatgtccagagcacagcctcgcagccctctcagccagggtcatg
tcggcccttgcagccctgtgctcaggctgtgccgtgtgccagggaacatgaaggtgtccctccatctcctgtctgataacatgattaatagtaagaatatt
aggatggagaaacactaggaatttactcagtgccagtgtgcctgactggcattgccagcttaaaatgtatcagcagaaccaggaaaagccctgcagctcactgcacaccta
ctttgccgggcaagtcccatcaaggtcagtgcgtcagttaccccctccactttctgagatgggcattaagattggtaaagatgggcattaagattgcctatttgcaacttacta
ctgtcaacagagttacacagagtttacttcgcggcgaggacccaaggtggtaaagattggtaaagattggtcaaacatgaaggcattaaagatttgccatggttgcaaaggttta
actcagctcaaaatggattggagaaaaaagattaaattgctcactcttgccaaatatttgctcaagatgaagggcaaaggtgtaaaaaaaggaaccc
ttgtattctaaggaggcaaaagtaccctttgtttcaggattttagtttgcacaactcttgtcagcaacaaaaaatcaatagacacgcctaagaaaaatcagggaaaagt
aatacattttagtctttctccctttttgttttgataaattatttttgtcagacaacaaaaaatcaatagacacgcctaagaaaaatcagggaaaagt
gaagtgtacctatttgctatgtagaagaggcagcttactgagaagcttagagtct
```

Rearranged human IGKV3-11+J1 nucleic acid sequence 3051bp (SEQ ID NO: 36)
V3-11 Promoter    1-2000
V3-11             2001-2516
J1                2517-2551    (the first 3 nucleotides in J1 are deleted)
Human 3' UTR sequence    2552-3051

```
caggagtgagcctggtttgatgcctctcccaacacgatagaagtgtggcacaaatcttgaaaaattcagtttcccgtgcaacaactacc
tgggactgaaaacttcttccctcgctccttctctcacaccccacttccacctcatctgtgactcatctgtcaggaaagattctgga
aaaagcaaagagagacttccttagaggtgtcagagattcctgtaccagcatctgtccatctctagagggtttgtgagtatgaggagcagcttgt
caatctttacttgctttcactgctttatttccactcccactgtatttcctaacagcaacagccatatcatcacagaggaccctctcttactttccaagg
ctttatttcagtaaatctgctctaccctctatctcaggcagctagaaagctagaagtttgatactcataactactgcagtttcattaattgaaa
```

FIG. 32 (Continued)

```
agtagacaagactcagtgtaatgcaggcattccttatgccagtcagcattcagttttgatcatcattgcacacatataccaccatgtgtctaata
tatatgtaaaaatccatgaagcaagagtcataatagctagcatttgatattgtattgtatttcctctatatcatcttcctttcgtcctaaaa
aaaatctgttcaagtcagtcctaaattattggatgatagtagataaaatcttttattgataacacattgacccaatgaatgttcttttgca
agacatagtcctcacttcacaaagataacaagcctgacaaaattatactggacaagtaatgatgtgtagctttcctttattgtcagtcctgg
ggcaaaaataagacaaaagattaatgcgttagacagagatgggcgggaatttaattgactgttgataaaacaaaacattcttggatcataggatt
ataatggatgatgagaatttgtacagttagtgataatgcgttagacagagatgggcgggaatttaattgactgttgataaaacaaaacattcttggatt
ttaagagttgtgtacatatttttatctttatctttaaactgtctacagcaatcggcaagcatctatgtcaggcaagcaccagtattgtcacagttacacagatatgtaaacagaagttttaa
aagtaagtatatgtttttatctttatctttaaactgtctacagcaatcggcaagcatctatgtcaggcaagcaccagtattgtcacagttacacagatatgtaaacagaagttttaa
ctgtaaatgttttaactcaaagagggtatgtgtctgcatcgatcaaatatgcacttaggagatgactggcatatgtgaggagaagaaatgaaaacacag
cccttataatattgttcttaacaggctgtgtgccaaacatcctctggtgaattaggtgattgaggagaagaaacatggagaatgaaattctctgagca
caaggagaaaagttctacactcagactgagccaacagactttctgcctgacaacagtcagggtggcgcaggttgctcagtgcaggccagtcagtgccatatcaatgcctgtcagag
ggtctctgggagctgaagctgccagttagggaactggtcaggaaccatgaagcccaagtggagttctgtcttcttaatccgaggctactctggctccagagtgcagag
ccctgggagaactgctcagttagggaaccatgaagcccaagtggagttctgtcttcttaatccgaggctactctggctccagagtgcagag
acatgaggtggttttgcacattagtgaaaactcttggccacctgctcagaagaaatatatcaaagtatatcacaattggcttctac
tcaaagacagttggtttgatcttgattacatgagtgctattctgttttctgttcattctgcaggcagcagttgctcagcaggcatccgagagcttctaactgaagtgttaccaacagtctccag
ccaaccctgtctctttgtctccagggaaagagagccttccctcagctgcatccaacaggcagcatccaacaggccagcatccaacagggccagcatccgtggaactctgctctcac
caggctcccaggctcctagagcctgaagattttcagtttattgtcagcagccatgcgtcagcagccgtcaatgttggttctgatgatgcaacttagctttagagggcttaaatagaagtttggtaaagattggtaa
aacgtaagtaattttcactattgtcctgaagttgccatggttgcatgggttgcaaagattttctaactcagctcaaaagttaaactcagctcaaaagttccctttgtatttctaaggagcaaaagtaaatcattttt
atgaggcattaaaaaaagtgtaactaaacagaaaagtggaaaaatcaggaaaaagtgaaaattcaggaaaaagtgaaaaatcaggaaaaagtgaaaaatcaggaaaaagtga
cacaagtaaaaaaaagtgtaactaaacagaaaagtggaaaaatcaggaaaaagtgaaaatcaggaaaaagtgaaaaatcaggaaaaagtgaaaaatcaggaaaaa
tggttgttgctgattatgcatgatacagccctaagaacagcccctttgctatttgtacctattggaaatcagcagcaatgtt
aaaatcaatagcacgccctaagaaatcagcaagaaaatcaggaaaaagtgaaaatcagc
gtttttagagtct Rearranged human IGK V3-20+J1 nucleic acid sequence 3072bp (SEQ ID NO: 37)
V3-20 promoter              1-2000
V3-20                       2001-2535 (the last 2 nucleotides in V3-20 are deleted)
J1                          2536-2572 (the first nucleotides in J1 is deleted)
Human 3' UTR sequence       2573-3072 agccagtggatgactatttcttcctgagactgatgactggcatcatccaacccaatggtccaaactacatggtccagtgtaatggtcatgcaggcctttct
gccacctcttgctatattttaccaactcatggccactgccaaacagtctgatcaggaaatagcaacgagtgactgactattaaagc
atccctctgtggagaaaaggactatgccaacagcttgcaacagccagttcactcagtcaataatgtcactcagtcaataaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtcactcagtctaagagacaaaatatgtccatgaccaccctt
```

FIG. 32 (Continued)

```
gagatgaactttatgccatgtgtttttggatgccactgagactttgctttgaccaaggaaagttctttactgcccaaatgacgtcaatggacactctc
atggacatgatgattttccatacagtcgattcttgttatccaccttgtttgaccaatggccaacagctgactcacacggaaagacgctcaatgaagagtgta
catcagggcaacctgctagtagagttgtaccccatctgactactctgaccattaaacactgcactgccactgcagagcactgccactcagtgaaatccaaactcagtgtttccaa
gcaggttgaaaacactgagttgagtgagtgaagaagttgggggtgttgttgcagtcagttaggccaagtgcagtttcctgcaccagtccaccagcaggcctcctaggtaggagggtcatctgattcctccattagg
tcccctgggtgcctctatggtcgtccacaggatcaagaaaatatcaggtgtgttaattccctctgcctgtgaggtgtttctagaactggacaaccgagggtgaaaggactggatcaagcaacaatg
gtggatgacgttatcagacatgtcaatgttctacagtacttgacctgctctgcaatgacagactgtctcagaacacctgtggatgagttgaggggatg
caatgggtgcccaaagagtagttgctcagaacagggagtagtctcagaacaggagatctcaatctgatctgctgtcatctgcttcgcttcatgtctgatgagtagttgggatg
cctgagatctggggtggatgggaggtgggcactgatctgtcaaactggctacacactgatctgtgcaccttgccatcaagcaaaccatct
gtaaggctcttccagccaacagatatatttgacaaaacactgtatctgtcactcagcaaagaaatagttcagaccctgaaactcattgcttgctgcatgaccatcttgtgaaagctactcacaccagttgtgag
ctaggtaagtaacactatacagaattggtatctcactaccctgaggatttggacctgctcacttctgtgtcagttgtgcagtcctcacaccagtgctgag
tctgtctttaaggaagctaacagtgttgtatcactaccctgaggatttggagccacagcttcagccctcaaagaatctctggaccctcacttatctgtgtcagttgtgaaagatcactaacagtgttcactaacaagtatatccggaa
gttaattgaatgttactcttttaatttctgcaaagaatgagacagcttcagccatcatttaggagagctgactcatcttgggctcaatctgtggctcaatacagtgttgggagcagaagacaggggttaaattctgtgg
gataaagttgtataagactcttcctttcaacctgatccatcatcgctgtggctcaatcttctgtggctcaatcgcctttctgcatgtcctcccaggccgagctgagcttggtccccgaagccgatggtgtgagggga
cagccttcaggggaggtagttctcaggggaggtctcaccctcagccgtctaccctcagacctcagaccgccaacgcctgttgcagtagccacagcgaagaaccatggaaactccaagtccctccccgaccaaaacgcctcgacgtccctcgaggta
cgtctctgcagctgcagagctgctcagtgctccatgcagtgcaatgtggcctcagtagggaccagaggaaccatggtgaaaaccccctcgttactgttcaactcttcaatataaagca
ctctgtgagaaagagctgctcagttagcaccagaggaaccatggtgaaaaccccctcgttacctgttcaactctcctgtcagtcggcaactctgctctcagttcttatttccaatctcagatacaccggagaaattg
acatggatggttttgcatgtcagtgaagaacaatggggtttgattttagattacacaagggaaaagaagagaccacctctctcgttcaggccagtcagattgttagccagcagttcagtggccagtggtc
tgttgacggcagtctcagaaacctggccaggcctccagcagtgaccaccatctcagacagactggagctgaactggttttcaggcacctatgtgagagatattttgcagtgtatattgaagttcttgagcatgtaattctctgtt
tggacagacttcactctccaccatcagccagcagctggagcctgagcccgagagatttgtctcactatttgccatggtctgatgccagtatggccagttgccagtattgactttgagttgaaaaaagatt
aagggaccaaggttgtaaagattggtaaatgagggcattgtaaaaactccaagaaactggtgggttgtcaaaaaaggtaaactgcagcttcaaaatgatggagaaagattgattggaaaagatt
gagtttgtgtctaaactgctaatgacacaagtgaaatgacacaaaatcaggtcatgaaaactccaagaaactggttgtcaaaaaagggaaaagcccttgtatttctaaggaaccccttgtatttctaaggagcaaaagtaaattttatttgtt
aaattgctctaaacattgtgtttgtctgcagcttgtgttgtctgattatgcatgatacagaaaatcaggggccccaagaaaatcaggggaaaagtgaagtgttgcatggccagggtcctcctcactctcctccctttttgtataaa
ttatttttgtcagacagcagcttcactctccaccaacagactaatcaataaaaatcagcacgccccaagaaaatcaggggaaaaatcagggaaaagtgaagtgtaccatttgctcatttgctatttgtagaaaggcagcttac
ttgaaaatcagcagcaatgttgttttagagtct
```

Amino acid sequence of common light chain VL encoded by human IGKV1-39/IGKJ4 (SEQ ID NO: 38)
DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTF
GGGTKVEIK Amino acid sequence of common light chain VL encoded by human IGKV3-11/IGKJ1 (SEQ ID NO: 39)

FIG. 32 (Continued)

EIVLTQSPATLSLSPGERATLSCRASQSVSSYLAWYQQKPGQAPRLLIYDASNRATGIPARFSGSGSGTDFTLTISSLEPEDFAVYYCQQRSNWPPTF
GQGTKVEIK

Amino acid sequence of common light chain VL encoded by human IGKV3-20/IGKJ1 (SEQ ID NO: 40)
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPWT
FGQGTKVEIK

Mouse kappa chain constant domain (SEQ ID NO: 41)
RADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPI
VKSFNRNEC

GENETICALLY MODIFIED NON-HUMAN ANIMALS WITH COMMON LIGHT CHAIN IMMUNOGLOBULIN LOCUS

CLAIM OF PRIORITY

Pursuant to 35 U.S.C. § 119(e), this application is a continuation of International Application PCT/CN2021/097652, with an international filing date of Jun. 1, 2021, which claims the benefit of PCT Application No. PCT/CN2020/094000, filed on Jun. 2, 2020, and PCT Application No. PCT/CN2021/085839, filed on Apr. 7, 2021. The entire contents of the foregoing are incorporated herein by reference.

SEQUENCE LISTING

This application contains a sequence listing that has been submitted electronically in XML format and is hereby incorporated by reference in its entirety. Said XML file is named 44835-0059001.xml. The xml file, created on Sep. 26, 2022, is 64,191 bytes in size.

TECHNICAL FIELD

This disclosure relates to genetically modified animals and cells with humanized light chain immunoglobulin locus and/or humanized heavy chain immunoglobulin locus.

BACKGROUND

Antibodies are immunological proteins that bind a specific antigen. Generally, antibodies are specific for targets, have the ability to mediate immune effector mechanisms, and have a long half-life in serum. Such properties make antibodies powerful therapeutics. Monoclonal antibodies are used therapeutically for the treatment of a variety of conditions including cancer, infectious disease, autoimmune disease, and inflammatory disorders. Many new antibody formats have been proposed for various treatment purposes. For example, bispecific antibodies can bind to two different targets or two different epitopes on a target, creating additive or synergistic effect superior to the effect of monoclonal antibodies. However, it is challenging to manufacture bispecific antibodies because of the mispairing problems.

In addition, these therapeutic antibodies are usually human or humanized antibodies. The human or humanized antibodies can be generated by humanization of a rodent antibody (e.g., a mouse antibody) or by using phage libraries. The antibodies that are generated by these methods often have suboptimal binding affinities and biophysical attributes, leading to difficulties in manufacture and poor pharmacokinetics. Particularly, the humanization process may adversely affect the binding affinity and introduce immunogenic epitopes to the antibodies, and antibodies discovered using phage libraries show limited diversity and non-native pairing of immunoglobulin heavy and light chains. Iterative and time-consuming experiments are often required to improve the properties. And in some cases, these antibodies can also be immunogenic in patients.

There is a need for efficient and cost-effective methods of producing humanized antibodies, and particularly a platform to generate humanized bispecific antibodies for various treatment purposes.

SUMMARY

The present disclosure relates to genetically modified animals and cells with humanized heavy chain and light chain immunoglobulin locus. In some embodiments, the genetically modified animals have a limited set of human IGKV and IGKJ genes at the endogenous light chain immunoglobulin gene locus. In one aspect, the genetic modified animals as described herein can produce immunoglobulin light chain variable domains that can pair with a rather diverse family of heavy chain variable domains, including e.g., affinity matured or somatically mutated variable domains.

In one aspect, the disclosure provides a genetically-modified, non-human animal comprising at the endogenous light chain immunoglobulin locus, an exogenous light chain variable region gene sequence. In some embodiments, the exogenous light chain variable region gene sequence comprises no more than three human IGKV genes and no more than two human IGKJ genes. In some embodiments, the no more than three human IGKV genes and the no more than two human IGKJ genes are operably linked to an endogenous light chain constant domain gene.

In some embodiments, the no more than three human IGKV genes are selected from Table 1, and the no more than two human IGKJ genes are selected from Table 2.

In some embodiments, the exogenous light chain variable region gene sequence comprises one human IGKV gene and one human IGKJ gene.

In some embodiments, the exogenous light chain variable region gene sequence further comprises a human IGKJ 3'-UTR sequence. In some embodiments, the exogenous light chain variable region gene in one or more cells of the animal can subject to somatic hypermutations.

In some embodiments, the somatic hypermutations can result in up to one, two, or three amino acid changes in light chain variable regions in the one or more cells of the animal.

In some embodiments, exogenous light chain variable region gene sequence comprises one human IGKV gene and one human IGKJ gene. In some embodiments, the human IGKV gene is selected from the group consisting of IGKV3-20, IGKV3-11, and IGKV1-39. In some embodiments, the human IGKV gene and the human IGKJ gene are operably linked. In some embodiments, the human IGKV gene is IGKV3-11. In some embodiments, the human IGKJ gene is selected from the group consisting of IGKJ1 and IGKJ4. In some embodiments, the human IGKV gene is IGKV1-39 and the human IGKJ gene is IGKJ4. In some embodiments, the human IGKV gene is IGKV3-11 and the human IGKJ gene is IGKJ1. In some embodiments, the human IGKV gene is IGKV3-20 and the human IGKJ gene is IGKJ1. In some embodiments, the animal further comprises a promoter sequence that is operably linked to the human IGKV gene. In some embodiments, the promoter sequence is within 2500 or 3000 bp of the human IGKV gene. In some embodiments, the promoter is an IGKV3-20 promoter, an IGKV3-11 promoter, or an IGKV1-39 promoter.

In some embodiments, the animal comprises a disruption in the animal's endogenous light chain immunoglobulin gene locus. In some embodiments, the animal is a mouse and the disruption in the animal's endogenous light chain immunoglobulin gene locus comprises a deletion of one or more mouse IGKV genes in Table 3 and one or more mouse IGKJ genes in Table 4. In some embodiments, the animal is a mouse and the disruption in the animal's endogenous light chain immunoglobulin gene locus comprises a deletion of a sequence starting from mouse IGKV2-137 to mouse IGKJ5.

In some embodiments, the animal comprises an endogenous IGKC. In some embodiments, the animal further comprises a kappa intronic enhancer 5' with respect to the endogenous IGKC and/or a kappa 3' enhancer.

In some embodiments, the human light chain variable region is a rearranged sequence.

In some embodiments, the animal is homozygous with respect to the light chain immunoglobulin gene locus. In some embodiments, the animal is heterozygous with respect to the light chain immunoglobulin gene locus. In some embodiments, the animal comprises a disruption in the animal's endogenous lambda light chain immunoglobulin gene locus.

In some embodiments, the animal is a rodent (e.g., a mouse).

In some embodiments, the animal further comprises at an endogenous heavy chain immunoglobulin gene locus, one or more human IGHV genes, one or more human IGHD genes, and one or more human IGHJ genes. In some embodiments, the human IGHV genes, the human IGHD genes, and the human IGHJ genes are operably linked and can undergo VDJ rearrangement.

In some embodiments, the animal comprises at least 150 human IGHV genes selected from Table 5, at least 20 human IGHD genes selected from Table 6, and at least 5 human IGHJ genes selected from Table 7. In some embodiments, the animal comprises all human IGHV genes, all human IGHD genes, and all human IGHJ genes at the endogenous heavy chain immunoglobulin gene locus of human chromosome 14 of a human subject. In some embodiments, the animal comprises all human IGHV genes, all human IGHD genes, and all human IGHJ genes at the endogenous heavy chain immunoglobulin gene locus of human chromosome 14 of a human cell. In some embodiments, the animal comprises an unmodified human sequence derived from a human heavy chain immunoglobulin gene locus. In some embodiments, the unmodified human sequence is at least 800 kb.

In some embodiments, the animal comprises an unmodified human sequence derived from a human heavy chain immunoglobulin gene locus starting from human IGHV(III)-82 to human IGHV1-2. In some embodiments, the animal comprises an unmodified human sequence derived from a human heavy chain immunoglobulin gene locus starting from human IGHV(III)-82 to human IGHV6-1. In some embodiments, the animal comprises an unmodified human sequence derived from a human heavy chain immunoglobulin gene locus starting from human IGHD1-1 to human IGHJ6. In some embodiments, the animal comprises an unmodified human sequence derived from a human heavy chain immunoglobulin gene locus starting from human IGHV(III)-82 to human IGHJ6. In some embodiments, the animal comprises IGHV(III)-82, IGHV7-81, IGHV4-80, IGHV3-79, IGHV(II)-78-1, IGHV5-78, IGHV7-77, IGHV(III)-76-1, IGHV3-76, IGHV3-75, and IGHV(II)-74-1. In some embodiments, the animal comprises IGHV5-10-1 and IGHV3-64D.

In some embodiments, the animal further comprises at an endogenous heavy chain immunoglobulin gene locus, a first sequence comprising one or more human IGHV genes; a second sequence comprising an endogenous sequence; and a third sequence comprising one or more human IGHD genes, and one or more human IGHJ genes. In some embodiments, the first sequence, the second sequence, and the third sequence are operably linked.

In some embodiments, the first sequence comprises at least 150 human IGHV genes selected from Table 5. In some embodiments, the first sequence comprises at least 20 human IGHD genes selected from Table 6. In some embodiments, the first sequence is an unmodified sequence derived from a human heavy chain immunoglobulin gene locus. In some embodiments, the first sequence is at least 800 kb. In some embodiments, the second sequence comprises an endogenous sequence that is at least 3 kb. In some embodiments, the third sequence comprises at least 20 human IGHD genes selected from Table 6, and at least 5 human IGHJ genes selected from Table 7.

In some embodiments, the third sequence comprises all human IGHD genes in Table 6, and all human IGHJ genes in Table 7. In some embodiments, the third sequence is an unmodified sequence derived from a human heavy chain immunoglobulin gene locus. In some embodiments, the third sequence is at least 50 kb. In some embodiments, the animal comprises a disruption in the animal's endogenous heavy chain immunoglobulin gene locus.

In some embodiments, the animal is a mouse and the disruption in the animal's endogenous heavy chain immunoglobulin gene locus comprises a deletion of one or more mouse IGHV genes in Table 8, one or more mouse IGHD genes in Table 9, and one or more mouse IGHJ genes in Table 10. In some embodiments, the animal is a mouse and the disruption in the animal's endogenous heavy chain immunoglobulin gene locus comprises a deletion of a sequence starting from mouse IGHV1-85 to mouse IGHJ4. In some embodiments, the animal comprises one or more endogenous IGHM, IGHδ, IGHG3, IGHG1, IGHG2b, IGHG2a, IGHE, and IGHA genes.

In some embodiments, the animal is homozygous with respect to the heavy chain immunoglobulin gene locus. In some embodiments, the animal is heterozygous with respect to the heavy chain immunoglobulin gene locus.

In one aspect, the disclosure provides a genetically-modified, non-human animal whose genome comprises an endogenous light chain immunoglobulin locus comprising: a replacement of one or more endogenous IGKV with one or more human IGKV genes selected from Table 1; and a replacement of one or more endogenous IGKJ genes with one or more human IGKJ genes selected from Table 2. In some embodiments, the human IGKV gene and the human IGKJ gene are operably linked to an endogenous IGKC gene.

In some embodiments, the one or more human IGKV genes are selected from the group consisting of IGKV3-20, IGKV3-11, and IGKV1-39. In some embodiments, the human IGKV gene is IGKV3-11. In some embodiments, the one or more human IGKJ genes are selected from the group consisting of IGKJ1 and IGKJ4. In some embodiments, the animal further comprises an insertion of a human IGKJ 3'-UTR sequence. In some embodiments, the human IGKV gene is IGKV1-39 and the human IGKJ gene is IGKJ4. In some embodiments, the human IGKV gene is IGKV3-11 and the human IGKJ gene is IGKJ1. In some embodiments, the human IGKV gene is IGKV3-20 and the human IGKJ gene is IGKJ1. In some embodiments, all endogenous IGKV genes are replaced by the one or more human IGKV genes. In some embodiments, all endogenous IGKJ genes are replaced by the one or more human IGKJ genes.

In some embodiments, the animal further comprises a promoter sequence before the human IGKV gene. In some embodiments, the promoter sequence is within 3000 bp of the human IGKV gene. In some embodiments, the animal further comprises a kappa intronic enhancer at the 5' of the endogenous IGKC. In some embodiments, the animal further comprises a kappa 3' enhancer.

In some embodiments, the genome of the animal further comprises an endogenous heavy chain immunoglobulin locus comprising: a replacement of one or more endogenous IGHV, endogenous IGHD, and endogenous IGHJ genes with one or more human IGHV, human IGHD, and human IGHJ genes. In some embodiments, the one or more human IGHV, human IGHD, and human IGHJ genes are operably linked to one or more of endogenous IGHM, IGHδ, IGHG, IGHE, and IGHA genes. In some embodiments, the one or more endogenous IGHV, endogenous IGHD, and endogenous IGHJ genes are replaced by at least 150 human IGHV genes in Table 5, at least 20 human IGHD genes in Table 6, and at least 5 human IGHJ genes in Table 7.

In some embodiments, the animal is a mouse, and at least 180 mouse IGHV genes in Table 8, all mouse IGHD genes in Table 9, and all mouse IGHJ genes in Table 10 are replaced.

In some embodiments, the animal lacks an endogenous immunoglobulin heavy chain variable region locus that is capable of rearranging and forming a nucleic acid sequence that encodes an endogenous heavy chain variable domain (e.g., a mouse heavy chain variable domain). In some embodiments, the animal lacks an endogenous immunoglobulin light chain variable region locus that is capable of rearranging and forming a nucleic acid sequence that encodes an endogenous light chain variable domain (e.g., a mouse light chain variable domain).

In some embodiments, the animal can produce a humanized antibody. In some embodiments, the antibody comprises a light chain variable region encoded by the IGKV gene and IGKJ gene.

In one aspect, the disclosure provides a cell obtained from the animal as described herein. In some embodiments, the cell is a B cell that expresses a chimeric immunoglobulin light chain comprising an immunoglobulin light chain variable domain that is encoded by a human IGKV gene selected from the group consisting of IGKV3-20, IGKV3-11, and IGKV1-39, and a human IGKJ gene selected from the group consisting of IGKJ1 and IGKJ4. In some embodiments, the immunoglobulin light chain variable domain is operably linked to a non-human light chain constant region.

In some embodiments, the B cell that expresses a chimeric immunoglobulin heavy chain comprising an immunoglobulin heavy chain variable domain that is derived from a rearrangement of one or more human IGHV genes, one or more human IGHD genes, and one or more human IGHJ genes. In some embodiments, the immunoglobulin heavy chain variable domain is operably linked to a non-human heavy chain constant region.

In some embodiments, the cell is an embryonic stem (ES) cell.

In one aspect, the disclosure provides a method of making a chimeric antibody that specifically binds to an antigen, the method comprising exposing the animal as described herein to the antigen; producing a hybridoma from a cell collected from the animal; and collecting the chimeric antibody produced by the hybridoma.

In some embodiments, the method further comprises sequencing the genome of the hybridoma.

In one aspect, the disclosure provides a method of making an antibody that specifically binds to an antigen, the method comprising exposing the animal as described herein to the antigen; sequencing nucleic acids encoding human heavy and light chain immunoglobulin variable regions in a cell that expresses a hybrid antibody that specifically binds to the antigen; and operably linking in a cell the nucleic acid encoding the human heavy chain immunoglobulin variable region with a nucleic acid encoding a human heavy chain immunoglobulin constant region and the nucleic acid encoding the human light chain immunoglobulin variable region with a nucleic acid encoding a human light chain immunoglobulin constant region.

In one aspect, the disclosure provides a method of making an antibody that specifically binds to an antigen, the method comprising obtaining a nucleic acid sequence encoding human heavy and light chain immunoglobulin variable regions in a cell that expresses a hybrid antibody that specifically binds to the antigen, wherein the cell is obtained by exposing the animal as described herein to the antigen; operably linking the nucleic acid encoding the human heavy chain immunoglobulin variable region with a nucleic acid encoding a human heavy chain immunoglobulin constant region and the nucleic acid encoding the human light chain immunoglobulin variable region with a nucleic acid encoding a human light chain immunoglobulin constant region; and expressing the nucleic acid in a cell, thereby obtaining the antibody.

In one aspect, the disclosure provides a method of obtaining a nucleic acid that encodes an antibody binding domain that specifically binds to an antigen, the method comprising exposing the animal as described herein to the antigen; and sequencing nucleic acids encoding human heavy and light chain immunoglobulin variable regions in a cell that expresses a hybrid antibody that specifically binds to the antigen.

In one aspect, the disclosure provides a method of obtaining a sample, the method comprising exposing the animal as described herein to the antigen; and collecting the sample from the animal. In some embodiments, the sample is a spleen tissue, a spleen cell, or a B cell.

In one aspect, the disclosure provides a method of making a bispecific antibody, the method comprising expressing in a cell a nucleic acid sequence encoding a light chain polypeptide comprising a human VL, a nucleic acid sequence encoding a first heavy chain polypeptide comprising a first human VH, and a nucleic acid sequence encoding a second heavy chain polypeptide comprising a second human VH, wherein the sequence encoding the first VH is obtained from the animal as described herein after being exposed to a first antigen, and the sequence encoding the second VH is obtained from the animal or a different animal after being exposed to a second antigen.

In some embodiments, the first VH and the VL forms a first antigen-binding site that specifically binds to the first antigen. In some embodiments, the second VH and the VL forms a second antigen-binding site that specifically binds to the second antigen.

In one aspect, the disclosure provides an antibody or antigen binding fragment thereof comprising a human light chain variable region that has a sequence that is at least 90%, 95%, or 98% identical to SEQ ID NO: 38, 39, or 40.

In one aspect, the disclosure provides a plurality of antibodies or antigen binding fragments thereof, wherein each antibody or antigen binding fragment thereof comprises a human light chain variable region that has a sequence that is at least 90%, 95%, or 98% identical to SEQ ID NO: 38, 39, or 40.

In one aspect, the disclosure provides a method of making an antibody that specifically binds to a protein of interest, the method comprising exposing the animal as described herein to the protein of interest, wherein the animal does not express an endogenous protein that is homologous to the protein of interest; and sequencing nucleic acids encoding human heavy and light chain immunoglobulin variable regions in a cell that expresses an antibody that specifically binds to the protein of interest.

In some embodiments, a gene encoding the endogenous protein is disrupted in the animal. In some embodiments, the gene encoding the endogenous protein is knocked out.

In some embodiments, the endogenous protein is at least 80%, 90%, 95% homologous to the protein of interest. In some embodiments, the endogenous protein is at least 80%, 90%, or 95% identical to the protein of interest.

In some embodiments, the protein of interest is a human protein. In some embodiments, the protein of interest is PD-1, CTLA-4, LAG-3, BTLA, PD-L1, CD27, CD28, CD47, CD137, CD154, TIGIT, TIM-3, GITR, SIRPa, or OX40.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 15 shows a list of human distal Vκ cluster IGKV genes and a list of human proximal Vκ cluster IGKV genes.

FIG. 20 lists IMGT repertoire for human heavy chain immunoglobulin locus (IGH).

FIG. 21 lists IMGT repertoire for mouse IGH.

FIG. 22 lists IMGT repertoire for human kappa chain immunoglobulin locus (IGK).

FIG. 23 lists IMGT repertoire for mouse IGK.

FIG. 26F shows IGHV usage (frequency <1%) in naïve hVH$^{H/H}$/hcVL$^{K/K}$ mice.

FIG. 32 lists sequences that are described in the present disclosure.

DETAILED DESCRIPTION

Figure 1A:
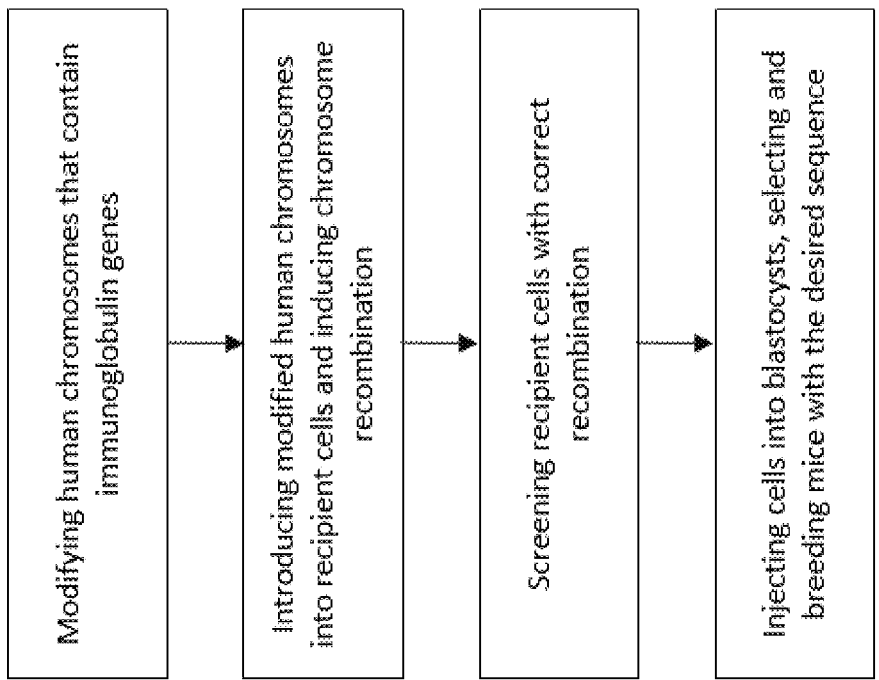
FIG. 1A is a flow chart of a method of introducing human immunoglobulin genes into the mouse genome.

A monoclonal antibody typically comprises two heavy chains, wherein each heavy chain monomer is associated with an identical light chain. Due to the target specificity of monoclonal antibodies, the monoclonal antibodies can usually bind to a single target. However, in drug development, there is a need for antibodies that can bind two different antigens or epitopes. For example, CD3-specific antibody has been commonly paired with various tumor-associated-antigen-specific antibodies to generate bispecific antibodies for treating cancers. The ability of bispecific antibodies to bind two different antigens or epitopes provide a wide range of clinical applications. To date, at least two bispecific antibodies are marketed and a large number of bispecific antibodies are in clinical trials.

A bispecific antibody usually has two different heavy chains and two different light chains. It is challenging to produce them in a single host cell because the random pairing of the two heavy and two light chains results in the expression of 10 different IgG species with only one being the format of interest. Knobs-into-holes has been proposed to modify heavy chains. Some other modifications have also been proposed for light chains. However, these additional modifications may adversely affect biochemical and/or biophysical properties, serum half-life, and/or stability, resulting in poor efficacy, instability and high immunogenicity. There is a need for methods of making bispecific antibodies that do not rely extensively on antibody engineering.

The present disclosure relates to genetically modified animals and cells with humanized light chain immunoglobulin locus (e.g., kappa chain locus) and/or humanized heavy chain immunoglobulin locus. In one aspect, the humanized light chain immunoglobulin locus has a limited set of IGKV genes and IGKJ genes. The genetically engineered animal, through the long and complex process of antibody selection within an organism, makes biologically appropriate choices in pairing a diverse collection of human heavy chain variable domains with a limited number of human light chain variable domain options. The animal is engineered to present a limited number of human light chain variable domain options in conjunction with a wide diversity of human heavy chain variable domain options. Upon challenge with an immunogen, the animal develops an antibody to the immunogen, limited largely or solely by the number of light chain options in its repertoire.

In various embodiments, antibodies produced in the genetically modified animal have heavy chains that can associate with identical or substantially identical light chains. This is particularly useful in making bispecific antibodies. For example, such an animal can be immunized with a first antigen to generate a B cell that expresses an antibody that specifically binds to the first antigen. The animal (or an animal with the same modification) can be immunized with a second antigen to generate a B cell that expresses an antibody that specifically binds the second antigen. VHs can be cloned from the first B cell and the second B cell. The two VHs can be paired with the same light chain VL to make a bispecific antibody. Thus, there is no need to associate a light chain with a particular heavy chain by antibody engineering (e.g., introducing modifications to the sequences). This can greatly increase the success rate of bispecific antibody development. In fact, the antibodies or sequences as described herein can be further combined with each other to make multi-specific antibodies.

To achieve a limited repertoire of light chain variable domain options, the animal is engineered to limit its ability to generate animal light chain variable domains with native diversity. The endogenous animal locus can then be modified by an exogenous suitable human light chain variable region gene sequence of choice, operably linked to the endogenous animal light chain constant domain, in a manner such that the rearranged exogenous human variable region gene sequence can encode a rearranged chimeric light chain (human variable, endogenous constant), or the unrearranged exogenous human variable region gene sequences with limited diversity can rearrange and recombine to encode a rearranged chimeric light chain.

The genetically modified animals described herein can have some additional advantages. For example, in some cases, the genetically modified animals described herein have complete human heavy chain variable region genes and rearranged human light chain variable region genes (e.g., human IGKV1-39/IGKJ4). Furthermore, because the entire heavy chain variable region at the human immunoglobulin locus are introduced into the animal genome (with no modifications or limited modifications), these genes can undergo the VDJ recombination in a way that is very similar to what happens in human. In addition, the antibody production can be very efficient and has a rate that is similar to the normal rates due to the efficient VDJ recombination.

As used herein, the term "antibody" refers to an immunoglobulin molecule comprising four polypeptide chains, two heavy (H) chains and two light (L) chains inter-connected by disulfide bonds. Each heavy chain comprises a heavy chain variable (VH) domain and a heavy chain constant region (CH). Each light chain comprises a light chain variable (VL) domain and a light chain constant region (CL). The VH and VL domains can be further subdivided into regions of hypervariability, termed complementarity determining regions (CDR), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-8}$ M or lower (e.g., about or lower than $1\times10^{-8}$ M, $1\times10^{-9}$ M, $1\times10^{-10}$ M, or $1\times10^{-11}$ M). In some embodiments, $K_D$ can be measured by surface plasmon resonance, e.g., BIACORE™ or ELISA.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')2, and Fv fragments.

As used herein, the term "human antibody" refers to an antibody that is encoded by a nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a mouse) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a human antibody and the constant domains of a non-human antibody. Additional examples of chimeric antibodies are described herein and are known in the art.

As used herein, the term "humanized antibody" refers to a non-human antibody which contains sequence derived from a non-human (e.g., mouse) immunoglobulin and contains sequences derived from a human immunoglobulin.

As used herein, the terms "subject" and "patient" are used interchangeably throughout the specification and describe an animal, human or non-human. Veterinary and non-veterinary applications are contemplated by the present disclosure. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

As used herein, the term "an unmodified human sequence" refers to a sequence that is derived from a human subject, a human cell, a cultured human cell or a human cell line, wherein the sequence is identical to the genetic sequence of a human subject, a human cell, a cultured human cell or a human cell line.

As used herein, the term "bispecific antibody" includes an antibody capable of selectively binding two or more epitopes. Bispecific antibodies generally comprise two non-identical heavy chains, with each heavy chain specifically binding a different epitope—either on two different molecules (e.g., different epitopes on two different immunogens) or on the same molecule (e.g., different epitopes on the same immunogen). Epitopes specifically bound by the bispecific antibody can be on the same or a different target (e.g., on the same or a different protein). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding or one or both of the heavy chains to one or both epitopes.

As used herein, the term "common light chain antibody" refers to an antibody having two or more than two identical light chains. In some embodiments, a common light chain antibody is a common light chain bispecific antibody.

Restricted Kappa Light Chain Immunoglobulin Locus

Kappa chain immunoglobulin locus (also known as IGK or immunoglobulin kappa locus) is a region on the chromosome (e.g., human chromosome 2) that contains genes for the light chains of human antibodies (or immunoglobulins). Similarly, the immunoglobulin light chain genes can also undergo a series rearrangement that lead to the production of a mature immunoglobulin light-chain nucleic acid (e.g., a kappa chain).

The joining of a V segment (also known as an IGKV gene) and a J segment (also known as an IGKJ gene) creates a continuous exon that encodes the whole of the light-chain variable domain. In the unrearranged DNA, the V gene segments (or IGKV gene cluster) are located relatively far away from the C region. The J gene segments (or IGKJ gene cluster) are located close to the C region. Joining of a V segment to a J gene segment also brings the V gene close to a C-region sequence. The J gene segment of the rearranged V region is separated from a C-region sequence only by an intron. To make a complete immunoglobulin light-chain messenger RNA, the V-region exon is joined to the C-region sequence by RNA splicing after transcription.

The human light chain immunoglobulin locus is located on human chromosome 2. Table 1 lists IGKV genes and its relative orders in this locus. There are several different groups for human IGKV genes, including IGKV1 genes (including all IGKV genes starting with IGKV1, also known as VκI), IGKV2 genes (including all IGKV genes starting with IGKV2, also known as VκII), IGKV3 genes (including all IGKV genes starting with IGKV3, also known as VκIII), IGKV4 genes (including all IGKV genes starting with IGKV4, also known as VκIV), IGKV5 genes (including all IGKV genes starting with IGKV5, also known as VκV), IGKV6 genes (including all IGKV genes starting with IGKV6, also known as VκVI), and IGKV7 genes (including all IGKV genes starting with IGKV7, also known as VκVII).

Figure 14:
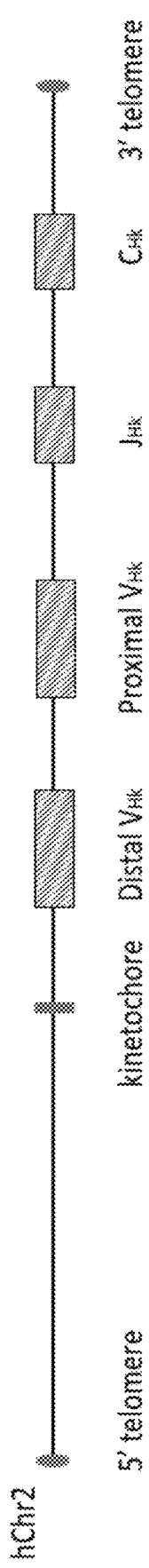
FIG. 14 is a schematic diagram of the human chromosome 2 highlighting the light chain immunoglobulin locus (not drawn to scale). $V_{HK}$ represents the segment for the IGKV gene cluster, $J_{HK}$ represents the segment for the IGKJ gene cluster, and $C_{HK}$ represents the IGKC gene.

These IGKV genes in human chromosome 2 also form two clusters, the proximal Vκ cluster and the distal Vκ cluster (FIG. 14). The sequences in the two clusters are similar but are not identical. This large segmental duplication of the sequence occurred since the divergence of the human lineage from the most recent shared ancestor with other great apes. The relevant IGKV genes in each cluster is summarized in FIG. 15.

TABLE 2

List of IGKV genes on human chromosome 2

| Gene names | Order |
| --- | --- |
| IGKV3D-7 | 1 |
| IGKV1D-8 | 2 |
| IGKV1D-43 | 3 |
| IGKV1D-42 | 4 |
| IGKV2D-10 | 5 |
| IGKV3D-11 | 6 |
| IGKV1D-12 | 7 |
| IGKV1D-13 | 8 |
| IGKV2D-14 | 9 |
| IGKV3D-15 | 10 |
| IGKV1D-16 | 11 |
| IGKV1D-17 | 12 |
| IGKV6D-41 | 13 |
| IGKV2D-18 | 14 |
| IGKV2D-19 | 15 |

TABLE 2-continued

List of IGKV genes on human chromosome 2

| Gene names | Order |
| --- | --- |
| IGKV3D-20 | 16 |
| IGKV6D-21 | 17 |
| IGKV1D-22 | 18 |
| IGKV2D-23 | 19 |
| IGKV2D-24 | 20 |
| IGKV3D-25 | 21 |
| IGKV2D-26 | 22 |
| IGKV1D-27 | 23 |
| IGKV2D-28 | 24 |
| IGKV2D-29 | 25 |
| IGKV2D-30 | 26 |
| IGKV3D-31 | 27 |
| IGKV1D-32 | 28 |
| IGKV1D-33 | 29 |
| IGKV3D-34 | 30 |
| IGKV1D-35 | 31 |
| IGKV2D-36 | 32 |
| IGKV1D-37 | 33 |
| IGKV2D-38 | 34 |
| IGKV1D-39 | 35 |
| IGKV2D-40 | 36 |
| IGKV2-40 | 37 |
| IGKV1-39 | 38 |
| IGKV2-38 | 39 |
| IGKV1-37 | 40 |
| IGKV2-36 | 41 |
| IGKV1-35 | 42 |
| IGKV3-34 | 43 |
| IGKV1-33 | 44 |
| IGKV1-32 | 45 |
| IGKV3-31 | 46 |
| IGKV2-30 | 47 |
| IGKV2-29 | 48 |
| IGKV2-28 | 49 |
| IGKV1-27 | 50 |
| IGKV2-26 | 51 |
| IGKV3-25 | 52 |
| IGKV2-24 | 53 |
| IGKV2-23 | 54 |
| IGKV1-22 | 55 |
| IGKV6-21 | 56 |
| IGKV3-20 | 57 |
| IGKV2-19 | 58 |
| IGKV2-18 | 59 |
| IGKV1-17 | 60 |
| IGKV1-16 | 61 |
| IGKV3-15 | 62 |
| IGKV2-14 | 63 |
| IGKV1-13 | 64 |
| IGKV1-12 | 65 |
| IGKV3-11 | 66 |
| IGKV2-10 | 67 |
| IGKV1-9 | 68 |
| IGKV1-8 | 69 |
| IGKV3-7 | 70 |
| IGKV1-6 | 71 |
| IGKV1-5 | 72 |
| IGKV2-4 | 73 |
| IGKV7-3 | 74 |
| IGKV5-2 | 75 |
| IGKV4-1 | 76 |

Figure 18:
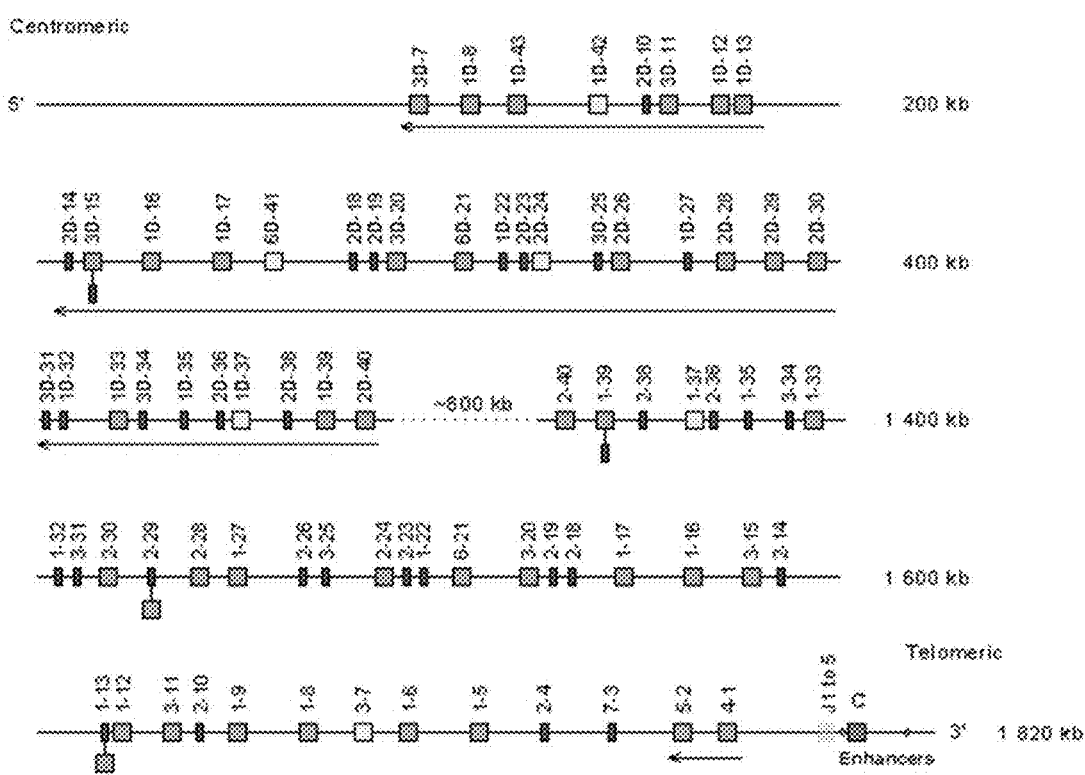
FIG. 18 is a schematic diagram showing human immunoglobulin kappa chain (IGK) locus on chromosome 2 (2p11.2).

Table 2 lists all IGKJ genes and its relative orders on human chromosome 2. The immunoglobulin kappa constant (IGKC) gene, which encodes the light chain immunoglobulin constant domains is located after the IGKV and IGKJ genes. These genes and the order of these genes are also shown in FIG. 18 and FIG. 22.

TABLE 2

List of IGKJ genes on human chromosome 2

| Gene names | Order |
| --- | --- |
| IGKJ1 | 77 |
| IGKJ2 | 78 |
| IGKJ3 | 79 |
| IGKJ4 | 80 |
| IGKJ5 | 81 |

The mouse light chain immunoglobulin locus is located on mouse chromosome 6. Table 3 lists IGKV genes and its relative orders in this locus.

TABLE 3

List of IGKV genes on mouse chromosome 6

| Gene names | Order |
| --- | --- |
| IGKV2-137 | 1 |
| IGKV1-136 | 2 |
| IGKV1-135 | 3 |
| | * |
| IGKV14-134-1 | 5 |
| IGKV17-134 | 6 |
| IGKV1-133 | 7 |
| IGKV1-132 | 8 |
| IGKV1-131 | 9 |
| IGKV14-130 | 10 |
| IGKV9-129 | 11 |
| IGKV9-128 | 12 |
| IGKV17-127 | 13 |
| IGKV14-126-1 | 14 |
| IGKV14-126 | 15 |
| IGKV11-125 | 16 |
| IGKV9-124 | 17 |
| IGKV9-123 | 18 |
| IGKV1-122 | 19 |
| IGKV17-121 | 20 |
| IGKV9-120 | 21 |
| IGKV9-119 | 22 |
| IGKV14-118-2 | 23 |
| IGKV14-118-1 | 24 |
| IGKV11-118 | 25 |
| IGKV1-117 | 26 |
| IGKV2-116 | 27 |
| IGKV1-115 | 28 |
| IGKV11-114 | 29 |
| IGKV2-113 | 30 |
| IGKV2-112 | 31 |
| IGKV14-111 | 32 |
| IGKV1-110 | 33 |
| IGKV2-109 | 34 |
| IGKV1-108 | 35 |
| IGKV2-107 | 36 |
| IGKV11-106 | 37 |
| IGKV2-105 | 38 |
| IGKV16-104 | 39 |
| IGKV15-103 | 40 |
| IGKV15-102 | 41 |
| IGKV20-101-2 | 42 |
| IGKV15-101-1 | 43 |
| IGKV15-101 | 44 |
| IGKV 14-100 | 45 |
| IGKV1-99 | 46 |
| IGKV12-98 | 47 |
| IGKV15-97 | 48 |
| IGKV10-96 | 49 |
| IGKV2-95-2 | 50 |
| IGKV2-95-1 | 51 |
| IGKV10-95 | 52 |
| IGKV10-94 | 53 |
| IGKV2-93-1 | 54 |
| IGKV19-93 | 55 |
| IGKV4-92 | 56 |
| IGKV4-91 | 57 |
| IGKV4-90 | 58 |

TABLE 3-continued

List of IGKV genes on mouse chromosome 6

| Gene names | Order |
|---|---|
| IGKV13-89-1 | 59 |
| IGKV12-89 | 60 |
| IGKV1-88 | 61 |
| IGKV13-87 | 62 |
| IGKV4-86 | 63 |
| IGKV13-85 | 64 |
| IGKV13-84 | 65 |
| IGKV4-83 | 66 |
| IGKV13-82 | 67 |
| IGKV4-81 | 68 |
| IGKV13-80-1 | 69 |
| IGKV4-80 | 70 |
| IGKV4-79 | 71 |
| IGKV13-78-1 | 72 |
| IGKV4-78 | 73 |
| IGKV4-77 | 74 |
| IGKV13-76 | 75 |
| IGKV4-75 | 76 |
| IGKV13-74-1 | 77 |
| IGKV4-74 | 78 |
| IGKV13-73-1 | 79 |
| IGKV4-73 | 80 |
| IGKV4-72 | 81 |
| IGKV13-71-1 | 82 |
| IGKV4-71 | 83 |
| IGKV4-70 | 84 |
| IGKV4-69 | 85 |
| IGKV4-68 | 86 |
| IGKV12-67 | 87 |
| IGKV12-66 | 88 |
| IGKV4-65 | 89 |
| IGKV13-64 | 90 |
| IGKV4-63 | 91 |
| IGKV13-62-1 | 92 |
| IGKV4-62 | 93 |
| IGKV13-61-1 | 94 |
| IGKV4-61 | 95 |
| IGKV4-59 | 96 |
| IGKV4-60 | 97 |
| IGKV4-58 | 98 |
| IGKV13-57-2 | 99 |
| IGKV4-57-1 | 100 |
| IGKV13-57-1 | 101 |
| IGKV4-57 | 102 |
| IGKV13-56-1 | 103 |
| IGKV4-56 | 104 |
| IGKV13-55-1 | 105 |
| IGKV4-55 | 106 |
| IGKV13-54-1 | 107 |
| IGKV4-54 | 108 |
| IGKV4-53 | 109 |
| IGKV4-52 | 110 |
| IGKV4-51 | 111 |
| IGKV4-50 | 112 |
| IGKV12-49 | 113 |
| IGKV5-48 | 114 |
| IGKV12-47 | 115 |
| IGKV12-46 | 116 |
| IGKV5-45 | 117 |
| IGKV12-44 | 118 |
| IGKV5-43 | 119 |
| IGKV12-42 | 120 |
| IGKV12-41 | 121 |
| IGKV5-40-1 | 122 |
| IGKV12-40 | 123 |
| IGKV5-39 | 124 |
| IGKV12-38 | 125 |
| IGKV5-37 | 126 |
| IGKV18-36 | 127 |
| IGKV1-35 | 128 |
| IGKV8-34 | 129 |
| IGKV7-33 | 130 |
| IGKV6-32 | 131 |
| IGKV8-31 | 132 |
| IGKV8-30 | 133 |
| IGKV6-29 | 135 |
| IGKV8-28 | 136 |
| IGKV8-27 | 137 |
| IGKV8-26 | 138 |
| IGKV6-25 | 139 |
| IGKV8-24 | 140 |
| IGKV8-23-1 | 141 |
| IGKV6-23 | 142 |
| IGKV8-22 | 143 |
| IGKV8-21 | 144 |
| IGKV6-20 | 145 |
| IGKV8-19 | 146 |
| IGKV8-18 | 147 |
| IGKV6-17 | 148 |
| IGKV8-16 | 149 |
| IGKV6-15 | 150 |
| IGKV6-14 | 151 |
| IGKV6-13 | 152 |
| IGKV3-12-1 | 153 |
| IGKV3-12 | 154 |
| IGKV3-11 | 155 |
| IGKV3-10 | 156 |
| IGKV3-9 | 157 |
| IGKV3-8 | 158 |
| IGKV3-7 | 159 |
| IGKV3-6 | 160 |
| IGKV3-5 | 161 |
| IGKV3-4 | 162 |
| IGKV3-3 | 163 |
| IGKV3-2 | 164 |
| IGKV3-1 | 165 |

Figure 19:
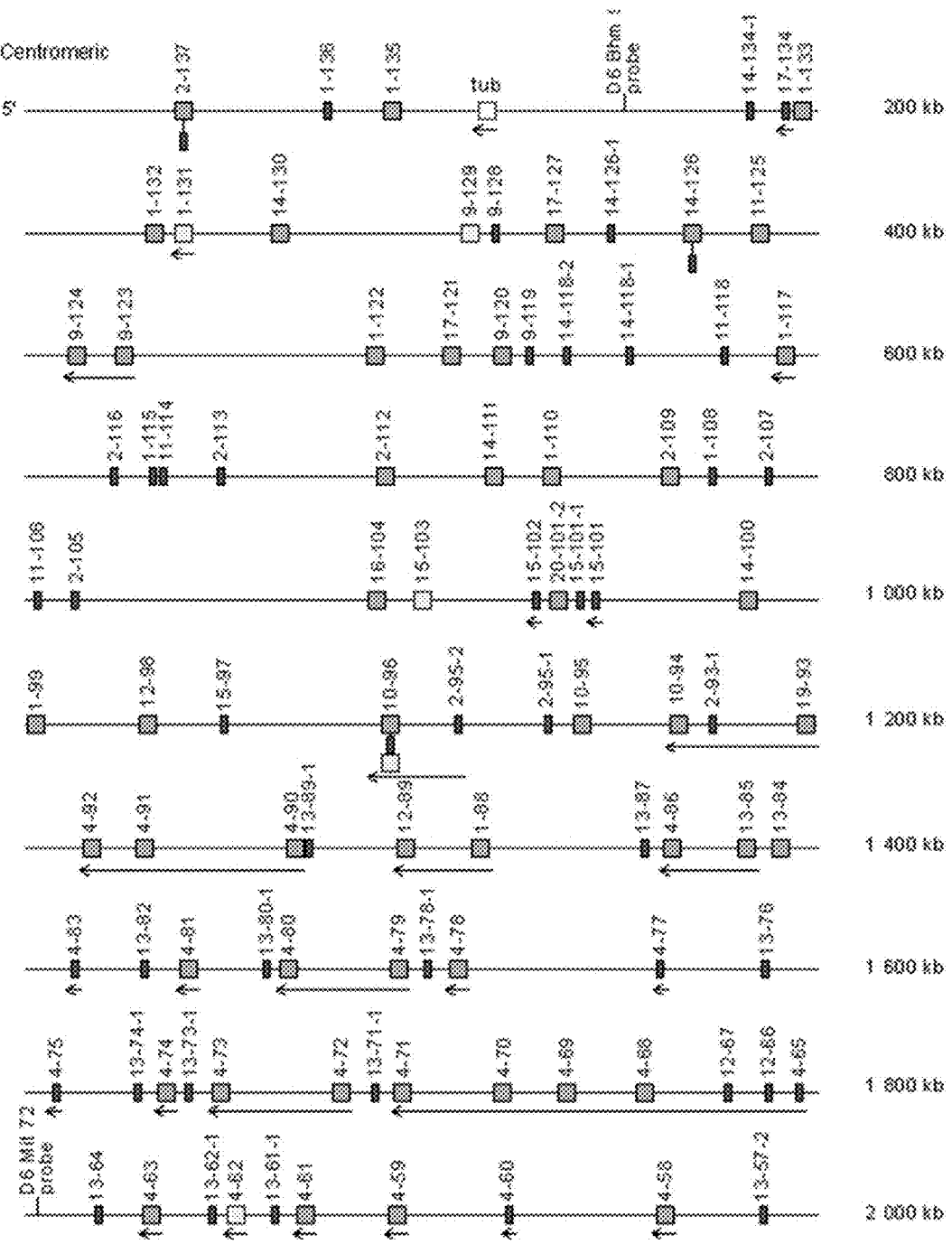
FIG. 19 is a schematic diagram showing mouse (*Mus musculus*) IGK locus on chromosome 6 (6C1).
Figure 19:
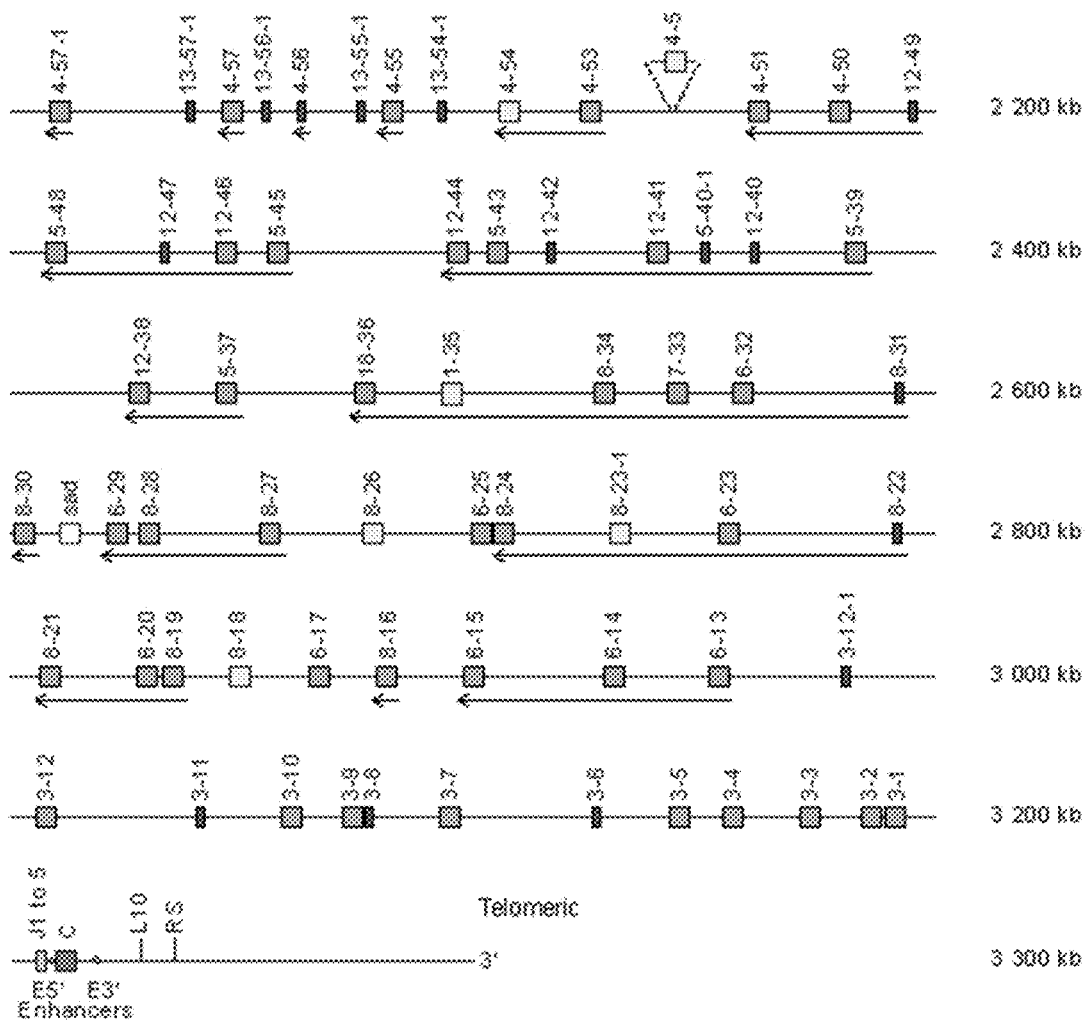

Gm9728 and Amd-ps2 are also located in this locus. The relative order of Gm9728 is 4, and the relative order of Amd-ps2 is 134. Table 4 lists all IGKJ genes and its relative orders on mouse chromosome 6. The IGKC gene, which encodes the light chain immunoglobulin constant domains are after the IGKV and IGKJ genes. These genes and the order of these genes are also shown in FIG. 19 and FIG. 23.

TABLE 4

List of IGKJ genes on mouse chromosome 6

| Gene names | Order |
|---|---|
| IGKJ1 | 166 |
| IGKJ2 | 167 |
| IGKJ3 | 168 |
| IGKJ4 | 169 |
| IGKJ5 | 170 |

The present disclosure provides a genetically-modified, non-human animal comprising one, two, three, or no more than three human IGKV genes and one, two, three, or no more than three human IGKJ genes. In some embodiments, the human IGKV gene and the human IGKJ gene are at endogenous light chain immunoglobulin gene locus. In some embodiments, the human IGKV gene and the human IGKJ gene are rearranged sequences. In some embodiments, they are unarranged sequences.

In some embodiments, the human IGKV genes are selected from any one of the IGKV genes in Table 1. In some embodiments, the human IGKJ genes are selected from any one of the IGKJ genes in Table 2.

In some embodiments, the animal only comprises one human IGKV gene and one human IGKJ gene. In some embodiments, the IGKV gene is selected from any one of the IGKV genes in Table 1. In some embodiments, the IGKJ gene is selected from any one of the IGKJ genes in Table 2.

In some embodiments, the animal comprises a human IGKV gene that is selected from IGKV3-20, IGKV1-39, IGKV1D-39, IGKV3-11, IGKV3-15, and IGKV4-1. In some embodiments, the animal comprises a human IGKJ gene that is selected from IGKJ1, IGKJ2, and IGKJ4.

In some embodiments, the animal comprises a human IGKV gene is selected from IGKV3-20, IGKV3-11, IGKV3-15, IGKV1-39, IGKV1D-39, and IGKV1-12, IGKV1D-12. In some embodiments, the animal comprises a human IGKJ gene that is selected from IGKJ1, IGKJ4, and IGKJ2.

In some embodiments, the animal comprises a human IGKV gene that is selected from IGKV3-20, IGKV3-11, and IGKV1-39. In some embodiments, the animal comprises a human IGKJ gene that is selected from IGKJ1, and IGKJ4.

In some embodiments, the animal comprises a promoter sequence before the first nucleotide of the human IGKV gene. In some embodiments, the promoter sequence is within or about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, or 5000 bp before the human IGKV gene. In some embodiments, the promoter is a human IGKV3-20 promoter, a human IGKV1-39 promoter, or a human IGKV3-11 promoter. In some embodiments, the promoter sequence is at least 80%, 85%, 90%, 95%, 96%, 97%, 98%, 99%, or 100% identical to nucleotides 1-2000 of SEQ ID NO: 35, nucleotides 1-2000 of SEQ ID NO: 36, or nucleotides 1-2000 of SEQ ID NO: 37.

In some embodiments, the animal comprises an auxiliary sequence after the last nucleotide of the human IGKJ gene. In some embodiments, the auxiliary sequence comprises a mouse IGKJ 3'UTR sequence, or a human IGKJ 3'UTR sequence. In some embodiments, the sequence is at least 80%, 85%, 90%, 95%, 96%, 97%, 98%, 99%, or 100% identical to SEQ ID NO: 6 or SEQ ID NO: 7.

In various embodiments, the appropriate enhancer(s) can be retained in the animal. For example, in modifying a kappa locus to replace endogenous kappa variable region gene segments with human kappa variable region gene segments, the kappa intronic enhancer and kappa 3' enhancer are functionally maintained, or undisrupted. In some embodiments, the modified kappa locus can be subject to somatic hypermutations. In some embodiments, the degree of somatic hypermutations is about the same or similar to the wildtype kappa locus. In some embodiments, at least 50%, 60%, 70%, 80%, 90%, or 95% of the human light chain variable regions in antibodies (before or after antigen immunization) have at least 1 somatic mutation. In some embodiments, at least 50%, 60%, 70%, 80%, 90%, or 95% of the human light chain variable regions in antibodies (before or after antigen immunization) have at least 2 somatic mutations. In some embodiments, at least 50%, 60%, 70%, 80%, 90%, or 95% of the human light chain variable regions in antibodies (before or after antigen immunization) have at least 3 somatic mutations.

In some embodiments, the animal comprises an endogenous IGKC. In some embodiments, the IGKV genes and/or the IGKJ genes are operably linked together to the IGKC gene (e.g., endogenous IGKC gene).

In some embodiments, the IGKV gene and the IGKJ gene are operably linked together.

In some embodiments, the animal comprises an endogenous IGKC. In some embodiments, the IGKV genes and/or the IGKJ genes are operably linked together. The VJ recombination can occur among these genes and produce functional antibodies. In some embodiments, the IGKV gene and the IGKJ gene are rearranged at the endogenous Kappa chain immunoglobulin locus.

In some embodiments, the animal comprises a disruption in the animal's endogenous light chain immunoglobulin gene locus. In some embodiments, the disruption in the animal's endogenous light chain immunoglobulin gene locus comprises a deletion of one or more endogenous IGKV genes, and one or more endogenous IGKJ genes.

In some embodiments, the animal is a mouse. The disruption in the animal's endogenous light chain immunoglobulin gene locus comprises a deletion of at least or about 1, 2, 3, 4, 5, 6, 7, 8, 9, 10, 20, 30, 40, 50, 60, 70, 80, 90, 100, 110, 120, 130, 140, 150, 151, 152, 153, 154, 155, 156, 157, 158, 159, 160, 161, 162, or 163 mouse IGKV genes (e.g., genes as shown in Table 3). In some embodiments, the disruption compromises a deletion of about or at least 1, 2, 3, 4, 5, 6, 7, 8, 9, or 10 mouse IGKV genes selected from IGKV2-137, IGKV1-136, IGKV1-135, IGKV14-134-1, IGKV17-134, IGKV1-133, IGKV1-132, IGKV1-131, IGKV14-130, and IGKV9-129. In some embodiments, the mouse still compromises about or at least 1, 2, 3, 4, 5, 6, 7, 8, 9, or 10 mouse IGKV genes selected from IGKV2-137, IGKV1-136, IGKV1-135, IGKV14-134-1, IGKV17-134, IGKV1-133, IGKV1-132, IGKV1-131, IGKV14-130, and IGKV9-129.

In some embodiments, the disruption compromises a deletion of about or at least 1, 2, 3, 4, 5, 6, 7, 8, 9, or 10 mouse IGKV genes selected from IGKV3-10, IGKV3-9, IGKV3-8, IGKV3-7, IGKV3-6, IGKV3-5, IGKV3-4, IGKV3-3, IGKV3-2, and IGKV3-1. In some embodiments, the mouse still compromises about or at least 1, 2, 3, 4, 5, 6, 7, 8, 9, or 10 mouse IGKV genes selected from IGKV3-10, IGKV3-9, IGKV3-8, IGKV3-7, IGKV3-6, IGKV3-5, IGKV3-4, IGKV3-3, IGKV3-2, and IGKV3-1.

In some embodiments, the disruption compromises a deletion of about or at least 1, 2, 3, 4, or 5 mouse IGKJ genes selected from IGKJ1, IGKJ2, IGKJ3, IGKJ4, and IGKJ5. In some embodiments, the mouse still compromises about or at least 1, 2, 3, 4, or 5 mouse IGKJ genes selected from IGKJ1, IGKJ2, IGKJ3, IGKJ4, and IGKJ5 (e.g., IGKJ5).

In some embodiments, the disruption in the animal's endogenous kappa light chain immunoglobulin gene locus comprises a deletion of about or at least 500 kb, 600 kb, 700 kb, 800 kb, 900 kb, 1000 kb, 1500 kb, 2000 kb, 2500 kb, 3000 kb or 3500 kb of an endogenous sequence.

In some embodiments, the deleted sequence starts from IGKV2-137 to IGKJ4, from IGKV1-136 to IGKJ4, from IGKV1-135 to IGKJ4, from IGKV2-137 to IGKJ5, from IGKV1-136 to IGKJ5, or from IGKV1-135 to IGKJ5 (e.g., from IGKV2-137 to IGKJ5).

In some embodiments, the animal comprises about or at least 1, 2, 3, 4, 5, 6, 7, 8, 9, or 10 sequences that are at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence in the human light chain immunoglobulin gene locus. In some embodiments, the sequence has a length of about or at least 2 or 3 kb. In some embodiments, the sequence has a length of no more than 4 kb.

In some embodiments, the animal comprises one or more (e.g., 1, 2, 3, 4, 5, 6, 7, 8, 9, or 10) rearranged human IGKV/IGKJ sequences. In some embodiments, the rearranged human IGKV/IGKJ sequence is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 35 (e.g., nucleotides 2001-2512 of SEQ ID NO: 35). In some embodiments, the rearranged human IGKV/IGKJ sequence is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 36 (e.g., nucleotides 2001-2551 of SEQ ID NO: 36). In some embodiments, the rearranged human IGKV/IGKJ sequence is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 37 (e.g., nucleotides 2001-2572 of SEQ ID NO: 37).

In some embodiments, the rearranged human IGKV/IGKJ sequence has a length of about or at least 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4500, or 5000 bp. In some embodiments, the rearranged human IGKV/IGKJ sequence is less than 1500, 1600, 1700, 1800, 1900, 2000, 2100, 2200, 2300, 2400, 2500, 2600, 2700, 2800, 2900, 3000 or 3100 bp.

In some embodiments, the animal can produce an immunoglobulin (e.g., IgG) comprising a light chain variable region that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 38. In some embodiments, the animal can produce an immunoglobulin (e.g., IgG) comprising a light chain variable region that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39. In some embodiments, the animal can produce an immunoglobulin (e.g., IgG) comprising a light chain variable region that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 40. In some embodiments, the light chain variable region can have 1, 2, 3, 4, or 5 mutations as compared to SEQ ID NO: 38, 39, or 40. In some embodiments, the light chain constant domain has a sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41.

In some embodiments, the animal can have one, two, three, four, five, six, seven, eight, nine, or ten unmodified human sequences. In some embodiments, the unmodified human sequence has a length of about or at least 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 kb.

In some embodiments, the light chain variable region has a sequence of SEQ ID NO: 38 with 0, 1, or 2 mutations. In some embodiments, the light chain variable region has a sequence of SEQ ID NO: 39 with 0, 1, or 2 mutations. In some embodiments, the light chain variable region has a sequence of SEQ ID NO: 40 with 0, 1, or 2 mutations.

Furthermore, in some cases, the entire mouse IGKV genes, and IGKJ genes (all none-pseudo genes) are knocked out, and the light chain variable region will not have any sequence that is encoded by a sequence derived from the mouse, thereby minimizing immunogenicity in humans. In various embodiments, the light chain variable region is capable of being somatically mutated.

Genetically Modified Heavy Chain Immunoglobulin Locus

Heavy chain immunoglobulin locus (also known as IGH or immunoglobulin heavy locus) is a region on the chromosome (e.g., human chromosome 14) that contains genes for the heavy chains of human antibodies (or immunoglobulins).

This region represents the germline organization of the heavy chain locus. The locus includes V (variable), D (diversity), J (joining), and C (constant) segments. The genes in the V region form a V gene cluster (also known as IGHV gene cluster). The genes in the D region form a D gene cluster (also known as IGHD gene cluster). The genes in the J region form a J gene cluster (also known as IGHJ gene cluster).

During B cell development, a recombination event at the DNA level joins a single D segment (also known as an IGHD gene) with a J segment (also known as an IGHJ gene); the fused D-J exon of this partially rearranged D-J region is then joined to a V segment (also known as an IGHV gene). The rearranged V-D-J region containing a fused V-D-J exon is then transcribed and fused at the RNA level to the IGHM constant region; this transcript encodes a mu heavy chain. Later in development B cells generate V-D-J-Cmu-Cdelta pre-messenger RNA, which is alternatively spliced to encode either a mu or a delta heavy chain. Mature B cells in the lymph nodes undergo switch recombination, so that the fused V-D-J gene segment is brought in proximity to one of the IGHG, IGHA, or IGHE gene segments and each cell expresses either the gamma, alpha, or epsilon heavy chain. Potential recombination of many different IGHV genes with several IGHJ genes provides a wide range of antigen recognition. Additional diversity is attained by junctional diversity, resulting from the random addition of nucleotides by terminal deoxynucleotidyl transferase, and by somatic hypermutation, which occurs during B cell maturation in the spleen and lymph nodes. Several V, D, J, and C segments are known to be incapable of encoding a protein and are considered pseudogenous gene segments (often simply referred to as pseudogenes).

The human heavy chain immunoglobulin locus is located on human chromosome 14. Table 5 lists IGHV genes and its relative orders in this locus.

TABLE 5

| List of IGHV genes on human chromosome 14 | |
|---|---|
| Gene names | Order |
| IGHV(III)-82 | 1 |
| IGHV7-81 | 2 |
| IGHV4-80 | 3 |
| IGHV3-79 | 4 |
| IGHV(II)-78-1 | 5 |
| IGHV5-78 | 6 |
| IGHV7-77 | 7 |
| IGHV(III)-76-1 | 8 |
| IGHV3-76 | 9 |
| IGHV3-75 | 10 |
| IGHV(II)-74-1 | 11 |
| IGHV3-74 | 12 |
| IGHV3-73 | 13 |
| IGHV3-72 | 14 |
| IGHV3-71 | 15 |
| IGHV2-70 | 16 |
| IGHV1-69D | 17 |
| IGHV1-69-2 | 18 |
| IGHV3-69-1 | 19 |
| IGHV2-70D | 20 |
| IGHV1-69 | 21 |
| IGHV1-68 | 22 |
| IGHV(III)-67-4 | 23 |
| IGHV(III)-67-3 | 24 |
| IGHV(III)-67-2 | 25 |
| IGHV(II)-67-1 | 26 |
| SLC20A1P1 (GLVR1) | 27 |
| IGHV1-67 | 28 |
| IGHV3-66 | 29 |
| IGHV(II)-65-1 | 30 |

TABLE 5-continued

List of IGHV genes on human chromosome 14

| Gene names | Order |
|---|---|
| IGHV3-65 | 31 |
| IGHV3-64 | 32 |
| GOLGA4P3 (Golgin) | 33 |
| IGHV3-63 | 34 |
| IGHV(II)-62-1 | 35 |
| IGHV3-62 | 36 |
| IGHV4-61 | 37 |
| IGHV(II)-60-1 | 38 |
| IGHV3-60 | 39 |
| IGHV4-59 | 40 |
| IGHV1-58 | 41 |
| IGHV3-57 | 42 |
| IGHV7-56 | 43 |
| IGHV4-55 | 44 |
| IGHV3-54 | 45 |
| IGHV(II)-53-1 | 46 |
| IGHV3-53 | 47 |
| IGHV3-52 | 48 |
| IGHV(II)-51-2 | 49 |
| IGHV(III)-51-1 | 50 |
| IGHV5-51 | 51 |
| IGHV3-50 | 52 |
| IGHV(II)-49-1 | 53 |
| IGHV3-49 | 54 |
| IGHV3-48 | 55 |
| IGHV(III)-47-1 | 56 |
| IGHV3-47 | 57 |
| IGHV(II)-46-1 | 58 |
| IGHV1-46 | 59 |
| IGHV1-45 | 60 |
| IGHV(II)-44-2 | 61 |
| IGHV(IV)-44-1 | 62 |
| IGHV(III)-44 | 63 |
| IGHV(II)-43-1 | 64 |
| IGHV3-43 | 65 |
| IGHV3-42 | 66 |
| IGHV3-41 | 67 |
| IGHV(II)-40-1 | 68 |
| IGHV7-40 | 69 |
| IGHV4-39 | 70 |
| IGHV1-38-4 | 71 |
| IGHV(III)-38-1D | 72 |
| IGHV3-38-3 | 73 |
| IGHV(III)-44D | 74 |
| IGHV(II)-43-1D | 75 |
| IGHV3-43D | 76 |
| IGHV3-42D | 77 |
| IGHV7-40D | 78 |
| IGHV4-38-2 | 79 |
| IGHV(III)-38-1 | 80 |
| IGHV3-38 | 81 |
| IGHV3-37 | 82 |
| IGHV3-36 | 83 |
| IGHV3-35 | 84 |
| IGHV7-34-1 | 85 |
| IGHV4-34 | 86 |
| IGHV3-33-2 | 87 |
| IGHV(II)-33-1 | 88 |
| IGHV3-33 | 89 |
| GOLGA4P1 (Golgin) | 90 |
| IGHV3-32 | 91 |
| IGHV(II)-31-1 | 92 |
| IGHV4-31 | 93 |
| IGHV3-30-52 | 94 |
| IGHV(II)-30-51 | 95 |
| IGHV3-30-5 | 96 |
| IGHV3-30-42 | 97 |
| IGHV(II)-30-41 | 98 |
| IGHV4-30-4 | 99 |
| IGHV3-30-33 | 100 |
| IGHV(II)-30-32 | 101 |
| IGHV3-30-3 | 102 |
| IGHV3-30-22 | 103 |
| IGHV(II)-30-21 | 104 |
| IGHV4-30-2 | 105 |
| IGHV4-30-1 | 106 |
| IGHV3-30-2 | 107 |
| IGHV(II)-30-1 | 108 |
| IGHV3-30 | 109 |
| GOLGA4P2 (Golgin) | 110 |
| IGHV3-29 | 111 |
| IGHV(II)-28-1 | 112 |
| IGHV4-28 | 113 |
| IGHV7-27 | 114 |
| IGHV(II)-26-2 | 115 |
| IGHV(III)-26-1 | 116 |
| IGHV2-26 | 117 |
| IGHV(III)-25-1 | 118 |
| IGHV3-25 | 119 |
| IGHV1-24 | 120 |
| IGHV3-23D | 121 |
| IGHV(III)-22-2D | 122 |
| IGHV(II)-22-1D | 123 |
| IGHV3-23 | 124 |
| IGHV(III)-22-2 | 125 |
| IGHV(II)-22-1 | 126 |
| IGHV3-22 | 127 |
| IGHV3-21 | 128 |
| IGHV(II)-20-1 | 129 |
| IGHV3-20 | 130 |
| IGHV3-19 | 131 |
| IGHV1-18 | 132 |
| SLC20A1P2 | 133 |
| IGHV1-17 | 134 |
| IGHV(III)-16-1 | 135 |
| IGHV3-16 | 136 |
| IGHV(II)-15-1 | 137 |
| IGHV3-15 | 138 |
| IGHV1-14 | 139 |
| IGHV(III)-13-1 | 140 |
| IGHV3-13 | 141 |
| IGHV1-12 | 142 |
| IGHV(III)-11-1 | 143 |
| IGHV3-11 | 144 |
| IGHV2-10 | 145 |
| IGHV3-9 | 146 |
| IGHV1-8 | 147 |
| IGHV5-10-1 | 148 |
| IGHV3-64D | 149 |
| IGHV3-7 | 150 |
| IGHV3-6 | 151 |
| IGHV(III)-5-2 | 152 |
| IGHV(III)-5-1 | 153 |
| IGHV2-5 | 154 |
| IGHV7-4-1 | 155 |
| IGHV4-4 | 156 |
| IGHV1-3 | 157 |
| IGHV(III)-2-1 | 158 |
| IGHV1-2 | 159 |
| * | |
| * | |
| IGHV(II)-1-1 | 162 |
| IGHV6-1 | 163 |
| * | |

Figure 16:
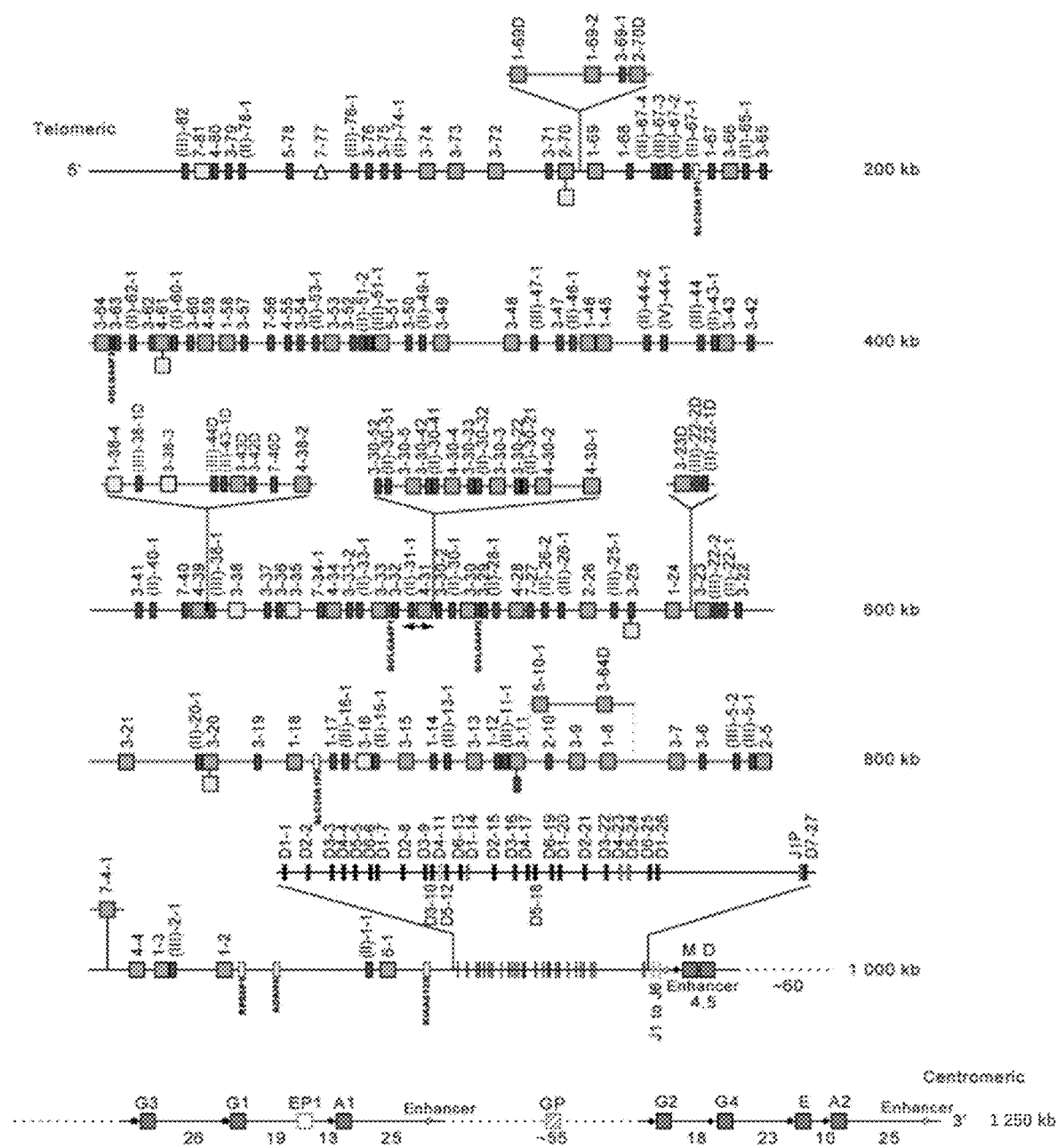
FIG. 16 is a schematic diagram showing human immunoglobulin heavy chain (IGH) locus on chromosome 14 (14q32.33).

RPS8P1, ADAM6, and KIAA0125 are also located in this locus. The relative order of RPS8P1 is 160, the relative order of ADAM6 is 161, and the relative order of KIAA0125 is 164. Table 6 lists all IGHD genes and its relative orders on human chromosome 14. Table 7 lists all IGHJ genes and its relative orders on human chromosome 14. The genes for immunoglobulin constant domains are located after the IGHV, IGHD, and IGHJ genes. These genes include (as shown in the following order): immunoglobulin heavy constant mu (IGHM), immunoglobulin heavy constant delta (IGH δ), immunoglobulin heavy constant gamma 3 (IGHG3), immunoglobulin heavy constant gamma 1 (IGHG1), immunoglobulin heavy constant epsilon P1 (pseudogene) (IGHEP1), immunoglobulin heavy constant alpha 1 (IGHA1), immunoglobulin heavy constant gamma P (non-functional) (IGHGP), immunoglobulin heavy constant gamma 2 (IGHG2), immunoglobulin heavy constant gamma 4 (IGHG4), immunoglobulin heavy constant epsilon (IGRE), and immunoglobulin heavy constant alpha 2 (IGHA2). These genes and the order of these genes are also shown in FIG. 16 and FIG. 20.

TABLE 6

List of IGHD genes on human chromosome 14

| Gene names | Order |
|---|---|
| IGHD1-1 | 165 |
| IGHD2-2 | 166 |
| IGHD3-3 | 167 |
| IGHD4-4 | 168 |
| IGHD5-5 | 169 |
| IGHD6-6 | 170 |
| IGHD1-7 | 171 |
| IGHD2-8 | 172 |
| IGHD3-9 | 173 |
| IGHD3-10 | 174 |
| IGHD4-11 | 175 |
| IGHD5-12 | 176 |
| IGHD6-13 | 177 |
| IGHD1-14 | 178 |
| IGHD2-15 | 179 |
| IGHD3-16 | 180 |
| IGHD4-17 | 181 |
| IGHD5-18 | 182 |
| IGHD6-19 | 183 |
| IGHD1-20 | 184 |
| IGHD2-21 | 185 |
| IGHD3-22 | 186 |
| IGHD4-23 | 187 |
| IGHD5-24 | 188 |
| IGHD6-25 | 189 |
| IGHD1-26 | 190 |
|  | * |
| IGHD7-27 | 192 |

TABLE 7

List of IGHJ genes on human chromosome 14

| Gene names | Order |
|---|---|
| IGHJ1P | 191 |
| IGHJ1 | 193 |
| IGHJ2 | 194 |
| IGHJ2P | 195 |
| IGHJ3 | 196 |
| IGHJ4 | 197 |
| IGHJ5 | 198 |
| IGHJ3P | 199 |
| IGHJ6 | 200 |

The mouse heavy chain immunoglobulin locus is located on mouse chromosome 12. Table 8 lists IGHV genes and its relative orders in this locus.

TABLE 8

List of IGHV genes on mouse chromosome 12

| Gene names | Order |
|---|---|
| IGHV1-86 | 1 |
| IGHV1-85 | 2 |
| IGHV1-84 | 3 |
| IGHV1-83 | 4 |
| IGHV1-82 | 5 |
| IGHV1-81 | 6 |
| IGHV1-80 | 7 |

TABLE 8-continued

List of IGHV genes on mouse chromosome 12

| Gene names | Order |
|---|---|
| IGHV1-79 | 8 |
| IGHV1-78 | 9 |
| IGHV1-77 | 10 |
| IGHV8-16 | 11 |
| IGHV1-76 | 12 |
| IGHV8-15 | 13 |
| IGHV1-75 | 14 |
| IGHV8-14 | 15 |
| IGHV1-74 | 16 |
| IGHV1-73 | 17 |
| IGHV8-13 | 18 |
| IGHV1-72 | 19 |
| IGHV1-71 | 20 |
| IGHV1-70 | 21 |
| IGHV8-12 | 22 |
| IGHV1-69 | 23 |
| IGHV1-68 | 24 |
| IGHV1-67 | 25 |
| IGHV1-66 | 26 |
| IGHV8-11 | 27 |
| IGHV1-65 | 28 |
| IGHV8-10 | 29 |
| IGHV1-64 | 30 |
| IGHV1-63 | 31 |
| IGHV8-9 | 32 |
| IGHV1-62-3 | 33 |
| IGHV1-62-2 | 34 |
| IGHV1-62-1 | 35 |
| IGHV1-62 | 36 |
| IGHV1-61 | 37 |
| IGHV1-60 | 38 |
| IGHV1-59 | 39 |
| IGHV1-58 | 40 |
| IGHV8-8 | 41 |
| IGHV1-57 | 42 |
| IGHV8-7 | 43 |
| IGHV1-56 | 44 |
| IGHV1-55 | 45 |
| IGHV1-54 | 46 |
| IGHV8-6 | 47 |
| IGHV1-53 | 48 |
| IGHV1-52 | 49 |
| IGHV1-51 | 50 |
| IGHV1-50 | 51 |
| IGHV8-5 | 52 |
| IGHV1-49 | 53 |
| IGHV1-48 | 54 |
| IGHV8-4 | 55 |
| IGHV8-3 | 56 |
| IGHV1-47 | 57 |
| IGHV1-46 | 58 |
| IGHV1-45 | 59 |
| IGHV1-44 | 60 |
| IGHV1-43 | 61 |
| IGHV1-42 | 62 |
| IGHV1-41 | 63 |
| IGHV1-40 | 64 |
| IGHV1-39 | 65 |
| IGHV1-38 | 66 |
| IGHV1-37 | 67 |
| IGHV1-36 | 68 |
| IGHV1-35 | 69 |
| IGHV1-34 | 70 |
| IGHV1-33 | 71 |
| IGHV1-32 | 72 |
| IGHV1-31 | 73 |
| IGHV1-30 | 74 |
| IGHV1-29 | 75 |
| IGHV1-28 | 76 |
| IGHV1-27 | 77 |
| IGHV1-26 | 78 |
| IGHV1-25 | 79 |
| IGHV1-24 | 80 |
| IGHV1-23 | 81 |
| IGHV1-22 | 82 |
| IGHV1-21 | 83 |

TABLE 8-continued

List of IGHV genes on mouse chromosome 12

| Gene names | Order |
|---|---|
| IGHV1-21-1 | 84 |
| IGHV1-20 | 85 |
| IGHV1-19 | 86 |
| IGHV1-19-1 | 87 |
| IGHV1-18 | 88 |
| IGHV1-17 | 89 |
| IGHV1-17-1 | 90 |
| IGHV1-16 | 91 |
| IGHV1-15 | 92 |
| IGHV1-14 | 93 |
| IGHV1-13 | 94 |
| IGHV1-12 | 95 |
| IGHV1-11 | 96 |
| IGHV1-10 | 97 |
| IGHV1-9 | 98 |
| IGHV15-2 | 99 |
| IGHV1-8 | 100 |
| IGHV10-4 | 101 |
| IGHV1-7 | 102 |
| IGHV1-6 | 103 |
| IGHV10-3 | 104 |
| IGHV1-5 | 105 |
| IGHV10-2 | 106 |
| IGHV1-4 | 107 |
| IGHV1-3 | 108 |
| IGHV10-1 | 109 |
| IGHV1-2 | 110 |
| IGHV8-2 | 111 |
| IGHV6-7 | 112 |
| IGHV6-6 | 113 |
| IGHV6-5 | 114 |
| IGHV6-4 | 115 |
| IGHV6-3 | 116 |
| IGHV12-3 | 117 |
| IGHV13-2 | 118 |
| IGHV1-1 | 119 |
| IGHV8-1 | 120 |
| IGHV3-8 | 121 |
| IGHV5-21 | 122 |
| IGHV3-7 | 123 |
| IGHV9-4 | 124 |
| IGHV3-6 | 125 |
| IGHV13-1 | 126 |
| IGHV3-5 | 127 |
| IGHV3-4 | 128 |
| IGHV7-4 | 129 |
| IGHV3-3 | 130 |
| IGHV14-4 | 131 |
| IGHV15-1 | 132 |
| IGHV7-3 | 133 |
| IGHV9-3 | 134 |
| IGHV12-2 | 135 |
| IGHV9-2 | 136 |
| IGHV12-1 | 137 |
| IGHV9-1 | 138 |
| IGHV6-2 | 139 |
| IGHV16-1 | 140 |
| IGHV14-3 | 141 |
| IGHV11-2 | 142 |
| IGHV3-2 | 143 |
| IGHV4-2 | 144 |
| IGHV14-2 | 145 |
| IGHV11-1 | 146 |
| IGHV3-1 | 147 |
| IGHV4-1 | 148 |
| IGHV14-1 | 149 |
| IGHV7-2 | 150 |
| IGHV7-1 | 151 |
| IGHV5-19 | 152 |
| IGHV2-9 | 153 |
| IGHV2-8 | 154 |
| IGHV5-18 | 155 |
| IGHV5-17 | 156 |
| IGHV5-16 | 157 |
| IGHV5-15 | 158 |
| IGHV2-7 | 159 |

TABLE 8-continued

List of IGHV genes on mouse chromosome 12

| Gene names | Order |
|---|---|
| IGHV2-6-8 | 160 |
| IGHV2-9-1 | 161 |
| IGHV5-12-4 | 162 |
| IGHV5-9-1 | 163 |
| IGHV2-6 | 164 |
| IGHV5-12 | 165 |
| IGHV5-11 | 166 |
| IGHV2-5 | 167 |
| IGHV5-10 | 168 |
| IGHV5-9 | 169 |
| IGHV5-8 | 170 |
| IGHV2-4 | 171 |
| IGHV5-7 | 172 |
| IGHV5-6 | 173 |
| IGHV5-5 | 174 |
| IGHV2-3 | 175 |
| IGHV6-1 | 176 |
| IGHV5-4 | 177 |
| IGHV5-3 | 178 |
| IGHV2-2 | 179 |
| IGHV5-2 | 180 |
| IGHV2-1 | 181 |
| IGHV5-1 | 182 |

Figure 17:
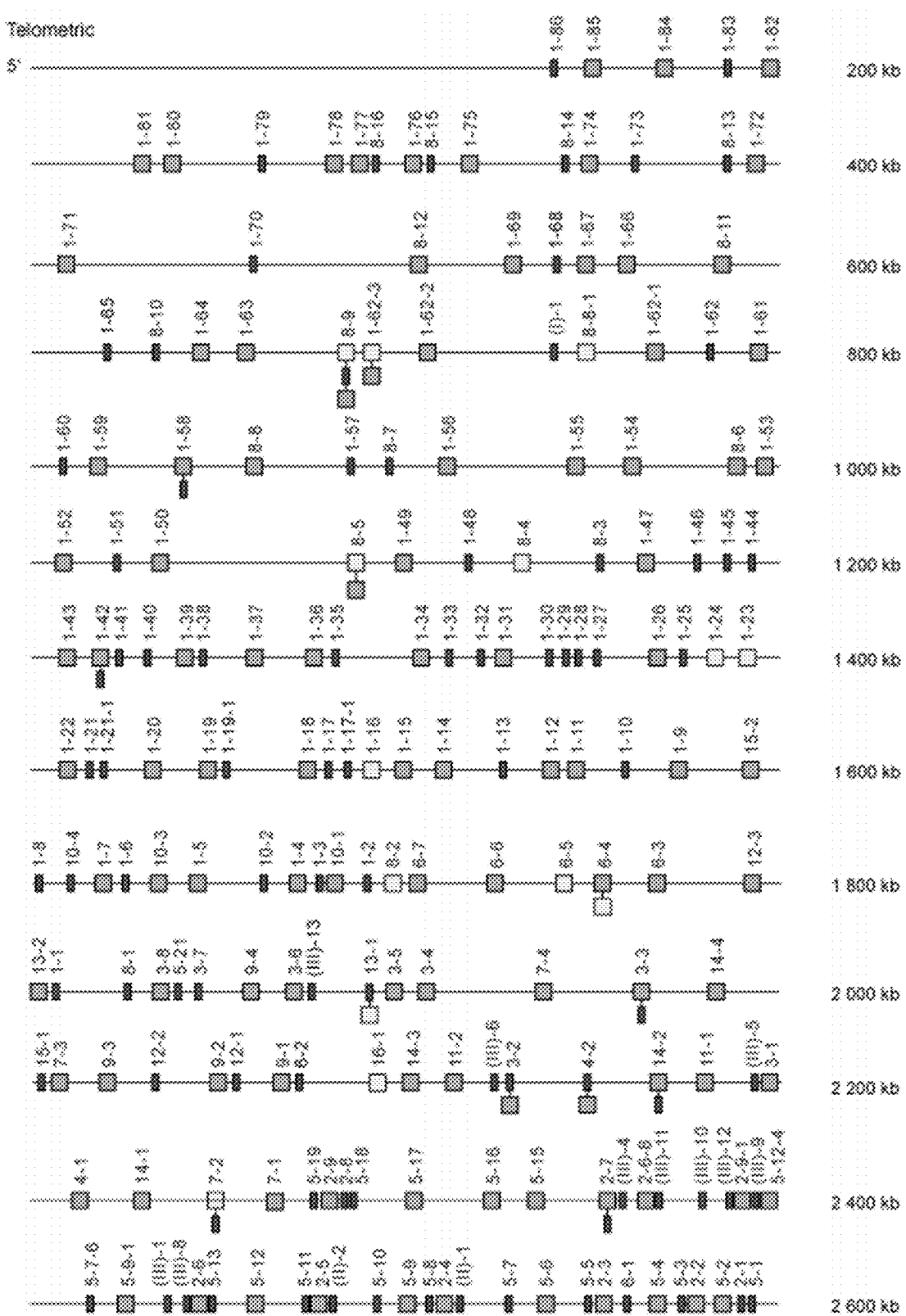
FIG. 17 is a schematic diagram showing mouse (*Mus musculus*) IGH locus on chromosome 12 (12F2) (strain C57BL/6).
Figure 17:
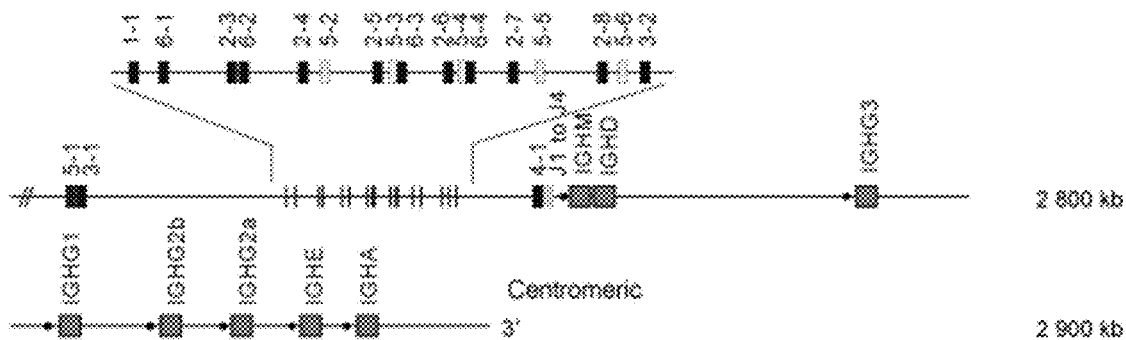

Table 9 lists all IGHD genes and its relative orders on mouse chromosome 12. Table 10 lists all IGHJ genes and its relative orders on mouse chromosome 12. The genes for immunoglobulin constant domains are after the IGHV, IGHD, and IGHJ genes. These genes include (as shown in the following order): immunoglobulin heavy constant mu (IGHM), immunoglobulin heavy constant delta (IGH δ), immunoglobulin heavy constant gamma 3 (IGHG3), immunoglobulin heavy constant gamma 1 (IGHG1), immunoglobulin heavy constant gamma 2b (IGHG2b), immunoglobulin heavy constant gamma 2a (IGHG2a), immunoglobulin heavy constant epsilon (IGRE), and immunoglobulin heavy constant alpha (IGHA) genes. These genes and the order of these genes are also shown in FIG. 17 and FIG. 21.

TABLE 9

List of IGHD genes on mouse chromosome 12

| Gene names | Order |
|---|---|
| IGHD5-1 | 183 |
| IGHD3-1 | 184 |
| IGHD1-1 | 185 |
| IGHD6-1 | 186 |
| IGHD2-3 | 187 |
| IGHD6-2 | 188 |
| IGHD2-4 | 189 |
| IGHD2-5 | 191 |
| IGHD5-3 | 192 |
| IGHD5-7 | 193 |
| IGHD2-6 | 194 |
| IGHD5-4 | 195 |
| IGHD5-8 | 196 |
| IGHD2-7 | 197 |
| IGHD5-5 | 198 |
| IGHD2-8 | 199 |
| IGHD5-6 | 200 |
| IGHD3-2 | 201 |
| IGHD4-1 | 202 |

TABLE 10

List of IGHJ genes on mouse chromosome 12

| Gene names | Order |
|---|---|
| IGHJ1 | 203 |
| IGHJ2 | 204 |
| IGHJ3 | 205 |
| IGHJ4 | 206 |

The present disclosure provides genetically-modified, non-human animal comprising one or more human IGHV genes, one or more human IGHD genes, and/or one or more human IGHJ genes.

The genetically modified animals can be made by introducing human immunoglobulin genes into the genome of non-human animals to produce animals that can express humanized antibodies or chimeric antibodies. FIG. 1A shows the methods of making the humanized mice. In some embodiments, the methods first involve modifying the human immunoglobulin region on the human chromosome. The modified human chromosomes are then introduced into the mouse recipient cell. The human immunoglobulin variable region is then introduced into the corresponding region of the mouse genome by direct replacement (e.g., in one step replacement). The recipient cells are then screened, preferably for the cells that do not contain the human chromosomes. The cells are then injected to blastocysts to prepare chimeric animals (e.g., mice). Subsequent breeding can be performed to obtain animals containing intact humanized immunoglobulin locus.

In some embodiments, the human IGHV genes, the human IGHD genes, and the human IGHJ genes are operably linked together and can undergo VDJ rearrangement. In some embodiments, the human IGHV genes, the human IGHD genes, and the human IGHJ genes are at the endogenous heavy chain immunoglobulin gene locus.

In some embodiments, the animal compromises about or at least 1, 2, 3, 4, 5, 6, 7, 8, 9, 10, 20, 30, 40, 50, 60, 70, 80, 90, 100, 110, 120, 130, 140, 150, 151, 152, 153, 154, 155, 156, 157, 158, 159, 160 or 161 human IGHV genes (e.g., genes as shown in Table 5).

In some embodiments, the animal compromises 1, 2, 3, 4, 5, 6, 7, 8, 9, or 10 genes selected from IGHV(III)-82, IGHV7-81, IGHV4-80, IGHV3-79, IGHV(II)-78-1, IGHV5-78, IGHV7-77, IGHV(III)-76-1, IGHV3-76, and IGHV3-75.

In some embodiments, the animal compromises 1, 2, 3, 4, 5, 6, 7, 8, 9, or 10 genes selected from IGHV(III)-5-2, IGHV(III)-5-1, IGHV2-5, IGHV7-4-1, IGHV4-4, IGHV1-3, IGHV(III)-2-1, IGHV1-2, IGHV(II)-1-1, and IGHV6-1.

In some embodiments, the animal compromises an unmodified human sequence comprising a sequence starting from a gene selected from IGHV(III)-82, IGHV7-81, IGHV4-80, IGHV3-79, IGHV(II)-78-1, IGHV5-78, IGHV7-77, IGHV(III)-76-1, IGHV3-76, and IGHV3-75, and ending at a gene selected from IGHV(III)-5-2, IGHV(III)-5-1, IGHV2-5, IGHV7-4-1, IGHV4-4, IGHV1-3, IGHV(III)-2-1, IGHV1-2, IGHV(II)-1-1, and IGHV6-1. In some embodiments, the unmodified human sequence derived from a human heavy chain immunoglobulin gene locus starting from human IGHV(III)-82 to human IGHV1-2. In some embodiments, the unmodified human sequence derived from a human heavy chain immunoglobulin gene locus starting from human IGHV(III)-82 to human IGHV(II)-1-1. In some embodiments, the unmodified human sequence derived from a human heavy chain immunoglobulin gene locus starting from human IGHV(III)-82 to human IGHV-6-1.

In some embodiments, the animal compromises about or at least 1, 2, 3, 4, 5, 6, 7, 8, 9, 10, 11, 12, 13, 14, 15, 16, 17, 18, 19, 20, 21, 22, 23, 24, 25, 26, or 27 human IGHD genes (e.g., genes as shown in Table 6). In some embodiments, the animal compromises 1, 2, 3, 4, 5, 6, 7, 8, 9, or 10 genes selected from IGHD1-1, IGHD2-2, IGHD3-3, IGHD4-4, IGHD5-5, IGHD4-23, IGHD5-24, IGHD6-25, IGHD1-26, and IGHD7-27.

In some embodiments, the animal compromises about or at least 1, 2, 3, 4, 5, 6, 7, 8, or 9 human IGHJ genes (e.g., genes as shown in Table 7). In some embodiments, the animal compromises 1, 2, 3, 4, 5, 6, 7, 8, or 9 human IGHJ genes selected from IGHJ1P, IGHJ1, IGHJ2, IGHJ2P, IGHJ3, IGHJ4, IGHJ5, IGHJ3P, and IGHJ6.

In some embodiments, the animal compromises an unmodified human sequence comprising a sequence starting from a gene selected from IGHD1-1, IGHD2-2, IGHD3-3, IGHD4-4, IGHD5-5, IGHD4-23, IGHD5-24, IGHD6-25, IGHD1-26, and IGHD7-27, and ending at a gene selected from IGHJ1P, IGHJ1, IGHJ2, IGHJ2P, IGHJ3, IGHJ4, IGHJ5, IGHJ3P, and IGHJ6. In some embodiments, the unmodified human sequence derived from a human heavy chain immunoglobulin gene locus starting from human IGHD1-1 to human IGHJ6.

In some embodiments, the unmodified human sequence derived from a human heavy chain immunoglobulin gene locus starting from human IGHD1-1 to human IGHD7-27.

In some embodiments, the unmodified human sequence derived from a human heavy chain immunoglobulin gene locus starting from human IGHJ1P to human IGHJ6. In some embodiments, the unmodified human sequence derived from a human heavy chain immunoglobulin gene locus starting from human IGHJ1 to human IGHJ6.

In some embodiments, the unmodified human sequence derived from a human heavy chain immunoglobulin gene locus starting from human IGHV(III)-82 to human IGHJ6. In some embodiments, the unmodified human sequence derived from a human heavy chain immunoglobulin gene locus starting from human IGHV1-2 to human IGHJ6. In some embodiments, the unmodified human sequence derived from a human heavy chain immunoglobulin gene locus starting from human IGHV(II)-1-1 to human IGHJ6. In some embodiments, the unmodified human sequence derived from a human heavy chain immunoglobulin gene locus starting from human IGHV6-1 to human IGHJ6.

In some embodiments, the animal can have one, two, three, four, five, six, seven, eight, nine, or ten unmodified human sequences. In some embodiments, the unmodified human sequence has a length of about or at least 10, 20, 30, 40, 50, 60, 70, 80, 90, 100, 200, 300, 400, 500, 600, 700, 800, 900, or 1000 kb.

In some embodiments, the animal comprises one or more endogenous genes selected from the group consisting of immunoglobulin heavy constant mu (IGHM), immunoglobulin heavy constant delta (IGHδ), immunoglobulin heavy constant gamma 3 (IGHG3), immunoglobulin heavy constant gamma 1 (IGHG1), immunoglobulin heavy constant gamma 2b (IGHG2b), immunoglobulin heavy constant gamma 2a (IGHG2a), immunoglobulin heavy constant epsilon (IGHE), and immunoglobulin heavy constant alpha (IGHA) genes. In some embodiments, these endogenous genes are operably linked together. In some embodiments, these endogenous genes have the same order as in a wildtype animal. In some embodiments, isotype switching (immunoglobulin class switching) can occur in the animal.

In some embodiments, the IGHV genes, the IGHD genes, and/or the IGHJ genes are operably linked together. The VDJ recombination can occur among these genes and produce functional antibodies. In some embodiments, these genes are arranged in an order that is similar to the order in human heavy chain immunoglobulin locus. This arrangement offers various advantages, e.g., the arrangement of these genes allow the production of heavy chain variable domains with a diversity that is very similar to the diversity of the heavy chain variable domains in human. As some random sequences may be inserted to the sequence during VDJ recombination, in some embodiments, the complete human antibody repertoires with no or minimum modifications can reduce the likelihood that non-human sequence is inserted during the VDJ recombination.

In some embodiments, the IGHV genes, the IGHD genes, and/or the IGHJ genes are operably linked together to one or more genes (e.g., all genes) selected from IGHM, IGHδ, IGHG3, IGHG1, IGHG2b, IGHG2a, IGHE, and IGHA genes.

In some embodiments, the animal comprises a disruption in the animal's endogenous heavy chain immunoglobulin gene locus. In some embodiments, the disruption in the animal's endogenous heavy chain immunoglobulin gene locus comprises a deletion of one or more endogenous IGHV genes, one or more endogenous IGHD genes, and one or more endogenous IGHJ genes.

In some embodiments, the animal is a mouse. The disruption in the animal's endogenous heavy chain immunoglobulin gene locus comprises a deletion of at least or about 1, 2, 3, 4, 5, 6, 7, 8, 9, 10, 20, 30, 40, 50, 60, 70, 80, 90, 100, 110, 120, 130, 140, 150, 160, 170, 171, 172, 173, 174, 175, 176, 177, 178, 179, 180, 181, or 182 mouse IGHV genes (e.g., genes as shown in Table 8). In some embodiments, the disruption compromises a deletion of about or at least 1, 2, 3, 4, 5, 6, 7, 8, 9, or 10 mouse IGHV genes selected from IGHV1-86, IGHV1-85, IGHV1-84, IGHV1-83, IGHV1-82, IGHV1-81, IGHV1-80, IGHV1-79, IGHV1-78, and IGHV1-77. In some embodiments, the mouse still compromises about or at least 1, 2, 3, 4, 5, 6, 7, 8, 9, or 10 mouse IGHV genes selected from IGHV1-86, IGHV1-85, IGHV1-84, IGHV1-83, IGHV1-82, IGHV1-81, IGHV1-80, IGHV1-79, IGHV1-78, and IGHV1-77 (e.g., IGHV1-86).

In some embodiments, the disruption compromises a deletion of about or at least 1, 2, 3, 4, 5, 6, 7, 8, 9, or 10 mouse IGHV genes selected from IGHV5-6, IGHV5-5, IGHV2-3, IGHV6-1, IGHV5-4, IGHV5-3, IGHV2-2, IGHV5-2, IGHV2-1, and IGHV5-1. In some embodiments, the mouse still compromises a deletion of about or at least 1, 2, 3, 4, 5, 6, 7, 8, 9, or 10 mouse IGHV genes selected from IGHV5-6, IGHV5-5, IGHV2-3, IGHV6-1, IGHV5-4, IGHV5-3, IGHV2-2, IGHV5-2, IGHV2-1, and IGHV5-1.

In some embodiments, the disruption in the animal's endogenous heavy chain immunoglobulin gene locus comprises a deletion of at least or about 1, 2, 3, 4, 5, 6, 7, 8, 9, 10, 11, 12, 13, 14, 15, 16, 17, 18, 19, or 20 mouse IGHD genes (e.g., genes as shown in Table 9). In some embodiments, the disruption compromises a deletion of about or at least 1, 2, 3, 4, 5, 6, 7, 8, 9, or 10 mouse IGHD genes selected from IGHD5-1, IGHD3-1, IGHD1-1, IGHD6-1, IGHD2-3, IGHD2-7, IGHD2-8, IGHD5-6, IGHD3-2, and IGHD4-1. In some embodiments, the mouse still compromises about or at least 1, 2, 3, 4, 5, 6, 7, 8, 9, or 10 mouse IGHD genes selected from IGHD5-1, IGHD3-1, IGHD1-1, IGHD6-1, IGHD2-3, IGHD2-7, IGHD2-8, IGHD5-6, IGHD3-2, and IGHD4-1.

In some embodiments, the disruption compromises a deletion of about or at least 1, 2, 3, or 4 mouse IGHJ genes selected from IGHJ1, IGHJ2, IGHJ3, and IGHJ4. In some embodiments, the mouse still compromises about or at least 1, 2, 3, or 4 mouse IGHJ genes selected from IGHJ1, IGHJ2, IGHJ3, and IGHJ4.

In some embodiments, the disruption in the animal's endogenous heavy chain immunoglobulin gene locus comprises a deletion of about or at least 500 kb, 600 kb, 700 kb, 800 kb, 900 kb, 1000 kb, 1500 kb, 2000 kb, 2500 kb, or 3000 kb of an endogenous sequence.

In some embodiments, the deleted sequence starts from IGHV1-86 to IGHJ4, from IGHV1-85 to IGHJ4, from IGHV1-84 to IGHJ4, from IGHV1-83 to IGHJ4, or from IGHV1-82 to IGHJ4 (e.g., from IGHV1-85 to IGHJ4).

In some embodiments, the animal comprises about or at least 1, 2, 3, 4, 5, 6, 7, 8, 9, or 10 sequences that are at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence in the human heavy chain immunoglobulin gene locus. In some embodiments, the sequence has a length of about or at least 10, 20, 30, 40, 50, 60, 70, 80, 90, 100, 200, 300, 400, 500, 600, 700, 800, 900, 1000, 1500, 2000, 2500, 3000 or 3500 kb. In some embodiments, the sequence starts from human IGHV(III)-82 to IGHV1-2. In some embodiments, the sequence starts from human IGHV7-81 to IGHV1-2. In some embodiments, the sequence starts from human IGHV(II)-1-1 to IGHVJ6. In some embodiments, the sequence starts from human IGHV6-1 to IGHVJ6.

The human IGHV genes, the human IGHD genes, and the human IGHJ genes are operably linked together and can undergo VDJ rearrangement. In some embodiments, the modified mouse has complete human IGHV, IGHD, and IGHJ gene repertoires (e.g., including all non-pseudo human IGHV, IGHD, and IGHJ genes). Thus, the modified mouse can produce a complete human antibody repertoire.

In some embodiments, the usage of IGHV3-15, IGHV1-18, IGHV3-21, IGHV5-51, IGHV3-74, IGHV3-30-3, IGHV3-43, IGHV1-24, IGHV3-7, IGHV4-4, IGHV3-53, IGHV4-59, IGHV6-1, IGHV3-23, IGHV3-33, IGHV3-30, IGHV3-48, IGHV4-39, IGHV4-34, or IGHV3-66 can be detected (e.g., with a frequency >1% among the rearranged sequences). In some embodiments, the usage of IGHV3-38-3, IGHV1-58, IGHV4-38-2, IGHV4-61, IGHV3-NL1, IGHV2-26, IGHV1-2, IGHV7-4-1, IGHV4-28, IGHV3-64, IGHV3-49, IGHV5-10-1, IGHV3-72, IGHV2-5, IGHV2-70, IGHV1-46, IGHV1-3, IGHV3-11, IGHV3-13, IGHV3-20, IGHV3-64D, IGHV1-69, IGHV3-73, IGHV4-30-2, IGHV4-31, or IGHV4-30-4 can be detected (e.g., with a frequency <1% among the rearranged sequences).

In some embodiments, the usage of IGHD5-24, IGHD2-8, IGHD6-25, IGHD1-14, IGHD4-23, IGHD3-16, IGHD1-20, IGHD2-15, IGHD2-21, IGHD1-1, IGHD5-12, IGHD3-22, IGHD7-27, IGHD4-11, IGHD3-9, IGHD3-3, IGHD2-2, IGHD5-18, IGHD4-17, IGHD3-10, IGHD6-6, IGHD1-26, IGHD1-7, IGHD6-19, or IGHD6-13 can be detected (e.g., with a frequency >1% among the rearranged sequences).

In some embodiments, the usage of IGHJ1, IGHJ2, IGHJ3, IGHJ4, IGHJ5, or IGHJ6 can be detected (e.g., with a frequency >1% among the rearranged sequences).

In some embodiments, the usage of IGHV1-24, IGHV4-30-2, IGHV1-18, IGHV3-43, IGHV4-30-4, IGHV5-51, IGHV3-21, IGHV4-31, IGHV3-7, IGHV3-30-3, IGHV3-

53, IGHV4-4, IGHV3-74, IGHV3-66, IGHV3-33, IGHV3-23, IGHV6-1, IGHV3-30, IGHV4-34, IGHV3-48, IGHV4-59, or IGHV4-39 can be detected (e.g., with a frequency >1% among the rearranged sequences).

In some embodiments, the usage of IGHV3-25, IGHV4-38-2, IGHV7-4-1, IGHV3-NL1, IGHV4-61, IGHV1-58, IGHV2-26, IGHV3-72, IGHV5-10-1, IGHV1-46, IGHV3-49, IGHV2-70, IGHV1-2, IGHV3-64, IGHV4-28, IGHV3-20, IGHV1-3, IGHV3-13, IGHV3-73, IGHV3-11, IGHV3-64D, IGHV1-69, IGHV2-5, or IGHV3-15 can be detected (e.g., with a frequency <1% among the rearranged sequences).

In addition, because V(D)J recombination may occur between endogenous IGHV, IGHD, IGHJ, IGKV and IGKJ genes and human genes, if the endogenous IGHV, IGHD, IGHJ, IGKV and IGKJ genes are incorporated in the rearranged heavy chain VDJ segment or the rearranged light chain VJ segment, it is likely that the antibodies generated by the antibody repertoires have immunogenic epitopes in human. The immunogenicity can lead to production of anti-drug-antibodies and may compromise efficacy. Here, in some embodiments, the endogenous IGHV, IGHD, IGHJ, IGKV and IGKJ genes have been effectively deleted. In some cases, the entire mouse IGHV genes, IGHD genes, and IGHJ genes (e.g., including all none-pseudo genes) are knocked out, and the heavy chain variable region will not have any sequence that is encoded by a sequence derived from the mouse.

It is less likely that the antibodies generated by the antibody repertoires are immunogenic in humans. Thus, the antibodies are more suitable for being used as therapeutics in humans. Therefore, the genetically modified animals provide an advantageous platform to produce humanized antibodies.

Genetically Modified Lambda Light Chain Immunoglobulin Locus

Lambda chain immunoglobulin locus (also known as IGL or immunoglobulin lambda locus) is a region on the chromosome (e.g., human chromosome 22) that contains genes for the light chains of human antibodies (or immunoglobulins). Similarly, the immunoglobulin light chain genes can also undergo a series rearrangement that lead to the production of a mature immunoglobulin light-chain nucleic acid (e.g., a lambda chain). In a healthy human individual, the total kappa to lambda ratio is roughly 2:1 in serum (measuring intact whole antibodies) or 1:1.5 if measuring free light chains. In mice, the total kappa to lambda ratio is roughly 9:1.

In some embodiments, the animal comprises a human lambda chain immunoglobulin locus.

In some embodiments, the animal comprises a disruption in the animal's endogenous lambda light chain immunoglobulin gene locus. In some embodiments, the disruption in the animal's endogenous light chain immunoglobulin gene locus comprises a deletion of one or more endogenous IGLV genes, one or more endogenous IGLJ genes, and/or one or more immunoglobulin lambda constant (IGLC) genes (e.g., IGLC1, IGLC2, IGLC3, and IGLC4).

The mouse lambda light chain immunoglobulin locus (IGL locus) is located on mouse chromosome 16. Table 11 lists IGLV, IGLJ, and IGLC genes and its relative orders in this locus.

TABLE 11

List of genes at mouse IGL locus

| IMGT Gene | Chromosomal localization | Gene orientation on chromosome | NCBI Gene ID | Reference GRCm38.p3 C57BL/6J | Gene positions in sequence |
|---|---|---|---|---|---|
| IGLV2 | 16A3 (11.93 cM) | REV | 110612 | NC_000082.6 | 19260403 . . . 19260844 |
| IGLV3 | 16A3 (11.91 cM) | REV | 404743 | NC_000082.6 | 19241208 . . . 19241679 |
| IGLJ2 | 16A3 (11.89 cM) | REV | 404739 | NC_000082.6 | 19200198 . . . 19200235 |
| IGLC2 | 16A3 (11.89 cM) | REV | 110786 | NC_000082.6 | 19198536 . . . 19198852 |
| IGLJ4 | 16A3 (11.89 cM) | REV | 404742 | NC_000082.6 | 19196495 . . . 19196536 |
| IGLC4 | 16A3 (11.89 cM) | REV | 404736 | NC_000082.6 | 19194999 . . . 19195312 |
| IGLV1 | 16A3 (11.82 cM) | REV | 16142 | NC_000082.6 | 19085017 . . . 19085460 |
| IGLJ3 | 16A3 (11.81 cM) | REV | 404740 | NC_000082.6 | 19067041 . . . 19067078 |
| IGLJ3P | 16A3 (11.81 cM) | REV | 404741 | NC_000082.6 | 19066371 . . . 19066408 |
| IGLC3 | 16A3 (11.81 cM) | REV | 110787 | NC_000082.6 | 19065365 . . . 19065681 |
| IGLJ1 | 16A3 (11.81 cM) | REV | 404737 | NC_000082.6 | 19063225 . . . 19063262 |
| IGLC1 | 16A3 (11.80 cM) | REV | 110785 | NC_000082.6 | 19061752 . . . 19062071 |

The disruption in the animal's endogenous lambda light chain immunoglobulin gene locus comprises a deletion of at least or about 1, 2, 3, 4, 5, 6, 7, 8, 9, 10, 11, or 12 mouse IGLV, IGLJ, and IGLC genes (e.g., genes as shown in Table 11). In some embodiments, the deletion compromises about or at least 1, 2, 3, or 4 mouse IGLC genes selected from IGLC1, IGLC2, IGLC3, and IGLC4. In some embodiments, the disruption compromises a deletion of about or at least 1, 2, or 3 mouse IGLV genes selected from IGLV1, IGLV2, and IGLV3. In some embodiments, the disruption compromises a deletion of about or at least 1, 2, 3, 4, or 5 mouse IGLJ genes selected from IGLJ1, IGLJ2, IGLJ3, IGLJ3P, and IGLJ4.

In some embodiments, the disruption in the animal's endogenous lambda light chain immunoglobulin gene locus comprises a deletion of about or at least 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 210 kb, 220 kb, 230 kb, 240 kb, 250 kb, 260 kb, 270 kb, 280 kb, 290 kb, 300 kb, 350 kb, 400 kb, 450 kb, 500 kb, or 1000 kb of nucleotides. In some embodiments, there is no disruption in the animal's endogenous lambda light chain immunoglobulin gene.

In some embodiments, the deleted sequence starts from IGLV2 to IGLC1, from IGLV3 to IGLC1, or from IGLJ2 to IGLC1.

A detailed description for genetically-modified animals and genetically modified heavy chain immunoglobulin locus can be found e.g., PCT/CN2020/075698, which is incorporated herein by reference in its entirety.

Genetically Modified Animals

In one aspect, the present disclosure provides genetically-modified, non-human animal comprising a humanized light chain immunoglobulin locus and/or humanized heavy chain immunoglobulin locus. The humanized light chain immunoglobulin locus comprises a limited set of human IGKV genes and/or one human IGKJ genes. In some embodiments, these genes are at the endogenous immunoglobulin gene locus.

In some embodiments, the animal comprises a human lambda chain immunoglobulin locus. In some embodiments, the animal comprises a disruption in the animal's endogenous lambda light chain immunoglobulin gene locus. In some embodiments, the animal does not have a disruption in the animal's endogenous lambda light chain immunoglobulin gene locus.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety. Thus, in various embodiments, human V, D, and/or J segments can be operably linked to non-human animal (e.g., rodent, mouse, rat, hamster) constant region gene sequences. During B cell development, these rearranged human V, D, and/or J segments are linked to the non-human animal immunoglobulin constant region.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57 background (e.g., a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola). In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S6/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized animal is made.

Genetically modified non-human animals that comprise a modification of an endogenous non-human immunoglobulin gene locus. In some embodiments, the modification can comprise a human nucleic acid sequence encoding at least a portion of a human protein (e.g., at least 10%, 20%, 30%, 40%, 50%, 60%, 70%, 80%, 90%, 95%, 96%, 97%, 98%, or 99% identical to the human heavy chain variable domain or light chain variable domain sequence). Although genetically modified cells are also provided that can comprise the modifications described herein (e.g., ES cells, somatic cells), in many embodiments, the genetically modified non-human animals comprise the modification of the endogenous locus in the germline of the animal.

Genetically modified animals can express a humanized antibody and/or a chimeric antibody from endogenous mouse loci, wherein one or more endogenous mouse immunoglobulin genes have been replaced with human immunoglobulin genes and/or a nucleotide sequence that is at least 10%, 20%, 30%, 40%, 50%, 60%, 70%, 80%, 90%, 95%, 96%, 97%, 98%, or 99% identical to the human immunoglobulin gene sequences (e.g., IGHV, IGHD, IGHJ, IGKV and/or IGKJ genes). In various embodiments, an endogenous non-human immunoglobulin gene locus is modified in whole or in part to comprise human nucleic acid sequence.

Genetic, molecular and behavioral analyses for the non-human mammals described above can performed. The present disclosure also relates to the progeny produced by the non-human mammal provided by the present disclosure mated with the same or other genotypes. Non-human mammals can be any non-human animal known in the art and which can be used in the methods as described herein. Preferred non-human mammals are mammals, (e.g., rodents). In some embodiments, the non-human mammal is a mouse.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human or humanized immunoglobulins can be detected by a variety of methods.

There are many analytical methods that can be used to detect exogenous DNA or modifications on the genomic DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized proteins.

Antibodies and Antigen Binding Fragments

The present disclosure provides antibodies and antigen-binding fragments thereof (e.g., humanized antibodies or chimeric antibodies) that are produced by the methods described herein.

In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or subclasses including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgG4, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, rat, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain.

In some embodiments, the scFV has one heavy chain variable domain, and one light chain variable domain. In some embodiments, the scFV has two heavy chain variable domains, and two light chain variable domains. In some embodiments, the scFV has two antigen binding regions, and the two antigen binding regions can bind to the respective target antigens.

The antibodies and antigen-binding fragments thereof (e.g., humanized antibodies or chimeric antibodies) that are produced by the methods described herein have various advantages. In some embodiments, no further optimization is required to obtain desired properties (e.g., binding affinities, thermal stabilities, and/or limited aggregation).

In some implementations, the antibody (or antigen-binding fragments thereof) specifically binds to a target with a dissociation rate (koff) of less than $0.1\ s^{-1}$, less than $0.01\ s^{-1}$, less than $0.001\ s^{-1}$, less than $0.0001\ s^{-1}$, or less than $0.00001\ s^{-1}$. In some embodiments, the dissociation rate (koff) is greater than $0.01\ s^{-1}$, greater than $0.001\ s^{-1}$, greater than $0.0001\ s^{-1}$, greater than $0.00001\ s^{-1}$, or greater than $0.000001\ s^{-1}$. In some embodiments, the koff of the majority of these antibodies (e.g., >50%, >60%, >70%, or >80%) is between $1\times10^{-2}/S$ and $1\times10^{-3}/S$.

In some embodiments, kinetic association rates (kon) is greater than $1\times10^2/Ms$, greater than $1\times10^3/Ms$, greater than $1\times10^4/Ms$, greater than $1\times10^5/Ms$, or greater than $1\times10^6/Ms$. In some embodiments, kinetic association rates (kon) is less than $1\times10^5/Ms$, less than $1\times10^6/Ms$, or less than $1\times10^7/Ms$. In some embodiments, the kon of the majority of these antibodies (e.g., >50%, >60%, >70%, or >80%) is between $1\times10^5/Ms$ and $1\times10^6/Ms$.

Affinities can be deduced from the quotient of the kinetic rate constants (KD=koff/kon). In some embodiments, KD is less than $1\times10^{-6}$ M, less than $1\times10^{-7}$ M, less than $1\times10^{-8}$ M, less than $1\times10^{-9}$ M, or less than $1\times10^{-10}$ M. In some embodiments, the KD is less than 50 nM, 40 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1\times10^{-7}$ M, greater than $1\times10^{-8}$ M, greater than $1\times10^{-9}$ M, greater than $1\times10^{-10}$ M, greater than $1\times10^{-11}$ M, or greater than $1\times10^{-12}$ M. In some embodiments, the antibody binds to a target with KD less than or equal to about 0.9 nM, 0.8 nM, 0.7 nM, 0.6 nM, 0.5 nM, 0.4 nM, 0.3 nM, 0.2 nM, or 0.1 nM. In some embodiments, the KD of the majority of these antibodies (e.g., >50%, >60%, >70%, or >80%) is between 0.10 nM and 100.00 nM (e.g., between 1 nM and 100 nM).

In some embodiments, the heavy chain CDR3 length of the antibodies produced by the animal as described herein has a median of 13~15 amino acids. In some embodiments, the heavy chain CDR3 length of the majority of these antibodies (e.g., >50%, >60%, >70%, or >80%) is between 9 and 18 amino acids, or between 10 and 17 amino acids.

In some embodiments, less than 30%, 20% or 15% of the heavy chain CDR3 in the antibodies produced by the animal as described herein has a cysteine residue (e.g., one cysteine residues or two cysteine residues). In some embodiments, the heavy chain CDR3 is no more than 21 amino acid residues.

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

As IgG can be described as a multi-domain protein, the melting curve sometimes shows two transitions, or three transitions, with a first denaturation temperature, Tm D1, and a second denaturation temperature Tm D2, and optionally a third denaturation temperature Tm D3.

In some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D3 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2, Tm D3 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibodies or antigen binding fragments as described herein do not form aggregation when the temperate is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

Methods of Making Genetically Modified Animals

The genetically modified animals can be made by introducing human immunoglobulin genes into the genome of non-human animals to produce animals that can express humanized antibodies or chimeric antibodies. FIG. 1A shows the methods of making the humanized animals. In some embodiments, the methods first involve modifying the human immunoglobulin locus on the human chromosome. The modified human chromosomes are then introduced into the mouse recipient cell. The human immunoglobulin variable region is then introduced into the corresponding region of the mouse genome by direct replacement. Then, the recipient cells are screened. In some embodiments, the cells do not contain the human chromosomes. The cells are then injected to blastocysts to prepare chimeric mice. Subsequent breeding can be performed to obtain mice containing intact humanized immunoglobulin locus.

Several other techniques may be used in making genetically modified animals, including, e.g., nonhomologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

The genetic modification process can involve replacing endogenous sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous sequence with human sequence.

In some embodiments, the methods for making a genetically modified, humanized animal, can include the step of replacing at an endogenous locus (or site), a nucleic acid (e.g., V, D, J regions, or V, J regions) with a corresponding region of human sequence. The sequence can include a region (e.g., a part or the entire region) of IGHV, IGHD, IGHJ, IGKV, and/or IGKJ genes. In some embodiments, the replacement is mediated by homologous recombination. In some embodiments, the replacement is mediated by Cre recombinase.

In some embodiments, the modification on mouse light chain immunoglobulin locus can be directly performed. In some embodiments, a vector is directly used to replace the entire mouse light chain immunoglobulin variable region. In some embodiments, the vectors can be inserted at the upstream of the V region, and between the J region and the C region.

In some embodiments, the modification on mouse light chain immunoglobulin locus can be performed by more than one steps. In some embodiments, a first vector can be used to replace the entire mouse light chain immunoglobulin variable region. In some embodiments, the vector includes one or more selection markers. In some embodiments, the selection marker is a dominant selection marker (e.g., neomycin resistance gene, or Neo). In some embodiments, the selection marker is a negative selection marker (e.g., diphtheria toxin receptor gene, or DTR). In some embodiments, the first vector contains one or more dominant and/or one or more negative selection markers. In some embodiments, a second vector can be used to further replace a region include one or more selection markers as described herein.

Figure 4:
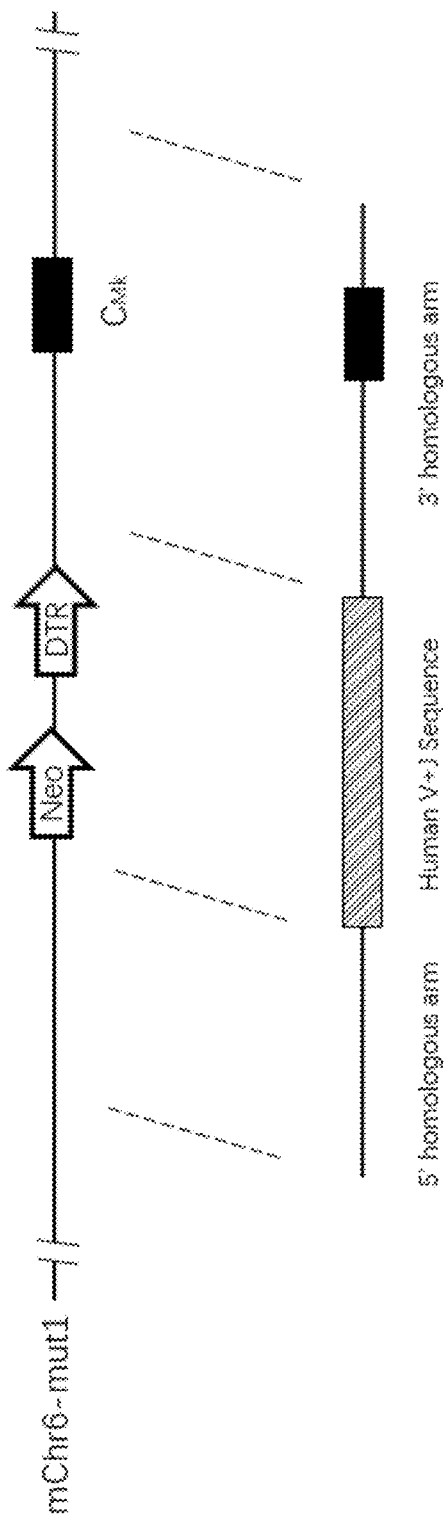
FIG. 4 is a schematic diagram showing the targeting strategy of kappa light chain gene humanization.
Figures 5A, 5B:
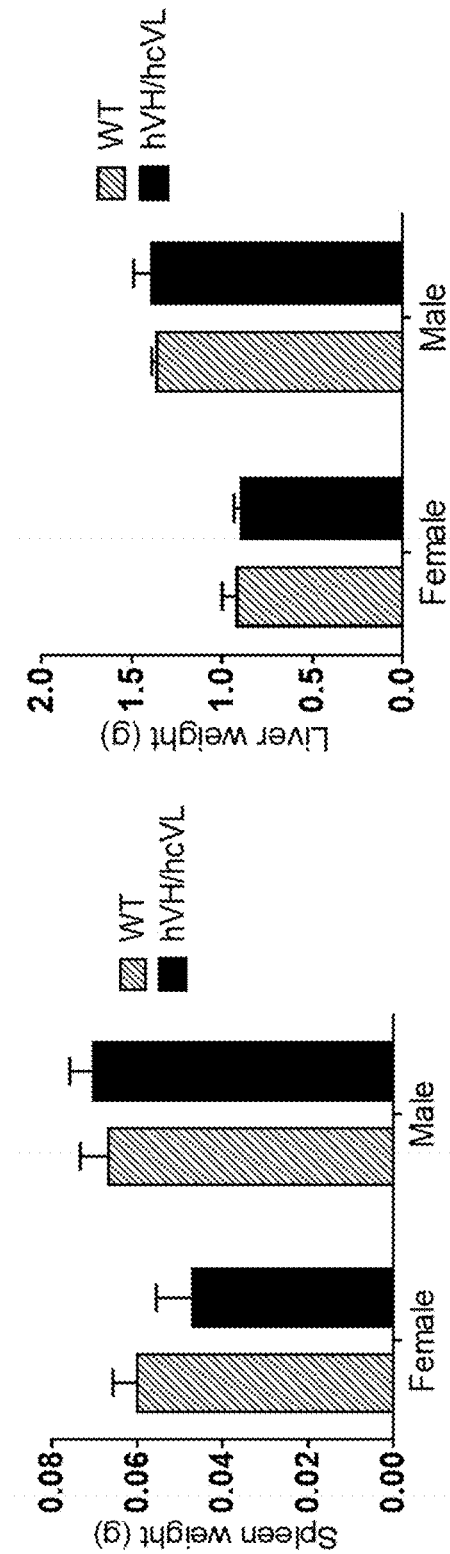
FIG. 5A is a histogram showing the body weight of wild-type (WT) and hVH/hcVL heterozygous mice.
FIG. 5B is a histogram showing the liver weight of wild-type (WT) and hVH/hcVL heterozygous mice.
Figure 5D:
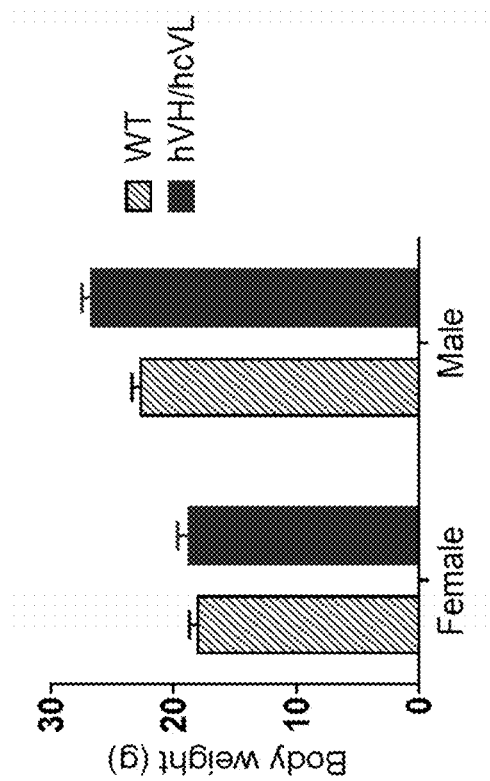
FIG. 5D is a histogram showing the spleen weight of wild-type (WT) and hVH/hcVL heterozygous mice.
Figure 5C:
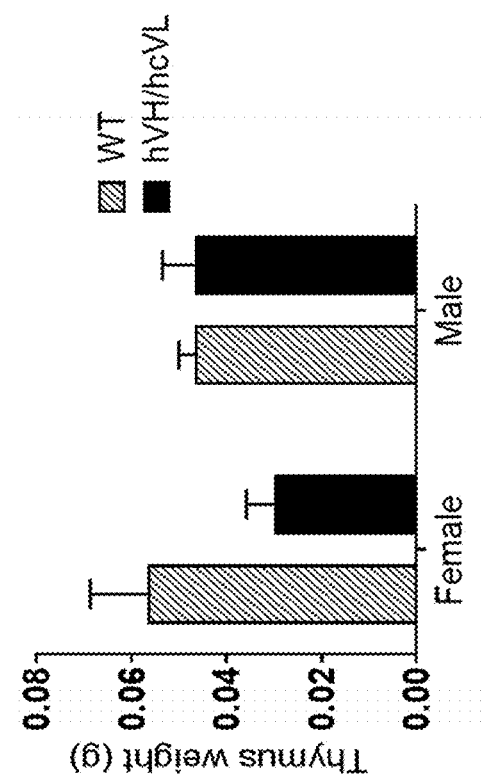
FIG. 5C is a histogram showing the thymus weight of wild-type (WT) and hVH/hcVL heterozygous mice.
Figure 5F:
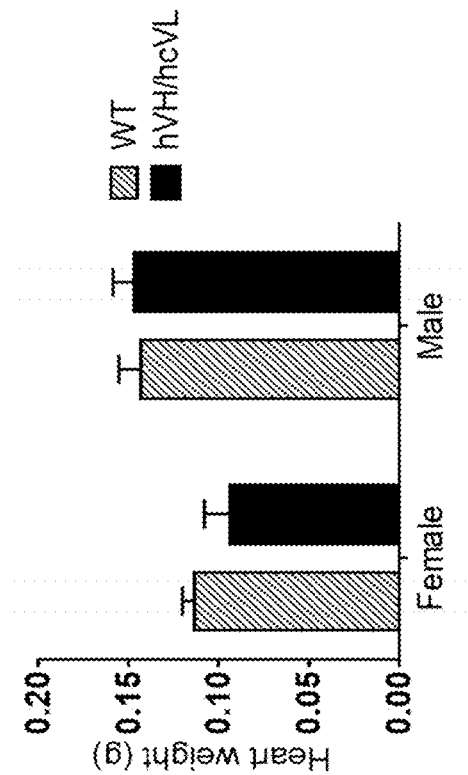
FIG. 5F is a histogram showing the heart weight of wild-type (WT) and hVH/hcVL heterozygous mice.
Figure 5E:
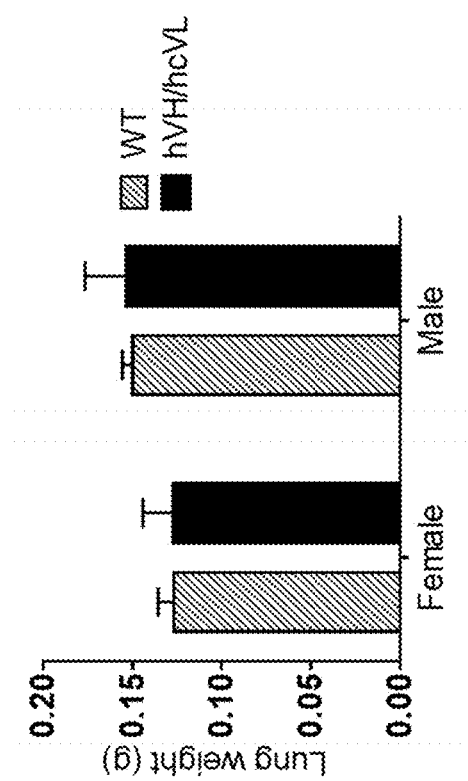
FIG. 5E is a histogram showing the lung weight of wild-type (WT) and hVH/hcVL heterozygous mice.
Figure 5G:
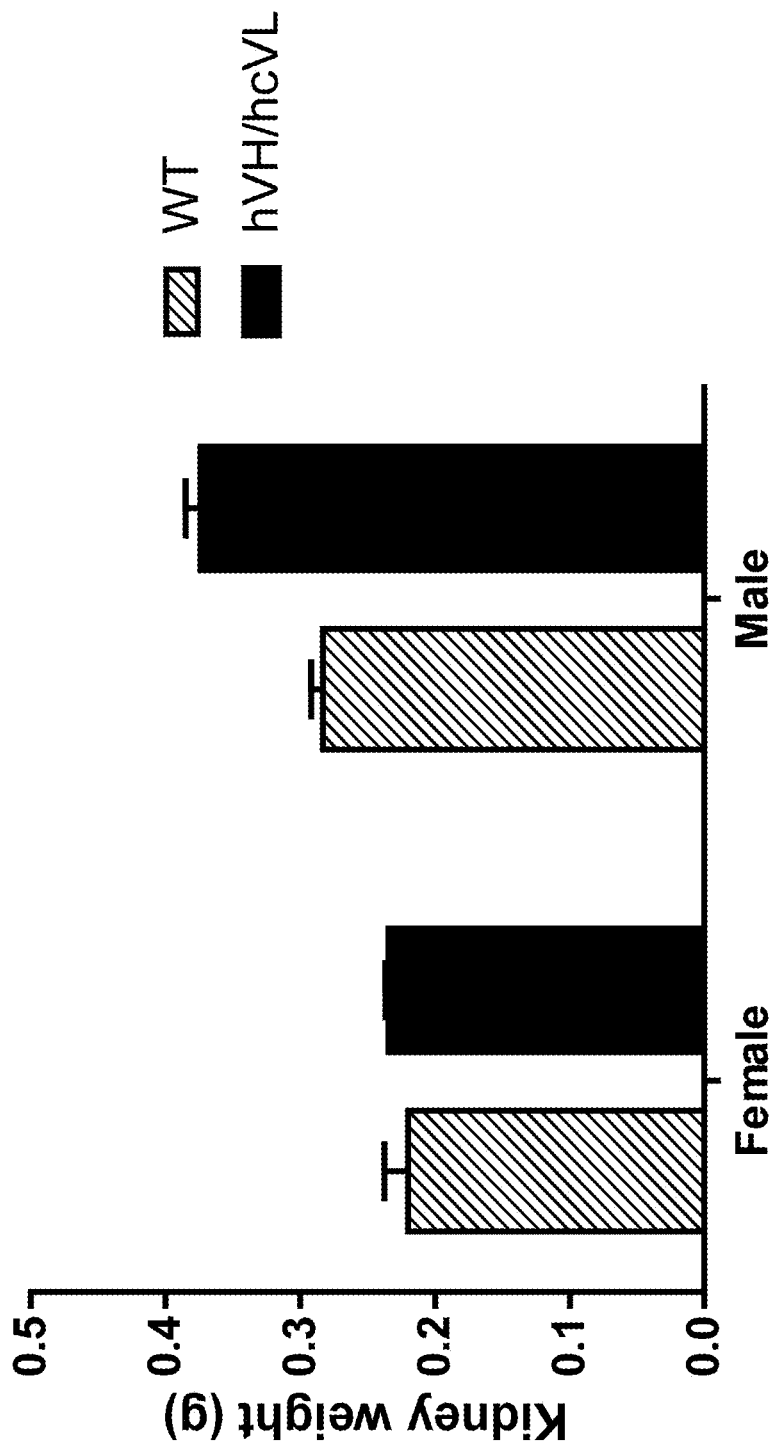
FIG. 5G is a histogram showing the kidney weight of wild-type (WT) and hVH/hcVL heterozygous mice.

FIG. 4 shows a targeting strategy for replacing the endogenous mouse light chain immunoglobulin variable region with human light chain variable region (e.g., rearranged or unrearranged human light chain variable region sequence). For example, the human light chain variable region can include a human IGKV gene that is selected from IGKV3-20, IGKV3-11, and IGKV1-39; and a human IGKJ gene that is selected from IGKJ1, and IGKJ4. In some embodiments, the entire mouse light chain variable region is replaced by a first vector comprising a Neo and a DTR selection marker gene. In some embodiments, a second vector has from 5' to 3' one or more of the following: a DNA homology arm sequence at upstream of the insertion site (5' homologous arm); the promoter sequence before the first nucleotide of the human IGKV gene (e.g., at least or about 2000 bp before the human IGKV gene); the human IGKV gene (e.g., IGKV3-20, IGKV3-11, or IGKV1-39); the human IGKJ gene (e.g., IGKJ1 or IGKJ4); the auxiliary sequence (e.g., a polyA sequence, a WPRE sequence, or 3'UTR sequence); and a DNA homology arm sequence at downstream of the insertion site (3' homologous arm).

These vectors can be integrated into the genome of the cells, and the cells can be selected by drug resistance markers or a combination thereof (e.g., Zeocin, G418, and/or Puromycin). In some embodiments, the PB transposase is expressed, and the genetic elements between the transposase target sequence can be deleted.

In some embodiments, these vectors are integrated into a human chromosome that has been modified. The human chromosome can be modified first, before the first and the second vectors are integrated into the genome. In some embodiments, one or more additional vectors can be added at various locations of the chromosome as needed. In some embodiments, the vector is added between the C region and the centromere.

The human chromosome can be obtained from human cell lines, cancer cells, primary cell culture, and/or human fibroblasts. In some embodiments, the human cell is introduced with a first vector and is then fused with a recipient cell. The modified chromosome is then separated and introduced into another appropriate recipient cell. Cells with the desired resistance are selected to obtain cells containing only one human chromosome. Then, a second vector is introduced into the cells, and the cells are selected by resistance. Then, if needed, a third vector, and/or a fourth vector can be introduced. The recipient cell can be a mammalian cell, a human cell, or a mouse cell. In some embodiments, the recipient cell is a CHO cell, or preferably an A9 cell. In some embodiments, the modified chromosomes are labeled by fluorescence and separated. And the modified chromosomes are injected into the recipient cells by chromosome microinjection. In some embodiments, the donor cells are induced to multinucleate their chromosomes. These nuclei are then forced through the cell membrane to create microcells, which can be fused to a recipient cell. In some embodiments, microcell-mediated chromosome transfer can also be used. The chromosome manipulation techniques are described e.g., in CN1200014A; CN109837307A; US20120093785A1; and US2009253902; Kuroiwa et al. "Manipulation of human minichromosomes to carry greater than megabase-sized chromosome inserts." Nature Biotechnology 18.10 (2000)): 1086-1090; Chinese patent CN1717483A; Paulis, Marianna. "Chromosome Transfer Via Cell Fusion." Methods in Molecular Biology 738(2011): 57; Genes, Chromosomes & Cancer 14: 126127 (1995); Tomizuka et al. "Functional expression and germline a transmission of a human chromosome fragment in chimaeric mice." Nature Genetics 16.2 (1997): 133-143; Somatic Cell and Molecular Genetics, Vol. 13, No. 3, 1987, pp. 279-284; each of which is incorporated herein by reference in its entirety.

LoxP recognition sequences can also be added to the human chromosome (e.g., human chromosome 2, 14, 22). The cells can also be treated with Cre enzyme, leading to the recombination of the loxP sites, thereby removing genomic DNA sequences. In some embodiments, spontaneous chromosome breakage can be used to remove genomic DNA sequences as well.

The mouse immunoglobulin variable region can be replaced by the human immunoglobulin variable region by replacement (e.g., homologous recombination, or Cre mediated recombination). In some embodiments, Cre recombination can be used to mediate the replacement. In some embodiments, the vectors can add LoxP recognition sequence into the human chromosome. Similar modifications can be made to the mouse chromosome, wherein two LoxP recognition sequences can be added to the chromosome. For example, Cre recombinase can then mediate the replacement of V, J regions on mouse chromosome with the V, J regions on human chromosome or the replacement of V, D, J regions on mouse chromosome with the V, D, J regions on human chromosome.

The cells can be further screened for cells that do not have human chromosomes (e.g., by DT). In some cases, cells that are not screened by DT may contain recombinant human chromosome fragments, but these fragments are small and are unstable in mouse cells (e.g., Shinohara et al. (2000) Chromosome Research, 8: 713-725), and will naturally disappear during cell proliferation. In some embodiments, a large fragment of the modified human chromosome is deleted, e.g., by Cre-mediated deletion or by spontaneous chromosomal breakage.

The 5' end homologous arm and/or the 3' end homologous arm can have a desired length to facilitate homologous recombination. In some embodiments, the homology arm is about or at least 1, 2, 3, 4, 5, 6, 7, 8, 9, 10, 20, 30, 40, or 50 kb (e.g., about 3 kb). In some embodiments, the homology arm is less than 1, 2, 3, 4, 5, 6, 7, 8, 9, 10, 20, 30, 40, or 50 kb.

In some embodiments, the vector may also optionally include a reporter protein, e.g., a luciferase (e.g., Gluc) or a fluorescent protein (e.g., EGFP, BFP, etc.).

These modifications can be performed in various cells. In some embodiments, the cell is a stem cell, an embryonic stem cell, or a fertilized egg cell.

The present disclosure further provides a method for establishing a humanized animal model, involving the following steps:

(a) providing the cell (e.g. a fertilized egg cell) based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, the non-human mammal in the foregoing method is a mouse (e.g., a C57 mouse, a BALB/c mouse, or a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Cells, tissues, and animals (e.g., mouse) are also provided that comprise the nucleotide sequences as described herein, as well as cells, tissues, and animals (e.g., mouse) that express humanized or chimeric antibodies from an endogenous non-human locus.

The present disclosure also provides various targeting vectors (e.g., vectors that are useful for making the genetically modified animals). In some embodiments, the vector can comprise: a) a DNA fragment homologous to the 5' end of a region to be altered (5' homology arm); b) a sequence comprising desired genetic elements (e.g., LoxP recognition site, drug resistance genes, and/or reporter genes etc.); and c) a second DNA fragment homologous to the 3' end of the region to be altered (3' homology arm). The disclosure also relates to a cell comprising the targeting vectors as described herein.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

The present disclosure further relates to methods for generating genetically modified animal model with two or more human or chimeric genes. The animal can comprise one or more human or humanized immunoglobulin locus and a sequence encoding an additional human or chimeric protein. In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (TNFRSF4 or OX40).

The methods of generating genetically modified animal model with additional human or chimeric genes (e.g., humanized genes) can include the following steps:

(a) using the methods as described herein to obtain a genetically modified non-human animal;
(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD47, CD137, CD154, TIGIT, TIM-3, GITR, SIRPa, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

The present disclosure further relates to methods for generating a knockout animal. In some embodiments, if the animal (e.g., mouse) expresses a protein that is very similar to the antigen of interest, it can be difficult to elicit an immune response in the animal. This is because during immune cell development, B-cells and T-cells that recognize MHC molecules bound to peptides of self-origin are deleted from the repertoire of immune cells. In those cases, the genetically engineered animal can be further modified. The corresponding gene in the animal can be knocked out, and the animal is then exposed to the antigen of interest. Because the animal does not go through negative selection for the gene product, the animal can generate an antibody that can specifically bind to the target easily. Thus, in some embodiments, the disclosure also provides methods of knocking out a gene of interest in the genetically modified animals. In some embodiments, the gene can be knocked out by various known gene-editing techniques, e.g., CRISPR-Cas system, TALEN, or ZFNs. In some embodiments, the genetically modified animal can be mated with another animal in which the gene of interest has been knocked-out. Once the animal with the knockout phenotype is created, the animal can be exposed to an antigen of interest to generate an antibody (e.g., an antibody with a common light chain). In some embodiments, the antigen of interest is a human protein. In some embodiments, the antigen of interest is PD-1, CTLA-4, LAG-3, BTLA, PD-L1, CD27, CD28, CD47, CD137, CD154, TIGIT, TIM-3, GITR, SIRPa, or OX40.

In some embodiments, the genetically modified animals can have a human ADAM6 gene, an endogenous ADAM6 gene or a modified ADAM6 gene (e.g., at its endogenous locus). The ADAM6 protein is a member of the ADAM family of proteins, where ADAM is an acronym for A Disintegrin And Metalloprotease. The human ADAM6 gene, normally found between human IGHV genes IGHV1-2 and IGHV6-1, is a pseudogene (FIG. 16). In mice, there are two ADAM6 genes, ADAM6a and ADAM6b. They are located in an intergenic region between mouse IGHV and IGHD gene clusters. The mouse ADAM6a is located between mouse IGHV5-1 and mouse IGHD5-1. The mouse ADAM6b is located between mouse IGHD3-1 and mouse IGHD1-1. Thus, in some embodiments, the genetically modified animals can have a human ADAM6 gene. In some embodiments, the genetically modified animals do not have an endogenous ADAM6 gene.

In some embodiments, the genetically modified animals are mice. In some embodiments, the mice are modified to include a nucleotide sequence that encodes an ADAM6 protein (e.g., ADAM6a or ADAM6b). In some embodiments, the sequence is placed at any suitable position. It can be placed in the intergenic region, or in any suitable position in the genome. In some embodiments, the nucleic acid encodes a sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a mouse ADAM6a gene (e.g., 113539230-113547024 of NC 000078.6) or a mouse ADAM6b gene (e.g., 113486188-113492125 of NC 000078.6). In some embodiments, the nucleic acid additionally includes the regulatory elements for the ADAM6a gene and ADAM6b gene (e.g., promoters).

In some embodiments, a functional mouse ADAM6 locus can be placed in the midst of human IGHV gene cluster. In some embodiment, the mouse ADAM6 locus is between two human IGHV genes. In some embodiments, the human ADAM6 pseudogene between human VH1-2 and human VH(II)-1-1 is replaced with the mouse ADAM6 locus. In some embodiments, the ADAM6a gene and the ADAM6b gene are located between human IGHV1-2 and human VH(II)-1-1 in the genome of the animal. In some embodiments, the location of the mouse ADAM6 sequence within the human gene sequence can approximate the position of the human ADAM6 pseudogene or can approximate the position of the mouse ADAM6 sequence (e.g., within the V-D intergenic region). In some embodiments, the genetic modified mice has a humanized heavy chain immunoglobulin locus. In some embodiments, the mouse ADAM6a and the mouse ADAM6b are located between human IGHV1-2 and IGHV6-1 genes. Placing the mouse ADAM6a and the mouse ADAM6b between human IGHV1-2 and IGHV6-1 genes can have various advantages. For example, because these genes replace the human ADAM6 gene at the same locus, it is likely that the replacement of human ADAM6 gene will have limited impact on the VDJ recombination and the mouse ADAM6a and the mouse ADAM6b gene can also function properly (as in a location that is similar to the endogenous locus).

Thus, in one aspect, the disclosure provides a genetically-modified animal comprising at an endogenous heavy chain immunoglobulin gene locus, a first sequence comprising one or more human IGHV genes; a second sequence comprising a ADAM6 gene; and a third sequence comprising one or more human IGHD genes, and one or more human IGHJ genes. In some embodiments, the first sequence, the second sequence, and the third sequence are operably linked.

In some embodiments, the first sequence comprises all human IGHV genes in Table 5 except IGHV2-10, IGHV3-9, IGHV1-8, IGHV(II)-1-1, and IGHV6-1. In some embodiments, the first sequence comprises all human IGHV genes in Table 5 except IGHV5-10-1 and IGHV3-64D, IGHV(II)-1-1, and IGHV6-1. In some embodiments, the first sequence comprises IGHV5-10-1 and IGHV3-64D. In some embodiments, the first sequence is an unmodified sequence derived from a human heavy chain immunoglobulin gene locus.

In some embodiments, the second sequence comprises either one or both of a mouse ADAM6a gene and a mouse ADAM6b gene. In some embodiments, the animal is a fertile male mouse. In some embodiments, the second sequence does not have a mouse ADAM6a gene or a mouse ADAM6b gene.

In some embodiments, the third sequence comprises all human IGHD genes in Table 6, and all human IGHJ genes in Table 7. In some embodiments, the third sequence comprises human IGHV6-1. In some embodiments, the third sequence comprises human IGHV(II)-1-1. In some embodiments, the third sequence is an unmodified sequence derived from a human heavy chain immunoglobulin gene locus.

In some embodiments, the AMAM6a and/or ADAM6b are endogenous sequences. In some embodiments, the AMAM6a and/or ADAM6b are not replaced, and/or located in its endogenous or native position. In some embodiments, the mouse IGHV genes before mouse IGHV1-2 in the heavy chain variable region locus are replaced with human IGHV genes. In some embodiments, the mouse IGHV, IGHD and IGHJ genes after mouse IGHV6-1 in the heavy chain variable region locus are replaced with one or more human IGHV genes, IGHD and/or IGHJ genes.

Thus, in some embodiments, the mouse IGHV, IGHD and IGHJ genes can be replaced with human IGHV, IGHD and IGHJ by more than one replacement. In the first step, a selected number of mouse IGHV genes on the 5' side of the ADAM6a (e.g., all mouse IGHV genes in Table 8) are replaced with human IGHV genes. In the second step, a selected number of mouse IGHD and IGHJ genes on the 3' side of the ADAM6b (e.g., all mouse IGHD genes in Table 9 except IGHD5-1 and IGHD3-1 and all IGHJ genes in Table 10) are replaced with human IGHD and human IGHJ genes. The replacement can be performed by homologous recombination or Cre-mediated recombination.

In some embodiments, the mice do not have mouse ADAM6a or ADAM6b genes. In some embodiments, the mice have human ADAM6 genes.

Various methods can be used to increase the fertility of the mice. In some embodiments, female mice with superovulation can be used in mating. In some embodiments, in vitro fertilization can be used. Superovulation can be induced by injecting serum gonadotropin and chorionic gonadotropin (e.g., human or mouse CG) into a mature female mouse. A mature male mouse can be sacrificed and its cauda epididymides can be isolated. The duct of cauda epididymis is cut open to release sperm. Next, a superovulating mature female mouse can be sacrificed and the oviducts can be isolated. Cumulus-oocyte-complexes (COCs) can be released from the oviduct. Next, sperm suspension can be added to the COCs and incubated for insemination. Pathenogenic oocytes containing only one pronucleus can be removed. After the incubation, embryos at 2-cell stage can be transferred to recipient females. Methods of increasing mouse fertility are known in the art.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 250, 300, 350, or 400 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of illustration, the comparison of sequences and determination of percent identity between two sequences can be accomplished by e.g., using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage. Thus, the present disclosure also provides an amino acid sequence that has at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% homology percentage to any amino acid sequence as described herein, or a nucleic acid encoding these amino acid sequences.

Methods of Using Genetic Modified Animals

The genetic modified animals can be used to generate humanized or chimeric antibodies that can bind specifically to a target. In some embodiments, the target (e.g., a protein or a fragment of the protein) can be used as an immunogen to generate antibodies in these animals using standard techniques for polyclonal and monoclonal antibody preparation. In some embodiments, the genetic modified animal is exposed to a selected antigen for a time and under conditions which permit the animal to produce antibody specific for the antigen.

Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence and encompasses an epitope of the protein such that an antibody raised against the peptide forms a specific immune complex with the protein.

An immunogen typically is used to prepare antibodies by immunizing a suitable subject (e.g., the genetically modified animal as described herein). An appropriate immunogenic preparation can contain, for example, a recombinantly-expressed or a chemically-synthesized polypeptide (e.g., a fragment of the protein). The preparation can further include an adjuvant, such as Freund's complete or incomplete adjuvant, or a similar immunostimulatory agent.

Polyclonal antibodies can be prepared as described above by immunizing a suitable subject with a polypeptide, or an antigenic peptide thereof (e.g., part of the protein) as an immunogen. The antibody titer in the immunized subject can be monitored over time by standard techniques, such as with an enzyme-linked immunosorbent assay (ELISA) using the immobilized polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

In one aspect, the disclosure provides a mouse that comprises a modification of an endogenous immunoglobulin heavy chain locus, wherein the mouse produces a B cell that comprises a rearranged immunoglobulin sequence operably linked to a heavy chain constant region gene sequence. In some embodiment, the rearranged immunoglobulin sequence operably linked to the heavy chain constant region gene sequence comprises a human heavy chain V, D, and/or J sequence. In some embodiments, the heavy chain constant region gene sequence comprises a human or a mouse heavy chain sequence selected from the group consisting of a CH1, a hinge, a CH2, a CH3, and a combination thereof.

In one aspect, the disclosure provides a mouse that comprises a modification of an endogenous immunoglobulin light chain (e.g., kappa or lambda) locus, wherein the mouse produces a B cell that comprises a rearranged immunoglobulin sequence operably linked to a light chain constant region gene sequence. In some embodiments, the rearranged immunoglobulin sequence operably linked to the light chain constant region gene sequence comprises a human light chain V and/or J sequence. In some embodiments, the light chain constant region gene sequence comprises a human or a mouse light chain constant region.

The mouse B cells or spleen cells can comprise a rearranged non-mouse immunoglobulin variable gene sequence, e.g., operably linked to a mouse immunoglobulin constant region gene. The sequences for encoding human heavy chain variable region and human light chain variable region are determined. The sequences can be determined by e.g., sequencing the hybridoma of interest or B cells. In some embodiments, single B cell screening is used. It can screen the natural antibody repertoire without the need for hybridoma fusion and combinatorial display. For example, B cells can be mixed with a panel of DNA-barcoded antigens, such that both the antigen barcode(s) and B-cell receptor (BCR) sequences of individual B cells are recovered via single-cell sequencing protocols.

The antibodies can be further modified to obtain a humanized antibody or a human antibody, e.g., by operably linking the sequence encoding human heavy chain variable region to a sequence encoding a human heavy chain constant region, and/or operably linking the sequence encoding human light chain variable region to a sequence encoding a human light chain constant region.

The disclosure also provides methods of making antibodies, nucleic acids, cells, tissues (e.g., spleen tissue). In some embodiments, the methods involve exposing the animal as described herein to the antigen. Antibodies (e.g., hybrid antibodies), nucleic acids encoding the antibodies, cells, and/or tissues (e.g., spleen tissue) can be obtained from the animal. In some embodiments, the nucleic acids encoding human heavy and light chain immunoglobulin variable regions are determined, e.g., by sequencing. In some embodiments, the nucleic acid encoding the human heavy chain immunoglobulin variable region can be operably linked with a nucleic acid encoding a human heavy chain immunoglobulin constant region. In some embodiments, the nucleic acid encoding the human light chain immunoglobulin variable region can be operably linked with a nucleic acid encoding a human light chain immunoglobulin constant region. In some embodiments, the cells containing the nucleic acids as described herein are cultured and the antibodies are collected.

In some embodiments, no mouse immunoglobulin V, D, J genes (e.g., no mouse IGHV, IGHD, IGHJ, IGKV, or IGKJ genes) contributes to the heavy chain and/or light chain variable region sequence. In some embodiments, the heavy chain and/or light chain variable region sequence produced by the animal are fully human, and are completely contributed by human immunoglobulin V, D, J genes (e.g., human IGHV, IGHD, IGHJ, IGKV, and IGKJ genes).

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

Additional modifications to the antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

Methods of Making Bispecific Antibodies with Common Light Chains

The present disclosure provides a genetically engineered animal that expresses a limited repertoire of light chains that can be associated with a diversity of heavy chains. In various embodiments, the endogenous kappa light chain variable region genes are deleted and replaced with a single, two, three, four, or five human light chain variable region genes, operably linked to the endogenous kappa constant region gene. In various embodiments, the animal also comprises a nonfunctional lambda light chain locus, or a deletion thereof or a deletion that renders the locus unable to make a lambda light chain.

In some embodiments, the animal comprises a light chain variable region locus lacking an endogenous light chain variable gene and comprising a rearranged human V/J sequence, operably linked to an endogenous constant region, and wherein the locus expresses a light chain comprising the human V/J sequence linked to the endogenous constant region.

The genetically engineered animal in various embodiments when immunized with an antigen of interest generates B cells that exhibit a diversity of rearrangements of human immunoglobulin heavy chain variable regions that express and function with a limited number (e.g., 1, 2, 3, 4, 5) of rearranged light chains, including embodiments where the one or two light chains comprise human light chain variable regions that comprise, e.g., 1 to 5 somatic mutations. In some embodiments, at least 50%, 60%, 70%, 80%, 90%, or 95% of the human light chain variable regions have at least 1 somatic mutation. In some embodiments, at least 50%, 60%, 70%, 80%, 90%, or 95% of the human light chain variable regions have at least 2 somatic mutations. In some embodiments, at least 50%, 60%, 70%, 80%, 90%, or 95% of the human light chain variable regions have at least 3 somatic mutations.

In some embodiments, the somatic hypermutations rate is relatively low. In some embodiments, no more than 30% or 40% of the human light chain variable regions have one or more than one somatic mutation. In some embodiments, no more than 20% of the human light chain variable regions have two or more than two somatic mutations.

In some embodiments, the animal as described herein can be immunized with a first immunogen to generate a B cell that expresses an antibody that specifically binds a first epitope. The animal can be immunized with a second immunogen to generate a B cell that expresses an antibody that specifically binds the second epitope. The heavy chain variable regions can be cloned from the B cells to a vector that is used to transfect a cell to express the rearrange human heavy chain variable region fused to a human heavy chain constant region, and the common light chain variable region fused to a human light chain constant region.

In some embodiments, the methods described here are designed to make a bispecific antibody. Bispecific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

In some embodiments, knob-into-hole (KIH) technology can be used, which involves engineering CH3 domains to create either a "knob" or a "hole" in each heavy chain to promote heterodimerization. The KIH technique is described e.g., in Xu, Yiren, et al. "Production of bispecific antibodies in 'knobs-into-holes' using a cell-free expression system." MAbs. Vol. 7. No. 1. Taylor & Francis, 2015, which is incorporated by reference in its entirety. In some embodiments, one heavy chain has a T366W, and/or S354C (knob) substitution (EU numbering), and the other heavy chain has an Y349C, T366S, L368A, and/or Y407V (hole) substitution (EU numbering). In some embodiments, one heavy chain has one or more of the following substitutions Y349C and T366W (EU numbering). The other heavy chain can have one or more the following substitutions E356C, T366S, L368A, and Y407V (EU numbering). In some embodiments, one heavy chain has a T366Y (knob) substitution, and the other heavy chain has one, two, or three of these substitutions T366S, L368A, Y407V (hole).

Furthermore, an anion-exchange chromatography can be used to purify bispecific antibodies. Anion-exchange chromatography is a process that separates substances based on their charges using an ion-exchange resin containing positively charged groups, such as diethyl-aminoethyl groups (DEAE). In solution, the resin is coated with positively charged counter-ions (cations). Anion exchange resins will bind to negatively charged molecules, displacing the counter-ion. Anion exchange chromatography can be used to purify proteins based on their isoelectric point (pI). The isoelectric point is defined as the pH at which a protein has no net charge. When the pH>pI, a protein has a net negative charge and when the pH<pI, a protein has a net positive charge. Thus, in some embodiments, different amino acid substitution can be introduced into two heavy chains, so that the pI for the homodimer comprising two Arm A and the pI for the homodimer comprising two Arm B is different. As used herein, the term "arm" in a bispecific antibody refers to an antigen-binding site in the bispecific antibody that specifically binds to a particular antigen (or epitope). The pI for the bispecific antibody having Arm A and Arm B will be somewhere between the two pIs of the homodimers. Thus, the two homodimers and the bispecific antibody can be released at different pH conditions. The present disclosure shows that a few amino acid residue substitutions can be introduced to the heavy chains to adjust pI. Thus, in some embodiments, the amino acid residue in the VH at Kabat numbering position 83 is lysine, arginine, or histidine. In some embodiments, the amino acid residues in the VH at one or more of the positions 1, 6, 43, 81, and 105 (Kabat numbering) is aspartic acid or glutamic acid. In some embodiments, the amino acid residues at one or more of the positions 13 and 105 (Kabat numbering) is aspartic acid or glutamic acid. In some embodiments, the amino acid residues at one or more of the positions 13 and 42 (Kabat numbering) is lysine, arginine, histidine, or glycine.

EXAMPLES

Example 1: Overview

Experiments were performed to introduce human immunoglobulin genes into the mouse genome to produce mice expressing humanized antibodies. FIG. 1A shows the methods of making the humanized mice. The methods first involve modifying the human immunoglobulin region on the human chromosome. The modified human chromosomes were then introduced into the mouse recipient cell.

The mouse immunoglobulin variable region was replaced by the human immunoglobulin variable region by direct replacement (e.g., homologous recombination, or Cre mediated recombination). In some cases, the human immunoglobulin variable region can be introduced into the mouse genome by a stepwise approach. Then, the recipient cells were screened for the correct replacement. The cells were then injected to blastocysts to prepare chimeric mice. Subsequent breeding was performed to obtain mice containing human or humanized immunoglobulin variable regions.

Because the mouse heavy chain gene and the two light chain genes are located on chromosomes 12, 6, and 16, respectively, mice containing the human heavy chain variable region or the human light chain variable region can be prepared separately. These mice can then be mated with each other to obtain mice that can express both the human heavy chain variable domain and the human common light chain variable domain.

Example 2: Modification of the Mouse Heavy Chain Immunoglobulin Locus

The heavy chain immunoglobulin locus is located on mouse chromosome 12. Two recombination sites were introduced on both sides of the variable region of the heavy chain immunoglobulin locus.

Figure 1B:
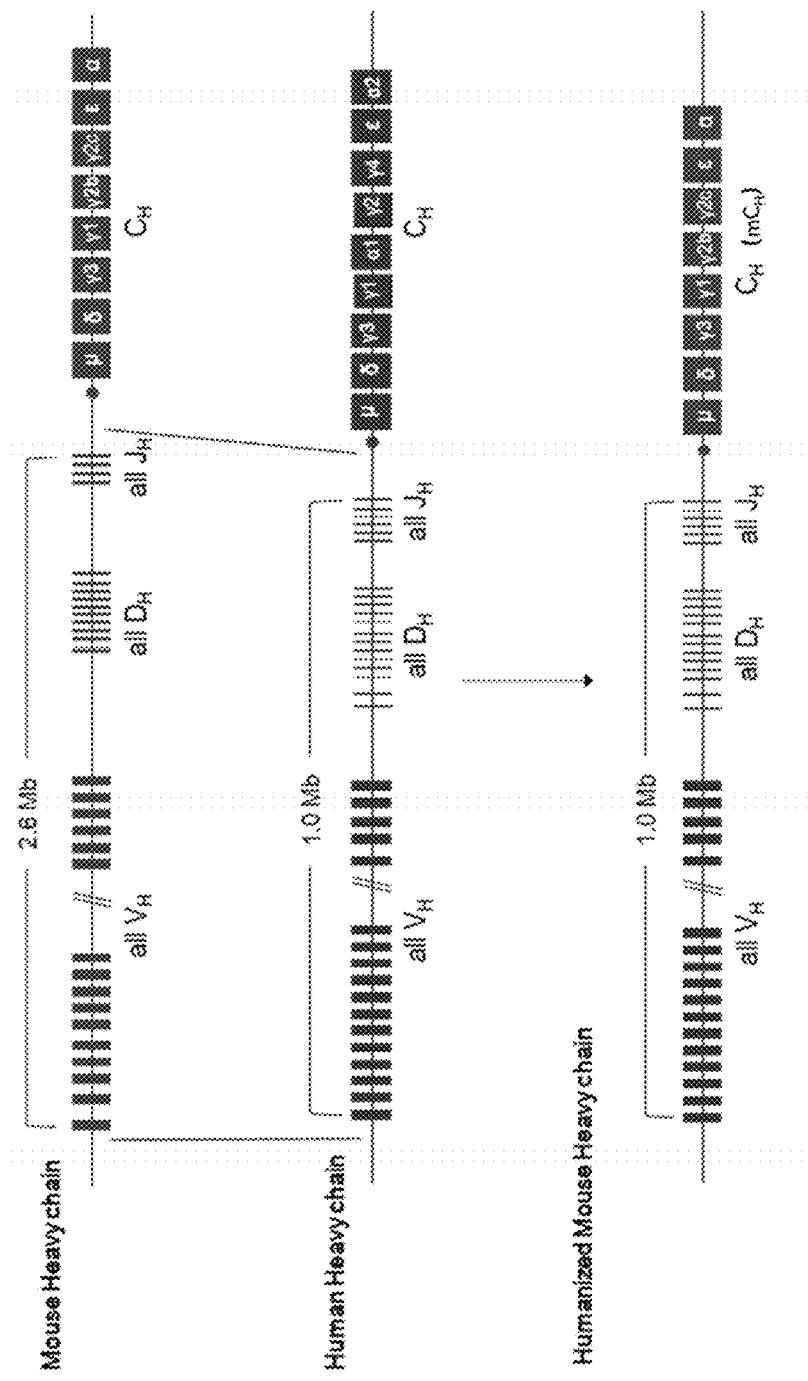
FIG. 1B is an overview of replacing mouse immunoglobulin heavy chain variable region with human immunoglobulin heavy chain variable region.

Experiments were also performed to generate a modified human chromosome. Two recombination sites were introduced on both sides of the variable region of the heavy chain immunoglobulin locus. The modified human chromosome was then introduced the into mouse cell. The cells were then screened. Only the cell containing only one human chromosome was selected. Cre recombinase then mediated the replacement of V, D, J regions on mouse chromosome with the V, D, J regions on human chromosome (FIG. 1B).

The positive clone cells were injected into the blastocysts of BALB/c mice by microinjection. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mice were then mated with mice having C57BL/6 background. PCR analysis was performed on the DNA obtained from the tail of the mice. The mice were further crossed with mice with BALB/c background several times (e.g., at least 5 times) to obtain humanized heavy chain immunoglobulin locus heterozygous mice with BALB/c background.

The heterozygous mice were then mated with each other to obtain a homozygous mouse. A detailed description regarding how to make humanized heavy chain immunoglobulin locus homozygous mice is provided in PCT/CN2020/075698, filed on Feb. 18, 2020, which is incorporated herein by reference in its entirety.

Example 3: Sequence Design for Light Chain VJ Regions

The utilization of human light chain variable region sequences in various antibodies was analyzed.

(1) Data were collected from the IMGT/GeneFrequency Database. Statistical analysis of the data showed that the top five highly utilized Kappa light chain V region genes were the following: IGKV3-20, IGKV1-39/IGKV1D-39, IGKV3-11, IGKV3-15, IGKV4-1. The top three highly utilized Kappa light chain J region genes were: IGKJ1, IGKJ2, IGKJ4.

TABLE 12

| Gene | Sequences assigned to one gene (colored part) | Sequences assigned to more than one gene (white part) | Total count |
|---|---|---|---|
| Variable genes | | | |
| IGKV3-20 | 816 | 3 | 819 |
| IGKV1D-39 | 21 | 490 | 511 |
| IGKV1-39 | 0 | 490 | 490 |
| IGKV3-11 | 299 | 7 | 306 |
| IGKV3-15 | 261 | 2 | 263 |
| IGKV4-1 | 216 | 0 | 216 |
| IGKV1-5 | 198 | 0 | 198 |
| IGKV1D-33 | 52 | 94 | 146 |
| IGKV2D-28 | 30 | 81 | 111 |
| IGKV1-33 | 3 | 94 | 97 |
| IGKV2-30 | 95 | 1 | 96 |
| IGKV2-28 | 12 | 81 | 93 |
| IGKV1-9 | 82 | 1 | 83 |
| IGKV2D-29 | 77 | 2 | 79 |
| IGKV1D-12 | 13 | 59 | 72 |
| IGKV1-12 | 12 | 59 | 71 |
| IGKV1-27 | 64 | 0 | 64 |
| IGKV1-16 | 49 | 1 | 50 |
| IGKV1-6 | 43 | 0 | 43 |
| IGKV1-17 | 40 | 0 | 40 |
| IGKV2-24 | 27 | 4 | 31 |
| IGKV1-8 | 24 | 0 | 24 |
| IGKV3D-15 | 14 | 2 | 16 |
| IGKV2-29 | 13 | 2 | 15 |
| IGKV1D-13 | 8 | 5 | 13 |
| IGKV3D-20 | 10 | 1 | 11 |
| IGKV1D-16 | 7 | 1 | 8 |
| IGKV2-40 | 2 | 6 | 8 |
| IGKV1-13 | 2 | 5 | 7 |
| IGKV2D-40 | 1 | 6 | 7 |
| IGKV3D-11 | 2 | 5 | 7 |
| IGKV1-NL1 | 5 | 0 | 5 |
| IGKV1D-17 | 5 | 0 | 5 |
| IGKV2D-30 | 4 | 1 | 5 |
| IGKV5-2 | 5 | 0 | 5 |
| IGKV2D-24 | 0 | 4 | 4 |
| IGKV6-21 | 1 | 3 | 4 |
| IGKV6D-21 | 1 | 3 | 4 |
| IGKV1D-8 | 3 | 0 | 3 |
| IGKV3D-7 | 1 | 0 | 1 |
| Total | 2518 | 1513 | 4031 |
| Joining genes | | | |
| IGKJ1 | 882 | 30 | 912 |
| IGKJ2 | 851 | 39 | 890 |
| IGKJ4 | 693 | 103 | 796 |
| IGKJ3 | 286 | 83 | 369 |
| IGKJ5 | 232 | 31 | 263 |
| Total | 2944 | 286 | 3230 |

Figure 2A:
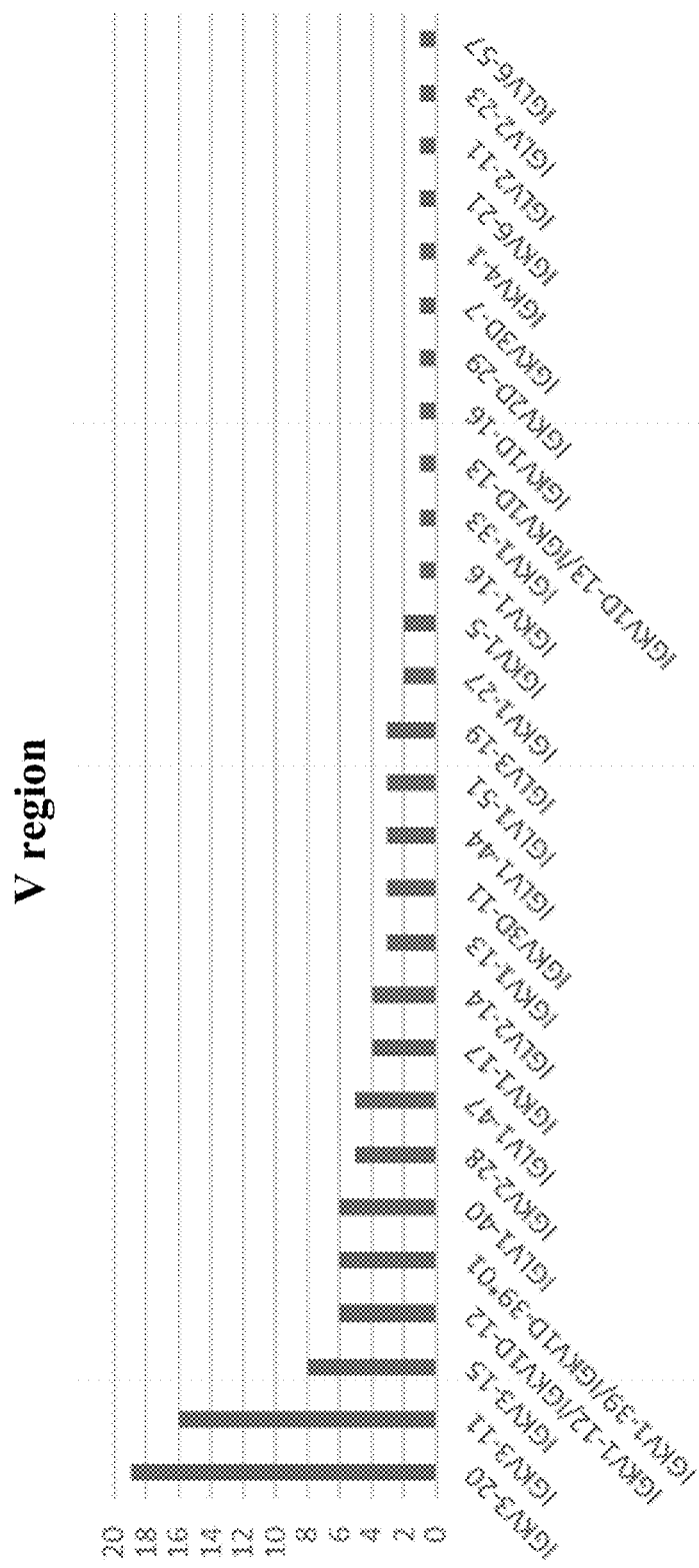
FIG. 2A shows top utilized human kappa chain V region genes.
Figure 2B:
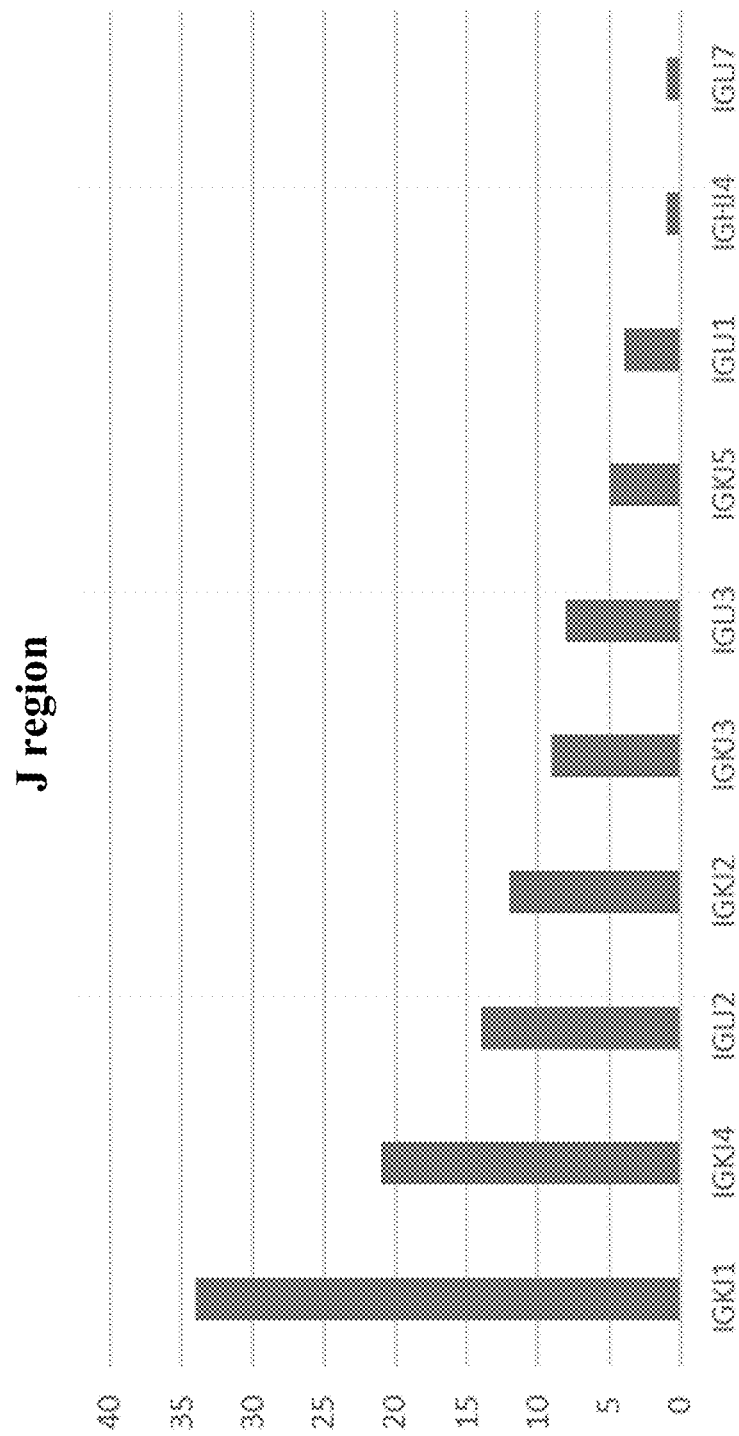
FIG. 2B shows top utilized human kappa chain J region genes.

2) Genetic information of the light chain from 110 antibody molecules were analyzed. The sequence information was collected from IMGT/mAb-DB database. Statistical analysis indicates that the top 5 Kappa light chain V region genes were IGKV3-20, IGKV3-11, IGKV3-15, IGKV1-39/IGKV1D-39, and IGKV1-12/IGKV1D-12; and the top 3 highly utilized Kappa light chain J region genes were: IGKJ1, IGKJ4, and IGKJ2 (FIGS. 2A-2B).

Based on the analysis, three human light chain V regions (IGKV3-20, IGKV3-11, and IGKV1-39) and two human light chain J regions (IGKJ1, and IGKJ4) were selected for the humanized light chain immunoglobulin locus.

Example 4: Preparation of Rearranged Light Chain Mice

Figure 3A:
FIG. 3A is a schematic diagram showing the mouse light chain immunoglobulin locus.
Figure 3B:
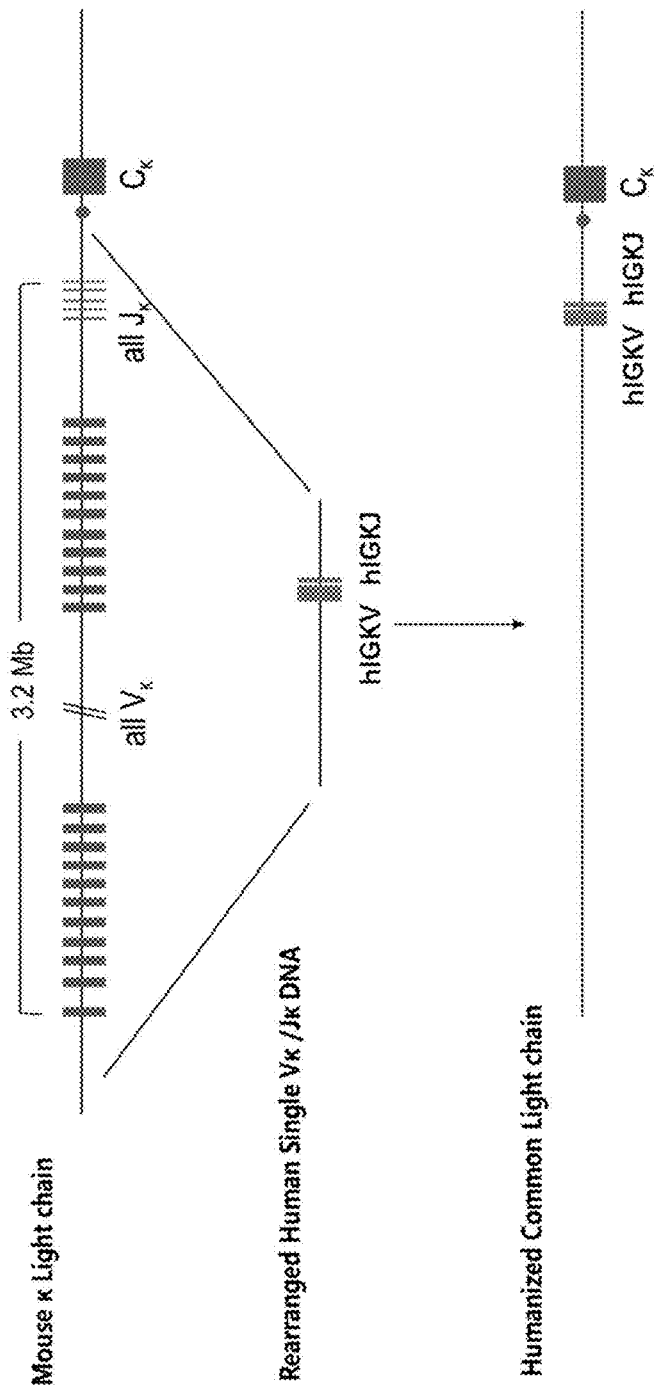
FIG. 3B is an overview of replacing mouse immunoglobulin light chain variable region genes with the rearranged human IGKV and IGKJ genes.

The mouse light chain immunoglobulin locus is located on mouse chromosome 6. FIG. 3A is a schematic diagram showing the mouse light chain immunoglobulin locus. The entire mouse VJ region of a wild-type mouse can be replaced with a sequence of rearranged human light chain VJ region (FIG. 3B). Alternatively, the process can be performed in steps, i.e., the mouse VJ region can be knocked out first (e.g., by replacement of the VJ region with a sequence containing Neo and DTR), and then sequence containing the rearranged human light chain VJ region can be inserted.

For example, the mouse chromosome 6 was modified by knocking out the entire sequence of the variable region of kappa light chain immunoglobulin locus. Three different rearranged human light chain VJ sequences were constructed, and were then inserted into mouse chromosome 6 Kappa chain VJ region.

A schematic diagram of the humanization strategy is shown in FIG. 4. Three targeting vectors for homologous recombination were constructed, sharing common sequence characteristics, i.e., each having an upstream and downstream homologous arm sequences and rearranged human light chain VJ sequences. For each vector, the rearranged human VJ sequence was selected differently. The three vectors contained rearranged human IGKV1-39/J4, IGKV3-11/J1, and IGKV3-20/J1 sequences, respectively, wherein IGKV1-39 (SEQ ID NO:1) is identical to nucleotide sequence 89319625 to 89320099 of NCBI accession number NC_000002.12; IGKV3-11 (SEQ ID NO:2) is identical to nucleotide sequence 89027171 to 89027684 of NCBI accession number NC_000002.12; IGKV3-20 (SEQ ID NO: 3) is identical to nucleotide sequence 89142574 to 89143108 of NCBI accession number NC_000002.12; IgKJ1 (SEQ ID NO:4) is identical to nucleotide sequence 88861886 to 88861923 of NCBI accession number NC_000002.12; IgKJ4 (SEQ ID NO:5) is identical to nucleotide sequence 88860886 to 88860923 of NCBI accession number NC_000002.12.

In addition, each rearranged human light chain VJ sequence also contained a human V promoter sequence of the light chain V region gene. The promoter sequence is about 2000 bp before the V region gene.

Further, there can be a separate auxiliary sequence after each rearranged human VJ sequence, e.g., a mouse 3'UTR sequence (SEQ ID NO: 6), or human 3'UTR sequence (SEQ ID NO: 7) following the human light chain VJ region.

The three vectors were introduced into cells by gene editing and the cells were selected by DT screening. The positive clones were confirmed by PCR and Southern Blot. The PCR assay was performed using the following primers:

TABLE 13

| NO. | Primer | | Sequence (5'-3') | Product size (bp) |
|---|---|---|---|---|
| | | | IGKV1-39/J4 | |
| 1 | IGKV1-39/J4 | L-GT-F | TCACACACTACAGCTTCCACCACAA (SEQ ID NO: 8) | 5196 |
| | | L-GT-R | TGGGCGCGCCAGACTCTAAA (SEQ ID NO: 9) | |
| 2 | IGKV1-39/J4 | R-GT-F | TGGGTCTGATGGCCAGTATTGACT (SEQ ID NO: 10) | 6607 |
| | | R-GT-R | GGCCTGGAAAACTCAGCTATCCTTT (SEQ ID NO: 11) | |
| 3 | m-5'loxp-L-GT-F | | GCCAAGGAATTTAAAAGGGGATTGAAAGCAA (SEQ ID NO: 12) | 6757 |
| | m-5'loxp-R-GT-R | | AGGGAGGGAATGGAATGAGGGTGAT (SEQ ID NO: 13) | |
| 4 | m-3'loxp-L-GT-F | | CCATGTGACCCATTCGAGTGTCCTG (SEQ ID NO: 14) | 3738 |
| | m-3'loxp-R-GT-R | | CTTACCATTTGCGGTGCCTGGTTTC (SEQ ID NO: 15) | |
| | | | IGKV3-11/J1 | |
| 5 | IGKV3-11/J1 | L-GT-F | TCACACACTACAGCTTCCACCACAA (SEQ ID NO: 16) | 5568 |
| | | L-GT-R | TGGGCGCGCCAGACTCTAAA (SEQ ID NO: 17) | |
| 6 | IGKV3-11/J1 | R-GT-F | TGGGTCTGATGGCCAGTATTGACT (SEQ ID NO: 18) | 6607 |
| | | R-GT-R | GGCCTGGAAAACTCAGCTATCCTTT (SEQ ID NO: 19) | |
| 7 | m-5'loxp-L-GT-F | | GCCAAGGAATTTAAAAGGGGATTGAAAGCAA (SEQ ID NO: 12) | 6757 |
| | m-5'loxp-R-GT-R | | AGGGAGGGAATGGAATGAGGGTGAT (SEQ ID NO: 13) | |
| 8 | m-3'loxp-L-GT-F | | CCATGTGACCCATTCGAGTGTCCTG (SEQ ID NO: 14) | 3738 |
| | m-3'loxp-R-GT-R | | CTTACCATTTGCGGTGCCTGGTTTC (SEQ ID NO: 15) | |

TABLE 13-continued

| NO. | Primer | Sequence (5'-3') | Product size (bp) |
|---|---|---|---|
| | | IGKV3-20/J1 | |
| 9 | IGKV3-20/J1 L-GT-F | TCACACACTACAGCTTCCACCACAA (SEQ ID NO: 20) | 5256 |
| | L-GT-R | TGGGCGCGCCAGACTCTAAA (SEQ ID NO: 21) | |
| 10 | IGKV3-20/J1 R-GT-F | TGGGTCTGATGGCCAGTATTGACT (SEQ ID NO: 22) | 6607 |
| | R-GT-R | GGCCTGGAAAACTCAGCTATCCTTT (SEQ ID NO: 23) | |
| 11 | m-5'loxp-L-GT-F | GCCAAGGAATTTAAAAGGGGATTGAAAGCAA (SEQ ID NO: 12) | 6757 |
| | m-5'loxp-R-GT-R | AGGGAGGGAATGGAATGAGGGTGAT (SEQ ID NO: 13) | |
| 12 | m-3'loxp-L-GT-F | CCATGTGACCCATTCGAGTGTCCTG (SEQ ID NO: 14) | 3738 |
| | m-3'loxp-R-GT-R | CTTACCATTTGCGGTGCCTGGTTTC (SEQ ID NO: 15) | |

In Table 13, L-GT-F is located on the 5' homologous arm; R-GT-R is located on the 3' homologous arm; L-GT-R and R-GT-F are located on the rearranged human light chain VJ sequence; m-5'loxp-L-GT-F, m-5'loxp-R-GT-R, m-3'lox-L-GT-F, and m-3'lox-R-GT-R primers are located on the humanized heavy chain chromosome.

The Southern Blot assay was performed using the following probes:

TABLE 14

| 5'Probe | F2 | AGACTTGATGGTGTGGAGTGGGGTA (SEQ ID NO: 24) |
|---|---|---|
| | R2 | TGGGCCCTGTACTTTGCTTGAACAT (SEQ ID NO: 25) |
| 3'Probe | F2 | TGATGGGTCAACCATGTTCCTGTGG (SEQ ID NO: 26) |
| | R2 | TCAGCCATTGLTTCTGCTTTCTCCT (SEQ ID NO: 27) |
| IGKV1-39 probe | F | GAAAAGTGGCTTTGATGGTGCAGGG (SEQ ID NO: 28) |
| | R | TGCCCATTTTTCTGCCCTTGGGTAT (SEQ ID NO: 29) |
| TGKV3-11 probe | F | AGGCATTCCTTATGCCAGTCAGCAT (SEQ ID NO: 30) |
| | R | TTTCCCATGTCCTGCTGCTTTCCTT (SEQ ID NO: 31) |
| TGKV3-20 probe | F | CATTTAGGGAGCTGACTGGGCACAA (SEQ ID NO: 32) |
| | R | TCTGGGTCCTAACTGAGCAGCTCTT (SEQ ID NO: 33) |

In Table 14, the 5' probe is located on the outside of the 5' homologous arm; the 3' probe is located on the outside of the 3' homologous arm; the IGKV1-39 probe, IGKV3-11 probe and IGKV3-20 probe are located on the humanized fragments.

The positive clone cells were injected into the blastocysts of BALB/c mice by microinjection. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The chimeric mice were selected to mate with the heavy chain gene humanized homozygous mice, producing the F1 generation mice. PCR and southern analysis was performed on the DNA obtained from the tail of the F1 generation mice to confirm whether the positive heterozygous mice were obtained.

Example 5: Common Light Chain Expression

The mRNA sequences of the light chain variable region in mice were analyzed by sequencing. Unimmunized (not exposed to a particular antigen) humanized mice (heterozygous humanized heavy and heterozygous rearranged light chain) were selected, and RNA was extracted from retro-orbital blood. A 5' RACE kit (SMARTer RACE 5'/3' Kit, Takara Bio USA, Inc., Cat #634858) was used to perform reverse transcription to obtain cDNA. The obtained cDNA was amplified using the IGKC-R primer and the UPM primer of the 5' RACE kit. The heavy chain variable region sequence fragment was then sequenced. The IGKC-R primer sequence was 5'-CTAACACTCATTCCTGTT-GAAGCTCTTGAC-3' (SEQ ID NO: 34). The sequencing result was compared with NCBI Ig Blast tool to identify human immunoglobulin sequences to identify the usage of human Vκ and Jκ region genes. Results indicated that 89% of the 577 clones from the three versions of mice (randomly selected) were expressing human Vκ and Jκ, and the ratio of human Vκ and Jκ in each mouse exceeded 60%. This indicated that after the endogenous κ chain variable region locus was entirely replaced by the rearranged sequence of the human immunoglobulin light chain sequences, the human Vκ and Jκ genes in the humanized mice were efficiently and predominantly expressed. In contrast, the wild-type κ chain was not expressed or had a relatively low expression level in heterozygous mice.

TABLE 15

| Sample Number | Gender | Positive clone number | Negative clone number | Ratio of positive clone (%) |
|---|---|---|---|---|
| IGKV3-11/J1#18 | male | 30 | 1 | 96.77% |
| IGKV3-11/J1#25 | male | 24 | 5 | 82.76% |
| IGKV3-11/J1#30 | male | 31 | 0 | 100.00% |
| IGKV3-11/J1#50 | female | 33 | 1 | 97.06% |
| IGKV3-11/J1#53 | male | 37 | 1 | 97.37% |
| IGKV3-11/J1#72 | female | 33 | 4 | 89.19% |
| IGKV1-39/J4#1 | male | 5 | 2 | 71.43% |
| IGKV1-39/J4#4 | male | 8 | 0 | 100.00% |
| IGKV1-39/J4#5 | male | 13 | 2 | 86.67% |
| IGKV1-39/J4#6 | female | 24 | 1 | 96.00% |
| IGKV1-39/J4#7 | male | 19 | 0 | 100.00% |
| IGKV1-39/J4#8 | female | 11 | 0 | 100.00% |
| IGKV3-20/J4#1 | male | 11 | 0 | 100.00% |
| IGKV3-20/J4#2 | male | 27 | 0 | 100.00% |
| IGKV3-20/J4#4 | female | 23 | 1 | 95.83% |
| IGKV3-20/J4#5 | female | 22 | 3 | 88.00% |
| IGKV3-20/J4#7 | male | 19 | 6 | 76.00% |
| IGKV3-20/J4#8 | male | 16 | 5 | 76.19% |
| IGKV3-20/J4#12 | female | 13 | 3 | 81.25% |
| IGKV3-20/J4#13 | female | 12 | 3 | 80.00% |
| IGKV3-20/J4#14 | female | 26 | 4 | 86.67% |
| IGKV3-20/J4#15 | female | 28 | 17 | 62.22% |

Example 6: B-Cell Development in hVH/hcVL Mice

The F1 generation mice were mated with each other. The homozygous humanized heavy chain immunoglobulin locus and heterozygous humanized common light chain immunoglobulin locus (humanized $VH^{H/H}/cVL^{K/+}$ mice, or indicated as $hVH^{H/H}/hcVL^{K/+}$ mice) were used to test B-cell development. The mice with humanized VH locus (heterozygous or homozygous) and common light chain immunoglobulin locus (heterozygous or homozygous) are also referred as hVH/hcVL mice. Experiments were performed to compare the immune systems of the $hVH^{H/H}/hcVL^{K/+}$ mice and the wild-type mice before immunization. The body weight and weight of some organs, e.g., spleen, thymus, liver, heart, lung and kidney, were measured in wild-type and hVH/hcVL heterozygous mice (FIGS. 5A-5G). No significant differences in average body weight and organ (spleen, thymus, liver, heart, lung, and kidney) weight were detected between the wild-type and hVH/hcVL heterozygous mice.

Figure 6A:
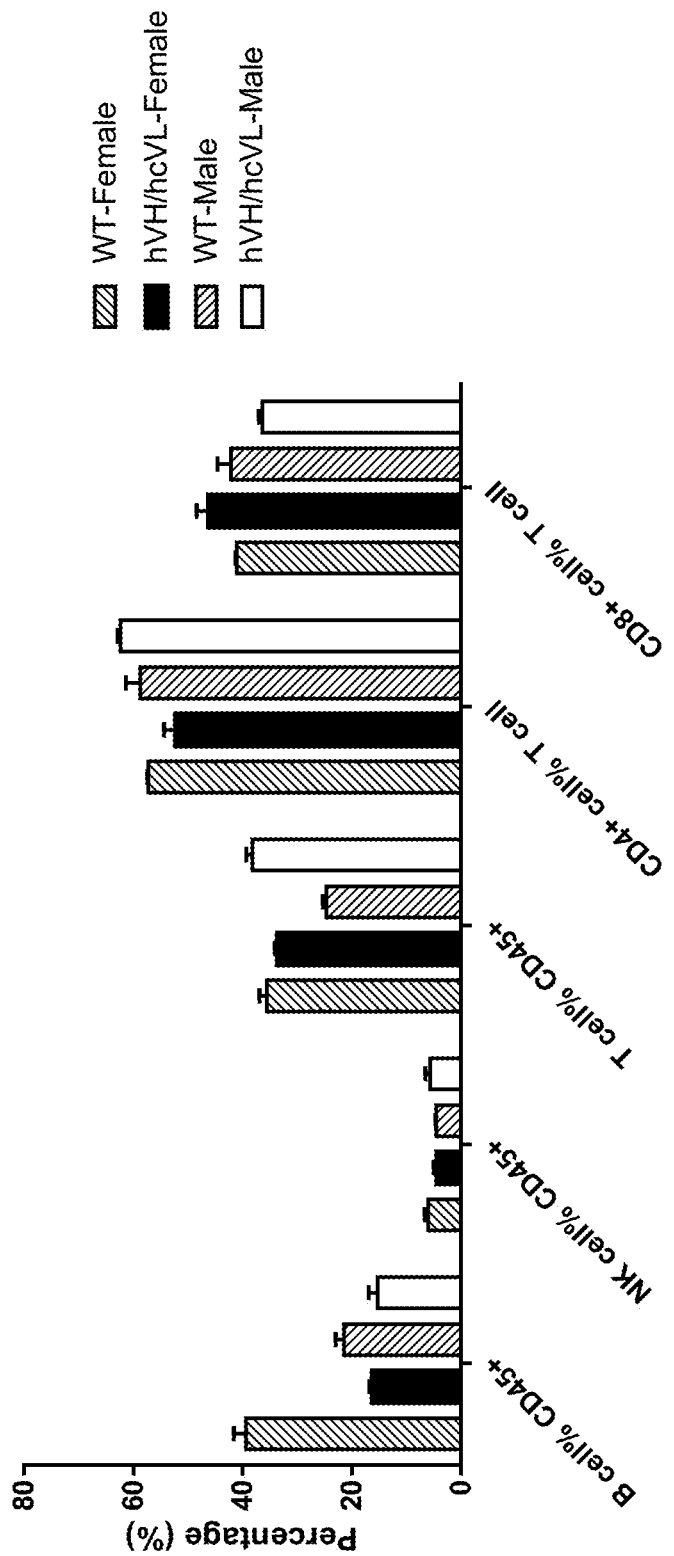
FIG. 6A is a histogram showing the blood immune cell percentage by flow cytometry. The blood immune cells were from wild-type or hVH/hcVL mice.
Figure 6B:
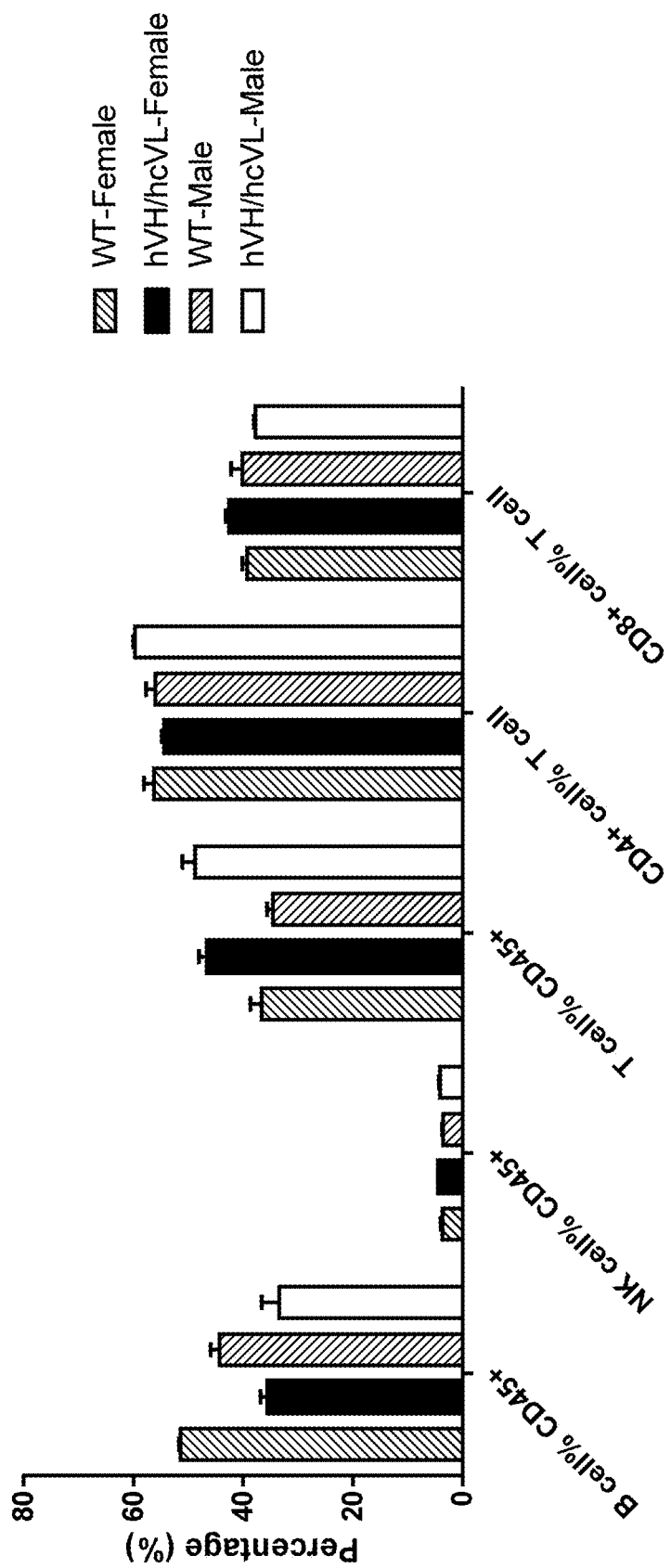
FIG. 6B is a histogram showing the immune cell percentage in the spleens by flow cytometry. The immune cells were from wild-type or hVH/hcVL mice.
Figure 7:
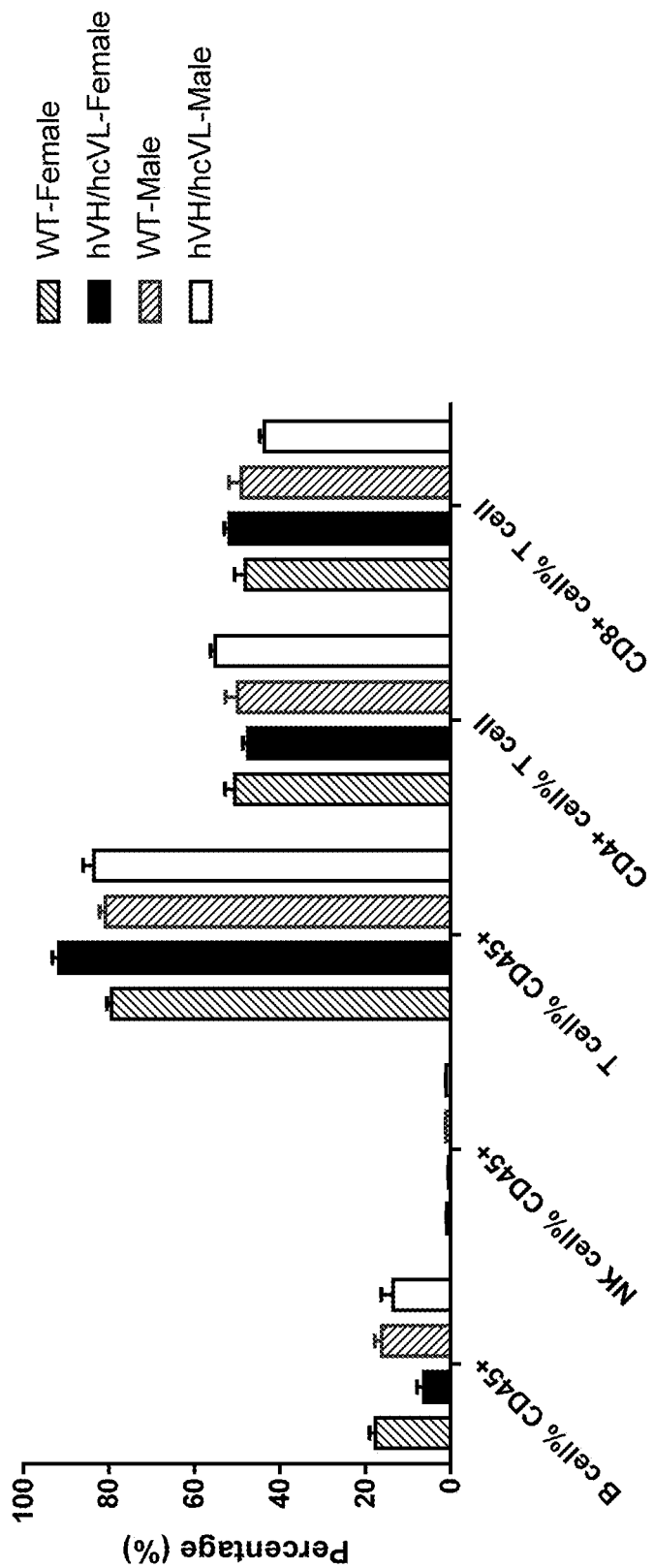
FIG. 7 is a histogram showing the lymph node immune cell percentage by flow cytometry. The lymph node immune cells were from wild-type or hVH/hcVL mice.

Flow cytometry was performed to analyze lymphocyte populations and distribution in the blood (FIG. 6A), the spleen (FIG. 6B) and lymph nodes (FIG. 7) of the wild-type and hVH/hcVL heterozygous mice. The results showed that in hVH/hcVL heterozygous mice, the percentage of B cells, T cells, NK cells, CD4+ T cells and CD8+ T cells in blood, in the spleen and in lymph nodes were almost identical to those of wild type mice. In the results, the leukocytes included: B cells (e.g., characterized by CD45+, CD19+, TCR−), T cells, and natural killer (NK) cells (e.g., characterized by CD45+, TCR−, NK1.1+). T cells were further characterized by CD45+, CD19−, TCR+. CD4+ T Cells (CD4) were characterized by CD45+, CD19−, TCR+, CD4+, CD8−. And CD8+ T cells (CD8) were characterized by CD45+, CD19−, TCR+, CD4−, CD8+. Only intact, single, live leukocytes were included in the flow cytometry analysis.

Figure 8A:
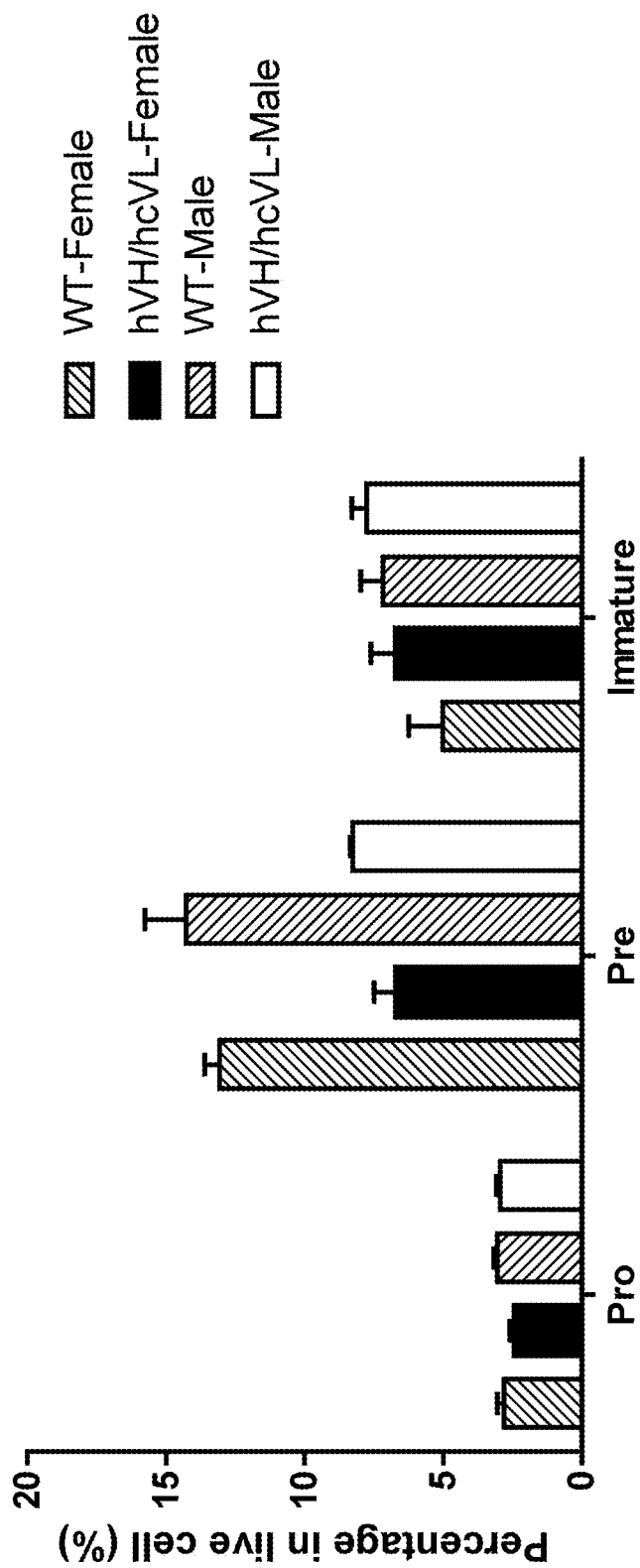
FIG. 8A shows percentage of Pro-B-cell ($B220^{low}CD43^{high}IgM^{low}$) Pre-B-cell ($B220^{low}CD43^{int}IgM^{low}$), and Immature-B-cell ($B220^{high}CD43^{low}IgM^{high}$) population in bone marrow B cells. The bone marrow B cells were from wild-type or hVH/hcVL mice.
Figure 8B:
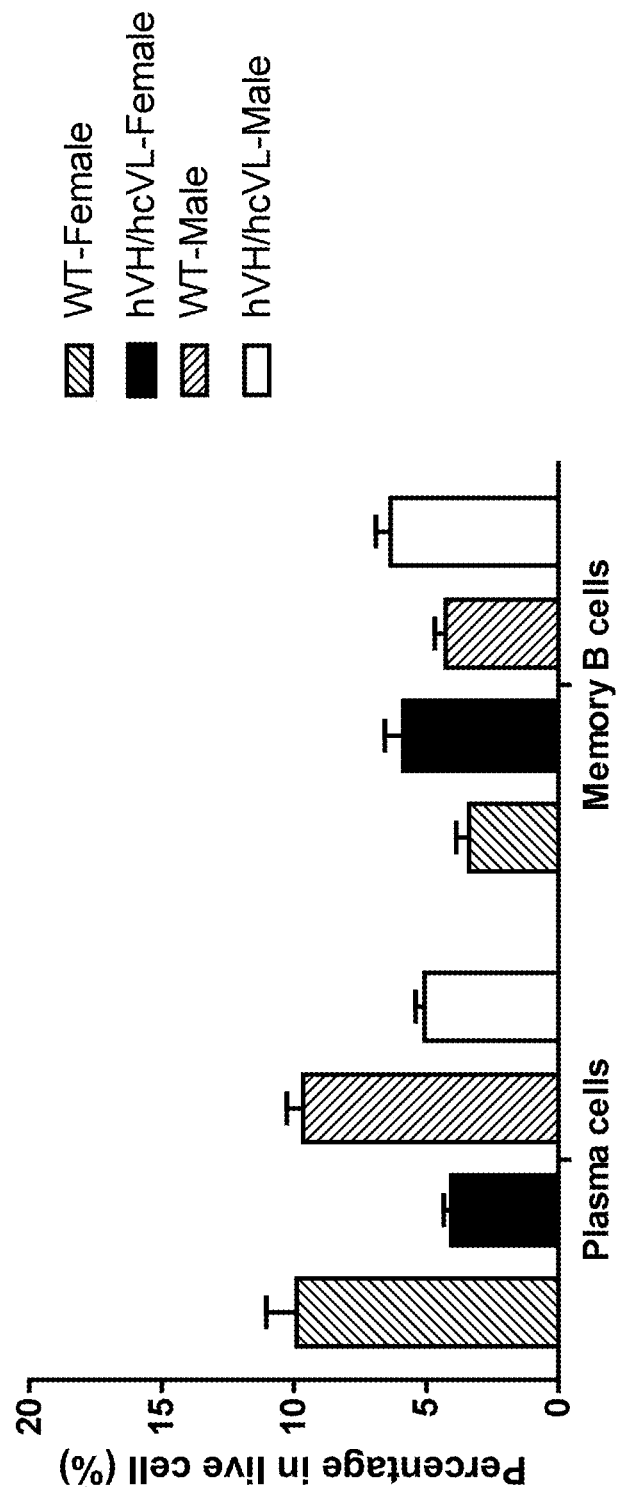
FIG. 8B shows percentage of Plasma cell ($B220^{low}IgM^-IgD^-CD138^+$) and Memory B cell ($B220^+IgM^+IgD^-CD38^+$) population in bone marrow B cells. The bone marrow B cells were from wild-type or hVH/hcVL mice.

FIG. 8A indicated percentages of B cells at different developmental stages in bone marrows. B cell progenitor cells in bone marrow were analyzed by flow cytometry. Based on expression levels of B220 and CD43, B cell progenitor cells in bone marrow can be divided into 3 cell populations pro-B-cells (characterized by $B220^{low}CD43^{high}Igm^{low}$), pre-B-cells (characterized by $B220^{low}CD43^{int}IgM^{low}$) and immature-B-cells (characterized by $B220^{high}CD43^{low}IgM^{high}$). No significant differences were observed between the wild-type mice and hVH/hcVL mice. In addition, B cell development were also evaluated in bone marrow by flow cytometry to selectively stain plasma cells ($B220^{low}IgM^-IgD^-CD138^+$) and memory B cells ($B220^+IgM^+IgD^-CD38^+$) (FIG. 8B). No significant difference was observed between the wild-type mice and hVH/hcVL mice.

Figure 9:
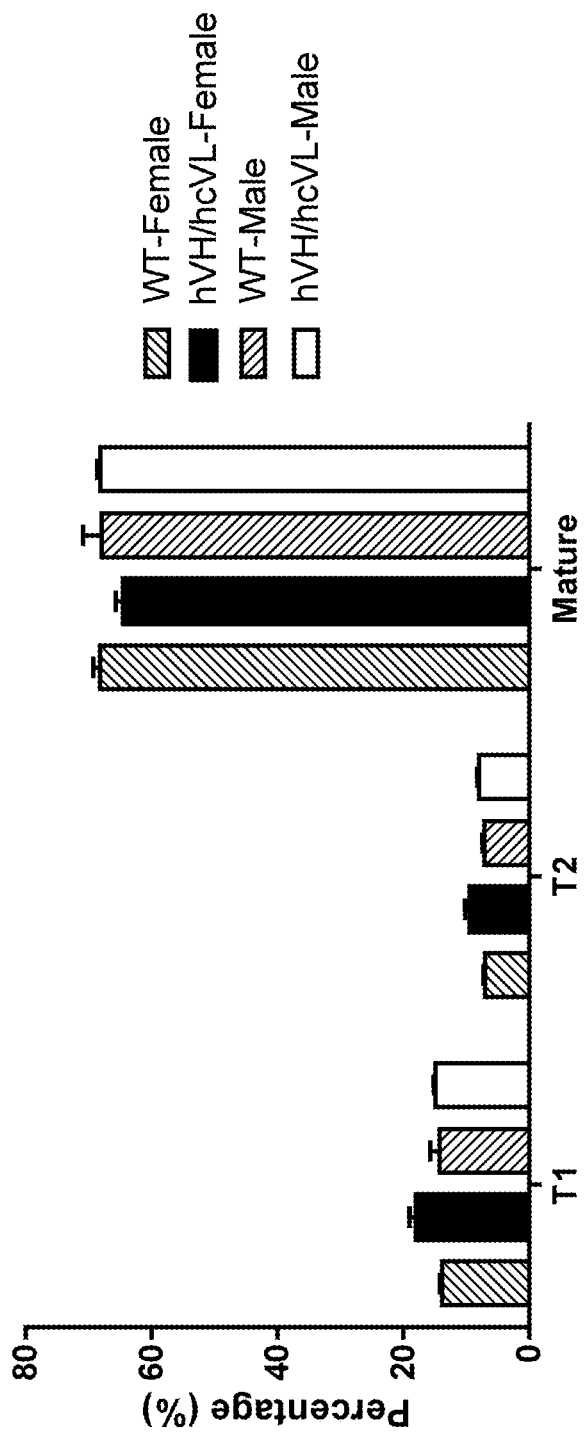
FIG. 9 shows percentage of transitional type 1 (T1, $B220^+IgM^+IgD^-$), transitional type 2 (T2, $B220^+IgM^+IgD^+$) and mature B cell (M, $B220^+IgM^{low}IgD^+$) population in spleen B cells. The spleen B cells were from wild-type or hVH/hcVL mice.

FIG. 9 indicated percentages of B cells at different developmental stages. The development stages of B cells in spleen were categorized into T1 (Transitional type 1 B cell, characterized by $B220^+IgM^+IgD^-$), T2 (Transitional type 2 B cell, characterized by $B220^+IgM^+IgD^+$) and mature B cells (characterized by $B220^+IgM^{low}IgD^+$). No significant difference was observed between the wild-type mice and hVH/hcVL mice.

Figure 10A:
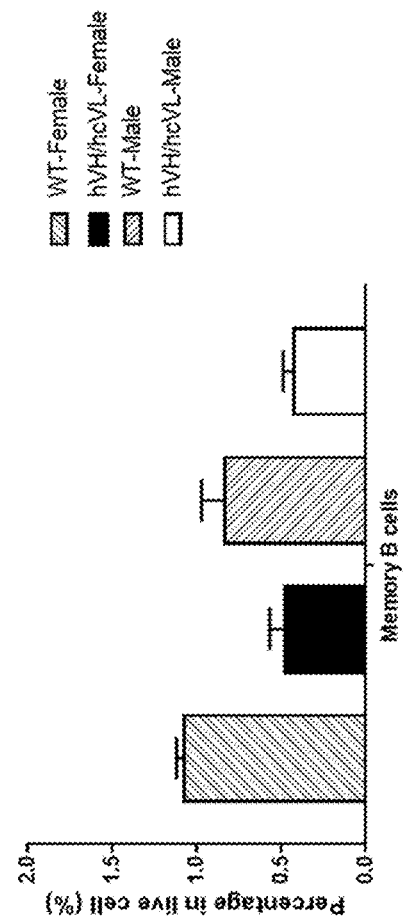
FIG. 10A shows percentage of Plasma cell ($B220^{low}IgM^-IgD^-CD138^+$) population in spleen B cells. The spleen B cells were from wild-type or hVH/hcVL mice.
Figure 10B:
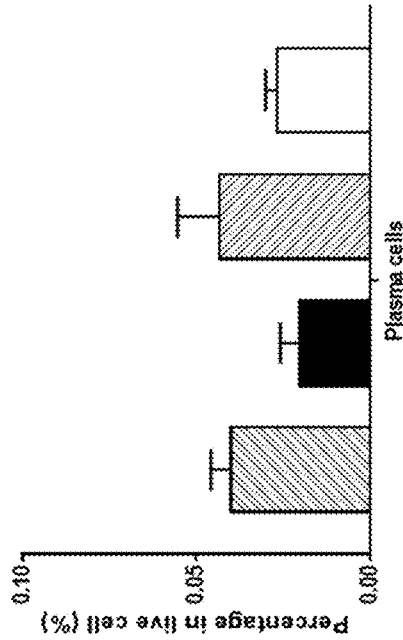
FIG. 10B shows percentage of Memory B cell ($B220^+IgM^+IgD^-CD38^+$) population in spleen B cells. The spleen B cells were from wild-type or hVH/hcVL mice.
Figure 10C:
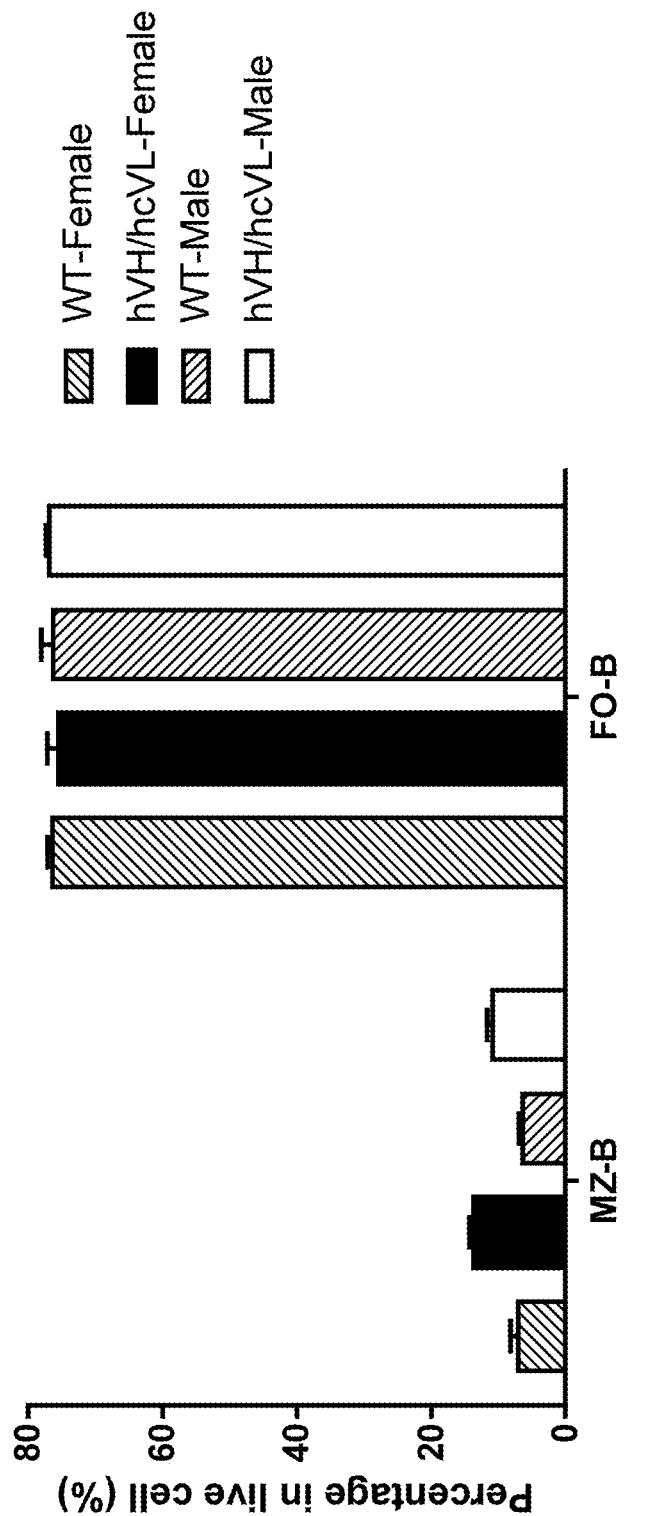
FIG. 10C shows percentage of Marginal-zone B cell (MZ, $B220^+CD21^+CD23^-$) and Follicular B cell (F0, $B220^+CD21^{low}CD23^+$) population in spleen B cells. The spleen B cells were from wild-type or hVH/hcVL mice.
Figures 11A, 11B:
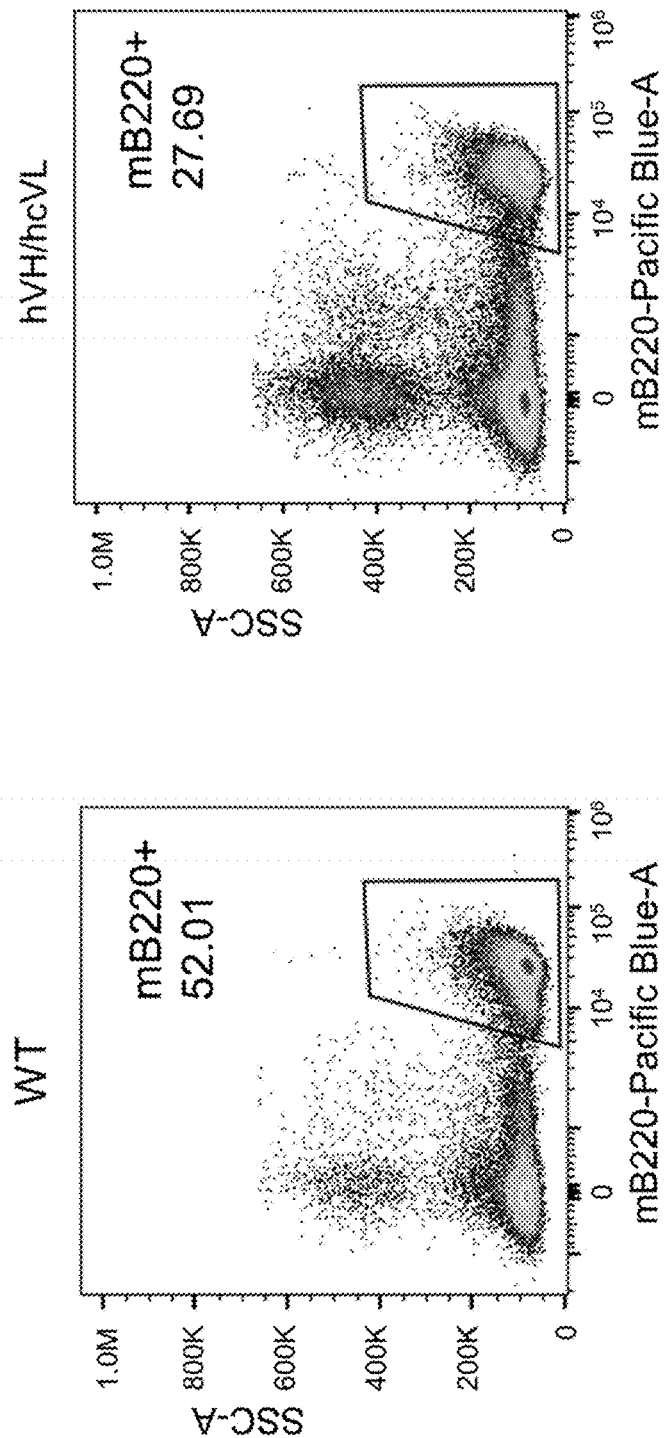
FIG. 11A shows a flow cytometry result of spleen B cells labeled by mB220 in wild-type female mice.
FIG. 11B shows a flow cytometry result of spleen B cell labeled by mB220 in hVH/hcVL female mice.
Figures 11C, 11D:
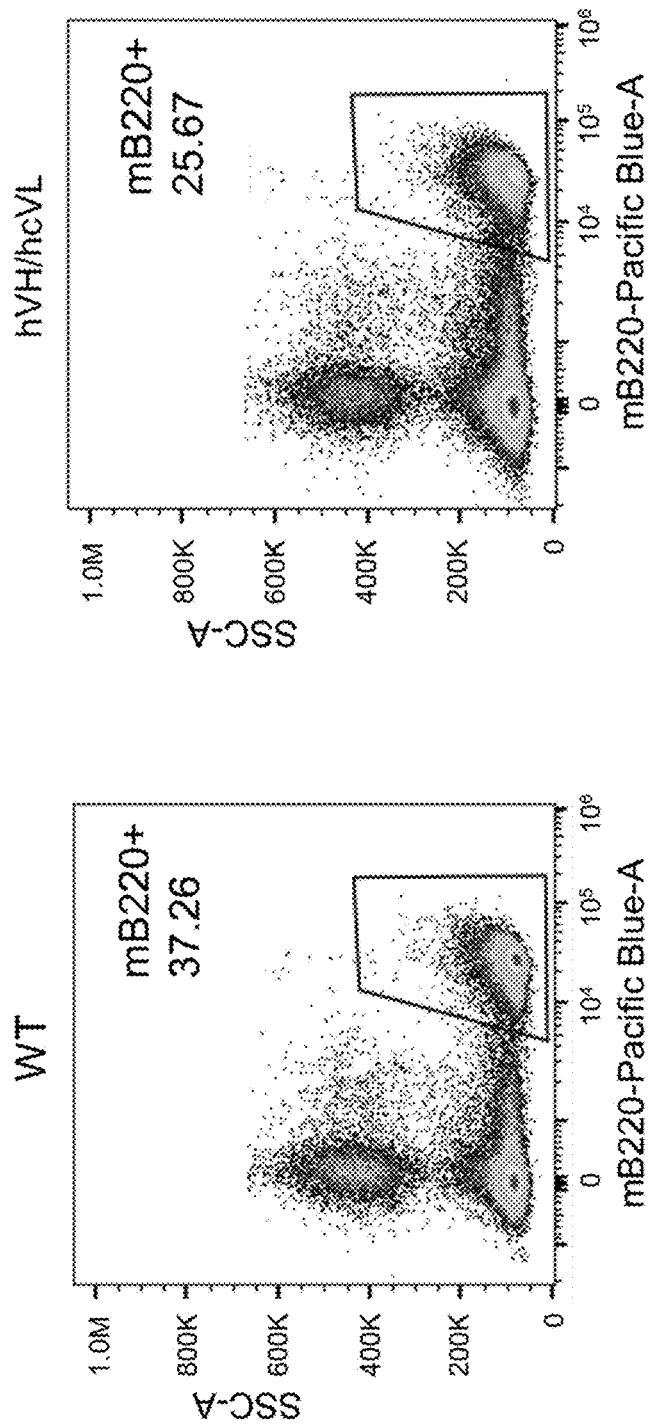
FIG. 11C shows a flow cytometry result of spleen B cells labeling by mB220 in wild-type male mice.
FIG. 11D shows a flow cytometry result of spleen B cell labeling by mB220 in hVH/hcVL male mice.
Figure 11F:
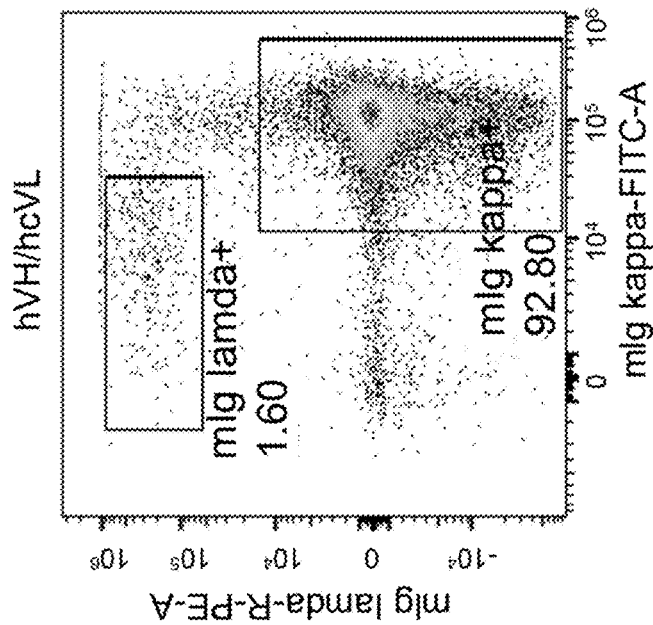
FIG. 11F shows a flow cytometry result of spleen B cells labeled by mIgG kappa-FITC and mIgG lambda-PE in hVH/hcVL female mice.
Figure 11E:
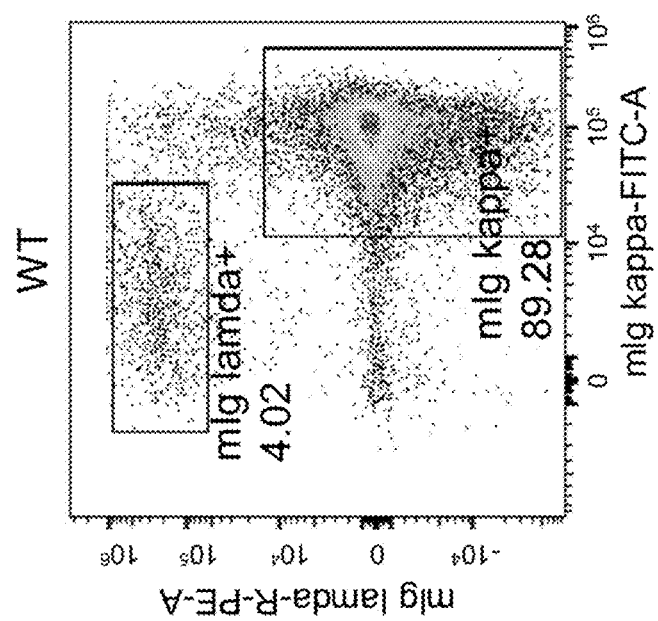
FIG. 11E shows a flow cytometry result of spleen B cells labeled by mIgG kappa-FITC and mIgG lambda-PE in wild-type female mice.
Figure 11H:
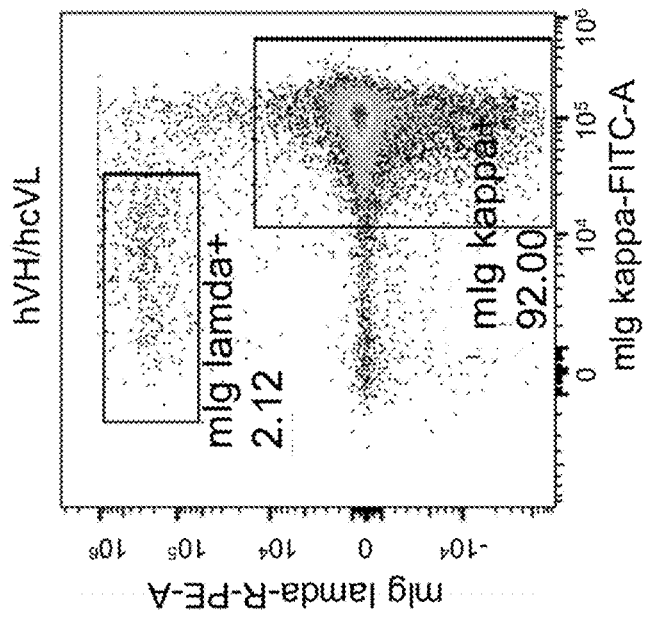
FIG. 11H shows a flow cytometry result of spleen B cells labeled by mIgG kappa-FITC and mIgG lambda-PE in hVH/hcVL male mice.
Figure 11G:
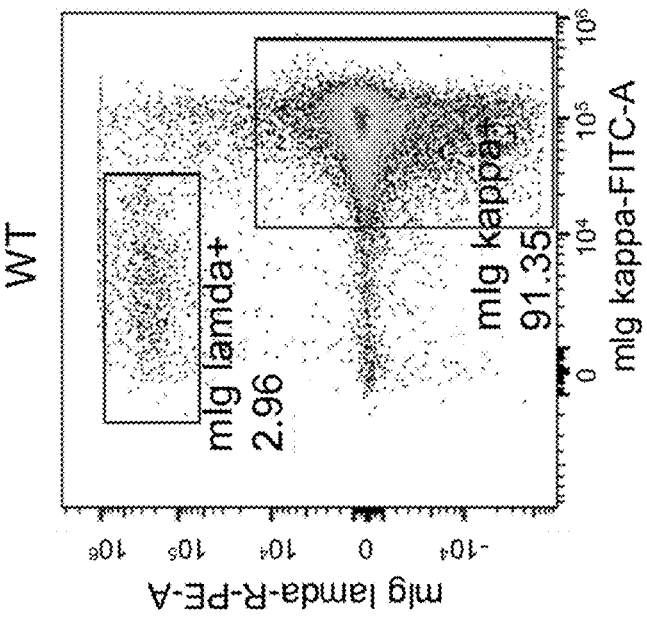
FIG. 11G shows a flow cytometry result of spleen B cells labeled by mIgG kappa-FITC and mIgG lambda-PE in wild-type male mice.
Figure 11:
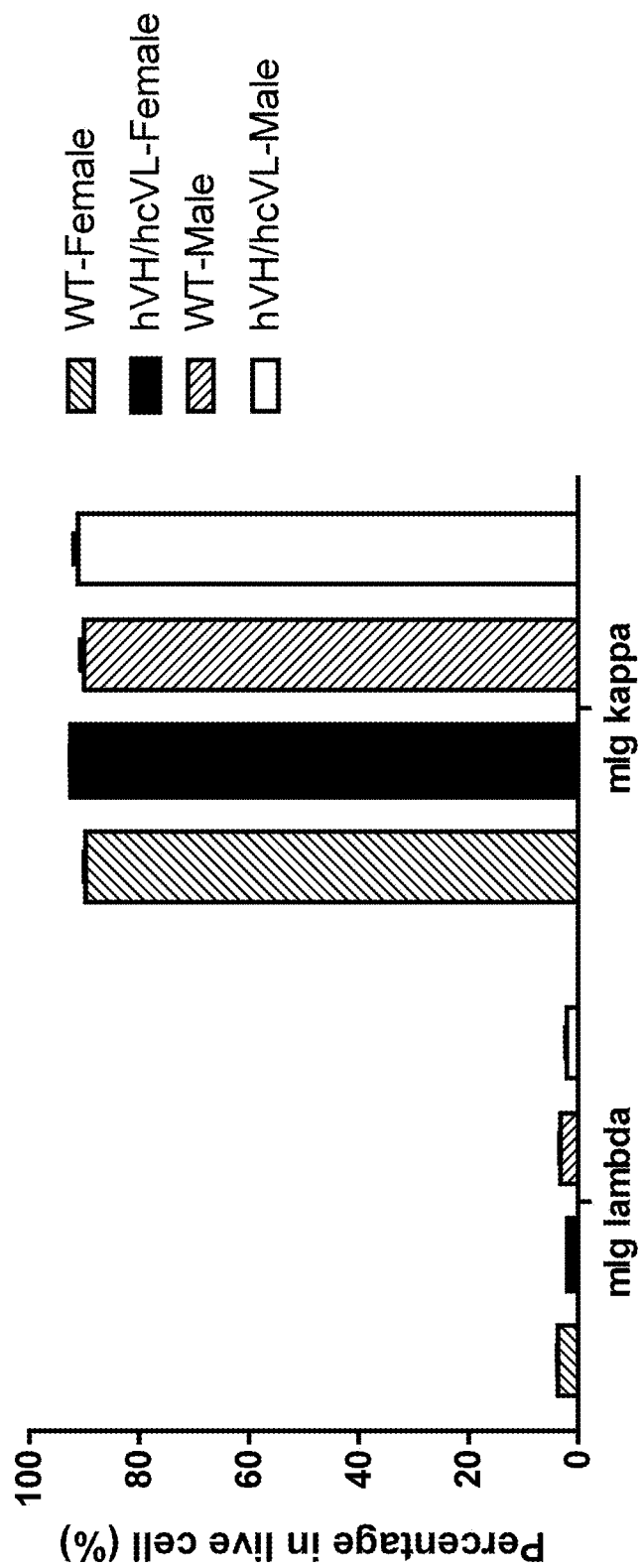
FIG. 11I is a histogram showing percentage of mIgG lambda-PE labeled B cells (mIg lambda) and mIgG kappa-FITC labeled spleen B cells (mIg kappa).

B cell development were also evaluated in spleen by flow cytometry to selectively stain plasma cells ($B220^{low}IgM^-IgD^-CD138^+$) and memory B cells ($B220^+IgM^+IgD^-CD38^+$) (FIGS. 10A-10B). No significant difference was observed between the wild-type mice and hVH/hcVL mice. In addition, B cell development were also evaluated at the spleen marginal zone (Marginal-zone B cell, MZ-B, characterized by $B220^+CD21^+CD23^-$) and follicular zone (Follicular B cell, referred to as FO-B, characterized by $B220^+CD21^{low}CD23^+$). FIG. 10C shows percentages of splenic B cells at spleen marginal zone (MZ-B) and follicular zone (FO-B). No significant differences were observed between the wild-type mice and hVH/hcVL mice.

The light chain utilization of B cells were evaluated in spleen by flow cytometry. B cells were first selectively labeled by mB220 (Pacific Blue™ anti-mouse/human CD45R/B220 Antibody, BioLegend, Cat #103227), followed by mIgG kappa-FITC (FITC anti-mouse Ig light chain κ Antibody, BioLegend, Cat #409509) and mIgG lambda-PE (PE anti-mouse Ig light chain λ Antibody, BioLegend, Cat #407307) labeling. No significant differences were observed between the wild-type mice and hVH/hcVL mice. The results indicated that humanization did not affect the expression radio of κ chain and λ chain in the spleen of hVH/hcVL heterozygous mice (FIGS. 11A-11I).

Figure 12A:
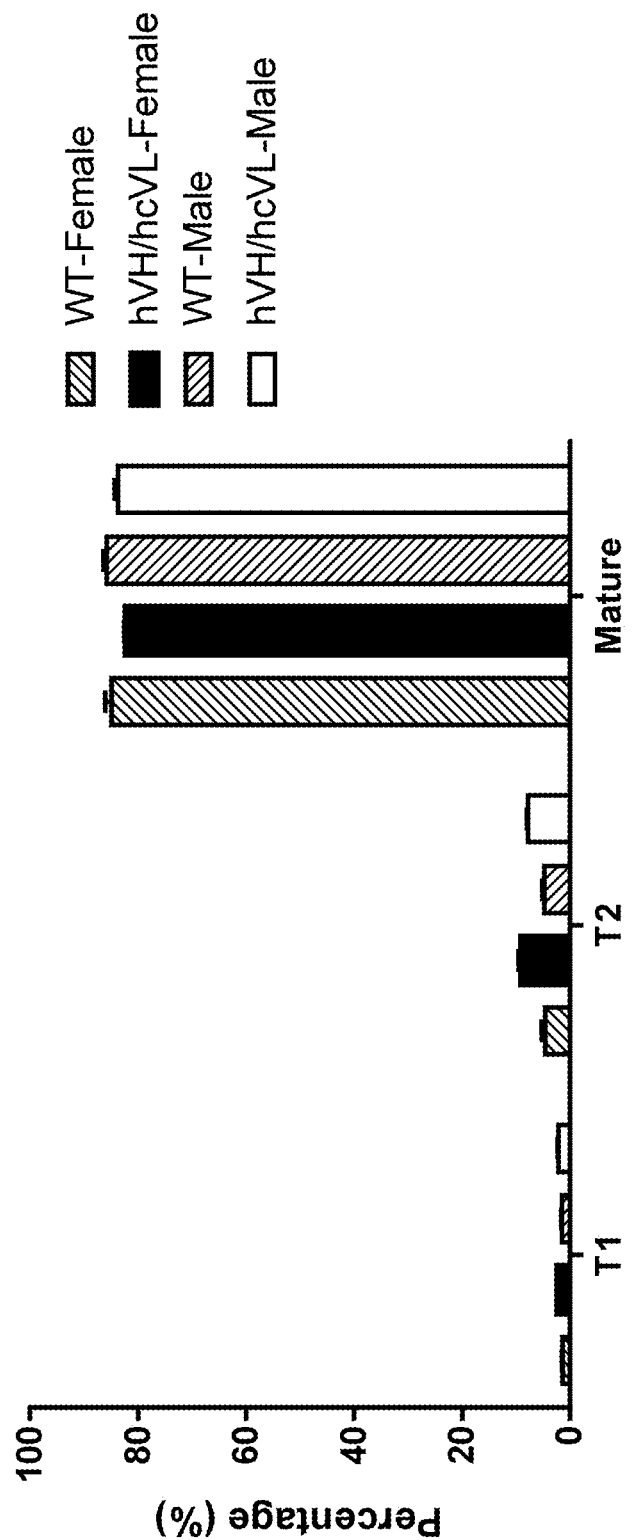
FIG. 12A shows percentage of transitional type 1 (T1, $B220^+IgM^+IgD^-$), transitional type 2 (T2, $B220^+IgM^+IgD^+$) and mature B cell (M, $B220^+IgM^{low}IgD^+$) population in lymph node B cells. The lymph node B cells were from wild-type or hVH/hcVL mice.
Figure 12B:
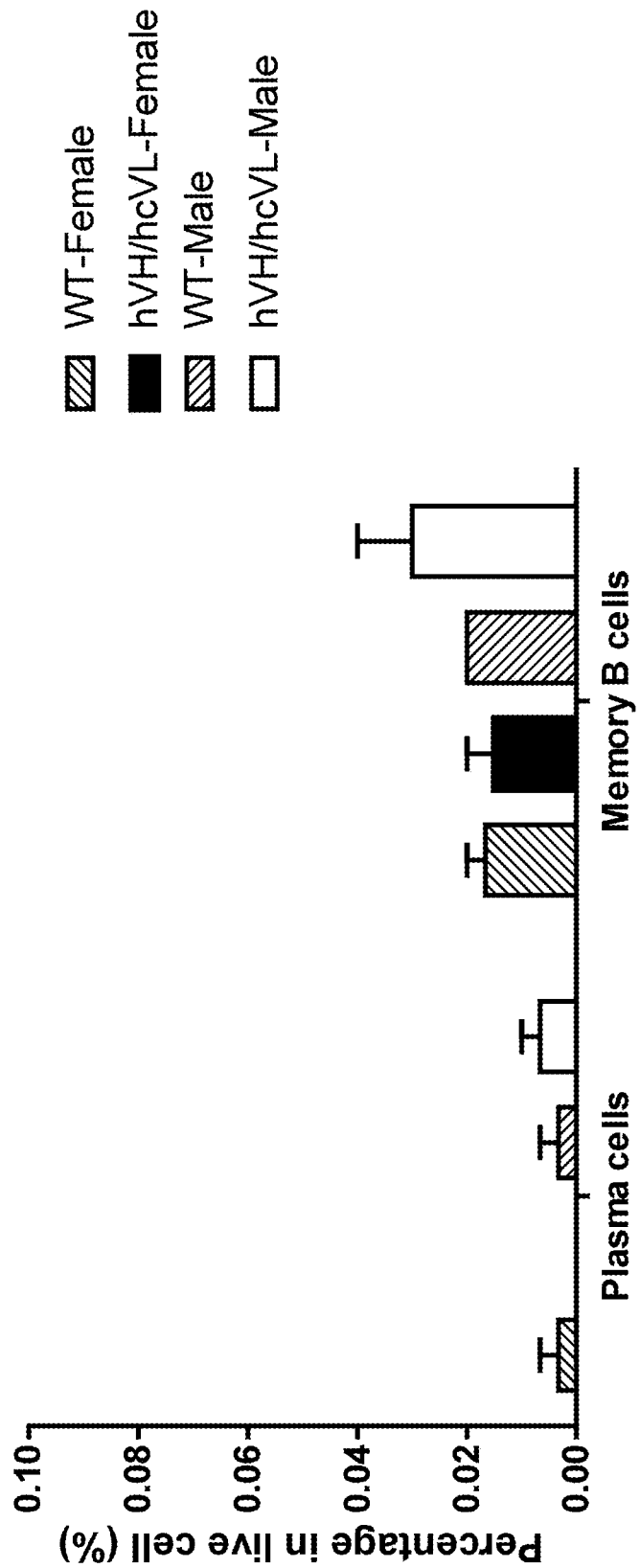
FIG. 12B shows percentage of Plasma cell ($B220^{low}IgM^-IgD^-CD138^+$) and Memory B cell ($B220^+IgM^+IgD^-CD38^+$) population in lymph node B cells. The lymph node B cells were from wild-type or hVH/hcVL mice.

FIG. 12A indicated percentages of B cells at different developmental stages. The development stages of B cells in lymph node were categorized into T1 (Transitional type 1 B cell, characterized by $B220^+IgM^+IgD^-$), T2 (Transitional type 2 B cell, characterized by $B220^+IgM^+IgD^+$) and mature B cells (characterized by $B220^+IgM^{low}IgD^+$). No significant difference was observed between the wild-type mice and hVH/hcVL mice. B cell development were also evaluated in lymph node by flow cytometry to selectively stain plasma cells ($B220^{low}IgM^-IgD^-CD138^+$) and memory B cells ($B220^+IgM^+IgD^-CD38^+$) (FIG. 12B). No significant difference was observed between the wild-type mice and hVH/hcVL mice.

The light chain utilization of B cells were evaluated in lymph node by flow cytometry. B cells were first selectively labeled by mB220, followed by mIgG kappa-FITC and mIgG lambda-PE labeling. No significant differences were observed between the wild-type mice and hVH/hcVL mice. The results indicated that humanization did not affect the expression radio of κ chain and λ chain in the spleen of hVH/hcVL heterozygous mice (FIGS. 13A-13I).

Figures 13A, 13B:
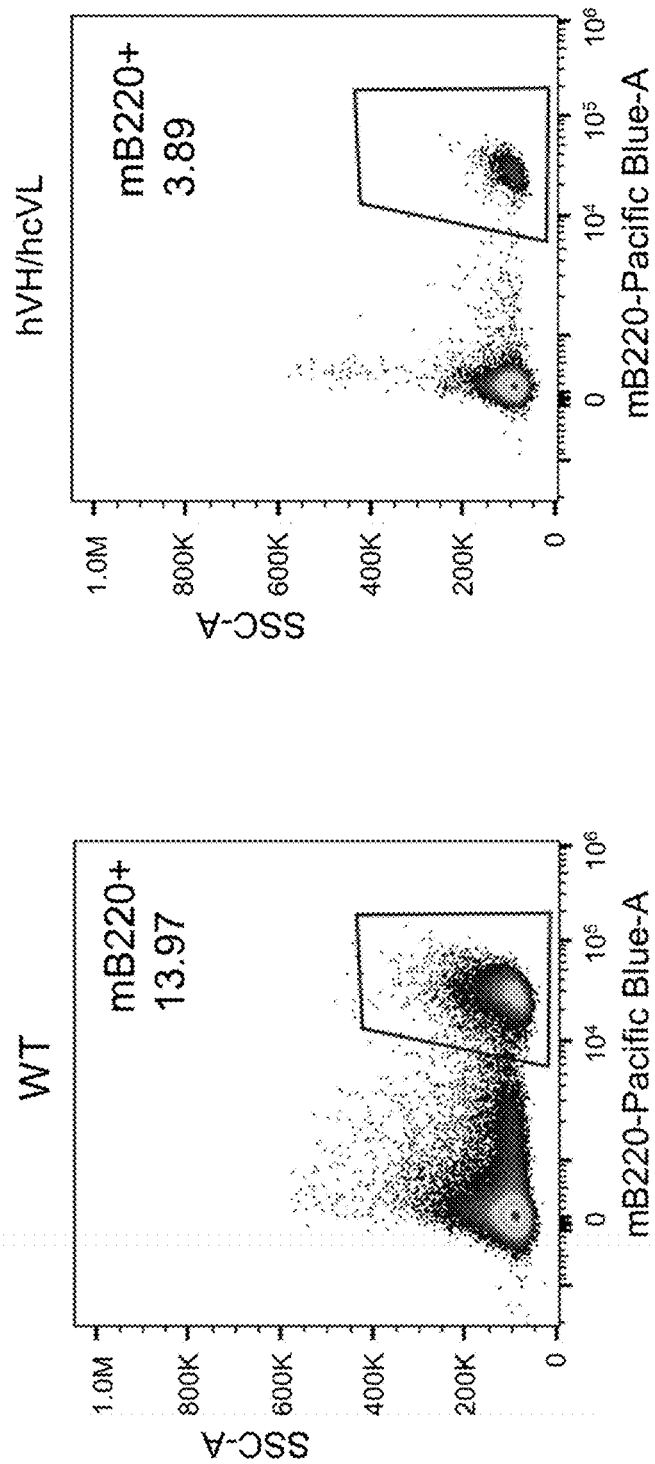
FIG. 13A shows a flow cytometry result of lymph node B cells labeled by mB220 in wild-type female mice.
FIG. 13B shows a flow cytometry result of lymph node B cell labeled by mB220 in hVH/hcVL female mice.
Figure 13D:
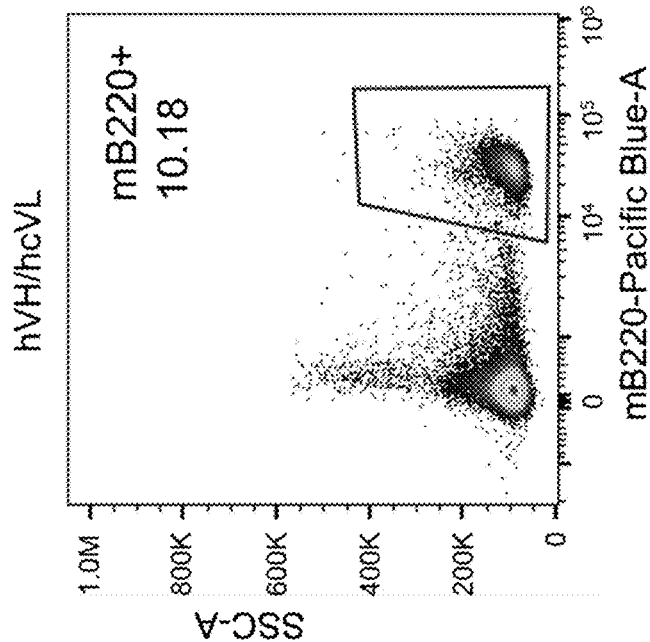
FIG. 13D shows a flow cytometry result of lymph node B cell labeling by mB220 in hVH/hcVL male mice.
Figure 13C:
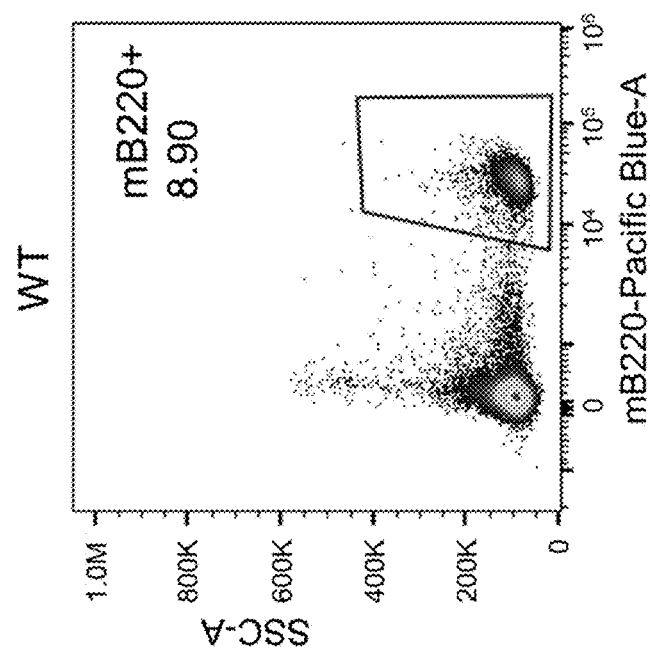
FIG. 13C shows a flow cytometry result of lymph node B cells labeling by mB220 in wild-type male mice.
Figure 13F:
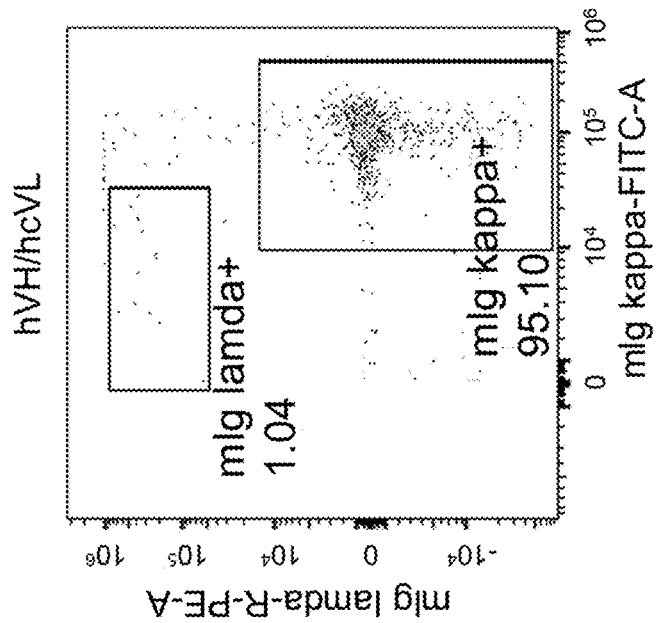
FIG. 13F shows a flow cytometry result of lymph node B cells labeled by mIgG kappa-FITC and mIgG lambda-PE in hVH/hcVL female mice.
Figure 13E:
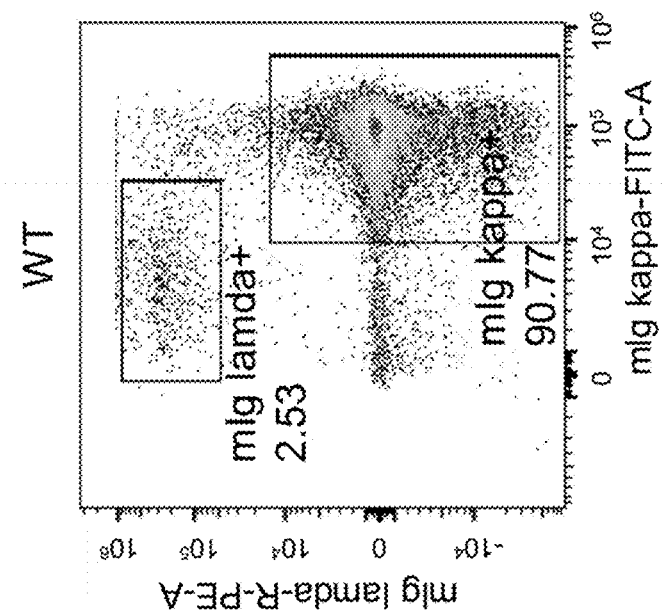
FIG. 13E shows a flow cytometry result of lymph node B cells labeled by mIgG kappa-FITC and mIgG lambda-PE in wild-type female mice.
Figures 13G, 13H:
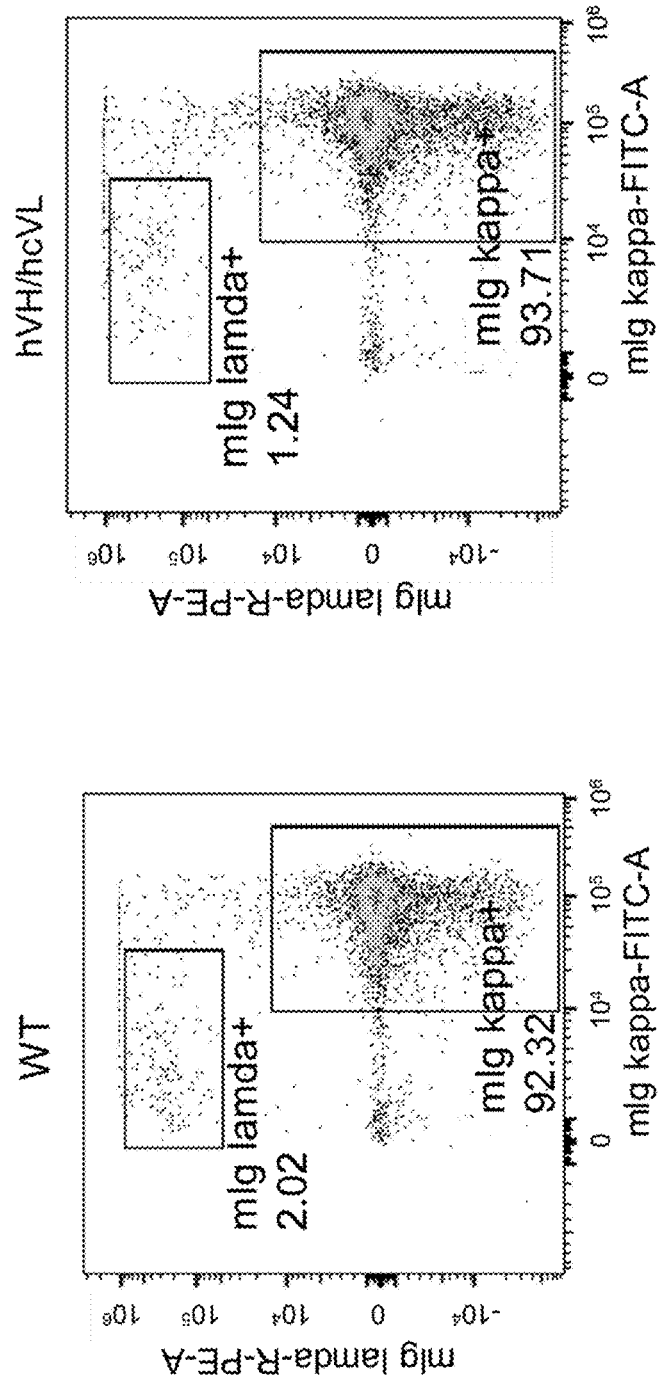
FIG. 13G shows a flow cytometry result of lymph node B cells labeled by mIgG kappa-FITC and mIgG lambda-PE in wild-type male mice.
FIG. 13H shows a flow cytometry result of lymph node B cells labeled by mIgG kappa-FITC and mIgG lambda-PE in hVH/hcVL male mice.
Figure 13I:
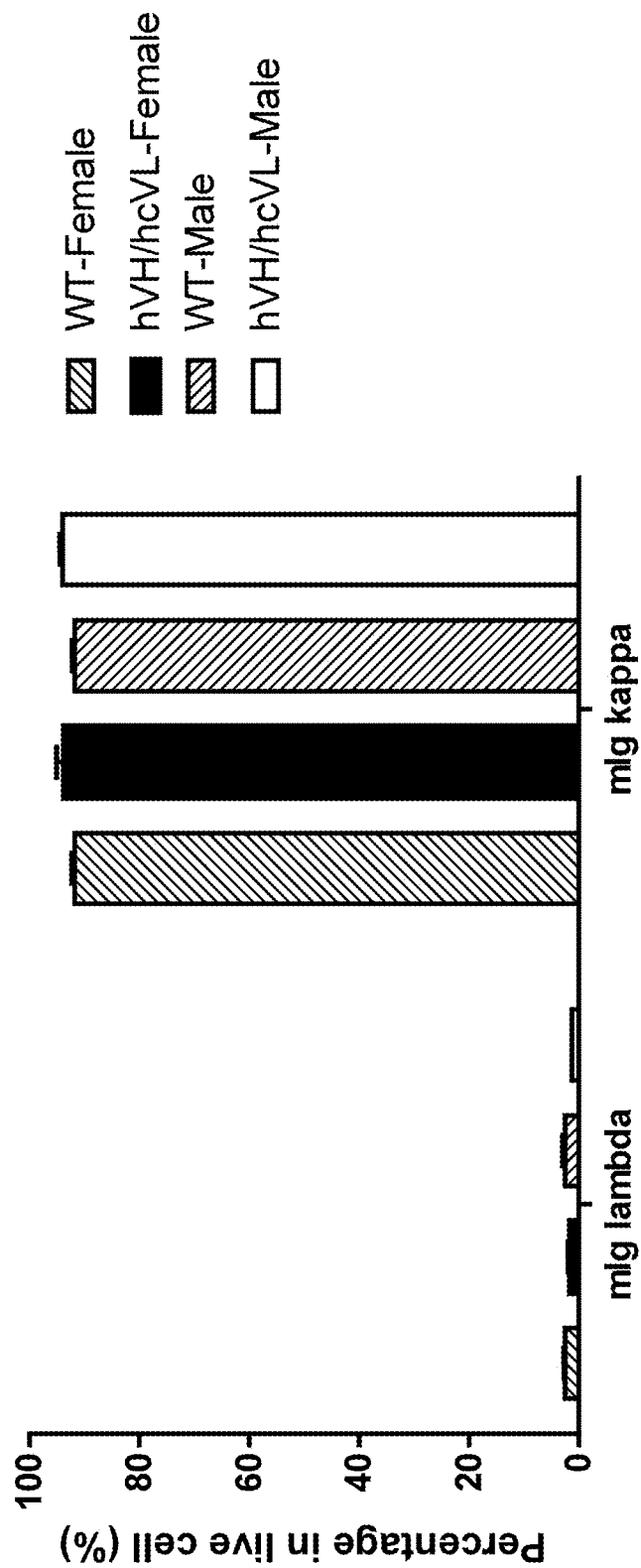
FIG. 13I is a histogram showing percentage of mIgG lambda-PE labeled B cells (mIg lambda) and mIgG kappa-FITC labeled lymph node B cells (mIg kappa).
Figure 13J:
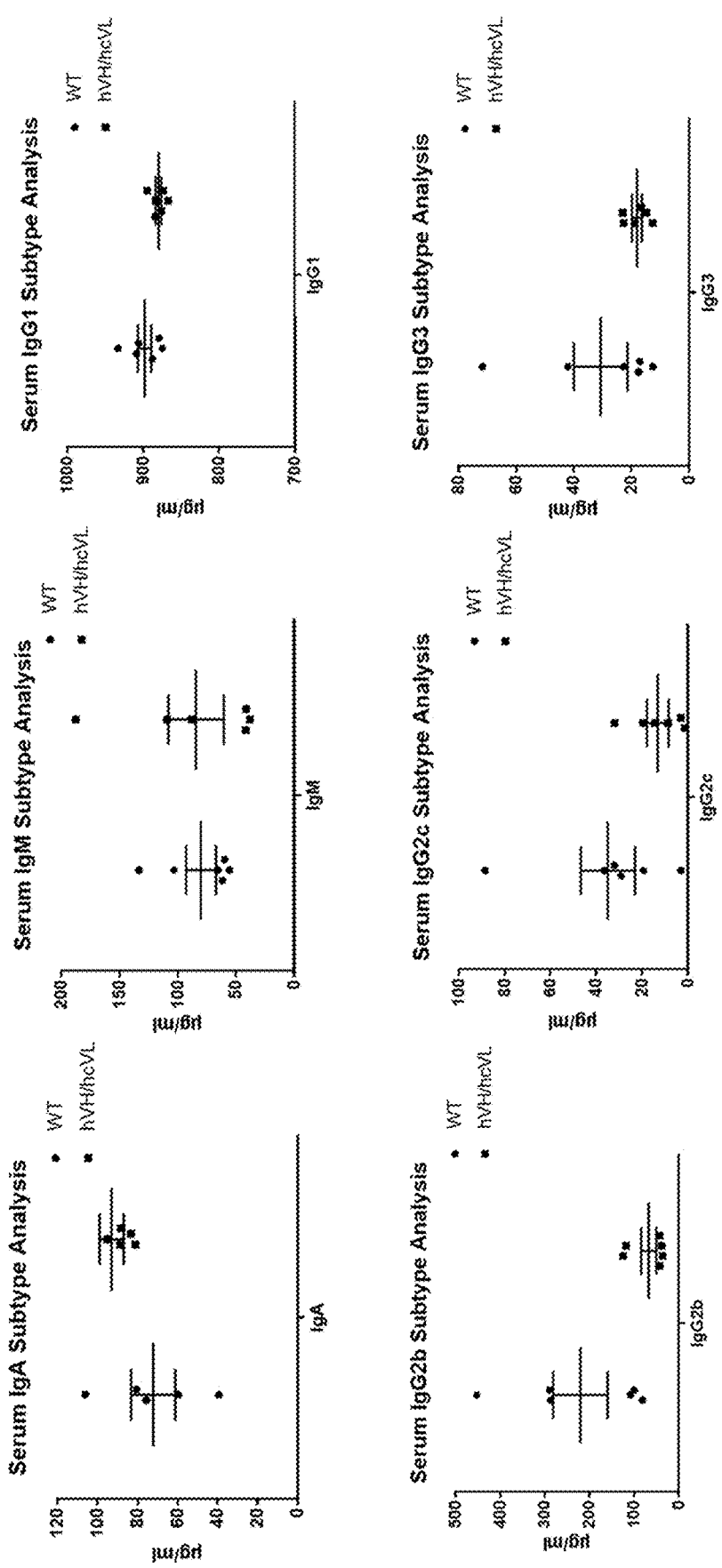
FIG. 13J shows concentration of serum immunoglobulin (Ig) subtypes in wild-type (WT) or hVH/hcVL mice before antigen immunization. The Ig subtype concentrations were determined by ELISA.

Experiments were performed to evaluate B cell development in the hVH$^{H/H}$/hcVL$^{K/K}$ mice. No significant differences in B cell development and average immune organ (e.g., spleen) weight were detected between wild-type and hVH$^{H/H}$/hcVL$^{K/K}$ mice. As shown in FIG. 13J, different immunoglobulin (Ig) subtypes in the serum of hVH$^{H/H}$/hcVL$^{K/K}$ and wild-type mice were quantitatively measured by ELISA before antigen immunization. No significant differences were observed.

Figure 13K:
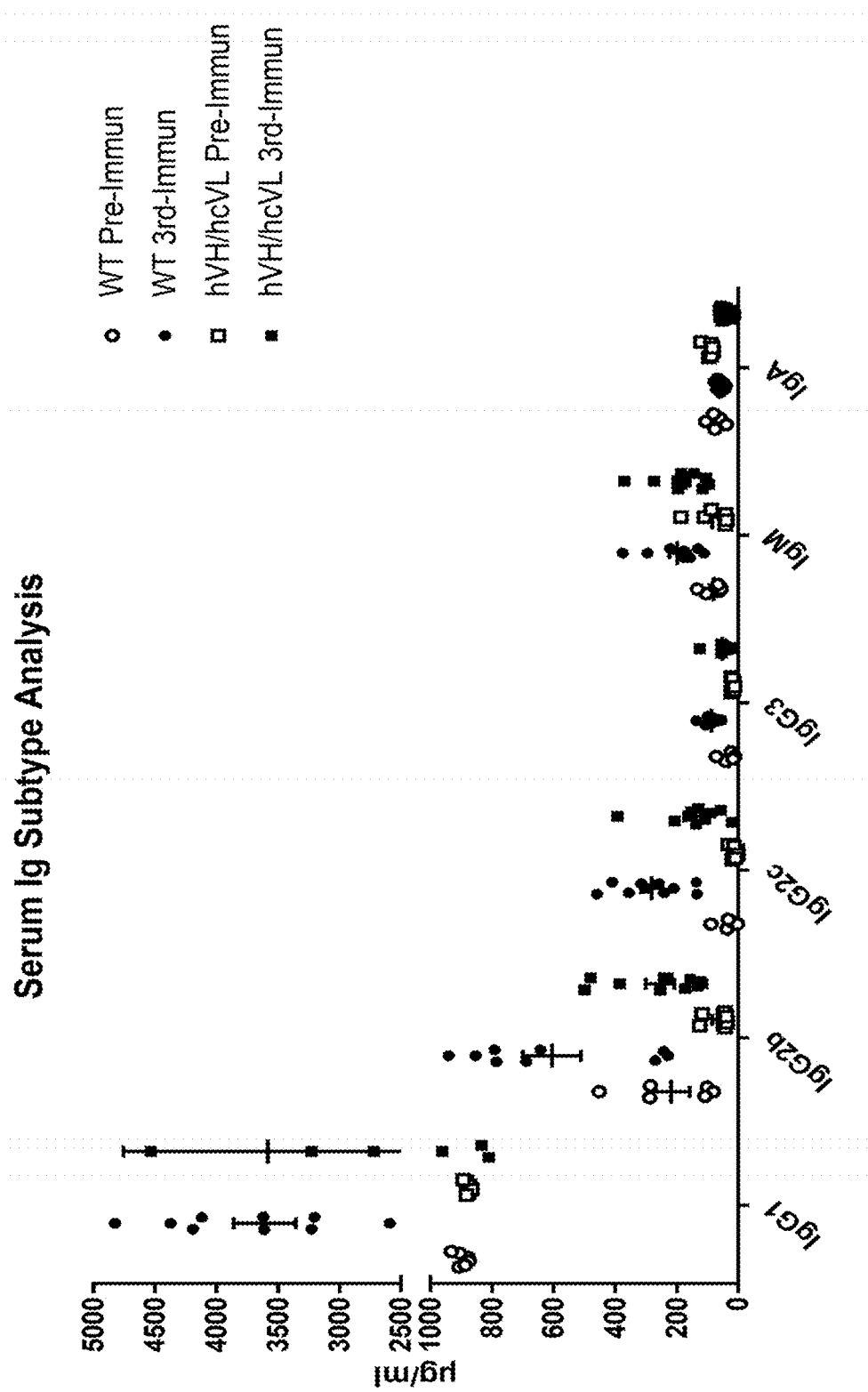
FIG. 13K shows serum Ig subtypes in wild-type (WT) or hVH/hcVL mice before and after immunization.

In another similar experiment, the Ig subtypes of hVH$^{H/H}$/hcVL$^{K/K}$ mice and wild-type mice before and after immunization were analyzed. No significant difference was found (FIG. 13K).

Example 7: Antibody Production in hVH/hcVL Mice

Experiments were performed to evaluate whether B cells were developed normally in hVH/hcVL mice. Antigen-specific antibody titers in the serum of immunized hVH/hcVL mice and wild-type mice were measured.

The hVH$^{H/H}$/hcVL$^{K/+}$ mice and wild-type (C57BL/6) mice were immunized by two different antigens for a total of three times. In the first immunization, complete Freund's adjuvant (CFA) and 20 ug of the antigen were administered. Two weeks later, incomplete Freund's adjuvant (IFA) and 20 ug of the antigen were administered. Two weeks later, the mice were administered with 20 ug of the antigen in combination with IFA. About one week after the third immunization, blood was collected and the antigen-specific antibody titers of the wild-type mice and hVH/hcVL mice were analyzed by ELISA. The hVH$^{H/H}$/hcVL$^{K/+}$ mice dominantly expressed antibodies with the humanized common light chain variable region.

The ELISA was performed as follows. The his-tagged antigen was diluted in 1×PBS to 0.5 μg/ml and added to a 96-well plate with 0.1 ml/well, followed by incubation at 37° C. for 2 hours. After the incubation, each well was washed with 300 μl 1×PBST for three times, and then blocked by 250 μl 1×PBS supplemented with 5% non-fat milk at 37° C. for 1 hour. Each well was then washed by 300 μl 1×PBST twice. Serum samples from the hVH/hcVL mice or wild-type mice were first diluted using 1×PBS at 1:500, 1:2000, 1:8000, 1:32000, 1:128000, 1:512000, or 1:2048000, and then added to the 96-well plate. Serum samples from unimmunized mice were also diluted at 1:500 and added to the plate as a blank control. The diluted serum samples (120 μl/well) were incubated at 37° C. in the 96-well plate for 1 hour. After the incubation, the plate was washed with 300 μl/well of 1×PBST for five times. The plate was then incubated with 0.1 ml/well of 1:20000 diluted goat-anti-mouse IgG Fc (HRP) at 37° C. for 1 hour. After the incubation, the plate was washed with 300 μl/well of 1×PBST for five times. Next, 0.1 ml TMB developing solution was added to each well and the plate was kept in dark at room temperature for 10 minutes, followed by adding 0.1 ml stop solution to each well. OD450 and OD570 were measured by a plate reader and the standard OD value in FIGS. 24-25 were calculated as: standard OD value=OD450−OD570.

Figure 24:
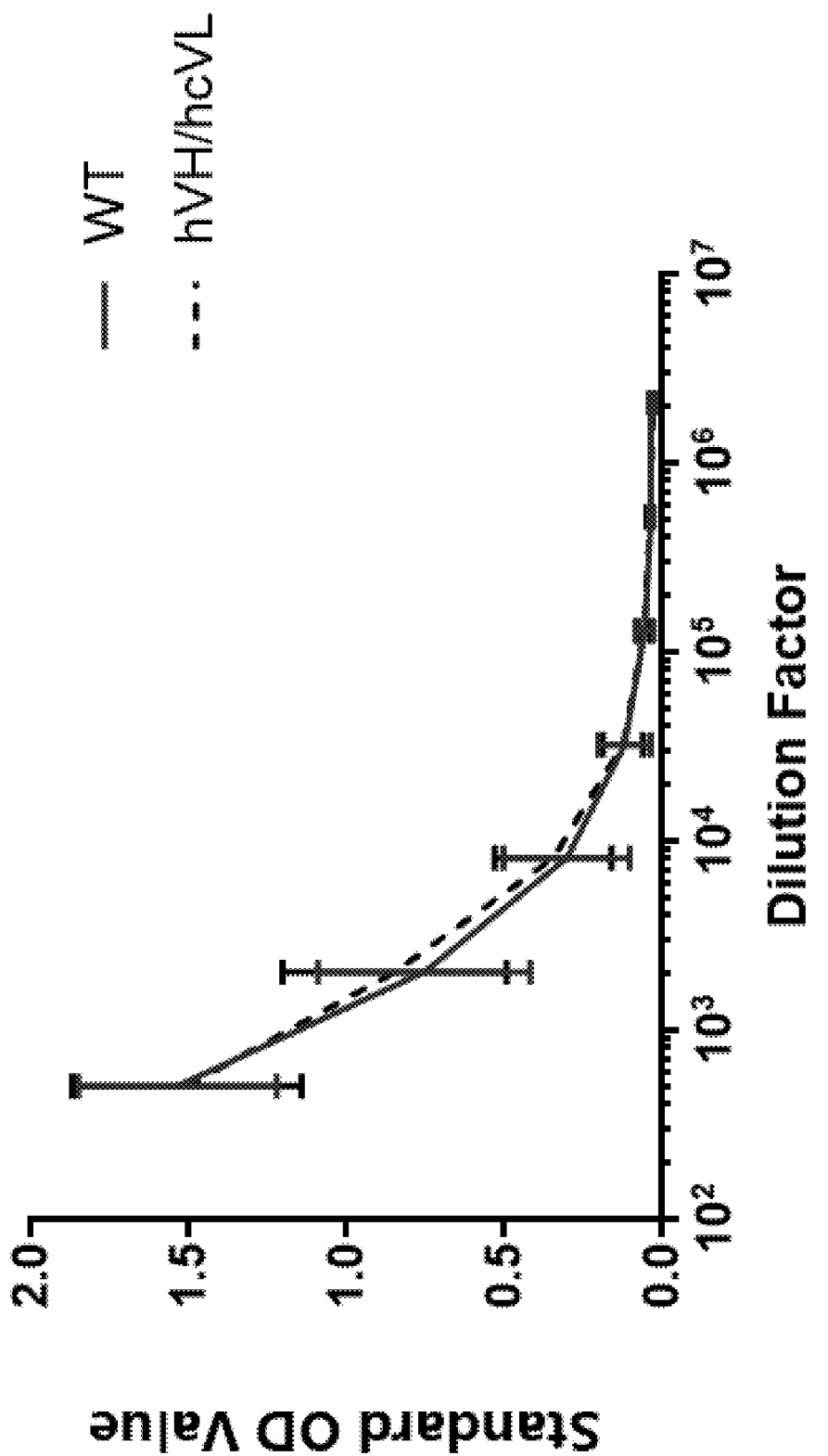
FIG. 24 shows antigen-specific antibody titer after three immunizations with a first test antigen in wild-type and hVH$^{H/H}$/hcVL$^{K/+}$ mice.
Figure 25:
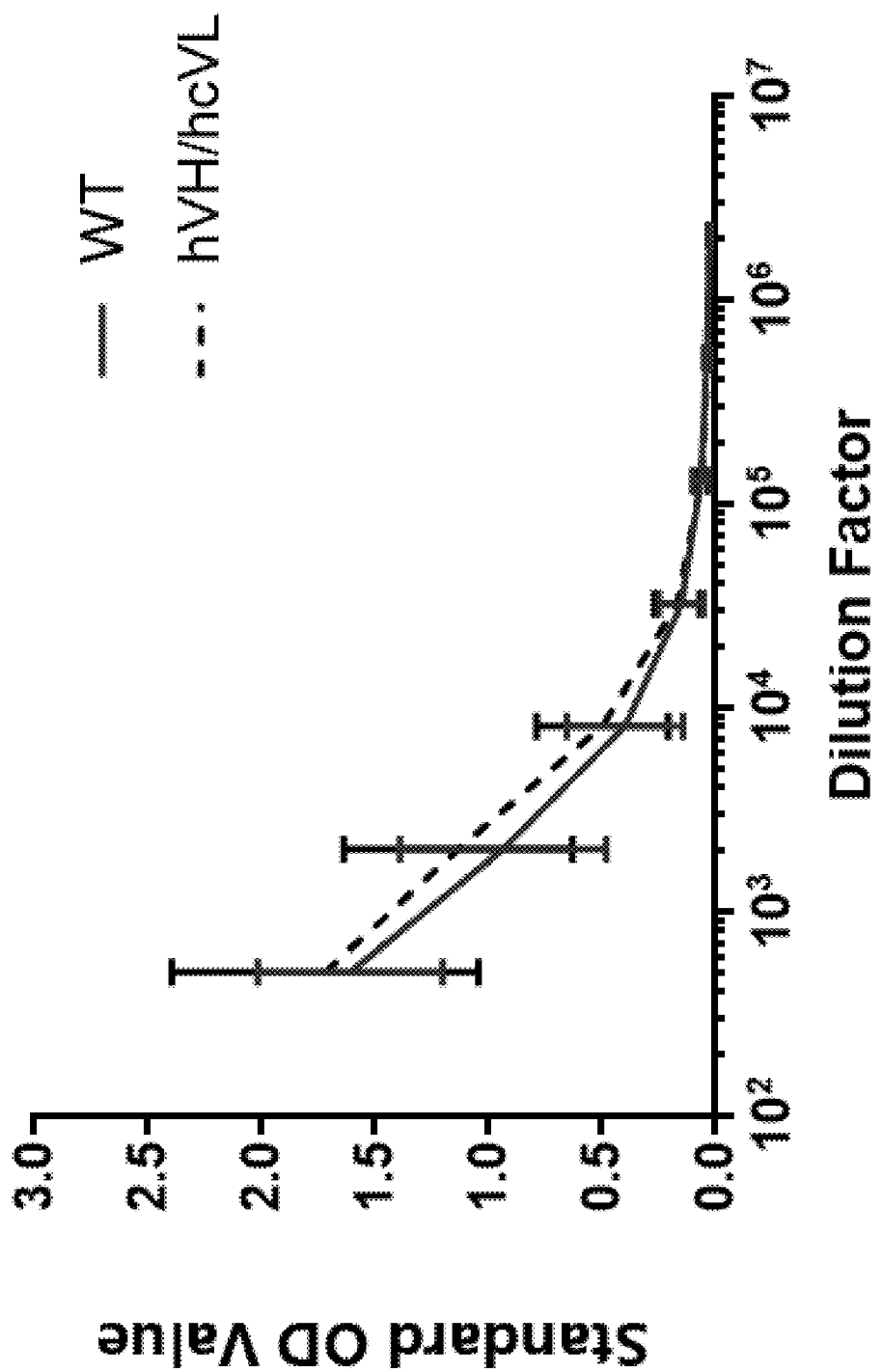
FIG. 25 shows antigen-specific antibody titer after three immunizations with a second test antigen in wild-type and hVH$^{H/H}$/hcVL$^{K/+}$ mice.

Results for the antigen-specific antibody titers after the third immunization are shown in FIG. 24 and FIG. 25, respectively. The results showed that hVH/hcVL mice can produce antibodies that specifically binds to the antigen, and the immune response in the wild-type and hVH/hcVL mice were similar. Particularly, the serum antibody titers were similar to the wild-type.

Example 8: Antibody Production in hVH/hcVL Mice

TFR1 and Ova were used to immunize of hVH$^{H/H}$/hcVL$^{K/K}$ mice and wild-type mice (3 for each group). Beacon® Optofluidic System was then used isolate the plasma cells that can produce antigen-specific monoclonal antibodies. The number of positive cells were shown below.

TABLE 16

| Mouse | Antigen | No. of positive cells |
|---|---|---|
| WT mice | TFR1 | 197 |
| hVH$^{H/H}$/hcVL$^{K/K}$ mice | TFR1 | 220 |
| WT mice | Ova | 356 |
| hVH$^{H/H}$/hcVL$^{K/K}$ mice | Ova | 448 |

Antigen A is a member of the tumor necrosis factor receptor superfamily. Antigen A was used to immunize of hVH$^{H/H}$/hcVL$^{K/K}$ mice. 42 human common light chain antibodies (IGKV3-11/J1) were obtained. The VH and VL of these antibodies were added to human IgG1 constant regions to obtain human antibodies. Biacore was then used to determine the affinity of 42 human common light chain antibodies (IGKV3-11/J1) produced against the antigen A.

Purified anti-antigen A antibodies were diluted to 1 ug/ml and then injected into the Biacore 8K biosensor at 10 μL/min for about 50 seconds to achieve a desired protein density (e.g., about 50 response units (RU)). His-tagged antigen A at concentrations of 200 nM was then injected at 30 μL/min for 120 seconds. Dissociation was monitored for 600 seconds. The chip was regenerated after the last injection of each titration with Glycine (pH 2.0, 30 μL/min for 30 seconds).

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore 8K Evaluation Software 3.0. Affinities were deduced from the quotient of the kinetic rate constants (KD=koff/kon).

As a person of ordinary skill in the art would understand, the same method with appropriate adjustments for parameters (e.g., antibody concentration) was performed for each tested antibody. The results showed that except for A-1C5-IgG1, A-1D10-IgG1 and A-1E1-IgG1, the binding affinity of these antibodies reached or even exceeded 10$^{-8}$ M, indicating that the methods can successfully generate antibodies with high binding affinity against an antigen.

TABLE 17

| | Protein | ka (1/Ms) | kd (1/s) | KD (M) |
|---|---|---|---|---|
| 1 | A-1A7-IgG1 | 2.7E+04 | 6.3E−04 | 2.4E−08 |
| 2 | A-1B1-IgG1 | 1.9E+05 | 1.4E−04 | 7.5E−10 |
| 3 | A-1B8-IgG1 | 1.6E+05 | 3.4E−04 | 2.1E−09 |
| 4 | A-1C5-IgG1 | 2.2E+02 | 7.6E−04 | 3.5E−06 |
| 5 | A-1D10-IgG1 | 1.8E+02 | 5.7E−04 | 3.1E−06 |
| 6 | A-1D12-IgG1 | 6.6E+04 | 1.6E−04 | 2.5E−09 |
| 7 | A-1E1-IgG1 | 1.8E+03 | 3.8E−04 | 2.1E−07 |
| 8 | A-1E12-IgG1 | 6.8E+04 | 1.4E−03 | 2.1E−08 |
| 9 | A-1E7-IgG1 | 3.1E+04 | 2.0E−03 | 6.3E−08 |
| 10 | A-1F9-IgG1 | 1.2E+05 | 6.0E−03 | 5.0E−08 |
| 11 | A-2A11-IgG1 | 2.3E+05 | 1.1E−03 | 4.6E−09 |
| 12 | A-2C11-IgG1 | 5.4E+04 | 4.1E−04 | 7.6E−09 |

TABLE 17-continued

| | Protein | ka (1/Ms) | kd (1/s) | KD (M) |
|---|---|---|---|---|
| 13 | A-2C12-IgG1 | 3.3E+04 | 3.8E-04 | 1.2E-08 |
| 14 | A-2C5-IgG1 | 1.4E+05 | 6.2E-04 | 4.5E-09 |
| 15 | A-2D4-IgG1 | 9.4E+04 | 1.4E-03 | 1.5E-08 |
| 16 | A-2F1-IgG1 | 3.0E+04 | 1.4E-04 | 4.7E-09 |
| 17 | A-2F10-IgG1 | 3.2E+04 | 4.3E-04 | 1.4E-08 |
| 18 | A-2F11-IgG1 | 3.3E+04 | 3.9E-04 | 1.2E-08 |
| 19 | A-2F12-IgG1 | 2.9E+04 | 2.5E-04 | 8.6E-09 |
| 20 | A-2F2-IgG1 | 1.1E+06 | 2.2E-02 | 2.0E-08 |
| 21 | A-2F5-IgG1 | 3.1E+05 | 1.4E-03 | 4.5E-09 |
| 22 | A-2F7-IgG1 | 6.4E+06 | 3.4E-02 | 5.4E-09 |
| 23 | A-2G11-IgG1 | 3.1E+06 | 6.6E-03 | 2.2E-09 |
| 24 | A-3A11-IgG1 | 7.7E+05 | 7.1E-03 | 9.2E-09 |
| 25 | A-3A4-IgG1 | 7.8E+04 | 7.2E-04 | 9.2E-09 |
| 26 | A-3B11-IgG1 | 8.6E+04 | 7.8E-04 | 9.1E-09 |
| 27 | A-3C7-IgG1 | 3.4E+04 | 3.2E-04 | 9.5E-09 |
| 28 | A-4A1-IgG1 | 3.5E+04 | 4.4E-04 | 1.3E-08 |
| 29 | A-4B2-IgG1 | 7.4E+04 | 5.6E-04 | 7.7E-09 |
| 30 | A-4B9-IgG1 | 3.7E+04 | 4.5E-04 | 1.2E-08 |
| 31 | A-4C10-IgG1 | 3.4E+04 | 5.2E-04 | 1.5E-08 |
| 32 | A-4C8-IgG1 | 5.7E+04 | 3.5E-03 | 6.2E-08 |
| 33 | A-4C9-IgG1 | 3.9E+04 | 3.3E-04 | 8.5E-09 |
| 34 | A-4E12-IgG1 | 2.7E+05 | 9.3E-03 | 3.4E-08 |
| 35 | A-4F2-IgG1 | 4.2E+04 | 5.5E-04 | 1.3E-08 |
| 36 | A-4F3-IgG1 | 1.9E+06 | 9.0E-03 | 4.8E-09 |
| 37 | A-4G2-IgG1 | 3.6E+04 | 4.2E-04 | 1.2E-08 |
| 38 | A-H8L8-IgG1 | 1.4E+05 | 3.9E-03 | 2.8E-08 |
| 39 | A-H7L7-IgG1 | 5.0E+04 | 2.4E-03 | 4.9E-08 |
| 40 | A-H10L10-IgG1 | 7.0E+04 | 5.6E-03 | 8.0E-08 |
| 41 | A-H3L3-IgG1 | 2.3E+05 | 4.8E-03 | 2.1E-08 |
| 42 | A-H6L6-IgG1 | 2.5E+05 | 3.7E-03 | 1.5E-08 |

Epitope Correlation Analysis

Relative positions of epitopes were analyzed through a surface plasmon resonance (SPR) competition experiment. A total of 15 monoclonal antibodies were used to study the binding inhibition (blocking) effect against each other: A-1B10-IgG1, A-1D7-IgG1, A-1C8-IgG1, A-1F2-IgG1, A-H6L6-IgG1, A-1F9-IgG1, A-1B1-IgG1, A-1D12-IgG1, A-1E7-IgG1, A-1A7-IgG1, A-1B8-IgG1, A-H7L7-IgG1, A-1E12-IgG1, A-H3L3-IgG1 and A-H8L8-IgG1. Another antibody against antigen A was also included as PC (positive control).

HBS-EP+ buffer (10 mM 4-(2-hydroxyethyl)-1-piperazineethanesulfonic acid (HEPES), 150 mM NaCl, 3 mM ethylenediaminetetraacetic acid (EDTA) and 0.05% P20, pH 7.4) was diluted from HBS-EP+ buffer (10×) as the running buffer throughout the experiment. Anti-His antibodies were fixed on the surface of a Series S sensor Chip CM5 by amino group coupling to generate an anti-His chip (i.e., CM5-Anti-His-Channel 1,8-Chip). Then, 1M ethanolamine, pH 8.5 was injected to block the remaining active carboxyl groups on the chip surface, followed by equilibration using the HBS-EP+ buffer for 2 hours. Recombinant Antigen A protein with His-tag (1 μg/ml) were injected into the Biacore 8K biosensor at 10 μL/min for 50 seconds and captured on the anti-His chip to achieve a desired protein density (i.e., 200 RU). A pair of antibodies (200 nM each) was continuously injected at 30 μL/min into the chip. The first injected antibody (analyte 1) had a binding time of 250 seconds, and then the second antibody (analyte 2) was injected with a binding time of 250 seconds. After injection of the antibodies in each analysis cycle, the chip was regenerated twice with a glycine buffer (pH 1.7; 30 μL/min for 30 seconds). Each pair of monoclonal antibodies was subjected to the same experimental steps to obtain the binding inhibition data when each monoclonal antibody was paired with another antibody.

Figure 31:
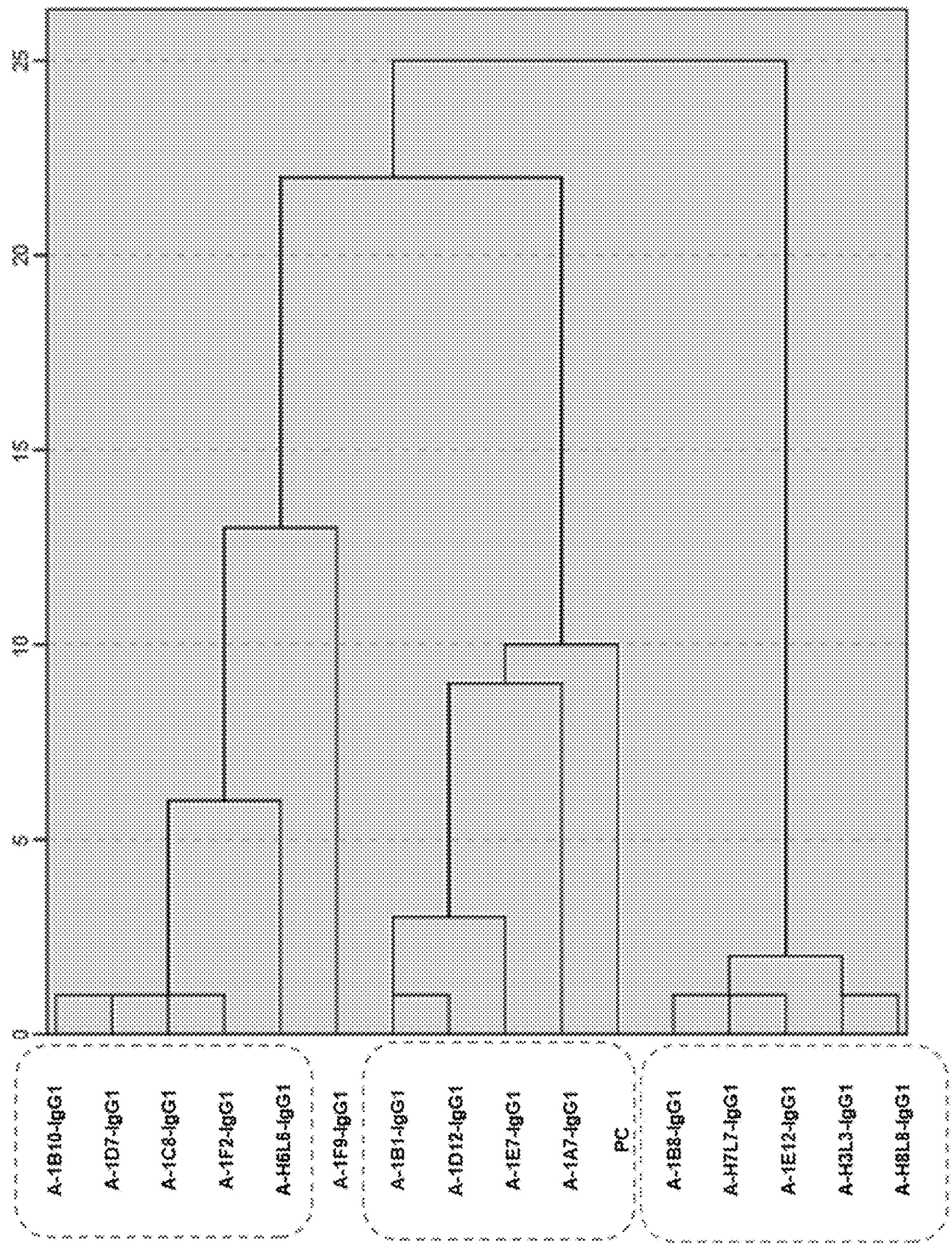
FIG. 31 shows epitope clustering results for 15 human anti-antigen A antibodies.

The binding value of each antibody was obtained using Biacore Insight Evaluation Software. To quantify the interference of one antibody binding to another, a binding ratio was calculated to compare each pair of antibodies. The binding ratio is defined as the binding value of the second antibody (analyte 2), divided by the binding value of the first antibody (analyte 1). A statistical software was also used for cluster analysis. Epitope correlation was analyzed and the 15 human anti-Antigen A antibodies were categorized into 4 epitope clusters (FIG. 31). In summary, A-1B10-IgG1, A-1D7-IgG1, A-1C8-IgG1 and A-1F2-IgG1 shared the same or overlapping epitopes; A-1B1-IgG1 and A-1D12-IgG1 shared the same or overlapping epitopes; A-1B8-IgG1, A-H7L7-IgG1 and A-1E12-IgG1 shared the same or overlapping epitopes; A-H3L3-IgG1 and A-H8L8-IgG1 shared the same or overlapping epitopes. The results indicate that hVH$^{H/H}$/hcVL$^{K/K}$ mice can produce antibodies that target various epitopes.

Thermal Stability Measurement

Thermal stability of 17 human anti-Antigen A antibodies were measured by a Protein Thermal Shift™ Dye Kit using QuantStudio™ 5 Real Time PCR Systems.

The experiments were performed according to the manufacturer's protocol. Reactions were performed continuously in two steps. Specifically, the first step was carried out at 1.6° C. per second at 25° C. for 2 minutes and the second step was carried out at 0.05° C. per second at 99° C. for 2 minutes. Melting temperature (Tm) of each anti-Antigen A antibody was determined, as shown in the table below.

TABLE 18

| Protein | Tm (° C.) |
|---|---|
| A-1A7-IgG1 | 69.6 |
| A-1B10-IgG1 | 71.2 |
| A-1B1-IgG1 | 68.9 |
| A-1B8-IgG1 | 74.2 |
| A-1C8-IgG1 | 73.6 |
| A-1D12-IgG1 | 70.0 |
| A-1D7-IgG1 | 72.8 |
| A-1E12-IgG1 | 76.6 |
| A-1E7-IgG1 | 73.5 |
| A-1F2-IgG1 | 73.1 |
| A-1F9-IgG1 | 72.3 |
| A-H3L3-IgG1 | 73.9 |
| A-H6L6-IgG1 | 68.7 |
| A-H7L7-IgG1 | 76.7 |
| A-H8L8-IgG1 | 76.7 |
| A-1E1-IgG1 | 75.8 |
| A-1E4-IgG1 | 70.8 |

The results show that Tm of the human anti-Antigen A antibodies are over or around 70° C., and these antibodies are thermally stable.

Example 9: Antibody Production in hVH/hcVL Mice

Antigen B is a Type II transmembrane serine protease. Antigen B was used to immunize of hVH$^{H/H}$/hcVL$^{K/K}$ mice (IGKV3-11/J1). Biacore was then used to detect the affinity of 8 human common light chain antibodies (IGKV3-11/J1) produced against the antigen B.

TABLE 19

| Antibody | Ka (1/Ms) | Kd (1/s) | KD (M) |
|---|---|---|---|
| B-3E10-hIgG1 | 1.2E+05 | 9.8E-06 | 8.1E-11 |
| B-3E4-hIgG1 | 2.0E+05 | 6.2E-05 | 3.1E-10 |
| B-1H9-hIgG1 | 1.8E+05 | 1.2E-04 | 6.9E-10 |
| B-1G2-hIgG1 | 2.9E+05 | 3.1E-04 | 1.1E-09 |
| B-1A1-hIgG1 | 1.9E+05 | 2.8E-04 | 1.5E-09 |

TABLE 19-continued

| Antibody | Ka (l/Ms) | Kd (l/s) | KD (M) |
|---|---|---|---|
| B-1E10-hIgG1 | 1.5E+05 | 2.7E−04 | 1.8E−09 |
| B-2D12-hIgG1 | 3.5E+04 | 5.3E−08 | 1.5E−12 |
| B-3D1-hIgG1 | 3.1E+04 | 3.4E−07 | 1.1E−11 |

Example 10. Blocking the Binding of Antigen C Ligand to Antigen C

Antigen C is an inhibitory receptor on antigen activated T-cells that plays a critical role in induction and maintenance of immune tolerance to self. Blocking assays were performed to determine whether the 129 anti-human Antigen C antibodies can block the binding between human Antigen C and its ligand. These antibodies were produced by hVH$^{H/H}$/hcVL$^{K/K}$ mice.

Anti-Antigen C antibodies were collected from CHO-S supernatant. 30 μl CHO cells (about $1\times10^5$) transiently transfected with human Antigen C Ligand were added to each well in a plate. The antibodies in supernatant (about 20-200 ug/ML) were collected and then were diluted 10 times and 100 times. The titrated antibodies (30 μl per well) and Bitoin-labeled human Antigen C (30 μl per well, with a final concentration of 1 μg/ml in each well) were added to each well at 30 μl per well at 4° C. The cells with Bitoin-labeled human Antigen C and the antibodies were incubated at 4° C. for 30 minutes.

After being washed with phosphate-buffered saline (PBS) twice, 50 μl of Alexa Fluor® 647-labeled Streptavidin (AF647 Streptavidin, Jackson Immuno research, Cat #016-600-084) at 1:1000 dilution were added into each well, and incubated for 15 minutes at 4° C., followed by PBS wash. The signals for AF647 was determined by flow cytometry (Thermo Attune NX). The result for the antibodies with percentage of tested cells that had Streptavidin signals in the flow cytometry analysis are summarized in the table below. As the antibody concentration decreases, the blocking rate decreases, indicating that these antibodies can block the binding between Antigen C and its ligand.

TABLE 20

| | | Blocking rate (%) | | | |
|---|---|---|---|---|---|
| No. | Antibody | Undiluted | Diluted 10X | Diluted 100X | Blocking activity |
| 1 | C-11A1-IgG4 | 85.8 | 69.9 | 41.8 | Y |
| 2 | C-11A2-IgG4 | 95.0 | 81.4 | 38.5 | Y |
| 3 | C-11A5-IgG4 | 95.0 | 77.7 | 35.7 | Y |
| 4 | C-11A9-IgG4 | 90.1 | 71.8 | 36.9 | Y |
| 5 | C-11B2-IgG4 | 95.6 | 77.8 | 51.3 | Y |
| 6 | C-11B3-IgG4 | 91.7 | 77.4 | 37.1 | Y |
| 7 | C-11B5-IgG4 | 97.0 | 86.5 | 37.8 | Y |
| 8 | C-11B6-IgG4 | 79.3 | 58.4 | 37.0 | Y |
| 9 | C-11B7-IgG4 | 95.4 | 84.3 | 41.6 | Y |
| 10 | C-11B9-IgG4 | 94.1 | 86.2 | 41.2 | Y |
| 11 | C-11C11-IgG4 | 96.3 | 77.9 | 36.4 | Y |
| 12 | C-11C1-IgG4 | 95.9 | 84.2 | 37.8 | Y |
| 13 | C-11C3-IgG4 | 87.7 | 60.0 | 39.0 | Y |
| 14 | C-11C4-IgG4 | 95.1 | 81.0 | 34.4 | Y |
| 15 | C-11C5-IgG4 | 96.3 | 78.7 | 37.5 | Y |
| 16 | C-11C8-IgG4 | 95.7 | 83.0 | 37.8 | Y |
| 17 | C-11C9-IgG4 | 94.0 | 86.0 | 48.5 | Y |
| 18 | C-11D1-IgG4 | 93.1 | 89.1 | 37.2 | Y |
| 19 | C-11D2-IgG4 | 95.0 | 65.5 | 37.1 | Y |
| 20 | C-12B5-IgG4 | 93.0 | 69.5 | 40.3 | Y |
| 21 | C-12B7-IgG4 | 93.8 | 76.8 | 49.4 | Y |
| 22 | C-12C5-IgG4 | 93.3 | 86.3 | 40.5 | Y |

TABLE 20-continued

| | | Blocking rate (%) | | | |
|---|---|---|---|---|---|
| No. | Antibody | Undiluted | Diluted 10X | Diluted 100X | Blocking activity |
| 23 | C-12D2-IgG4 | 94.2 | 70.3 | 39.5 | Y |
| 24 | C-12A1-IgG4 | 96.4 | 79.5 | 41.4 | Y |
| 25 | C-12A4-IgG4 | 94.2 | 84.6 | 42.2 | Y |
| 26 | C-12A11-IgG4 | 93.3 | 75.5 | 36.5 | Y |
| 27 | C-12A12-IgG4 | 88.4 | 63.2 | 36.2 | Y |
| 28 | C-12A6-IgG4 | 96.0 | 86.4 | 39.9 | Y |
| 29 | C-12A7-IgG4 | 95.3 | 89.8 | 45.7 | Y |
| 30 | C-12A9-IgG4 | 95.7 | 87.4 | 39.2 | Y |
| 31 | C-12C12-IgG4 | 96.9 | 86.2 | 37.6 | Y |
| 32 | C-12C3-IgG4 | 96.9 | 96.3 | 40.8 | Y |
| 33 | C-15H10-IgG4 | 86.5 | 71.9 | 36.1 | Y |
| 34 | C-16E9-IgG4 | 96.3 | 82.3 | 32.4 | Y |
| 35 | C-16F5-IgG4 | 96.9 | 85.5 | 35.7 | Y |
| 36 | C-16F8-IgG4 | 97.4 | 85.0 | 33.5 | Y |
| 37 | C-11A11-IgG4 | 97.3 | 87.9 | 40.1 | Y |
| 38 | C-11A3-IgG4 | 93.6 | 76.9 | 38.2 | Y |
| 39 | C-11B11-IgG4 | 96.3 | 83.9 | 35.9 | Y |
| 40 | C-11C10-IgG4 | 96.3 | 86.2 | 39.3 | Y |
| 41 | C-11C2-IgG4 | 78.7 | 61.6 | 34.2 | Y |
| 42 | C-11C7-IgG4 | 94.1 | 79.9 | 35.0 | Y |
| 43 | C-12A10-IgG4 | 97.4 | 54.4 | 32.0 | Y |
| 44 | C-12A5-IgG4 | 95.4 | 85.9 | 36.0 | Y |
| 45 | C-12B1-IgG4 | 96.4 | 82.6 | 33.3 | Y |
| 46 | C-12B4-IgG4 | 94.8 | 86.0 | 38.7 | Y |
| 47 | C-12B6-IgG4 | 95.8 | 80.0 | 36.9 | Y |
| 48 | C-12C1-IgG4 | 97.0 | 85.7 | 36.2 | Y |
| 49 | C-12C7-IgG4 | 96.7 | 80.1 | 34.3 | Y |
| 50 | C-15D10-IgG4 | 80.2 | 73.7 | 32.8 | Y |
| 51 | C-15D7-IgG4 | 82.5 | 72.2 | 36.9 | Y |
| 52 | C-15D9-IgG4 | 96.1 | 83.7 | 35.0 | Y |
| 53 | C-15E11-IgG4 | 95.9 | 80.9 | 32.3 | Y |
| 54 | C-15H3-IgG4 | 94.3 | 79.9 | 33.7 | Y |
| 55 | C-15H4-IgG4 | 96.2 | 82.8 | 35.9 | Y |
| 56 | C-15H11-IgG4 | 96.7 | 83.7 | 37.5 | Y |
| 57 | C-15H12-IgG4 | 96.1 | 83.2 | 35.0 | Y |
| 58 | C-15H9-IgG4 | 80.1 | 69.3 | 33.3 | Y |
| 59 | C-16B11-IgG4 | 96.6 | 76.9 | 35.5 | Y |
| 60 | C-16B8-IgG4 | 91.0 | 80.1 | 35.1 | Y |
| 61 | C-16C10-IgG4 | 95.3 | 83.1 | 33.9 | Y |
| 62 | C-16C3-IgG4 | 96.1 | 81.3 | 37.2 | Y |
| 63 | C-16C5-IgG4 | 96.8 | 80.5 | 36.2 | Y |
| 64 | C-16C8-IgG4 | 97.6 | 84.4 | 35.2 | Y |
| 65 | C-16C9-IgG4 | 96.2 | 80.1 | 39.8 | Y |
| 66 | C-16D12-IgG4 | 95.5 | 81.7 | 39.3 | Y |
| 67 | C-16D3-IgG4 | 97.1 | 83.0 | 44.1 | Y |
| 68 | C-16D6-IgG4 | 96.1 | 82.2 | 47.0 | Y |
| 69 | C-16E2-IgG4 | 96.2 | 79.4 | 37.2 | Y |
| 70 | C-16F10-IgG4 | 95.4 | 80.3 | 37.1 | Y |
| 71 | C-16F2-IgG4 | 96.5 | 81.8 | 42.3 | Y |
| 72 | C-16F3-IgG4 | 96.7 | 83.2 | 45.6 | Y |
| 73 | C-16F4-IgG4 | 95.9 | 81.8 | 38.2 | Y |
| 74 | C-16F6-IgG4 | 93.7 | 80.8 | 38.6 | Y |
| 75 | C-16G7-IgG4 | 93.6 | 81.3 | 42.4 | Y |
| 76 | C-15B10-IgG4 | 96.9 | 84.3 | 46.4 | Y |
| 77 | C-15B1-IgG4 | 95.8 | 80.6 | 37.2 | Y |
| 78 | C-15B6-IgG4 | 95.4 | 80.2 | 36.3 | Y |
| 79 | C-15C3-IgG4 | 95.0 | 83.1 | 41.0 | Y |
| 80 | C-15C5-IgG4 | 96.9 | 83.9 | 38.9 | Y |
| 81 | C-15DH-IgG4 | 96.1 | 80.5 | 37.6 | Y |
| 82 | C-15D3-IgG4 | 95.5 | 79.3 | 33.1 | Y |
| 83 | C-15D4-IgG4 | 96.1 | 81.9 | 36.7 | Y |
| 84 | C-15D5-IgG4 | 96.2 | 84.7 | 43.3 | Y |
| 85 | C-15E2-IgG4 | 96.0 | 79.7 | 38.0 | Y |
| 86 | C-15E3-IgG4 | 96.4 | 80.7 | 34.5 | Y |
| 87 | C-15E4-IgG4 | 95.9 | 82.8 | 37.3 | Y |
| 88 | C-16H1-IgG4 | 97.1 | 83.7 | 37.1 | Y |
| 89 | C-16H4-IgG4 | 95.3 | 79.3 | 38.1 | Y |
| 90 | C-16H5-IgG4 | 94.9 | 80.1 | 36.9 | Y |
| 91 | C-16H6-IgG4 | 96.3 | 82.6 | 39.6 | Y |
| 92 | C-16H7-IgG4 | 97.3 | 84.1 | 40.2 | Y |
| 93 | C-16H9-IgG4 | 93.9 | 79.8 | 77.7 | Y |
| 94 | C-15E10-IgG4 | 95.8 | 86.5 | 39.8 | Y |
| 95 | C-15F10-IgG4 | 95.0 | 85.9 | 38.9 | Y |
| 96 | C-15G10-IgG4 | 98.1 | 87.8 | 41.0 | Y |
| 97 | C-15G11-IgG4 | 97.5 | 83.1 | 37.9 | Y |

TABLE 20-continued

| No. | Antibody | Blocking rate (%) Undiluted | Diluted 10X | Diluted 100X | Blocking activity |
|---|---|---|---|---|---|
| 98 | C-15G12-IgG4 | 97.6 | 82.7 | 37.8 | Y |
| 99 | C-15G4-IgG4 | 97.3 | 78.8 | 39.9 | Y |
| 100 | C-15G8-IgG4 | 97.2 | 41.8 | 48.1 | Y |
| 101 | C-15G9-IgG4 | 97.8 | 85.1 | 38.0 | Y |
| 102 | C-15H1-IgG4 | 97.4 | 84.1 | 36.1 | Y |
| 103 | C-16A3-IgG4 | 97.6 | 81.6 | 39.7 | Y |
| 104 | C-16A4-IgG4 | 97.5 | 82.4 | 42.7 | Y |
| 105 | C-16A7-IgG4 | 97.8 | 87.2 | 44.4 | Y |
| 106 | C-16A8-IgG4 | 97.2 | 84.3 | 37.4 | Y |
| 107 | C-16A12-IgG4 | 97.3 | 84.2 | 40.3 | Y |
| 108 | C-16B12-IgG4 | 96.9 | 82.3 | 40.8 | Y |
| 109 | C-16B3-IgG4 | 96.6 | 85.1 | 41.1 | Y |
| 110 | C-16B4-IgG4 | 97.1 | 84.8 | 36.2 | Y |
| 111 | C-16B9-IgG4 | 92.4 | 79.3 | 39.6 | Y |
| 112 | C-16C1-IgG4 | 97.4 | 79.5 | 40.4 | Y |
| 113 | C-16C4-IgG4 | 97.9 | 84.2 | 42.4 | Y |
| 114 | C-16E12-IgG4 | 90.5 | 79.1 | 33.8 | Y |
| 115 | C-16E1-IgG4 | 86.0 | 74.3 | 39.3 | Y |
| 116 | C-16E6-IgG4 | 97.6 | 81.5 | 45.9 | Y |
| 117 | C-16G3-IgG4 | 83.5 | 72.8 | 40.2 | Y |
| 118 | C-16G4-IgG4 | 97.6 | 85.4 | 36.9 | Y |
| 119 | C-11B4-IgG4 | 88.8 | 78.4 | 40.0 | Y |
| 120 | C-15B12-IgG4 | 98.1 | 81.5 | 41.7 | Y |
| 121 | C-15B5-IgG4 | 98.3 | 86.3 | 41.5 | Y |
| 122 | C-15B7-IgG4 | 97.6 | 84.1 | 39.0 | Y |
| 123 | C-16A11-IgG4 | 97.8 | 84.3 | 40.6 | Y |
| 124 | C-16C11-IgG4 | 97.8 | 85.0 | 41.6 | Y |
| 125 | C-16D1-IgG4 | 98.1 | 86.4 | 42.6 | Y |
| 126 | C-16D2-IgG4 | 97.7 | 86.3 | 41.4 | Y |
| 127 | C-16D8-IgG4 | 97.8 | 86.6 | 40.9 | Y |
| 128 | C-16F1-IgG4 | 98.4 | 83.3 | 81.8 | Y |
| 129 | C-16G9-IgG4 | 97.5 | 80.6 | 46.1 | Y |

23 antibodies were selected to determine cross-reactivity with mouse Antigen C, monkey Antigen C, and canine Antigen C by flow cytometry. The results are shown below.

TABLE 21

| No. | Tested antibody | Human | Mouse | Monkey | Dog |
|---|---|---|---|---|---|
| 1 | C-9A2-IgG4 | Y | N | Y | Y |
| 2 | C-9A6-IgG4 | Y | N | Y | N |
| 3 | C-10B10-IgG4 | Y | N | Y | N |
| 4 | C-10B12-IgG4 | Y | N | Y | N |
| 5 | C-10B4-IgG4 | Y | N | Y | N |
| 6 | C-10B6-IgG4 | N | N | N | N |
| 7 | C-10B9-IgG4 | Y | Y | Y | N |
| 8 | C-10D5-IgG4 | Y | N | Y | Y |
| 9 | C-10C7-IgG4 | Y | N | Y | N |
| 10 | C-10E11-IgG4 | Y | N | Y | N |
| 11 | C-10E7-IgG4 | Y | N | Y | Y |
| 12 | C-10E8-IgG4 | Y | N | Y | N |
| 13 | C-10E9-IgG4 | Y | N | Y | Y |
| 14 | C-10F11-IgG4 | Y | N | Y | Y |
| 15 | C-10F12-IgG4 | Y | Y | Y | N |
| 16 | C-10F1-IgG4 | Y | N | Y | Y |
| 17 | C-10F7-IgG4 | Y | N | Y | Y |
| 18 | C-10F9-IgG4 | Y | N | Y | Y |
| 19 | C-10G4-IgG4 | Y | N | Y | N |
| 20 | C-9B10-IgG4 | Y | N | Y | N |
| 21 | C-9B3-IgG4 | Y | N | Y | N |
| 22 | C-9B8-IgG4 | Y | Y | Y | N |
| 23 | C-10E10-IgG4 | N | N | N | N |

Example 11: Antibody Diversity and Binding Affinity Distribution of hVH/hcVL Mice Antigen D and antigen E are Type I transmembrane receptor proteins. Antigen D and antigen E were used to immunize of hVH$^{H/H}$/hcVL$^{K/K}$ mice (IGKV3-11/J1) separately. Beacon® Optofluidic System was then used to isolate the plasma cells that can produce antigen-specific monoclonal antibodies.

Figure 33A:
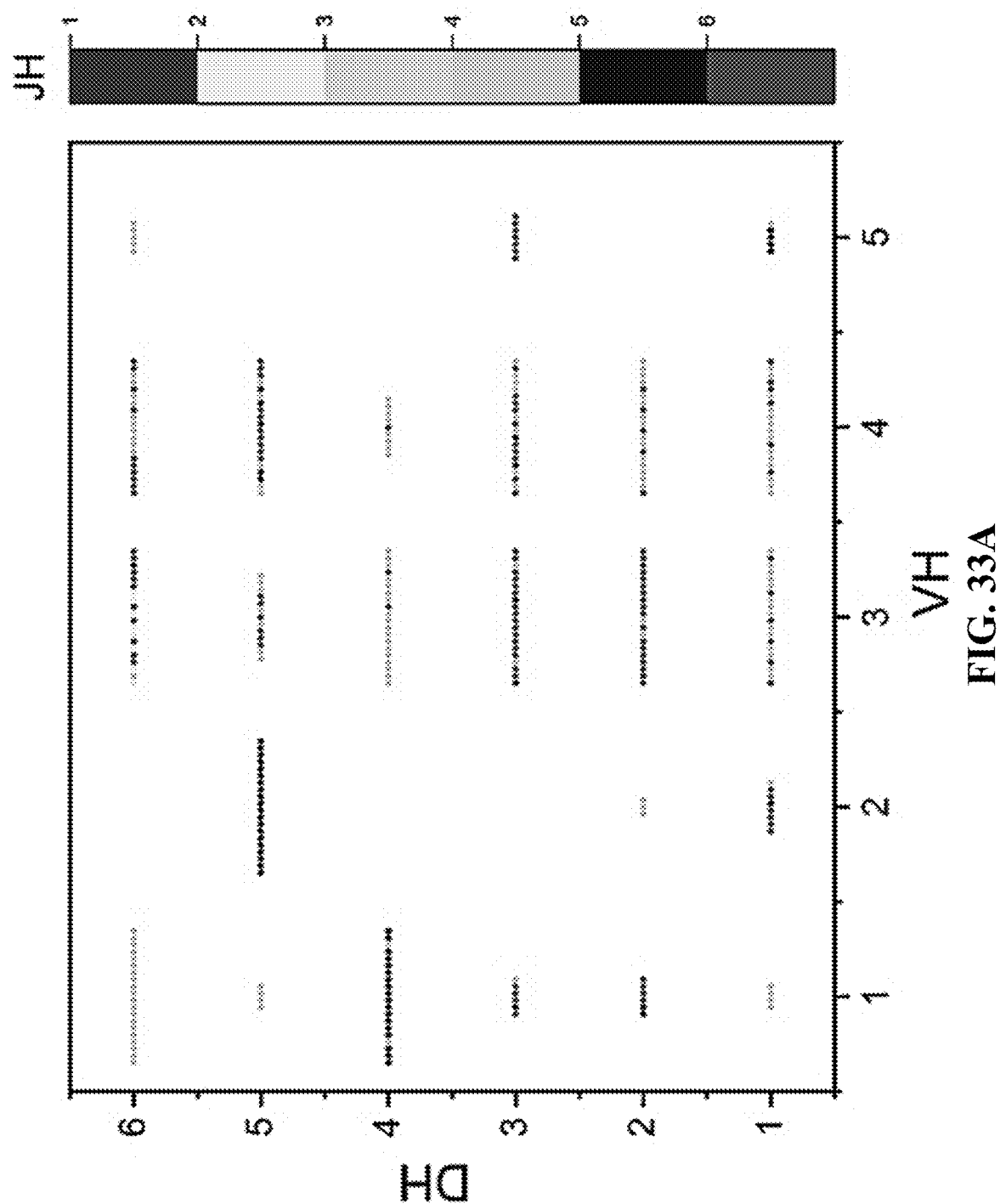
FIG. 33A shows heavy chain diversity by V-D-J recombination analysis of antibodies target Antigen D in hVH$^{H/H}$/hcVL$^{K/K}$ mice.
Figure 33B:
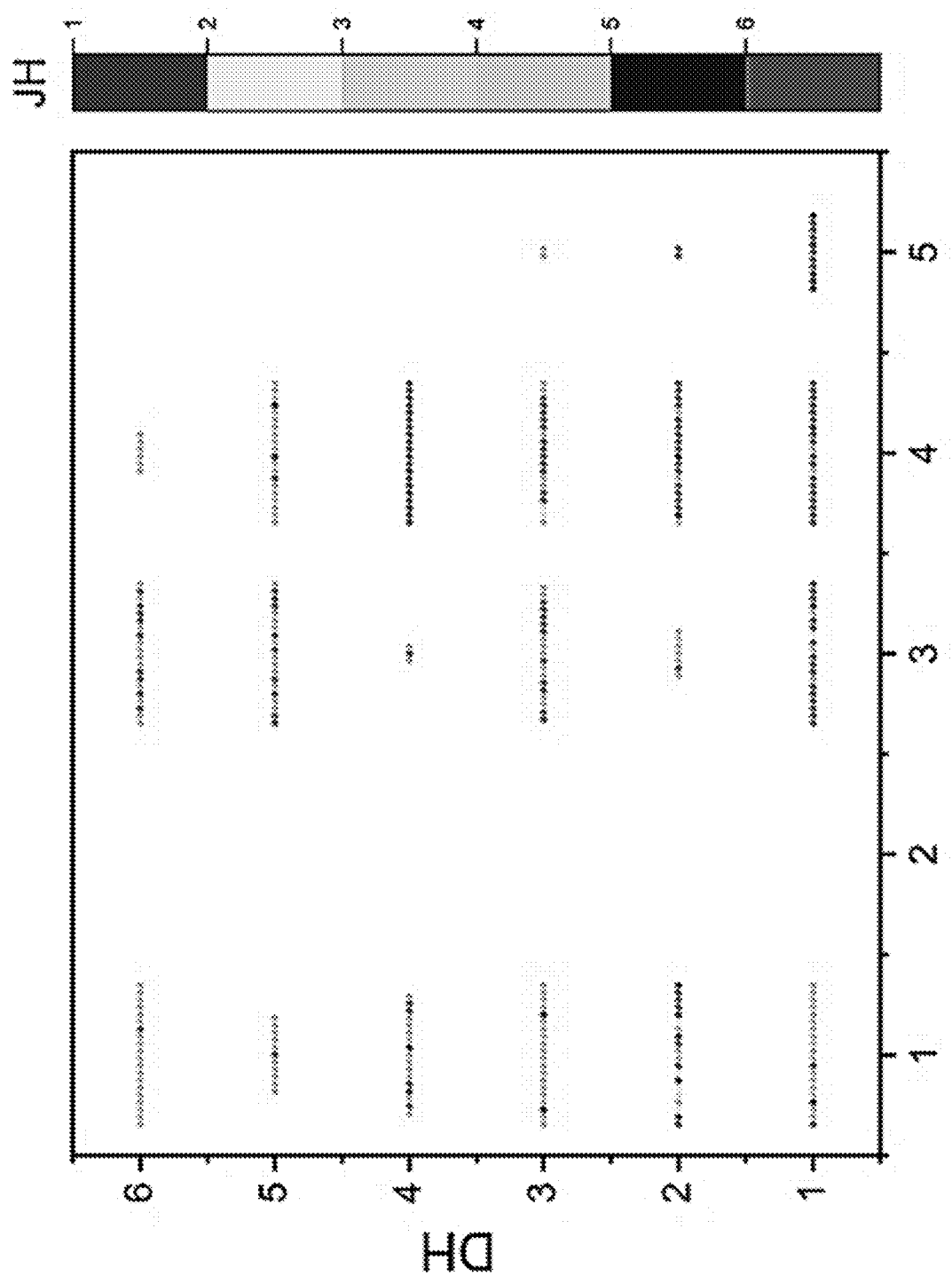
FIG. 33B shows heavy chain diversity by V-D-J recombination analysis of antibodies target Antigen E in hVH$^{H/H}$/hcVL$^{K/K}$ mice.

After extracting RNA from plasma cells, RNA was reverse transcribed into cDNA and sequenced. In the Antigen D group, a total of 1166 antibody heavy chain variable region sequences were obtained. In the Antigen E group, a total of 1290 heavy chain variable region antibody sequences were obtained. The human germline genes of these antibody heavy chain sequences were determined. The results are shown in FIGS. 33A-33B. Among them, the V region genes of all antibodies involve a total of 5 subgroups of VH1-VH5 (including IGHV1, IGHV2, IGHV3, IGHV4, and IGHV5; see the X axis shown in FIGS. 33A-33B). The D region genes involve a total of 6 subgroups of DH1-DH6 (including IGHD1, IGHD2, IGHD3, IGHD4, IGHD5, and IGHD6; see the left Y axis shown in FIGS. 33A-33B). The J region genes involve a total of 6 subgroups JH1-JH6 (including IGHJ1, IGHJ2, IGHJ3, IGHJ4, IGHJ5, and IGHJ6; see the right Y axis shown in FIGS. 33A-33B). The results show that the V\D\J diversity of the antibody heavy chain produced against Antigen D and Antigen E is very high. It demonstrates that in the humanized common light mice, the diversity of antibody heavy chain is not affected.

Biacore was then used to determine the affinity of these antibodies. The association rates (kon) and dissociation rates (koff) were obtained by fitting the data to a 1:1 Langmuir binding model (Karlsson, R. Roos, H. Fagerstam, L. Petersson, B., 1994. Methods Enzymology 6. 99-110). Affinities were deduced from the quotient of the kinetic rate constants (KD=koff/kon). Antibodies with KD less than $1 \times 10^{-8}$ M were analyzed. These antibodies included 805 human common light chain antibodies against the Antigen D and 1026 human common light chain antibodies against the Antigen E. The antibody binding affinity (KD), kon, and koff values were provided and sorted based on KD. Statistical analysis was performed. The distribution of KD, kon and koff are shown in FIGS. 34-35.

Figures 34A, 34C:
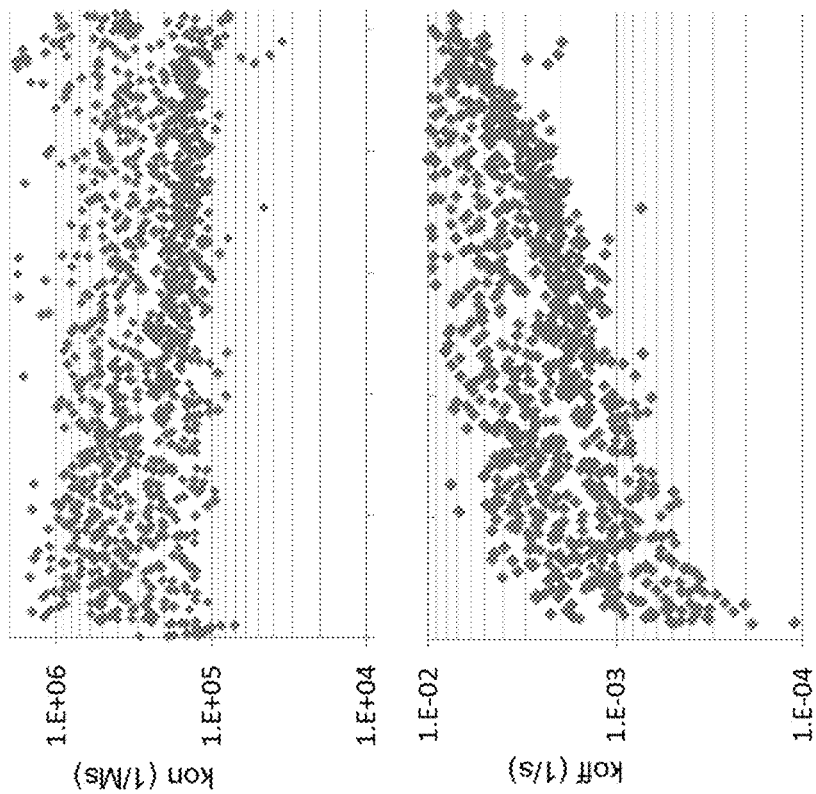
FIGS. 34A-34B show association rates (kon) and dissociation rates (koff) distribution of antibodies target Antigen D.
FIGS. 34C-34D show association rates (kon) and dissociation rates (koff) distribution of antibodies target Antigen E.
Figures 34B, 34D:
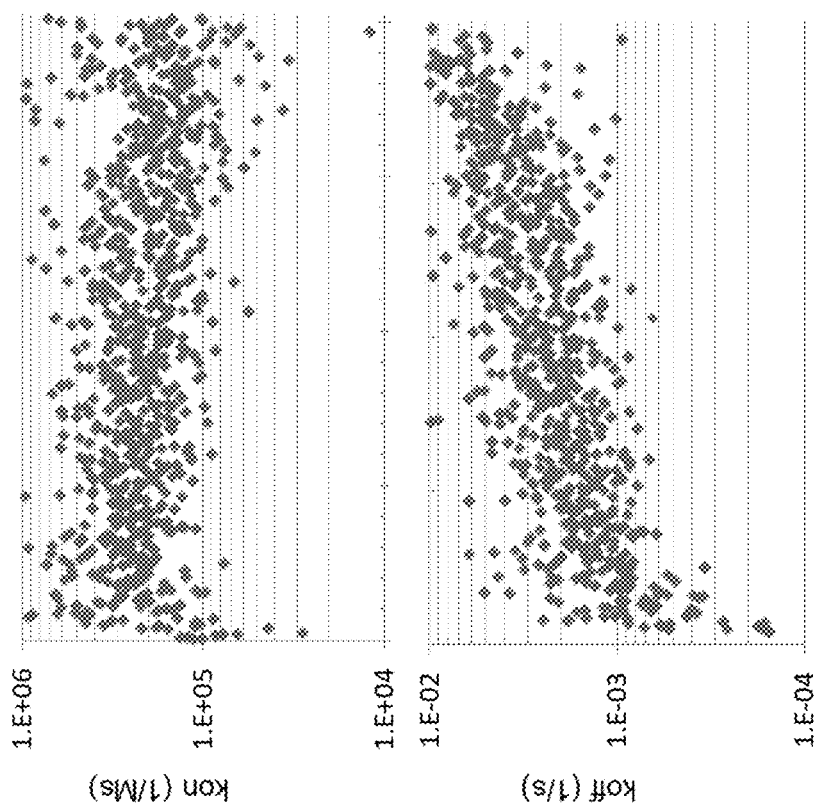
Figure 35A:
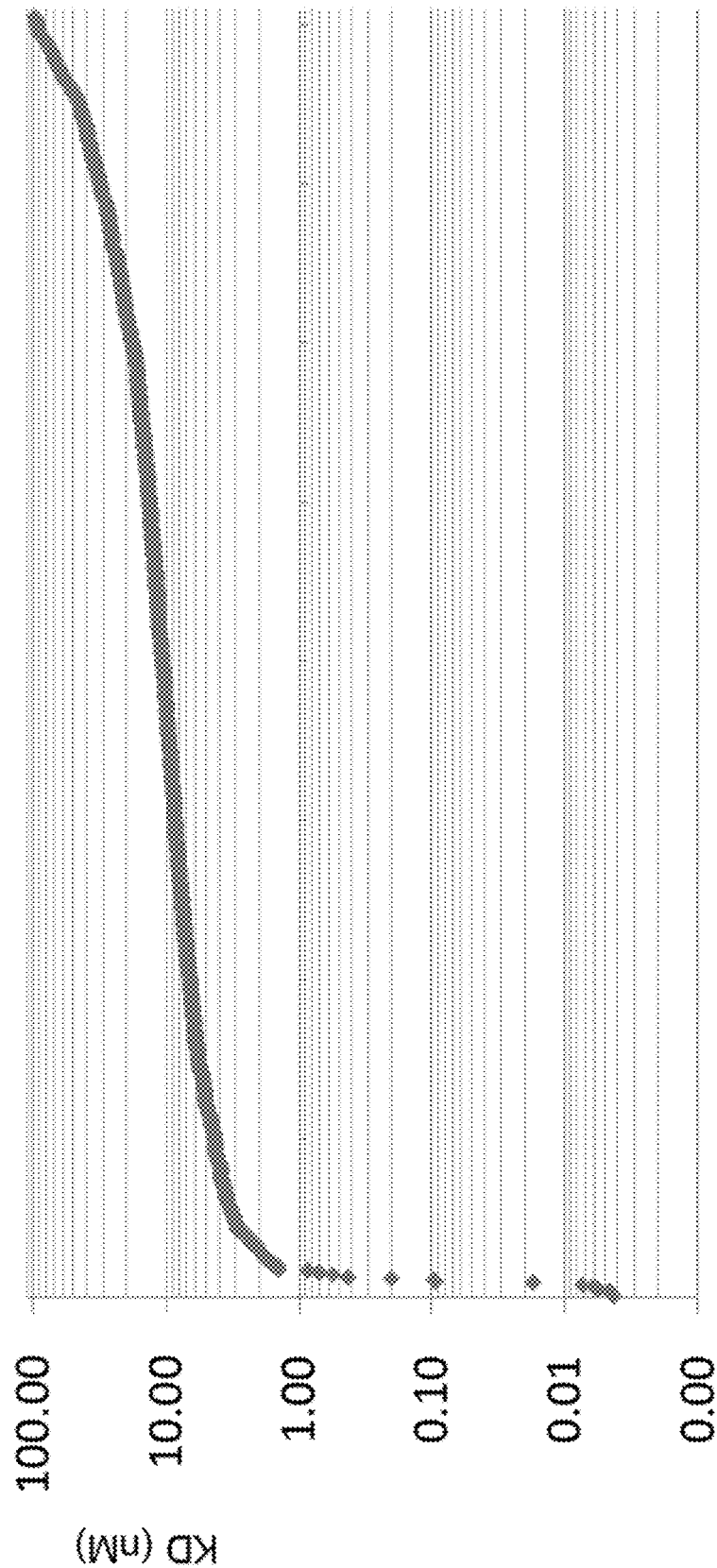
FIG. 35A shows binding affinity (KD) distribution of antibodies target Antigen D.
Figure 35B:
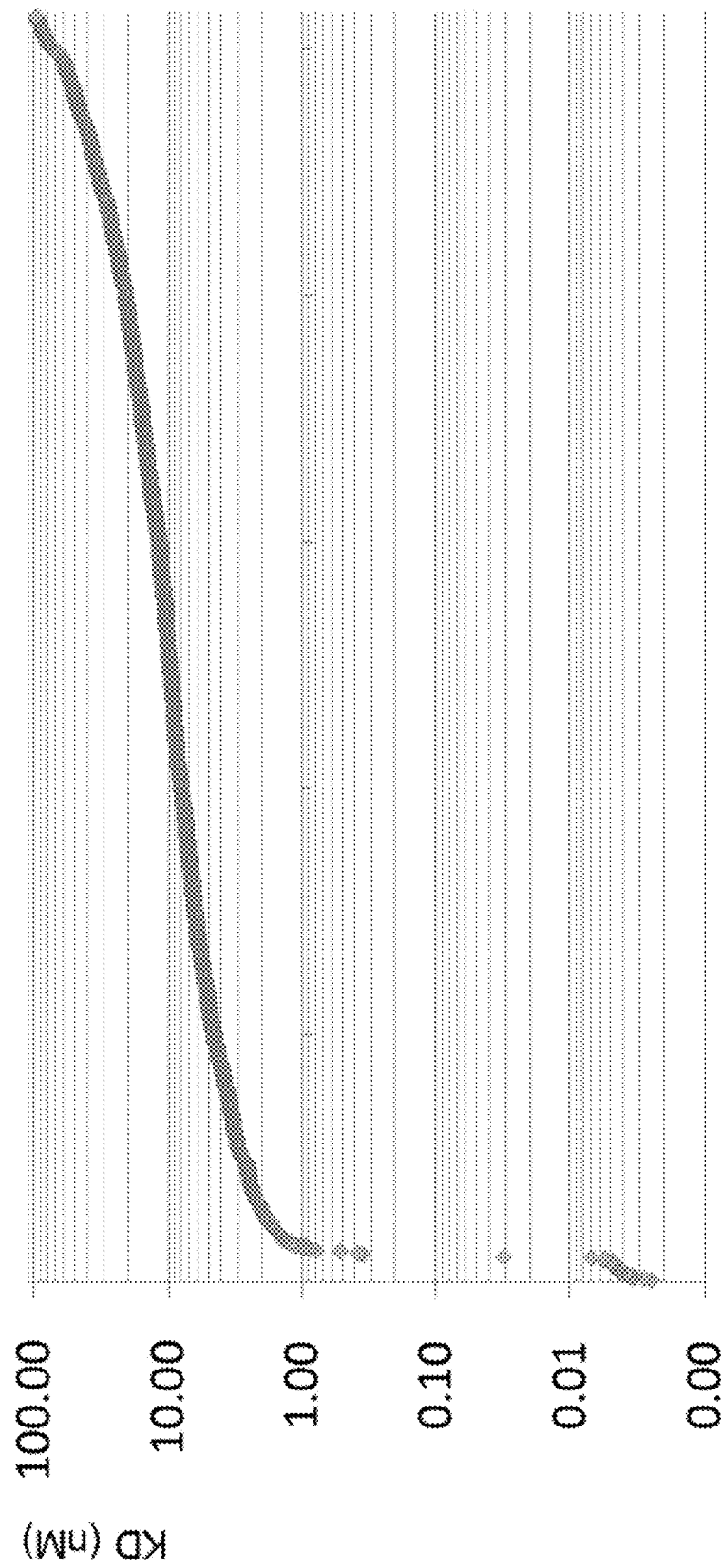
FIG. 35B shows binding affinity (KD) distribution of antibodies target Antigen E.

FIGS. 34A-34B are the kon and koff rate distribution for the antibodies against antigen D. FIGS. 34C-34D are kon and koff rate distribution for the antibodies against antigen E. FIG. 35 is the antibodies binding affinity distribution, which show that the kon rate of these antibodies are mainly concentrated between $1 \times 10^5$/Ms and $1 \times 10^6$/Ms, the koff are mainly concentrated between $1 \times 10^{-2}$/S and $1 \times 10^{-3}$/S, and the binding affinity (KD) are mainly concentrated between 0.10 nM~100.00 nM. These results are consistent with antibodies derived from natural immune responses. The data shows that hVH$^{H/H}$/hcVL$^{K/K}$ mice can produce diverse antibodies with high affinity for various antigens.

Example 12: Analysis of Germline Usage in hVH$^{H/}$$_H$hcVL$^{K/+}$ Mice

Transgenic mice with homozygous humanized heavy chain immunoglobulin locus and heterozygous humanized common light chain immunoglobulin locus (humanized VH$^{H/H}$/cVL$^{K/+}$ mice, or indicated as hVH$^{H/H}$/hcVL$^{K/+}$ mice) were selected for germline usage analysis. The hVH$^{H/H}$/hcVL$^{K/+}$ mice had the rearranged human IGKV3-11/J1 sequences. RNA was extracted from mouse splenocytes before antigen immunization. The extracted RNA was reversed transcribed and immunoglobulin heavy chain variable regions were amplified by PCR. More specifically, an upstream primer, i.e., a 5' rapid amplification of cDNA ends (RACE) primer, and a downstream primer targeting a region downstream of genes encoding IgM were used for PCR amplification. The amplified PCR product was purified and germline usage in naïve hVH$^{H/H}$/hcVL$^{K/+}$ mice was determined by next generation sequencing (NGS). A total of 131847 valid reads were obtained.

Figures 26A, 26B:
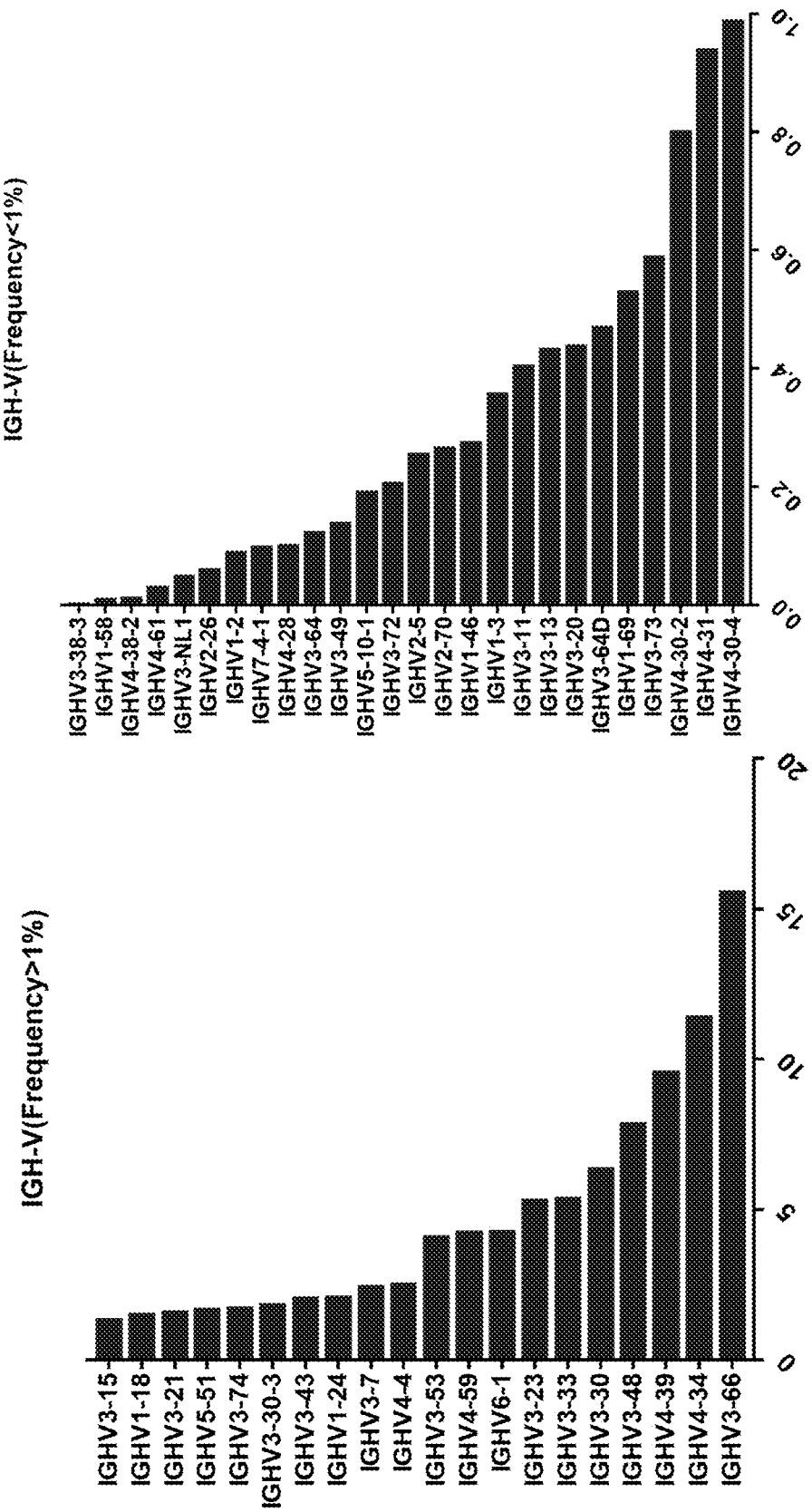
FIG. 26A shows IGHV usage (frequency >1%) in naïve hVH$^{H/H}$/hcVL$^{K/+}$ mice.
FIG. 26B shows IGHV usage (frequency <1%) in naïve hVH$^{H/H}$/hcVL$^{K/+}$ mice.
Figure 26C:
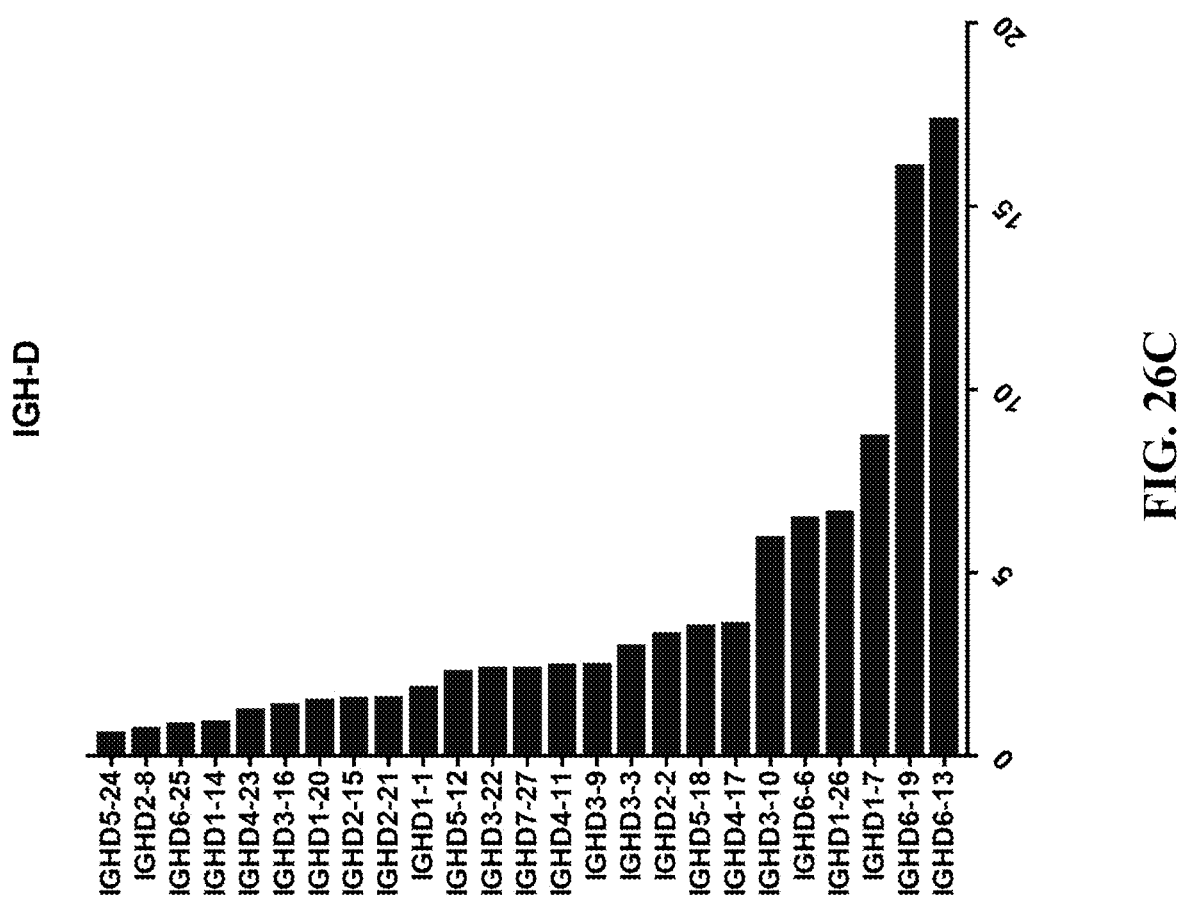
FIG. 26C shows IGHD usage in naïve hVH$^{H/H}$/hcVL$^{K/+}$ mice.
Figure 26D:
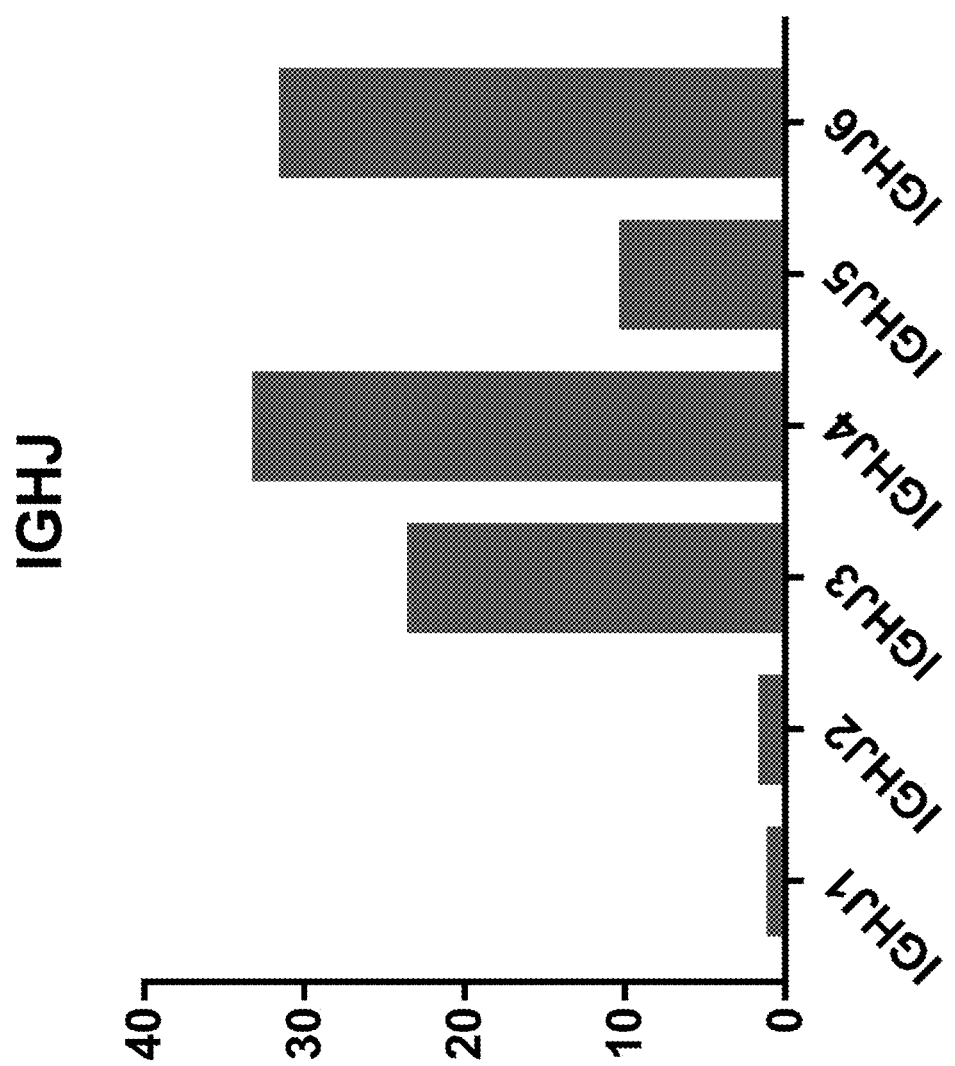
FIG. 26D shows IGHJ usage in naïve hVH$^{H/H}$/hcVL$^{K/+}$ mice.

The heavy chain IGHV, IGHD and IGHJ usage in the naïve hVH$^{H/H}$/hcVL$^{K/+}$ mouse was analyzed. The results are shown in FIGS. 26A-26D. Transcripts from 46 IGHV genes (including two pseudogenes) were detected. In addition, transcripts from 25 IGHD genes and 6 IGHJ genes were detected. For example, as shown in FIG. 26D, IGHJ3, IGHJ4, IGHJ5 and IGHJ6 were frequently used in naive hVH$^{H/H}$/hcVL$^{K/+}$ mice, while IGHJ1 and IGHJ2 were used less frequently. The IGHJ germline usage pattern is largely consistent with literature reports of human IGHJ germline usage in humans.

Figure 26E:
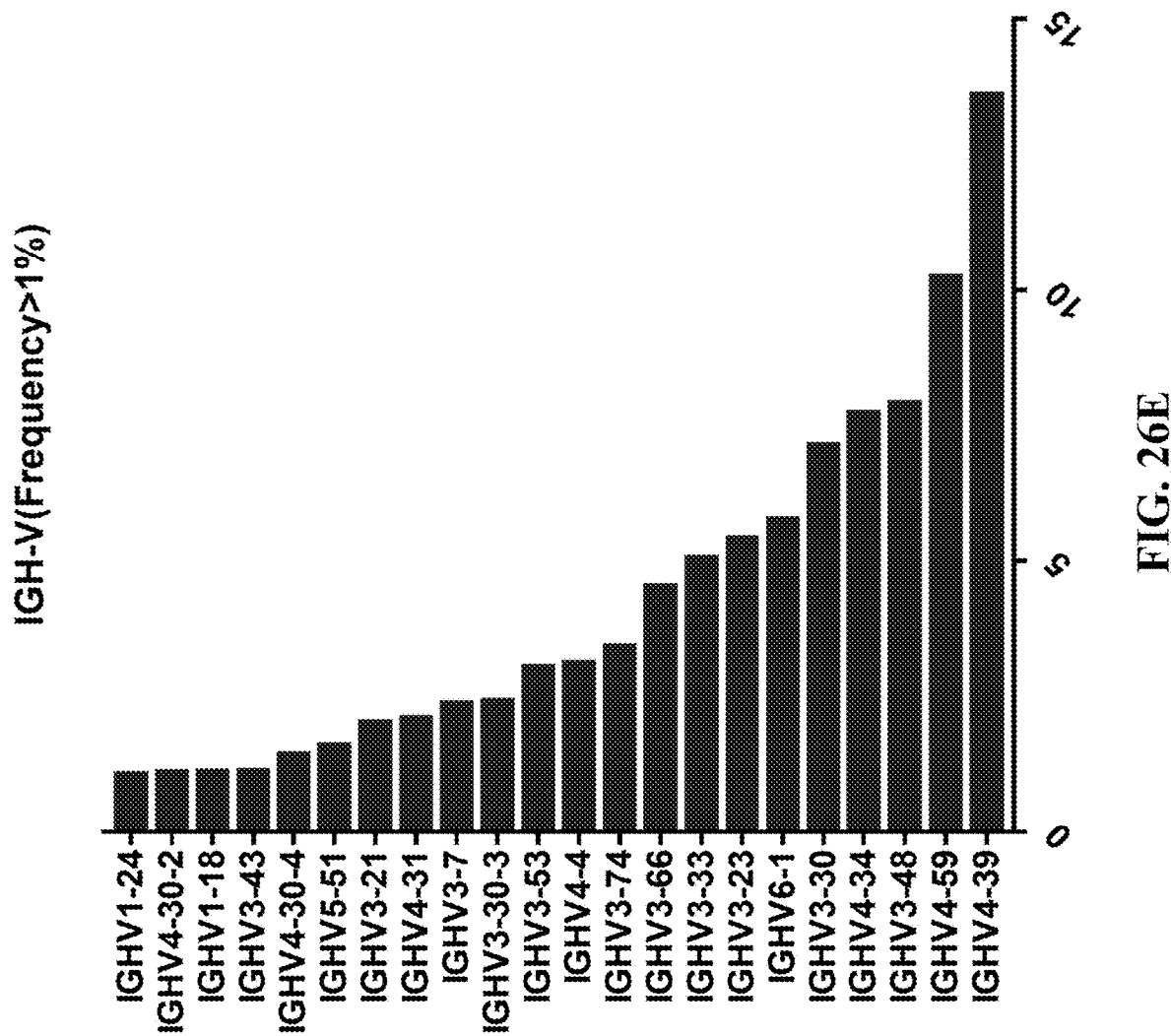
FIG. 26E shows IGHV usage (frequency >1%) in naïve hVH$^{H/H}$/hcVL$^{K/K}$ mice.
Figure 26G:
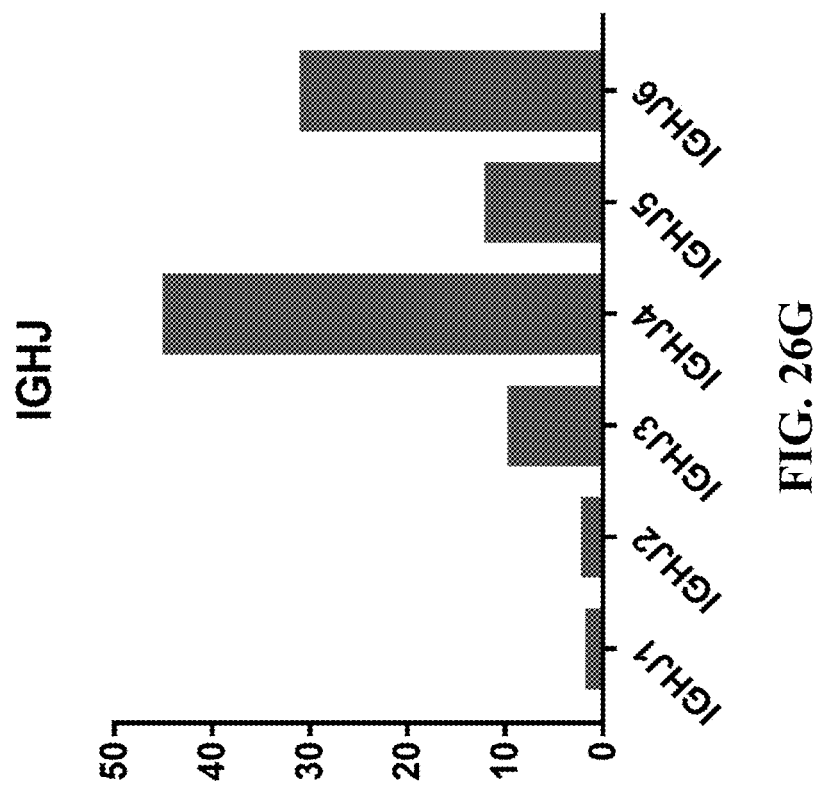
FIG. 26G shows IGHJ usage in naïve hVH$^{H/H}$/hcVL$^{K/K}$ mice.

The usage of heavy chain IGHV and IGHD in homozygous naïve hVH$^{H/H}$/hcVL$^{K/K}$ mice was also determined. A total of 123188 valid reads were obtained. The results are shown in FIGS. 26E-26G. Transcripts from 46 IGHV genes (including two pseudogenes IGHV1-NL1 and IGHV3-38-3) were detected. The test results are similar to the results of heterozygous mice.

TABLE 22

| |
|---|
| IGHV1-18 |
| IGHV1-2 |
| IGHV1-24 |
| IGHV1-3 |
| IGHV1-46 |
| IGHV1-58 |
| IGHV1-69 |
| IGHV2-26 |
| IGHV2-5 |
| IGHV2-70 |
| IGHV3-11 |
| IGHV3-13 |
| IGHV3-15 |
| IGHV3-20 |
| IGHV3-21 |
| IGHV3-23 |
| IGHV3-30 |
| IGHV3-30-3 |
| IGHV3-33 |
| IGHV3-43 |
| IGHV3-48 |
| IGHV3-49 |
| IGHV3-53 |
| IGHV3-64 |
| IGHV3-64D |
| IGHV3-66 |
| IGHV3-7 |
| IGHV3-72 |
| IGHV3-73 |
| IGHV3-74 |
| IGHV4-28 |
| IGHV4-30-2 |
| IGHV4-30-4 |
| IGHV4-31 |
| IGHV4-34 |
| IGHV4-38-2 |
| IGHV4-39 |
| IGHV4-4 |
| IGHV4-59 |
| IGHV4-61 |
| IGHV5-10-1 |
| IGHV5-51 |

TABLE 22-continued

| |
|---|
| IGHV6-1 |
| IGHV7-4-1 |
| IGHV1-NL1 |
| IGHV3-38-3 |

Figure 27A:
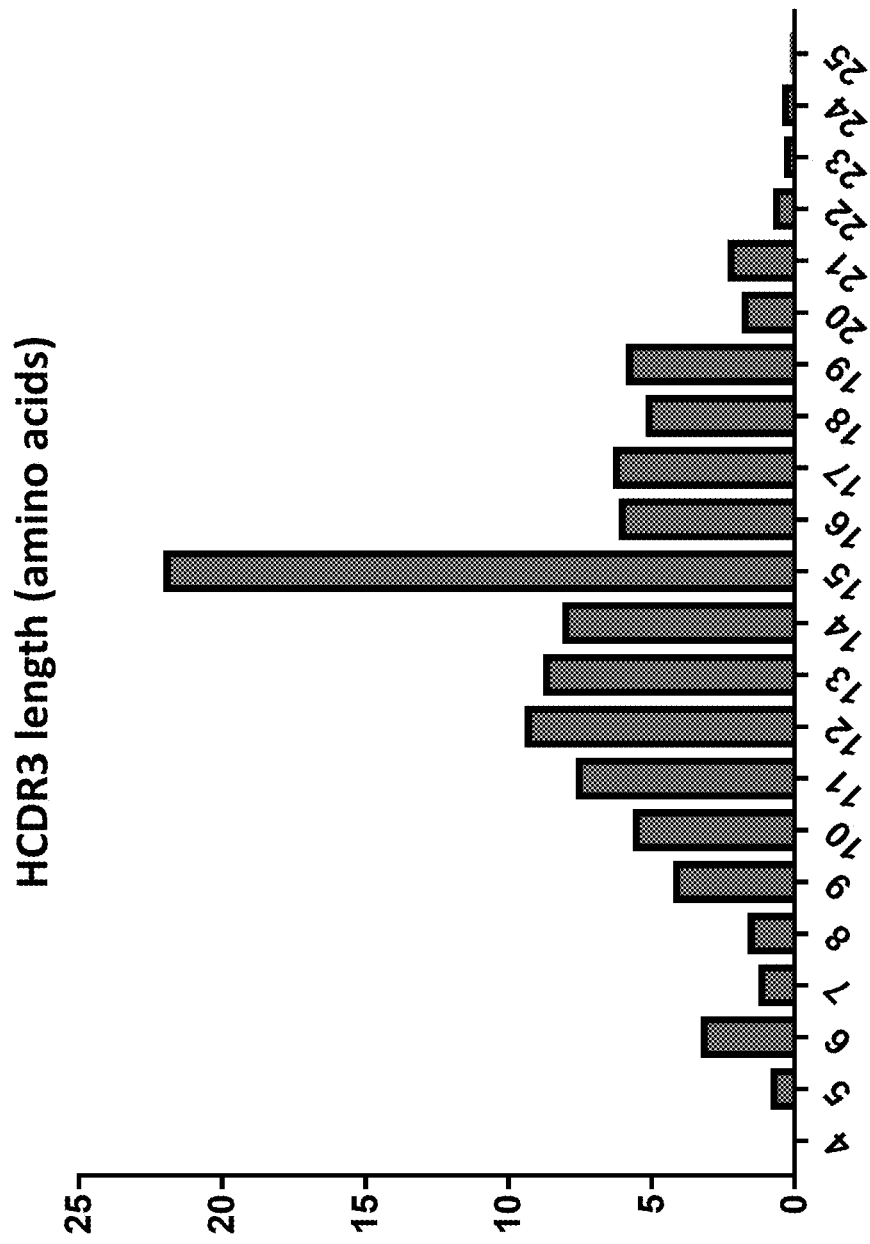
FIG. 27A is a histogram showing heavy chain CDR3 amino acid length distribution from naïve hVH$^{H/H}$/hcVL$^{K/+}$ mice.
Figure 27B:
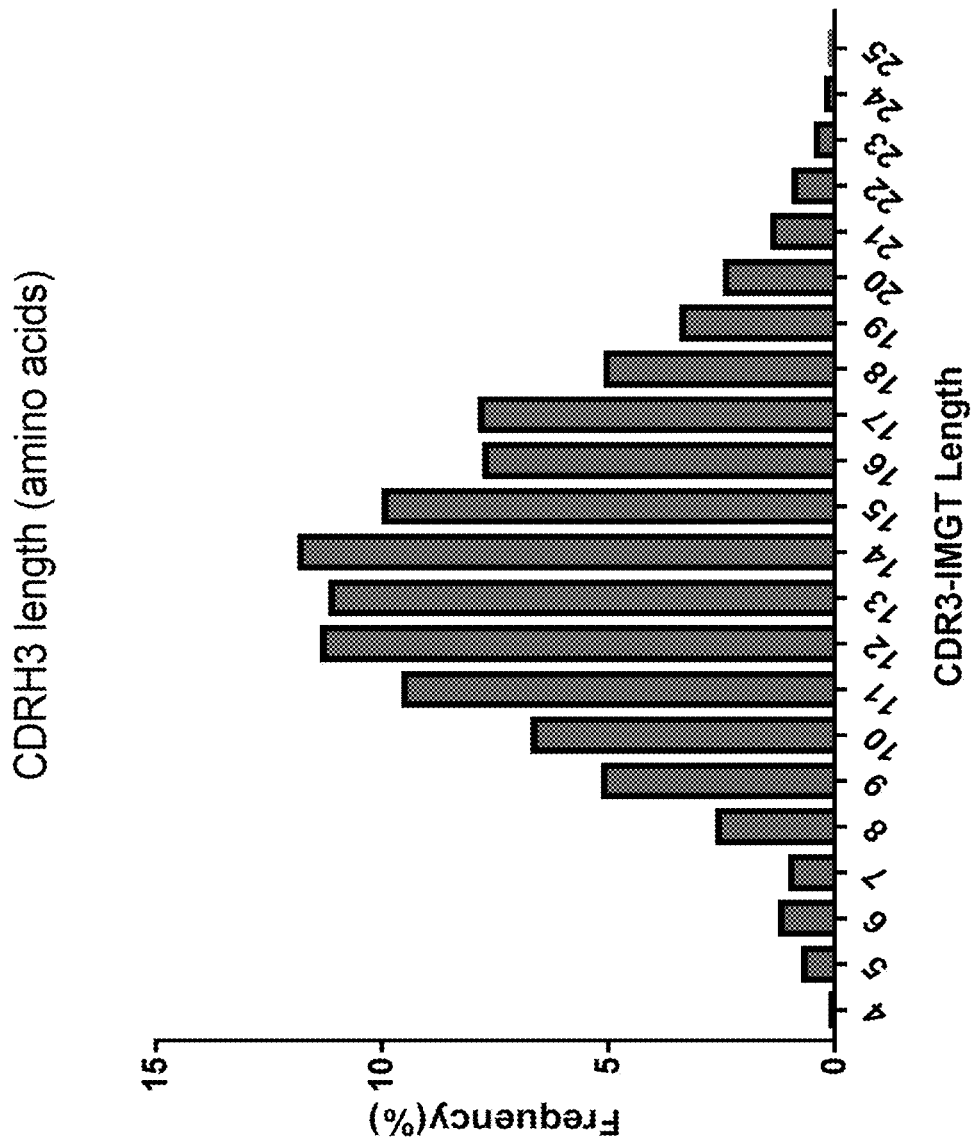
FIG. 27B is a histogram showing heavy chain CDR3 amino acid length distribution from naïve hVH$^{H/H}$/hcVL$^{K/K}$ mice.
Figure 28A:
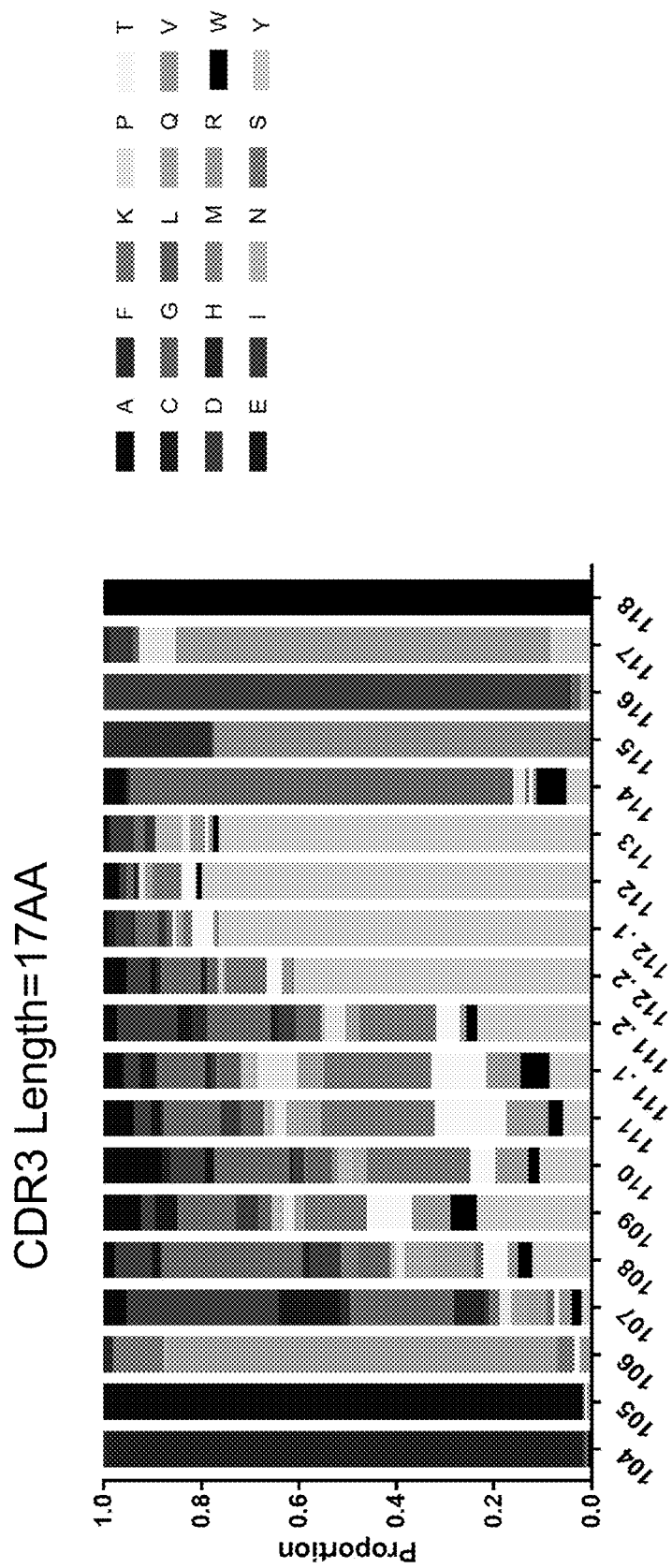
FIG. 28A shows amino acid frequency at heavy chain CDR3 (CDR3 length equals to 17 amino acids) in naïve hVH$^{H/H}$/hcVL$^{K/+}$ mice.
Figure 28B:
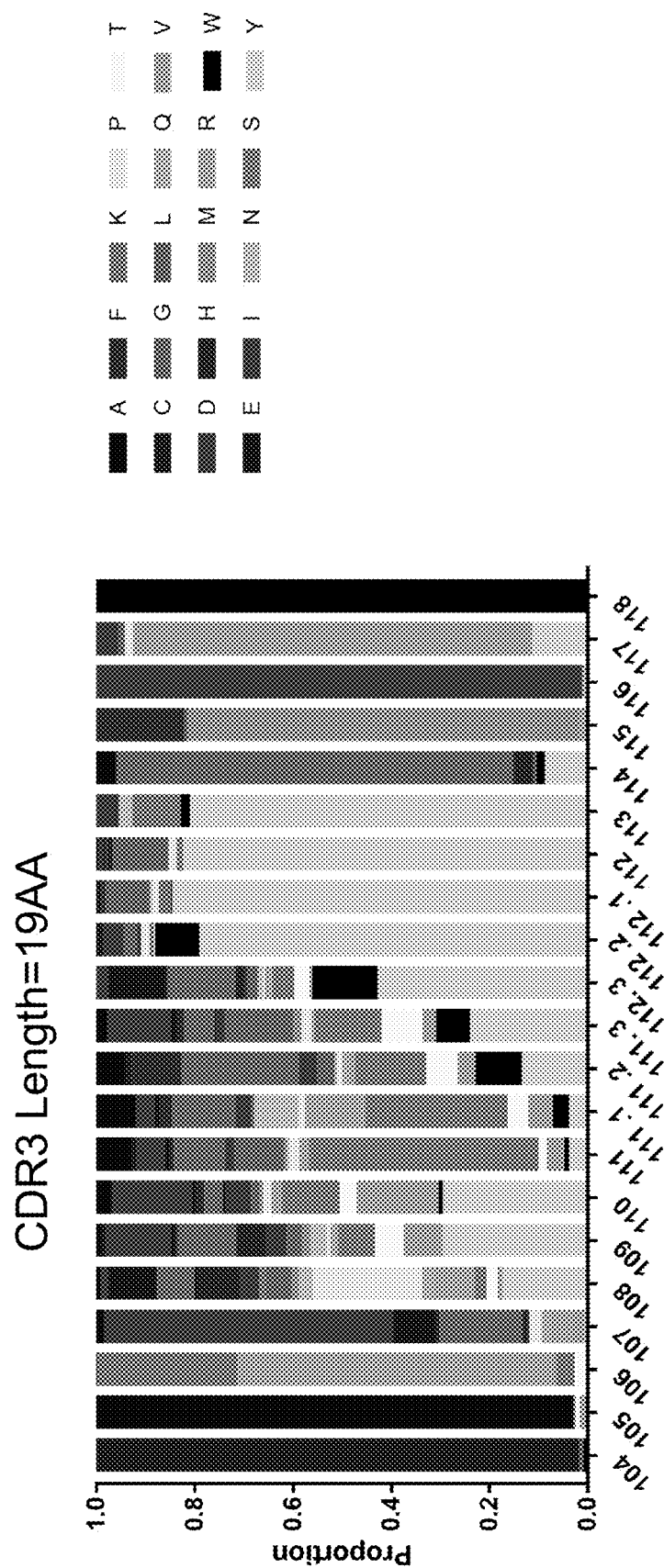
FIG. 28B shows amino acid frequency at heavy chain CDR3 (CDR3 length equals to 19 amino acids) in naïve hVH$^{H/H}$/hcVL$^{K/+}$ mice.
Figure 28C:
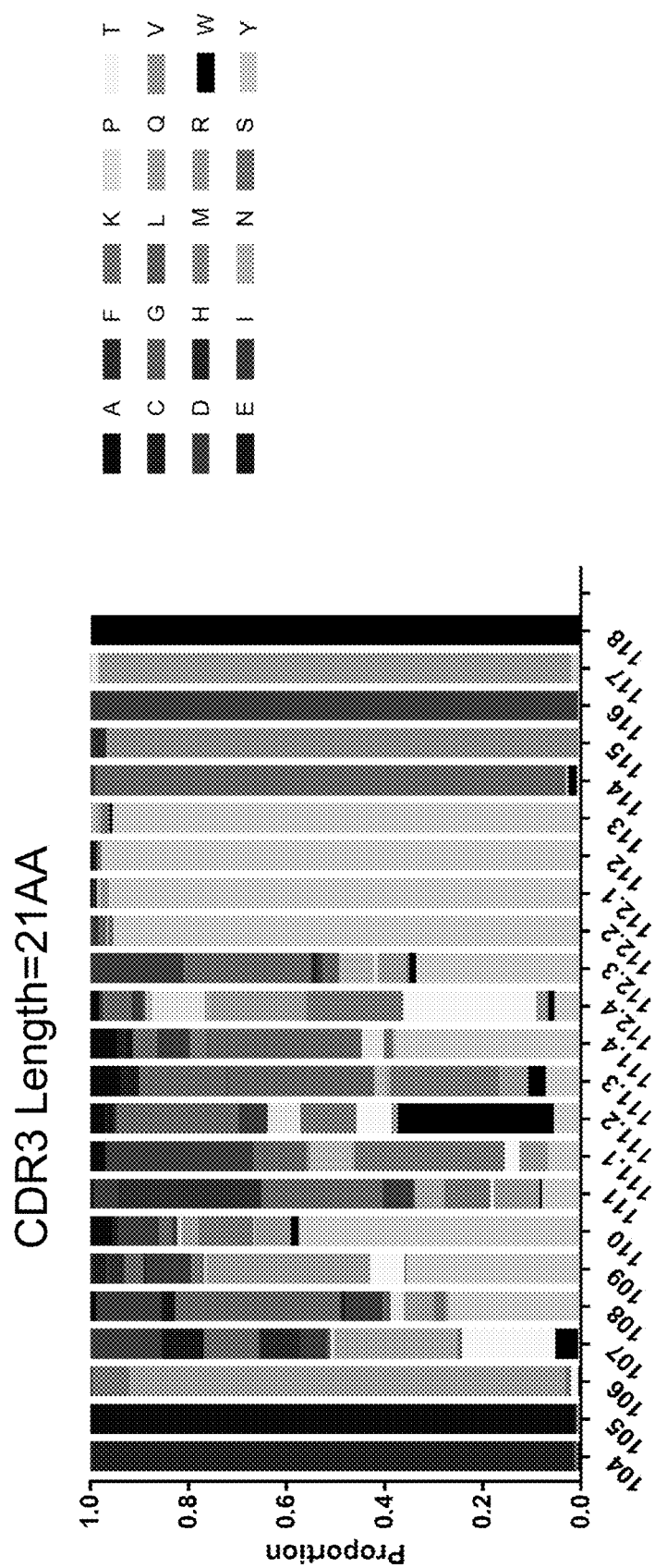
FIG. 28C shows amino acid frequency at heavy chain CDR3 (CDR3 length equals to 21 amino acids) in naïve hVH$^{H/H}$/hcVL$^{K/+}$ mice.
Figure 28D:
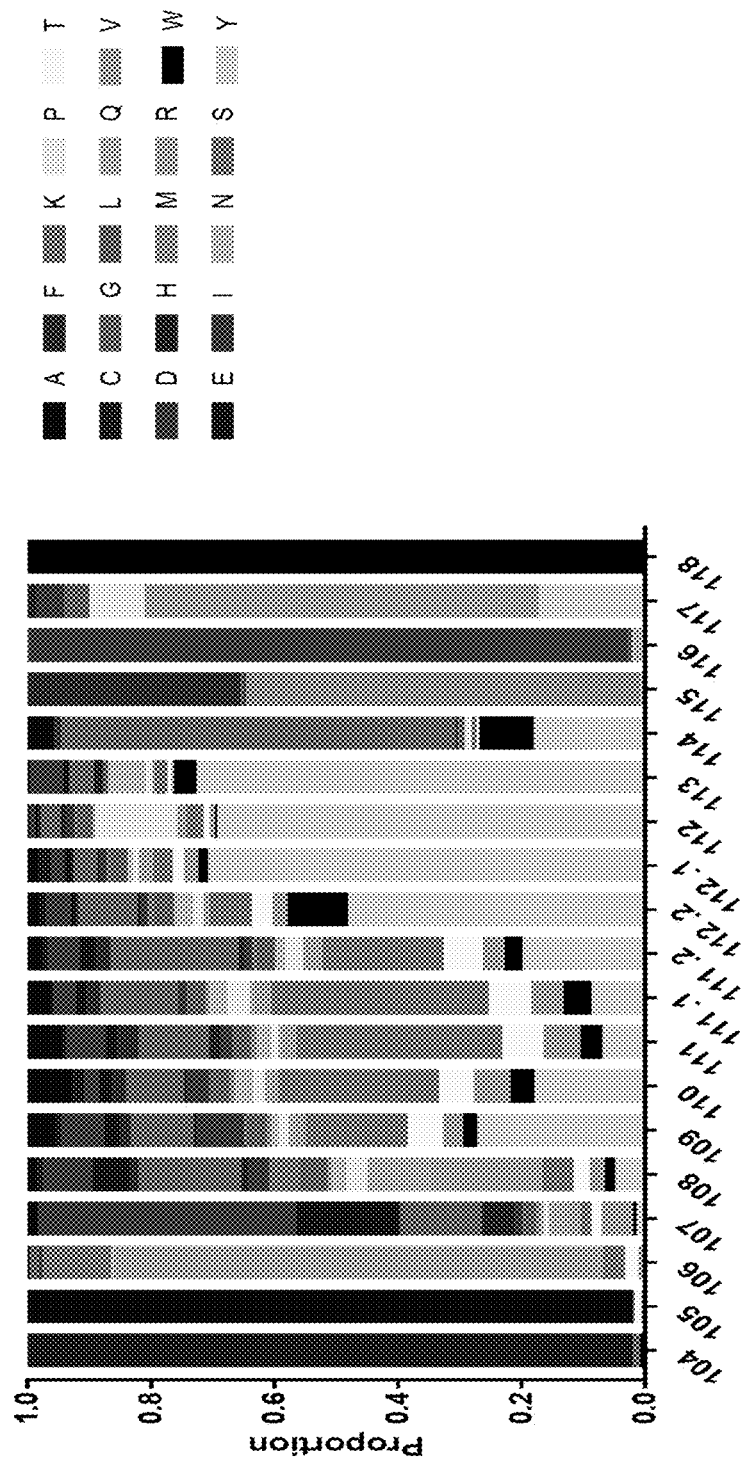
FIG. 28D shows amino acid frequency at heavy chain CDR3 (CDR3 length equals to 17 amino acids) in naïve hVH$^{H/H}$/hcVL$^{K/K}$ mice.

The heavy chain CDR3 length distribution was determined by NGS sequencing of immune repertoire from the splenocytes of naive hVH$^{H/H}$/hcVL$^{K/+}$ mice (n=1). As shown in FIG. 27A, the median length of CDR3 is around 13~15 amino acids. The results for homozygous naive hVH$^{H/H}$/hcVL$^{K/K}$ mice are shown in FIG. 27B. The results were also consistent with the median length of human heavy chain CDR3 in the human immune system.

The types of amino acids at each position of heavy chain CDR3 (HCDR3) were also analyzed (FIGS. 28A-28C, 28D). These patterns are similar to the amino acid composition in human HCDR3.

Figure 29:
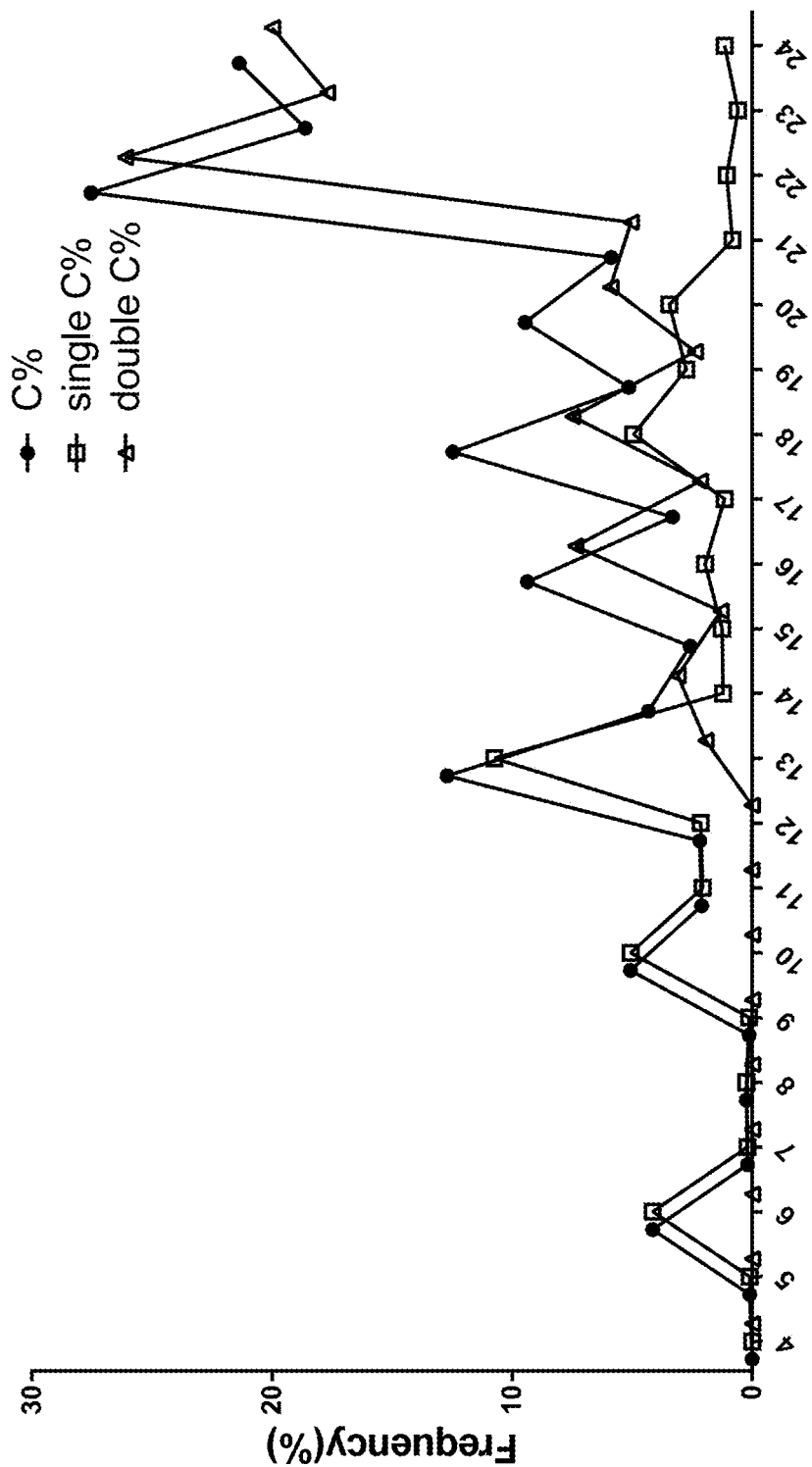
FIG. 29 shows the frequency of heavy chain CDR3 that contains cysteine residues, one cysteine residue, and two cysteine residues at CDR3 with different lengths in the naive hVH$^{H/H}$/hcVL$^{K/+}$ mice.

Cysteine residue can form disulfide bond. Human HCDR3 may contain one cysteine residue or two cysteine residues, while mouse HCDR3 typically contains no cysteine. Results in FIG. 29 show that the frequency of HCDR3 of the hVH$^{H/H}$/hcVL$^{K/+}$ mice that contains cysteine residues and the frequency increases as the length of HCDR3 increases. This result is consistent with the HCDR3 diversity in human peripheral blood mononuclear cells (PBMCs). The results indicate that the VDJ recombination in hVH/hcVL mice is working properly.

Example 13: Somatic Hypermutation Analysis in hVH$^{H/H}$/hcVL$^{K/+}$ Mice

Figures 30A, 30B:
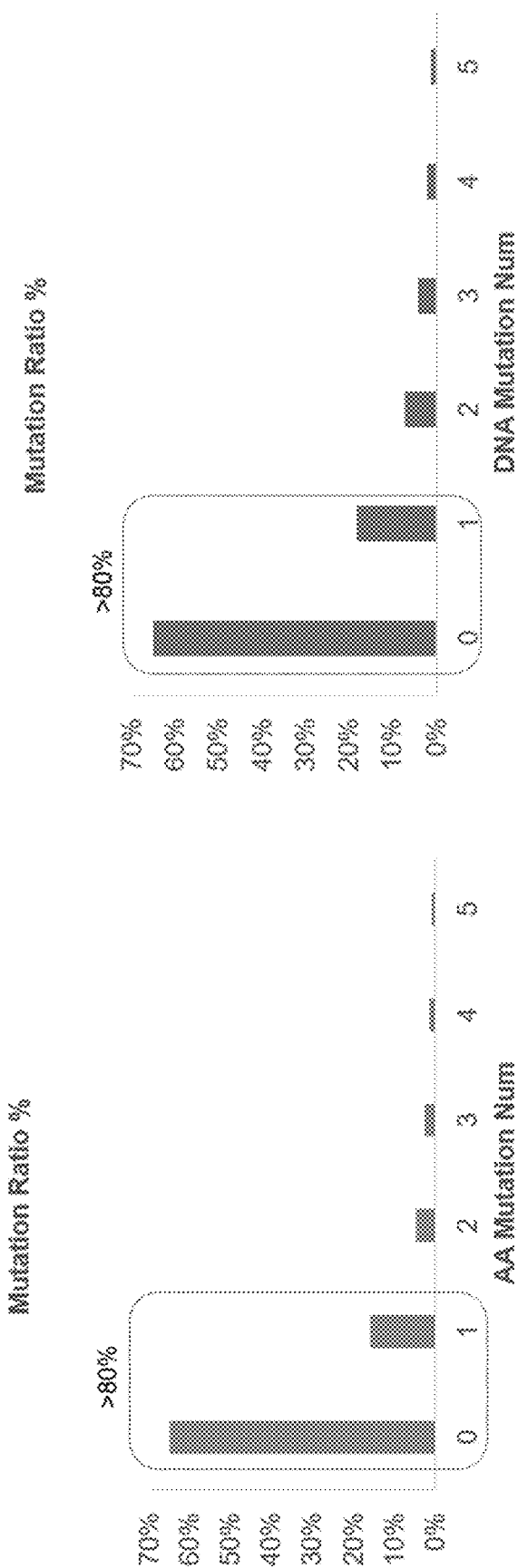
FIG. 30A shows amino acid (AA) somatic hypermutation ratio as encoded in the rearranged human IGKV3-11/J1 sequence in hVH$^{H/H}$/hcVL$^{K/+}$ mice.
FIG. 30B shows DNA somatic hypermutation ratio in the rearranged human IGKV3-11/J1 sequence in hVH$^{H/H}$/hcVL$^{K/+}$ mice.
Figure 30C:
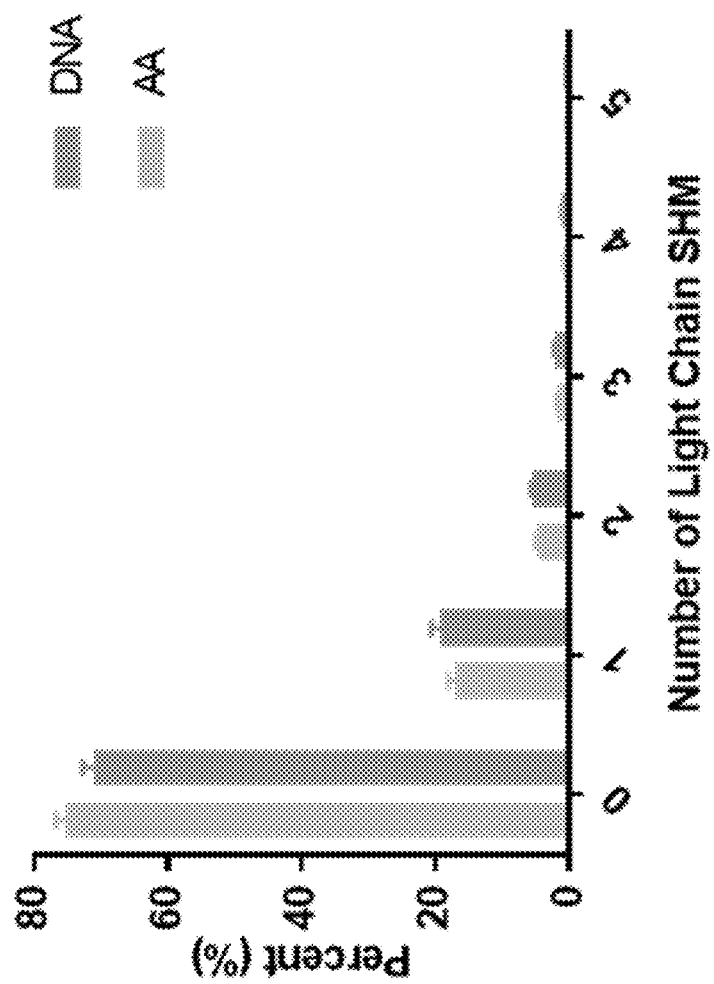
FIG. 30C shows DNA somatic hypermutation ratio in the rearranged human IGKV3-11/J1 sequence in hVH$^{H/H}$/hcVL$^{K/K}$ mice.

The hVH$^{H/H}$/hcVL$^{K/+}$ mice with rearranged human IGKV3-11/J1 sequences were selected for somatic hypermutation analysis. RNA was extracted from mouse splenocytes before antigen immunization. The extracted RNA was reversed transcribed to cDNA and the rearranged human IGKV3-11/J1 region was amplified by PCR using primers that are specific for human IGKV3-11 and IGJ1. The amplified PCR product was then processed for next generation sequencing (NGS). A total of 48326 valid reads were obtained and analyzed by IMGT/HighV-QUEST tool. As shown in FIGS. 30A-30B, the results indicate that somatic hypermutations can occur within the rearranged human light chain region, but most somatic hypermutations are limited to one or two amino acid changes. The results for homozygous naive hVH$^{H/H}$/hcVL$^{K/K}$ mice are shown in FIG. 30C. A total of 48541 valid reads were obtained and analyzed by IMGT/HighV-QUEST tool. Similar to the results of heterozygous mice, most somatic mutations are limited to 1-2 nucleotide changes, thus 1-2 amino acid changes. This indicates that in hVH$^{H/H}$/hcVL$^{K/K}$ mice, the somatic hypermutations rate is relatively low and is around 1-2 nucleotide (or amino acid) changes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises at the endogenous kappa light chain immunoglobulin locus, an exogenous kappa light chain variable region gene sequence,
   wherein the exogenous kappa light chain variable region gene sequence comprises only one human IGKV gene and only one human IGKJ gene,
   wherein the human IGKV gene and the one human IGKJ gene are operably linked to an endogenous light chain constant domain gene, and the endogenous kappa light chain variable region gene sequence is nonfunctional, wherein
   (1) the human IGKV gene is IGKV 1-39 and the human IGKJ gene is IGKJ4; or
   (2) the human IGKV gene is IGKV 3-11 and the human IGKJ gene is IGKJ1,
   wherein the mouse produces an antibody comprising a human light chain variable region (VL) in response to an antigen.

2. The mouse of claim 1, wherein the exogenous light chain variable region gene sequence further comprises a human IGKJ 3'-UTR sequence.

3. The mouse of claim 1, wherein the exogenous light chain variable region gene in one or more cells of the mouse is subject to somatic hypermutations.

4. The mouse of claim 1, wherein the human IGKV gene is IGKV1-39 and the human IGKJ gene is IGKJ4.

5. The mouse of claim 1, wherein the human IGKV gene is IGKV3-11 and the human IGKJ gene is IGKJ1.

6. The mouse of claim 1, wherein the mouse further comprises a promoter sequence that is operably linked to the human IGKV gene, wherein the promoter sequence is within 3000 bp of the human IGKV gene.

7. The mouse of claim 1, wherein the mouse comprises an endogenous IGKC.

8. The mouse of claim 1, wherein the mouse is homozygous or heterozygous with respect to the light chain immunoglobulin gene locus.

9. The mouse of claim 1, wherein the mouse further comprises at an endogenous heavy chain immunoglobulin gene locus, one or more human IGHV genes, one or more human IGHD genes, and one or more human IGHKJ genes, wherein the human IGHV genes, the human IGHD genes, and the human IGHJ genes are operably linked and can undergo VDJ rearrangement.

10. An isolated cell obtained from the mouse of claim 1.

11. The mouse of claim 1, wherein the mouse produces an antibody or antigen binding fragment thereof comprising a human light chain variable region that has an amino acid sequence that is at least 90% identical to SEQ ID NO: 38 or 39.

12. The mouse of claim 1, wherein the mouse produces an antibody or antigen binding fragment thereof comprising a human light chain variable region that comprises the amino acid sequence as set forth in SEQ ID NO: 38.

13. The mouse of claim 1, wherein the mouse produces an antibody or antigen binding fragment thereof comprising a human light chain variable region that comprises the amino acid sequence as set forth in SEQ ID NO: 39.

14. The mouse of claim 1, wherein the exogenous light chain variable region gene sequence can be detected by PCR using one or more primer pairs selected from the group consisting of:
   (a) SEQ ID NO: 8 and SEQ ID NO: 9;
   (b) SEQ ID NO: 10 and SEQ ID NO: 11;
   (c) SEQ ID NO: 16 and SEQ ID NO: 17; and
   (d) SEQ ID NO: 18 and SEQ ID NO: 19.

15. The mouse of claim 1, wherein the mouse comprises at the endogenous light chain immunoglobulin locus a nucleic acid sequence that is 95% identical to SEQ ID NO: 35.

16. The mouse of claim 1, wherein the mouse comprises at the endogenous light chain immunoglobulin locus a nucleic acid sequence that is identical to SEQ ID NO: 35.

17. The mouse of claim 1, wherein the mouse comprises at the endogenous light chain immunoglobulin locus a nucleic acid sequence that is 95% identical to SEQ ID NO: 36.

18. The mouse of claim 1, wherein the mouse comprises at the endogenous light chain immunoglobulin locus a nucleic acid sequence that is identical to SEQ ID NO: 36.

* * * * *

UNITED STATES PATENT AND TRADEMARK OFFICE
CERTIFICATE OF CORRECTION

| | | |
|---|---|---|
| PATENT NO. | : 11,997,994 B2 | Page 1 of 1 |
| APPLICATION NO. | : 17/969254 | |
| DATED | : June 4, 2024 | |
| INVENTOR(S) | : Yabo Zhang et al. | |

It is certified that error appears in the above-identified patent and that said Letters Patent is hereby corrected as shown below:

On the Title Page

Column 1, (30) Foreign Application Priority Data Line 1, delete "(WO)" and insert -- (CN) --.

Column 1, (30) Foreign Application Priority Data Line 2, delete "(WO)" and insert -- (CN) --.

Column 2, Other Publications Line 3, delete "Schlerosis," and insert -- Sclerosis, --.

Signed and Sealed this
Eighth Day of October, 2024

Katherine Kelly Vidal
*Director of the United States Patent and Trademark Office*

SEQUENCE LISTING

```
Sequence total quantity: 41
SEQ ID NO: 1                 moltype = DNA  length = 477
FEATURE                      Location/Qualifiers
misc_feature                 1..477
                             note = IGKV1-39
source                       1..477
                             mol_type = other DNA
                             organism = synthetic construct
SEQUENCE: 1
atggacatga gggtccccgc tcagctcctg gggctcctgc tactctggct ccgaggtaag    60
gatggagaac actaggaatt tactcagcca gtgtgctcag tactgactgg aacttcaggg   120
aagttctctg ataacatgat taatagtaag aatatttgtt tttatgtttc caatctcagg   180
tgccagatgt gacatccaga tgacccagtc tccatcctcc ctgtctgcat ctgtaggaga   240
cagagtcacc atcacttgcc gggcaagtca gagcattagc agctatttaa attggtatca   300
gcagaaacca gggaaagccc ctaagctcct gatctatgct gcatccagtt tgcaaagtgg   360
ggtcccatca aggttcagtg gcagtggatc tgggacagat ttcactctca ccatcagcag   420
tctgcaacct gaagattttg caacttacta ctgtcaacag agttacagta cccctcc      477

SEQ ID NO: 2                 moltype = DNA  length = 516
FEATURE                      Location/Qualifiers
misc_feature                 1..516
                             note = IGKV3-11
source                       1..516
                             mol_type = other DNA
                             organism = synthetic construct
SEQUENCE: 2
atggaagccc cagctcagct tctcttcctc ctgctactct ggctcccagg tgagggaac    60
atgaggtggt tttgcacatt agtgaaaact cttgccacct ctgctcagca agaaatataa   120
ttaaaattca aagtatatca acaatttggg ctctactcaa agacagttgg tttgatcttg   180
attacatgag tgcatttctg ttttatttcc aatttcagat accaccggag aaattgtgtt   240
gacacagtct ccagccaccc tgtctttgtc tccaggggaa agagccaccc tctcctgcag   300
ggccagtcag agtgttagca gctacttagc ctggtaccaa cagaaacctg gccaggctcc   360
caggctcctc atctatgatg catccaacag ggccactggc atcccagcca ggttcagtgg   420
cagtgggtct gggacagact tcactctcac catcagcagc ctagagcctg aagattttgc   480
agtttattac tgtcagcagc gtagcaactg gcctcc                             516

SEQ ID NO: 3                 moltype = DNA  length = 537
FEATURE                      Location/Qualifiers
misc_feature                 1..537
                             note = IGKV3-20
source                       1..537
                             mol_type = other DNA
                             organism = synthetic construct
SEQUENCE: 3
atggaaaccc cagcgcagct tctcttcctc ctgctactct ggctcccagg tgagggaac    60
atgggatggt tttgcatgtc agtgaaaacc ctcaagtc ctgttacctg caactctgc     120
tcagtcaata caataattaa agctcaatat aaagcaataa ttctggctct ctgggaaga   180
caatgggttt gatttagatt acatgggtga cttttctgtt ttatttccaa tctcagatac   240
caccggagaa attgtgttga cgcagtctcc aggcaccctg tctttgtctc caggggaaag   300
agccaccctc tcctgcaggg ccagtcagag tgttagcagc agctactag cctggtacca   360
gcagaaacct ggccaggctc ccaggctcct catctatggt gcatccagca gggccactgg   420
catcccagac aggttcagtg gcagtgggtc tgggacagac ttcactctca ccatcagcag   480
actggagcct gaagattttg cagtgtatta ctgtcagcag tatggtagct caccctcc    537

SEQ ID NO: 4                 moltype = DNA  length = 38
FEATURE                      Location/Qualifiers
misc_feature                 1..38
                             note = IGKJ1
source                       1..38
                             mol_type = other DNA
                             organism = synthetic construct
SEQUENCE: 4
gtggacgttc ggccaaggga ccaaggtgga aatcaaac                            38

SEQ ID NO: 5                 moltype = DNA  length = 38
FEATURE                      Location/Qualifiers
misc_feature                 1..38
                             note = IGKJ4
source                       1..38
                             mol_type = other DNA
                             organism = synthetic construct
SEQUENCE: 5
gctcactttc ggcggaggga ccaaggtgga gatcaaac                            38

SEQ ID NO: 6                 moltype = DNA  length = 1189
FEATURE                      Location/Qualifiers
source                       1..1189
                             mol_type = genomic DNA
```

```
                        organism = Mus musculus
SEQUENCE: 6
gtaagtacac ttttctcatc ttttttatg tgtaagacac aggttttcat gttaggagtt    60
aaagtcagtt cagaaaatct tgagaaaatg gagagggctc attatcagtt gacgtggcat   120
acagtgtcag atttttctgtt tatcaagcta gtgagattag gggcaaaaag aggctttagt   180
tgagaggaaa gtaattaata ctatggtcac catccaagag attggatcgg agaataagca   240
tgagtagtta ttgagatctg ggtctgactg caggtagcgt ggtcttctag acgtttaagt   300
gggagatttg gaggggatga ggaatgaagg aacttcagga tagaaaaggg ctgaagtcaa   360
gttcagctcc taaaatggat gtgggagcaa actttgaaga taaactgaat gacccagagg   420
atgaaacagc gcagatcaaa gaggggcctg gagctctgag aagagaagga gactcatccg   480
tgttgagttt ccacaagtac tgtcttgagt tttgcaataa aagtgggata gcagagttga   540
gtgagccgta ggctgagttc tctcttttgt ctcctaagtt tttatgacta caaaaatcag   600
tagtatgtcc tgaataatc attaagctgt ttgaaagtat gactgcttgc catgtagata    660
ccatggcttg ctgaataatc agaagaggtg tgactcttat tctaaaattt gtcacaaaat   720
gtcaaaatga gagactctgt aggaacgagt ccttgacaga cagctcaagg ggttttttc    780
ctttgtctca tttctacatg aaagtaaatt tgaaatgatc tttttattta taagagtaga   840
aatacagttg ggtttgaact atatgtttta atggccacgg ttttgtaaga catttggtcc   900
tttgttttcc cagttattac tcgattgtaa ttttatatcg ccagcaatgg actgaaacgg   960
tccgcaacct cttctttaca actgggtgac ctcgcggctg tgccagccat ttggcgttca  1020
ccctgccgct aagggccatg tgaaccccccg cggtagcatc ccttgctccg cgtgaccac   1080
tttcctgagg cacagtgata ggaacagagc cactaatctg aagagaacag agatgtgaca  1140
gactacacta atgtgagaaa aacaaggaaa gggtgactta ttggagatt               1189

SEQ ID NO: 7             moltype = DNA   length = 500
FEATURE                  Location/Qualifiers
source                   1..500
                         mol_type = genomic DNA
                         organism = Homo sapiens
SEQUENCE: 7
gtaagtaatt tttcactatt gtcttctgaa atttgggtct gatggccagt attgactttt    60
agaggcttaa ataggagttt ggtaaagatt ggtaaatgag ggcatttaag atttgccatg   120
ggttgcaaaa gttaaactca gcttcaaaaa tggatttgga gaaaaaaaga ttaaattgct   180
ctaaactgaa tgcacaaag taaaaaaaaa aagtgtaact aaaaaggaac ccttgtattt    240
ctaaggagca aaagtaaatt tattttgtt cactcttcgc aaatattgta ttggttgttg    300
ctgattatgc atgatacaga aaagtggaaa aatacatttt ttagtctttc tcccttttgt   360
ttgataaatt attttgtcag acaacaataa aaatcaatag cacgccctaa gaaaaatcag   420
ggaaaagtga agtgtaccta tttgctatgt agaagaggca gcttacttga aaatcagcag   480
caatgttgtt tttagagtct                                                500

SEQ ID NO: 8             moltype = DNA   length = 25
FEATURE                  Location/Qualifiers
misc_feature             1..25
                         note = Primer
source                   1..25
                         mol_type = other DNA
                         organism = synthetic construct
SEQUENCE: 8
tcacacacta cagcttccac cacaa                                           25

SEQ ID NO: 9             moltype = DNA   length = 20
FEATURE                  Location/Qualifiers
misc_feature             1..20
                         note = Primer
source                   1..20
                         mol_type = other DNA
                         organism = synthetic construct
SEQUENCE: 9
tgggcgcgcc agactctaaa                                                 20

SEQ ID NO: 10            moltype = DNA   length = 24
FEATURE                  Location/Qualifiers
misc_feature             1..24
                         note = Primer
source                   1..24
                         mol_type = other DNA
                         organism = synthetic construct
SEQUENCE: 10
tgggtctgat ggccagtatt gact                                            24

SEQ ID NO: 11            moltype = DNA   length = 25
FEATURE                  Location/Qualifiers
misc_feature             1..25
                         note = Primer
source                   1..25
                         mol_type = other DNA
                         organism = synthetic construct
SEQUENCE: 11
ggcctggaaa actcagctat cctttt                                          25
```

```
SEQ ID NO: 12              moltype = DNA   length = 31
FEATURE                    Location/Qualifiers
misc_feature               1..31
                           note = Primer
source                     1..31
                           mol_type = other DNA
                           organism = synthetic construct
SEQUENCE: 12
gccaaggaat ttaaaagggg attgaaagca a                                  31

SEQ ID NO: 13              moltype = DNA   length = 25
FEATURE                    Location/Qualifiers
misc_feature               1..25
                           note = Primer
source                     1..25
                           mol_type = other DNA
                           organism = synthetic construct
SEQUENCE: 13
agggagggaa tggaatgagg gtgat                                         25

SEQ ID NO: 14              moltype = DNA   length = 25
FEATURE                    Location/Qualifiers
misc_feature               1..25
                           note = Primer
source                     1..25
                           mol_type = other DNA
                           organism = synthetic construct
SEQUENCE: 14
ccatgtgacc cattcgagtg tcctg                                         25

SEQ ID NO: 15              moltype = DNA   length = 25
FEATURE                    Location/Qualifiers
misc_feature               1..25
                           note = Primer
source                     1..25
                           mol_type = other DNA
                           organism = synthetic construct
SEQUENCE: 15
cttaccattt gcggtgcctg gtttc                                         25

SEQ ID NO: 16              moltype = DNA   length = 25
FEATURE                    Location/Qualifiers
misc_feature               1..25
                           note = Primer
source                     1..25
                           mol_type = other DNA
                           organism = synthetic construct
SEQUENCE: 16
tcacacacta cagcttccac cacaa                                         25

SEQ ID NO: 17              moltype = DNA   length = 20
FEATURE                    Location/Qualifiers
misc_feature               1..20
                           note = Primer
source                     1..20
                           mol_type = other DNA
                           organism = synthetic construct
SEQUENCE: 17
tgggcgcgcc agactctaaa                                               20

SEQ ID NO: 18              moltype = DNA   length = 24
FEATURE                    Location/Qualifiers
misc_feature               1..24
                           note = Primer
source                     1..24
                           mol_type = other DNA
                           organism = synthetic construct
SEQUENCE: 18
tgggtctgat ggccagtatt gact                                          24

SEQ ID NO: 19              moltype = DNA   length = 25
FEATURE                    Location/Qualifiers
misc_feature               1..25
                           note = Primer
source                     1..25
                           mol_type = other DNA
                           organism = synthetic construct
SEQUENCE: 19
ggcctggaaa actcagctat ccttt                                         25
```

```
SEQ ID NO: 20            moltype = DNA   length = 25
FEATURE                  Location/Qualifiers
misc_feature             1..25
                         note = Primer
source                   1..25
                         mol_type = other DNA
                         organism = synthetic construct
SEQUENCE: 20
tcacacacta cagcttccac cacaa                                               25

SEQ ID NO: 21            moltype = DNA   length = 20
FEATURE                  Location/Qualifiers
misc_feature             1..20
                         note = Primer
source                   1..20
                         mol_type = other DNA
                         organism = synthetic construct
SEQUENCE: 21
tgggcgcgcc agactctaaa                                                     20

SEQ ID NO: 22            moltype = DNA   length = 24
FEATURE                  Location/Qualifiers
misc_feature             1..24
                         note = Primer
source                   1..24
                         mol_type = other DNA
                         organism = synthetic construct
SEQUENCE: 22
tgggtctgat ggccagtatt gact                                                24

SEQ ID NO: 23            moltype = DNA   length = 25
FEATURE                  Location/Qualifiers
misc_feature             1..25
                         note = Primer
source                   1..25
                         mol_type = other DNA
                         organism = synthetic construct
SEQUENCE: 23
ggcctggaaa actcagctat ccttt                                               25

SEQ ID NO: 24            moltype = DNA   length = 25
FEATURE                  Location/Qualifiers
misc_feature             1..25
                         note = Primer
source                   1..25
                         mol_type = other DNA
                         organism = synthetic construct
SEQUENCE: 24
agacttgatg gtgtggagtg gggta                                               25

SEQ ID NO: 25            moltype = DNA   length = 25
FEATURE                  Location/Qualifiers
misc_feature             1..25
                         note = Primer
source                   1..25
                         mol_type = other DNA
                         organism = synthetic construct
SEQUENCE: 25
tgggccctgt actttgcttg aacat                                               25

SEQ ID NO: 26            moltype = DNA   length = 25
FEATURE                  Location/Qualifiers
misc_feature             1..25
                         note = Primer
source                   1..25
                         mol_type = other DNA
                         organism = synthetic construct
SEQUENCE: 26
tgatgggtca accatgttcc tgtgg                                               25

SEQ ID NO: 27            moltype = DNA   length = 25
FEATURE                  Location/Qualifiers
misc_feature             1..25
                         note = Primer
source                   1..25
                         mol_type = other DNA
                         organism = synthetic construct
SEQUENCE: 27
```
tcagccattg cttctgcttt ctcct                                              25

SEQ ID NO: 28            moltype = DNA   length = 25
FEATURE                  Location/Qualifiers
misc_feature             1..25
                         note = Primer
source                   1..25
                         mol_type = other DNA
                         organism = synthetic construct
SEQUENCE: 28
gaaaagtggc tttgatggtg caggg                                              25

SEQ ID NO: 29            moltype = DNA   length = 25
FEATURE                  Location/Qualifiers
misc_feature             1..25
                         note = Primer
source                   1..25
                         mol_type = other DNA
                         organism = synthetic construct
SEQUENCE: 29
tgcccatttt tctgcccttg ggtat                                              25

SEQ ID NO: 30            moltype = DNA   length = 25
FEATURE                  Location/Qualifiers
misc_feature             1..25
                         note = Primer
source                   1..25
                         mol_type = other DNA
                         organism = synthetic construct
SEQUENCE: 30
aggcattcct tatgccagtc agcat                                              25

SEQ ID NO: 31            moltype = DNA   length = 25
FEATURE                  Location/Qualifiers
misc_feature             1..25
                         note = Primer
source                   1..25
                         mol_type = other DNA
                         organism = synthetic construct
SEQUENCE: 31
tttcccatgt cctgctgctt tcctt                                              25

SEQ ID NO: 32            moltype = DNA   length = 25
FEATURE                  Location/Qualifiers
misc_feature             1..25
                         note = Primer
source                   1..25
                         mol_type = other DNA
                         organism = synthetic construct
SEQUENCE: 32
catttaggga gctgactggg cacaa                                              25

SEQ ID NO: 33            moltype = DNA   length = 25
FEATURE                  Location/Qualifiers
misc_feature             1..25
                         note = Primer
source                   1..25
                         mol_type = other DNA
                         organism = synthetic construct
SEQUENCE: 33
tctgggtcct aactgagcag ctctt                                              25

SEQ ID NO: 34            moltype = DNA   length = 30
FEATURE                  Location/Qualifiers
misc_feature             1..30
                         note = Primer
source                   1..30
                         mol_type = other DNA
                         organism = synthetic construct
SEQUENCE: 34
ctaacactca ttcctgttga agctcttgac                                         30

SEQ ID NO: 35            moltype = DNA   length = 3012
FEATURE                  Location/Qualifiers
misc_feature             1..3012
                         note = Rearranged human IGKV1-39+J4 nucleic acid sequence
source                   1..3012
                         mol_type = other DNA
                         organism = synthetic construct

```
SEQUENCE: 35
gcaggcagca tatttataat gcacagtaaa cactaggagg aaacaaggca gtgagagagg    60
aaagagagca gcgataccga aaatgtcctc agcgagaagc taccacagag gatgaatgga   120
gatcaagccc acgtggaaac atgggaaaat gtctcagtat ttttccacct aagaagggag   180
ggagatgggg tatgtataca cctccctgtc ctcactgatt gagggctttc cgagaggatg   240
ctcattccag gtgctgtgat aggccatgtg tacaggcagg gctgccttct ccagcttcag   300
atagagcagt gaggaaaaga tatggccatg ggggtcagc agaagtacag caaagggaaa    360
agggaaaggg tagcaagagt gacaactata ttcacccccc ccacacacac acacacacac   420
acgaaattgt gtattgcaat ccagaactgc ttctctctga acctaaatct tagcaagcag   480
tttaccagta actgcccttg aaattcaggc ccctggaaag gagcaggggg ttgtgtacag   540
gctataccac agcagtctgc ccaccttag tgatgcatga gtaatgctcc ctggactccc    600
caggttctag tcttctcatg tcgatgtagt tgattccact tcccttgctg cacaaccagg   660
ctgggatgcc tgggcagagg cagacatgtg aggtataggg gttcaaatct gtttccaagt   720
tttatccagc ttcaaagcat ttctccgtgt acatgagcgg ttgcttgaca ggagatggag   780
actctctttc ctggatgtga ggcaaggagg caggcgtctg agtcaggatg atgtccctac   840
tcactgctaa agagaaaagt ggctttgatg gtgcagggca gggaaatgca ctgagtggtc   900
gccaccctca cagaagagaa agtgttcact gacctggcct ttcccaggg cctctccctc    960
ccattgcttt ccagaaagcc atgattttg agagccacac ctgaacactc acaaacatta   1020
tggtgggaaa agcagatcag agcattaggc aagttgcatt accttggcct tcttcctttg   1080
gagacaattg atgtggggtt ctagattgac ccagagtttc aagtttatcc tgattcaggc   1140
ttcaacagct ggaggaagaa acagagatgt ttttgaagt aaacagatct agcattacta    1200
atcaacccctt catactgatg acctatgga aataatacc aaggggcagaa aatgggcag    1260
aataagggga gccccaaacc aagacgaagc tgctgcccat tgagaccctg ggtattacag   1320
agacctatag ctctgcgataa tggaagatct atgagtggca caggcgctga ggaatcacag   1380
catcattatc gtgcatctgc agggaattgc ttgtaaatat actggtaatt acaaatgttt   1440
aaggtcacta caaatacttt ggagtgtatt aaatatgctt ctgataaaga ctgtttttct   1500
cacatgaaac aatgggaacc atgtgacaat cacagaggtg ttgttactat agcaaaaggg   1560
attgttactc tccacatccc tttaagtaac ttgaaggcct gatagaccca ccctctaaga   1620
cttcattaga cattccctac gaatggttat actctcctgt atactcccaa tacaactcta   1680
aaatatatta ttccatatag tccttaggtt tgtattaaag tttgacttttt ttccttcaaa   1740
atatctcttg tcaacacagc ggctctagag agaaatacat tccctccagg caaatctatg   1800
ctgcgctggt ctgacctggg accctgggga cattgcccct gtgctgagtt actaagatga   1860
gccagccctg cagctgtgct cagcctgccc catgccctgc tgattgattt gcatgttcca   1920
gagcacagcc ccctgccctg aagactttt tatgggctgg tcgcaccctg tgcaggagtc   1980
agtctcagtc aggacacagc atggacatga gggtccccgc tcagctcctg gggctcctgc   2040
tactctggct ccgaggtaag gatggagaac actaggaatt tactcagcca gtgtgctcag   2100
tactgactgg aacttcaggg aagttctctg ataacatgat taatagtaag aatatttgtt   2160
tttatgtttc caatctcagg tgccagatgt gacatccaga tgacccagtc tccatcctcc   2220
ctgtctgcat ctgtaggaga cagagtcacc atcacttgcc gggcaagtca gagcattagc   2280
agctatttaa attggtatca gcagaaacca gggaaagccc ctaagctcct gatctatgct   2340
gcatccagtt tgcaaagtgg ggtcccatca aggttcagtg gcagtggatc tgggacagat   2400
ttcactctca ccatcagcag tctgcaacct gaagattttg caacttacta ctgtcaacag   2460
agttacagta cccctctcac tttcggcgga gggaccaagg tggagatcaa acgtaagtaa   2520
tttttcacta ttgtcttctg aaatttgggt ctgatggcca gtattgactt ttagaggctt   2580
aaataggagt ttggtaaaga ttggtaaatg agggcattta agatttgcca tgggttgcaa   2640
aagttaaaact cagcttcaaa aatggatttg gagaaaaaaa gattaaattg ctctaaactg   2700
aatgacacaa agtaaaaaaa ctaaaaagga accccttgtat ttctaaggag              2760
caaaagtaaa tttattttttg ttcactcttg ccaaatattg tattggttgt tgctgattat   2820
gcatgataca gaaaagtgga aaaatacatt ttttagtctt tctccctttt gtttgataaa   2880
ttattttgtc agacaacaat aaaaatcaat agcacgccct aagaaaaatc agggaaaagt   2940
gaagtgtacc tatttgctat gtagaagagg cagcttactt gaaaatcagc agcaatgttg   3000
tttttagagt ct                                                       3012

SEQ ID NO: 36        moltype = DNA  length = 3051
FEATURE              Location/Qualifiers
misc_feature         1..3051
                     note = Rearranged human IGKV3-11+J1 nucleic acid sequence
source               1..3051
                     mol_type = other DNA
                     organism = synthetic construct
SEQUENCE: 36
caggagtgag cctggtttga tgcctctctc cccaacacga tagaagtgtg gcacaaatct    60
ttgaaaaatt cagtttcccc gtggcaacaa caactacctg ggactgaaaa cttcttccct   120
cgctctagtc ctttcttcta cacccacttc cacctcatca caatccttgt caatacttgt   180
caggaaagat tctggaaaaa gcaaagagac ttccttagag gtgtcagaga ttcctgtacc   240
agcatctgtc catctctaga gggggttgtg agtatgagga agagcagagc ttgtcaatct   300
tctacttgct ttcactccca ctgtatttcc taacaacagc aaccagagca acagccatat   360
catcacagga cgaaccctct ctacttccaa ggcttttatt tcagtaaatc tgctctacct   420
ctatctcagg cagctagaag ttttgatact catacaaata ctactgcagc tttctgttca   480
taattggaaa agtagacaag actcagtgta atgcaggcat tccttatgcc agtcagcatt   540
cagtttttgg atcatcattg cacacatata ccccaccatgt gtcaatata tatgtaaaaa   600
tccatgaagc aagagtcata atagctagca tttgatattg tattgtattt tcctcttata   660
tcatcttctc cttttcgtcc ttaaaaaaaa tctgttcaag tcagtctaaa ttaattattg   720
gatgataagt agataaaatc tttatttga taacacattg accaatgaa tatgttttctt    780
tgcaagacat agtcctcact tccaagataa caagcctgac aaaattatac tggagcaagt   840
ccacaagtaa tgatggtagc ttttccttat tgtcagtcct ggggcaaaaa taagacaaaa   900
gataacaagg tagactaaag attatgtaag aagaaggaa agcagcagga catgggaaac   960
tttcatagga taacattttg ataatggatg atgagaatta atgcgttaga cagagatggg  1020
cgggaatgat tgaaggtctg agcattttag cacagattaa gaccaaatca ttaggatttt  1080
```

```
aagagttgtg tacagttagt gaagaaaaag ccctagaatt taatttgact gttgataaaa    1140
cattcttgga ttagattgaa gactctttc tgtgccaagt aagtatattt atgataatga    1200
tgatgactgt agtgctaaat atttaatcaa taaaaacaaa aataattgcc gcatacataa    1260
tgtcctgagt actactgtaa atgttttatc ttatttct taaactgtct acagcactgt    1320
aaggtaggca ccagtattgt cacagttaca cagatatga aactgagaca cagggaagtt    1380
aagttagttg gtcaatttca agcaatcggc aagccatgga gcatctatgt cagggctgcc    1440
aggacatgtg actgtaaaca gaagttttaa cttttaact caaagagggt atgtgtctgg    1500
gttaatggaa agtttcagga ccctcagaaa acattactaa caagcaaatg aaaggtgtat    1560
ctggaagatt aagttctaac agactcctca tttccatcga tccaataatg cacttaggga    1620
gatgactggg catattgagg ataggaagag agaaatgaaa acacagcctt ttatattgtt    1680
cttaacaggc ttgtgccaaa catcatctgg gtgaatttag gtgattgagg agaagaaaga    1740
cataggaatg aaattctctg agcacaaggg agaagttcta cactcagact gagccaacag    1800
actttctgg cctgacaacc agggtggcgc aggatgctca gtgcagagag gaagaagcag    1860
gtggtctctg cagctggaag ctcagctccc acccagctgc tttgcatgtc cctcccagct    1920
gccctacctt ccagagccca tatcaatgcc tgtgtcagag ccctggggag gaactgctca    1980
gttaggaccc agagggaacc atggaagccc cagctcagct tctcttcctc ctgctactct    2040
ggctcccagg tgaggggaac atgaggtggt tttgcacatt agtgaaaact cttgccacct    2100
ctgctcagca agaaatataa ttaaaattca aagtatatca acaattttgg ctctactcaa    2160
agacagttgg tttgatcttg attacatgag tgcatttctg ttttatttcc aatttcagat    2220
accaccggag aaattgtgtt gacacagtct ccagccaccc tgtctttgtc tccaggggaa    2280
agagccaccc tctcctgcag ggccagtcag agtgttagca gctacttagc ctggtaccaa    2340
cagaaacctg gccaggctcc caggctcctc atctatgatg catccaacag ggccactggc    2400
atcccagcca ggttcagtgg cagtgggtct gggacagact tcactctcac catcagcagc    2460
ctagagcctg aagattttgc agtttattac tgtcagcagc gtagcaactg gcctccgacg    2520
ttcggccaag gaccaaggt ggaaatcaaa cgtaagtaat ttttcactat tgtcttctga    2580
aatttgggtc tgatggccag tattgacttt tagaggctta aataggagtt tggtaaagat    2640
tggtaaatga gggcatttaa gatttgccat gggttgcaaa agttaaactc agcttcaaaa    2700
atggatttgg agaaaaaaag attaaattgc tctaaactga atgacacaaa gtaaaaaaaa    2760
aaagtgtaac taaaaaggaa cccttgtatt tctaaggagc aaaagtaaat ttattttgt    2820
tcactcttgc caaatattgt attggttgtt gctgattatg catgatacag aaaagtggaa    2880
aaatacattt tttagtcttt ctcccttttg tttgataaat tattttgtca gacaacaata    2940
aaaatcaata gcacgcccta agaaaaatca gggaaaagtg aagtgtacct atttgctatg    3000
tagaagaggc agcttacttg aaaatcagca gcaatgttgt ttttagagtc t              3051

SEQ ID NO: 37            moltype = DNA   length = 3072
FEATURE                  Location/Qualifiers
misc_feature             1..3072
                         note = Rearranged human IGK V3-20+J1 nucleic acid sequence
source                   1..3072
                         mol_type = other DNA
                         organism = synthetic construct
SEQUENCE: 37
agccagtgga tgactatttt ctttcctgag actgataatg gtcattccac ccaatggtcc     60
aaactacatg cagtggtaat ggtcatgcag gcctttctgc cacctcttgc tatattttta    120
ccaactcatg ggccactgcc aacagtctag ctatctgatc aggaaaatag caaccgagtg    180
actgactat taaagcatcc cctctgtgga gaaaaggact atggcaacag cttgccacct    240
ataagagaca aatatgtcac tcagctggat gctgggtcta ccatgaccac ccttgagatg    300
aacttatgcc atgtttttgg atgcccactg agactttgct ttgaccaagg aaagttcttt    360
actgcccaaa tgacgtcaat ggacacactc tcatgggaca tgatggattt tccatacacc    420
ttgttatcca aaggccaatg gatctattta atgctagaac agctgactca cacggcaact    480
gaagagtgta catcagggca acctgctagt agagtgtgaa cccatctgac tacagcaatt    540
ggacattaaa cactgcactg cagagcaagg gaaagacggc acggaggtgc aggttgaaaa    600
acactgagtt gagtgaggaa gaagttgggc aaggccagtt tcctgataga gctgccactg    660
tgaaatccca aactcagtgt ttccaatcat ttttttcctt ttatagtgat gttcttgggg    720
gtgttgcagt ttaggccacc atgataaccc agacaggcct cctaactcta attggatgga    780
atgattcccc tgggtgcctt ctatgggttc cacaggatca agaaatatca gggtgttaat    840
ttccttctgc tggtaggagg gtcatctgat tcctccatta gggtggatga cgttatcaga    900
catgtcaatt ttctacagta cttgacctgc cttctagaac tggacaaccg agggtgaaag    960
gactggatca agcaacaatg gcaatgggtg cccaaaagag tagtagtctc agaacaggga   1020
gagacagact gagtcctcc actaactcag cccaacacct gtggatgagt agggatgcc    1080
tgagatcctg gggtggatgg gaggtggggc actgatctgt caatctgctt tttcttcaag   1140
gatcaggcag cagagaccca gaagcttcat gtctttgtaa ggctcttcca agccaacaca   1200
gataatttga caaaacactg tatctgcatc ccagacctca ccctgtcaca gactgaagtg   1260
gttgtttcat cctactaagg gtaaactata tcagctatac aagataaaaa actggatag    1320
tttagaggat cacccaagaa atagttcttt gcctgcatgg acaaaaccat cttctgtctt   1380
tagggaaatg gtatcactac cctgaggatt tggagcccag gtctcactta tctgtgcagt   1440
tgtgaaagtc ctcacacca cagtgctgag gttaattgaa tgttactctt ttaatttctg   1500
caaagaatga gacagcttct ggaccctcag gaaagatcaa taacaagtaa atacaagtat   1560
atccggaaga taaagttgta atagactctt cctttcaacc tgatccatca tgcattagg    1620
gagctgactg gcacaagtt ggagcagaaa gagaaaatg aaaccacagc cttctatttt   1680
gttctaaca gacttgtacc aaacattctg tggctcaatc taggtgatgg tgagacaaga   1740
ggacacaggg gttaaattct gtggccgcag gggagaagtt ctaccctcag actgagccaa   1800
cggccttttc tggcctgatc acctgggcat gggctgctga gagcagaaag ggagagaga   1860
ttgtctctgc agctgcaagc ccagcacccg cccagctgc tttgcatgtc cctcccagtc   1920
gccctgcagt ccagagccca tatcaatgcc tgggtcagag ctctggagaa gagctgctca   1980
gttaggaccc agagggaacc atggaaaccc cagcgcagct tctcttcctc ctgctactct   2040
ggctcccagg tgaggggaac atgggatggt tttgcatgtc agtgaaaacc ctctcaagtc   2100
ctgttacctg gcaactctgc tcagtcaata caataattaa agctcaatat aaagcaataa   2160
ttctggctct tctgggaaga caatgggttt gatttagatt acatgggtga ctttctgtt    2220
```

```
ttatttccaa tctcagatac caccggagaa attgtgttga cgcagtctcc aggcaccctg    2280
tctttgtctc caggggaaag agccaccctc tcctgcaggg ccagtcagag tgttagcagc    2340
agctacttag cctggtacca gcagaaacct ggccaggctc ccaggctcct catctatggt    2400
gcatccagca gggccactgg catcccagac aggttcagtg gcagtgggtc tgggacagac    2460
ttcactctca ccatcagcag actggagcct gaagattttg cagtgtatta ctgtcagcag    2520
tatggtagct cacccttggac gttcggccaa gggaccaagg tggaaatcaa acgtaagtaa   2580
tttttcacta ttgtcttctg aaatttgggt ctgatggcca gtattgactt ttagaggctt    2640
aaataggagt ttggtaaaga ttggtaaatg agggcattta agatttgcca tgggttgcaa    2700
aagttaaact cagcttcaaa aattggatttg gagaaaaaaa gattaaattg ctctaaactg   2760
aatgacacaa agtaaaaaaa aaaagtgtaa ctaaaaagga accettgtat ttctaaggag    2820
caaaagtaaa tttattttg ttcactcttg ccaaatattg tattggttgt tgctgattat     2880
gcatgataca gaaagtgga aaaatacatt ttttagtctt tctcccttt gtttgataaa      2940
ttatttgtc agacaacaat aaaaatcaat agcacgccct aagaaaaatc agggaaaagt     3000
gaagtgtacc tatttgctat gtagaagagg cagcttactt gaaaatcagc agcaatgttg    3060
tttttagagt ct                                                        3072

SEQ ID NO: 38          moltype = AA  length = 107
FEATURE                Location/Qualifiers
REGION                 1..107
                       note = common light chain VL encoded by human IGKV1-39/IGKJ4
source                 1..107
                       mol_type = protein
                       organism = synthetic construct
SEQUENCE: 38
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGG GTKVEIK                  107

SEQ ID NO: 39          moltype = AA  length = 107
FEATURE                Location/Qualifiers
REGION                 1..107
                       note = common light chain VL encoded by human IGKV3-11/IGKJ1
source                 1..107
                       mol_type = protein
                       organism = synthetic construct
SEQUENCE: 39
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPTFGQ GTKVEIK                  107

SEQ ID NO: 40          moltype = AA  length = 108
FEATURE                Location/Qualifiers
REGION                 1..108
                       note = common light chain VL encoded by human IGKV3-20/IGKJ1
source                 1..108
                       mol_type = protein
                       organism = synthetic construct
SEQUENCE: 40
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIK                 108

SEQ ID NO: 41          moltype = AA  length = 107
FEATURE                Location/Qualifiers
source                 1..107
                       mol_type = protein
                       organism = Mus musculus
SEQUENCE: 41
RADAAPTVSI FPPSSEQLTS GGASVVCFLN NFYPKDINVK WKIDGSERQN GVLNSWTDQD    60
SKDSTYSMSS TLTLTKDEYE RHNSYTCEAT HKTSTSPIVK SFNRNEC                  107
```